US012497622B2

(12) United States Patent
Zhang et al.

(10) Patent No.: US 12,497,622 B2
(45) **Date of Patent: *Dec. 16, 2025**

(54) NUCLEIC ACID, PHARMACEUTICAL COMPOSITION, CONJUGATE, PREPARATION METHOD, AND USE

(71) Applicant: SUZHOU RIBO LIFE SCIENCE CO., LTD., Jiangsu (CN)

(72) Inventors: Hongyan Zhang, Jiangsu (CN); Shan Gao, Jiangsu (CN); Daiwu Kang, Jiangsu (CN); Tao Liu, Jiangsu (CN)

(73) Assignee: SUZHOU RIBO LIFE SCIENCE CO., LTD., Jiangsu (CN)

( * ) Notice: Subject to any disclaimer, the term of this patent is extended or adjusted under 35 U.S.C. 154(b) by 979 days.

This patent is subject to a terminal disclaimer.

(21) Appl. No.: 17/612,912

(22) PCT Filed: May 21, 2020

(86) PCT No.: PCT/CN2020/091484

§ 371 (c)(1),
(2) Date: Nov. 19, 2021

(87) PCT Pub. No.: WO2020/233650

PCT Pub. Date: Nov. 26, 2020

(65) Prior Publication Data

US 2023/0193277 A1 Jun. 22, 2023

(30) Foreign Application Priority Data

May 22, 2019 (CN) ........................ 201910430588.7

(51) Int. Cl.

| | |
|---|---|
| ***A61K 31/713*** | (2006.01) |
| ***A61K 47/18*** | (2017.01) |
| ***A61K 47/24*** | (2006.01) |
| ***A61K 47/26*** | (2006.01) |
| ***A61P 7/00*** | (2006.01) |
| ***C12N 15/113*** | (2010.01) |

(52) U.S. Cl.

CPC .......... *C12N 15/1137* (2013.01); *A61K 47/18* (2013.01); *A61K 47/24* (2013.01); *A61K 47/26* (2013.01); *C12N 2310/11* (2013.01); *C12N 2310/14* (2013.01); *C12N 2310/314* (2013.01); *C12N 2310/315* (2013.01); *C12N 2310/3515* (2013.01)

(58) Field of Classification Search

CPC ........... C12N 15/1137; C12N 2310/11; C12N 2310/14; C12N 2310/314; C12N 2310/315; C12N 2310/3515; C12N 2310/321; C12N 2310/322; C12N 15/113; C12N 2310/3525; A61K 47/18; A61K 47/24; A61K 47/26; A61K 31/713; C12Y 304/21027; A61P 7/00; A61P 7/02; C07H 21/00

See application file for complete search history.

(56) References Cited

U.S. PATENT DOCUMENTS

| | | | | |
|---|---|---|---|---|
| 8,030,474 | B2 | 10/2011 | Khvorova et al. | |
| 8,106,022 | B2 | 1/2012 | Manoharan et al. | |
| 8,334,372 | B2 * | 12/2012 | Freier | C12N 15/1137 536/24.1 |
| 8,344,125 | B2 | 1/2013 | Manoharan et al. | |
| 9,428,751 | B2 | 8/2016 | Macdonald et al. | |
| 9,670,492 | B2 | 6/2017 | Freier et al. | |
| 10,130,651 | B2 | 11/2018 | Wooddell et al. | |
| 10,246,708 | B2 | 4/2019 | Kasperkovitz et al. | |
| 10,294,477 | B2 | 5/2019 | Swayze | |
| 10,370,453 | B2 | 8/2019 | Sexton et al. | |
| 10,934,544 | B2 | 3/2021 | Akinc et al. | |
| 11,084,884 | B2 | 8/2021 | Sexton et al. | |
| 11,414,661 | B2 * | 8/2022 | Zhang | A61P 3/06 |
| 11,414,665 | B2 * | 8/2022 | Zhang | C12N 15/1131 |
| 11,492,620 | B2 * | 11/2022 | Zhang | C12N 15/1131 |
| 11,633,482 | B2 * | 4/2023 | Zhang | A61P 31/20 514/25 |
| 11,660,347 | B2 * | 5/2023 | Zhang | A61K 47/549 536/1.11 |
| 11,896,674 | B2 * | 2/2024 | Zhang | A61K 47/555 |
| 11,918,600 | B2 * | 3/2024 | Zhang | A61K 31/712 |
| 12,084,661 | B2 * | 9/2024 | Zhang | C12N 15/1131 |
| 2003/0206887 | A1 | 11/2003 | Morrissey et al. | |

(Continued)

FOREIGN PATENT DOCUMENTS

| | | | |
|---|---|---|---|
| AU | 2014208251 | A1 | 8/2014 |
| CA | 2930393 | A1 | 6/2009 |

(Continued)

OTHER PUBLICATIONS

Jean-Rémi Bertrand, Mireille Pottier, Antoine Vekris, Paule Opolon, Andrei Maksimenko, Claude Malvy, Comparison of antisense oligonucleotides and siRNAs in cell culture and in vivo, Biochemical and Biophysical Research Communications, vol. 296, Issue 4, 2002, pp. 1000-1004, ISSN 0006-291X. (Year: 2002).*

Qui, S. et al., "Dickkopf 3 attenuates xanthine dehydrogenase expression to prevent oxidative stress-induced apoptosis," Genes to Cells, 2017, vol. 22, pp. 406-417. (cited in Extended European Search Report issued on Jan. 30, 2024, in European Patent Application No. 20813863.6).

Yasuda, T. et al., "Anti-Gout Agent Allopurinol Exerts Cytotoxicity to Human Hormone-Refractory Prostate Cancer Cells in Combination with Tumor Necrosis Factor-Related Apoptosis-Inducing Ligand," Mol Cancer Res, Dec. 2008, vol. 6, No. 12, pp. 1852-1860. (cited in Extended European Search Report issued on Jan. 30, 2024, in European Patent Application No. 20813863.6).

(Continued)

*Primary Examiner* — Abigail Vanhorn

(74) *Attorney, Agent, or Firm* — Panitch Schwarze Belisario & Nadel LLP

(57) ABSTRACT

Provided are an siRNA which inhibits plasma coagulation factor XI gene expression, a pharmaceutical composition containing the siRNA, a conjugate, a reagent kit, and a use of the siRNA, the pharmaceutical composition thereof and the conjugate in preparing a drug used for treating and/or preventing thrombotic diseases and ischemic strokes.

26 Claims, No Drawings

Specification includes a Sequence Listing.

(56) References Cited

U.S. PATENT DOCUMENTS

| | | | | |
|---|---|---|---|---|
| 2004/0266707 | A1* | 12/2004 | Leake | C12N 15/111 536/23.1 |
| 2005/0245475 | A1 | 11/2005 | Khvorova et al. | |
| 2005/0246794 | A1 | 11/2005 | Khvorova et al. | |
| 2005/0255487 | A1 | 11/2005 | Khvorova et al. | |
| 2008/0113351 | A1 | 5/2008 | Naito et al. | |
| 2008/0146788 | A1 | 6/2008 | Bhat et al. | |
| 2010/0063132 | A1 | 3/2010 | Kim et al. | |
| 2010/0137414 | A1 | 6/2010 | Freier et al. | |
| 2011/0015252 | A1 | 1/2011 | Fitzgerald et al. | |
| 2011/0039914 | A1 | 2/2011 | Pavco et al. | |
| 2011/0054005 | A1 | 3/2011 | Naito et al. | |
| 2012/0052487 | A9 | 3/2012 | Khvorova et al. | |
| 2012/0108803 | A1 | 5/2012 | Han et al. | |
| 2012/0172412 | A1 | 7/2012 | Rozema et al. | |
| 2012/0184595 | A1 | 7/2012 | Macdonald et al. | |
| 2012/0201756 | A1 | 8/2012 | Sexton | |
| 2012/0227119 | A1 | 9/2012 | Doran et al. | |
| 2013/0005793 | A1 | 1/2013 | Chin et al. | |
| 2013/0023579 | A1 | 1/2013 | Crooke et al. | |
| 2013/0041133 | A1 | 2/2013 | Aaronson et al. | |
| 2013/0096288 | A1 | 4/2013 | Han et al. | |
| 2013/0123482 | A1 | 5/2013 | Xi et al. | |
| 2013/0158021 | A1 | 6/2013 | Dong et al. | |
| 2013/0190484 | A1 | 7/2013 | Rozema et al. | |
| 2014/0099666 | A1 | 4/2014 | Rossomando et al. | |
| 2014/0128453 | A1 | 5/2014 | Mullick et al. | |
| 2014/0179768 | A1 | 6/2014 | Bettencourt et al. | |
| 2014/0194489 | A1 | 7/2014 | Bumcrot et al. | |
| 2014/0343123 | A1 | 11/2014 | Prakash et al. | |
| 2015/0093444 | A1 | 4/2015 | Zhang et al. | |
| 2015/0152436 | A1 | 6/2015 | Musunuru et al. | |
| 2015/0174260 | A1 | 6/2015 | Yang et al. | |
| 2015/0191726 | A1 | 7/2015 | Manoharan et al. | |
| 2015/0247143 | A1 | 9/2015 | Fitzgerald et al. | |
| 2015/0263948 | A1 | 9/2015 | Jan et al. | |
| 2015/0291958 | A1 | 10/2015 | Albaek et al. | |
| 2015/0315584 | A1 | 11/2015 | Macdonald et al. | |
| 2015/0315594 | A1 | 11/2015 | Prakash et al. | |
| 2016/0017335 | A1 | 1/2016 | Borodovsky et al. | |
| 2016/0186180 | A1 | 6/2016 | Bettencourt et al. | |
| 2016/0237438 | A1 | 8/2016 | Brown et al. | |
| 2016/0283653 | A1 | 9/2016 | Staudt et al. | |
| 2016/0354404 | A1 | 12/2016 | Hinkle et al. | |
| 2017/0000815 | A1 | 1/2017 | Fitzgerald et al. | |
| 2017/0002094 | A1 | 1/2017 | Sexton et al. | |
| 2017/0114341 | A1 | 4/2017 | Bradshaw et al. | |
| 2018/0087054 | A1 | 3/2018 | Querbes et al. | |
| 2018/0148722 | A1 | 5/2018 | Fitzgerald et al. | |
| 2018/0216114 | A1 | 8/2018 | Fitzgerald et al. | |
| 2018/0245077 | A1 | 8/2018 | Chiu et al. | |
| 2019/0062749 | A1 | 2/2019 | Zhang | |
| 2019/0078088 | A1 | 3/2019 | Li et al. | |
| 2019/0202855 | A1 | 7/2019 | Sakamuri et al. | |
| 2019/0255091 | A1 | 8/2019 | Li et al. | |
| 2019/0292547 | A1 | 9/2019 | Li et al. | |
| 2020/0199591 | A1 | 6/2020 | Fitzgerald et al. | |
| 2020/0338201 | A1 | 10/2020 | Zhang et al. | |
| 2020/0360522 | A1 | 11/2020 | Zhang et al. | |
| 2021/0032623 | A1 | 2/2021 | Zhang et al. | |
| 2021/0275564 | A1 | 9/2021 | Zhang et al. | |
| 2021/0277400 | A1 | 9/2021 | Zhang et al. | |
| 2021/0401994 | A1 | 12/2021 | Zhang et al. | |
| 2022/0049249 | A1 | 2/2022 | Zhang et al. | |
| 2022/0062427 | A1* | 3/2022 | Zhang | A61K 47/549 |
| 2022/0186221 | A1* | 6/2022 | Zhang | A61K 47/549 |
| 2022/0235359 | A1* | 7/2022 | Zhang | A61K 47/50 |
| 2022/0315929 | A1* | 10/2022 | Zhang | A61K 47/549 |
| 2022/0356474 | A1* | 11/2022 | Zhang | C12N 15/113 |
| 2022/0389428 | A1 | 12/2022 | Zhang et al. | |
| 2022/0395526 | A1 | 12/2022 | Zhang et al. | |
| 2023/0076803 | A1 | 3/2023 | Zhang et al. | |
| 2023/0132756 | A1* | 5/2023 | Zhang | A61P 29/00 514/44 A |
| 2023/0257827 | A1 | 8/2023 | Zhang et al. | |
| 2023/0313195 | A1* | 10/2023 | Zhang | A61P 1/16 514/44 A |
| 2024/0200060 | A1* | 6/2024 | Zhang | C12N 15/113 |
| 2024/0200076 | A1* | 6/2024 | Zhang | C12N 15/1137 |
| 2025/0057870 | A1 | 2/2025 | Liang et al. | |

FOREIGN PATENT DOCUMENTS

| | | | |
|---|---|---|---|
| CA | 2 677 068 | A1 | 3/2011 |
| CN | 101603042 | A | 12/2009 |
| CN | 102006890 | A | 4/2011 |
| CN | 102016036 | A | 4/2011 |
| CN | 102124107 | A | 7/2011 |
| CN | 102140458 | A | 8/2011 |
| CN | 102140459 | A | 8/2011 |
| CN | 102140460 | A | 8/2011 |
| CN | 102140461 | A | 8/2011 |
| CN | 102344477 | A | 2/2012 |
| CN | 102439148 | A | 5/2012 |
| CN | 102719434 | A | 10/2012 |
| CN | 102753186 | A | 10/2012 |
| CN | 102869774 | A | 1/2013 |
| CN | 103380113 | A | 10/2013 |
| CN | 102083983 | B | 4/2014 |
| CN | 103890000 | A | 6/2014 |
| CN | 104107437 | A | 10/2014 |
| CN | 104232644 | A | 12/2014 |
| CN | 104328121 | A | 2/2015 |
| CN | 104717982 | A | 6/2015 |
| CN | 104854242 | A | 8/2015 |
| CN | 104922141 | A | 9/2015 |
| CN | 105324485 | A | 2/2016 |
| CN | 105378082 | A | 3/2016 |
| CN | 105392488 | A | 3/2016 |
| CN | 105452465 | A | 3/2016 |
| CN | 105517556 | A | 4/2016 |
| CN | 105713092 | A | 6/2016 |
| CN | 105814204 | A | 7/2016 |
| CN | 106132442 | A | 11/2016 |
| CN | 106146591 | A | 11/2016 |
| CN | 106232831 | A | 12/2016 |
| CN | 106255755 | A | 12/2016 |
| CN | 106460025 | A | 2/2017 |
| CN | 107075516 | A | 8/2017 |
| CN | 107109405 | A | 8/2017 |
| CN | 107250362 | A | 10/2017 |
| CN | 107854478 | A | 3/2018 |
| CN | 108271386 | A | 3/2018 |
| CN | 108064294 | A | 5/2018 |
| CN | 108064313 | A | 5/2018 |
| CN | 108220293 | A | 6/2018 |
| CN | 108239644 | A | 7/2018 |
| CN | 108265052 | A | 7/2018 |
| CN | 108348541 | A | 7/2018 |
| CN | 110945131 | A | 3/2020 |
| CN | 110959011 | A | 4/2020 |
| CN | 111050807 | A | 4/2020 |
| CN | 111973617 | A | 11/2020 |
| CN | 111973618 | A | 11/2020 |
| CN | 111973619 | A | 11/2020 |
| CN | 111979237 | A | 11/2020 |
| CN | 112423795 | A | 2/2021 |
| CN | 113330117 | A | 8/2021 |
| EP | 1 752 536 | A1 | 2/2007 |
| EP | 2 194 128 | A1 | 6/2010 |
| EP | 2 213 738 | A2 | 8/2010 |
| EP | 2 376 641 | | 10/2011 |
| EP | 2 669 377 | A2 | 12/2013 |
| EP | 2 990 410 | A1 | 3/2016 |
| EP | 3 312 281 | A2 | 4/2018 |
| EP | 3 315 608 | A1 | 5/2018 |
| EP | 3 335 715 | A2 | 6/2018 |
| EP | 3409780 | A1 | 12/2018 |
| EP | 3 719 128 | A1 | 10/2020 |
| EP | 3 862 024 | A1 | 8/2021 |
| JP | 2013523149 | A | 6/2013 |
| JP | 2013537423 | A | 10/2013 |
| JP | 2016501195 | A | 1/2016 |
| JP | 2016523087 | A | 8/2016 |

(56) References Cited

FOREIGN PATENT DOCUMENTS

| | | | |
|---|---|---|---|
| JP | 2017521045 | A | 8/2017 |
| JP | 2017534290 | A | 11/2017 |
| RU | 2013 134 745 | A | 2/2015 |
| RU | 2 558 258 | C2 | 7/2015 |
| RU | 2015 133 167 | A | 3/2017 |
| TW | 201925471 | A | 7/2019 |
| TW | 201929905 | A | 8/2019 |
| WO | 00/27795 | A1 | 5/2000 |
| WO | 2004/045543 | A2 | 6/2004 |
| WO | 2004/078181 | A1 | 9/2004 |
| WO | 2005/116204 | A1 | 12/2005 |
| WO | 2006/006948 | A2 | 1/2006 |
| WO | 2006/096018 | A1 | 9/2006 |
| WO | 2007/134161 | A2 | 11/2007 |
| WO | 2008/011431 | A2 | 1/2008 |
| WO | 2008/109472 | A2 | 9/2008 |
| WO | 2009/073809 | A2 | 6/2009 |
| WO | 2009/082607 | A2 | 7/2009 |
| WO | 2009/134487 | A2 | 11/2009 |
| WO | 2010/012244 | A1 | 2/2010 |
| WO | 2010/045509 | A2 | 4/2010 |
| WO | 2010/068978 | A1 | 6/2010 |
| WO | 2010/083615 | A1 | 7/2010 |
| WO | 2010/101951 | A1 | 9/2010 |
| WO | 2010/121074 | A1 | 10/2010 |
| WO | 2010/131916 | A2 | 11/2010 |
| WO | 2010/147992 | A1 | 12/2010 |
| WO | 2011005793 | A1 | 1/2011 |
| WO | 2011/028938 | A1 | 3/2011 |
| WO | 2011/085271 | A2 | 7/2011 |
| WO | 2011/104169 | A1 | 9/2011 |
| WO | 2011126974 | A1 | 10/2011 |
| WO | 2011/139702 | A2 | 11/2011 |
| WO | 2011/154331 | A1 | 12/2011 |
| WO | 2012/013127 | A1 | 2/2012 |
| WO | 2012024170 | A2 | 2/2012 |
| WO | 2012/037254 | A1 | 3/2012 |
| WO | 2012/068176 | A1 | 5/2012 |
| WO | 2012/083185 | A2 | 6/2012 |
| WO | 2012/089352 | A1 | 7/2012 |
| WO | 2012/130086 | A1 | 10/2012 |
| WO | 2012/139081 | A2 | 10/2012 |
| WO | 2012/139469 | A1 | 10/2012 |
| WO | 2012/177784 | A2 | 12/2012 |
| WO | 2013/060261 | A1 | 5/2013 |
| WO | 2013/070771 | A1 | 5/2013 |
| WO | 2013061295 | A1 | 5/2013 |
| WO | 2013/166155 | A1 | 11/2013 |
| WO | 2014/025805 | A1 | 2/2014 |
| WO | 2014076195 | A1 | 5/2014 |
| WO | 2014/089313 | A1 | 6/2014 |
| WO | 2014/118267 | A2 | 11/2014 |
| WO | 2014/179626 | A2 | 11/2014 |
| WO | 2014/179627 | A2 | 11/2014 |
| WO | 2014/179629 | A2 | 11/2014 |
| WO | 2014205451 | A1 | 12/2014 |
| WO | 2015/006498 | A2 | 1/2015 |
| WO | 2015/006740 | A2 | 1/2015 |
| WO | 2015/015496 | A1 | 2/2015 |
| WO | 2015/031679 | A2 | 3/2015 |
| WO | 2015/051366 | A2 | 4/2015 |
| WO | 2015/100394 | A1 | 7/2015 |
| WO | 2015/113922 | A1 | 8/2015 |
| WO | 2015/148580 | A2 | 10/2015 |
| WO | 2015/168532 | A2 | 11/2015 |
| WO | 2015168589 | A1 | 11/2015 |
| WO | 2015/188197 | A2 | 12/2015 |
| WO | 2016/077321 | A2 | 12/2015 |
| WO | 2015188194 | A1 | 12/2015 |
| WO | 2015/011123 | A1 | 1/2016 |
| WO | 2016/028649 | A1 | 2/2016 |
| WO | 2016/040589 | A1 | 3/2016 |
| WO | 2016/081444 | A1 | 5/2016 |
| WO | 2016077349 | A1 | 5/2016 |
| WO | 2016/099982 | A2 | 6/2016 |
| WO | 2016/149331 | A2 | 9/2016 |
| WO | 2016/154127 | A2 | 9/2016 |
| WO | 2016/168286 | A1 | 10/2016 |
| WO | 2016/179342 | A2 | 11/2016 |
| WO | 2016/188473 | A1 | 12/2016 |
| WO | 2016/201301 | A1 | 12/2016 |
| WO | 2016/206626 | A1 | 12/2016 |
| WO | 2017/015175 | A1 | 1/2017 |
| WO | 2017/019660 | A1 | 2/2017 |
| WO | 2017/019891 | A2 | 2/2017 |
| WO | 2017/035340 | A1 | 3/2017 |
| WO | 2017/055627 | A1 | 4/2017 |
| WO | 2017/100542 | A1 | 6/2017 |
| WO | 2017/120397 | A1 | 7/2017 |
| WO | 2017131236 | A1 | 8/2017 |
| WO | 2017/184689 | A1 | 10/2017 |
| WO | 2017/189813 | A1 | 11/2017 |
| WO | 2018/027106 | A2 | 2/2018 |
| WO | 2018/035380 | A1 | 2/2018 |
| WO | 2018/044350 | A1 | 3/2018 |
| WO | 2018/075658 | A1 | 4/2018 |
| WO | 2018/140920 | A1 | 8/2018 |
| WO | 2018/191278 | A2 | 10/2018 |
| WO | 2018/209848 | A1 | 11/2018 |
| WO | 2018/223073 | A1 | 12/2018 |
| WO | 2019/105403 | A1 | 6/2019 |
| WO | 2019/105404 | A1 | 6/2019 |
| WO | 2019/105418 | A1 | 6/2019 |
| WO | 2019/105419 | A1 | 6/2019 |
| WO | 2019/105435 | A1 | 6/2019 |
| WO | 2019/105437 | A1 | 6/2019 |
| WO | WO-2019105414 | A1 * | 6/2019 ........... A61K 31/713 |
| WO | 2019/128611 | A1 | 7/2019 |
| WO | 2020038377 | A1 | 2/2020 |
| WO | 2020/063198 | A1 | 4/2020 |
| WO | 2020/093053 | A1 | 5/2020 |
| WO | 2020/135581 | A1 | 7/2020 |
| WO | 2020/147847 | A1 | 7/2020 |
| WO | 2020233651 | A1 | 11/2020 |
| WO | 2020233655 | A1 | 11/2020 |
| WO | 2020233680 | A1 | 11/2020 |
| WO | 2020238763 | A1 | 12/2020 |
| WO | 2020238766 | A1 | 12/2020 |

OTHER PUBLICATIONS

Hashimoto, K. et al., "Sulfotransferase-1A1-dependent bioactivation of aristolochic acid I and N-hydroxyaristolactam I in human cells," Carcinogenesis, 2016, vol. 37, No. 7, pp. 647-655. (cited in Extended European Search Report issued on Jan. 30, 2024, in European Patent Application No. 20813863.6).

Durnov, et al., "Children's Oncology", Paediatric Oncology, Second Edition, Moscow Publishing House Medicine, 2002, p. 139 and its English translation. Cited in Office Action issued on Oct. 10, 2022 in Russian Application No. 2020121741). (4 pages).

Dysop, "Chemistry of Synthetic Drugs", Publishing House MIR, 1964, pp. 12-19 and its English translation. Cited in Office Action issued on Oct. 10, 2022 in Russian Application No. 2020121741). (18 pages).

Belikov, V.G., "Pharmaceutical Chemistry", textbook, Moscow, 11th Edition, MEDpress-inform, 2007, pp. 27-29 and its English translation. (Cited in Office Action issued on Oct. 10, 2022 in Russian Application No. 2020121741). (8 pages).

Examination Report No. 2 issued on Feb. 3, 2023, by the Australian Government IP Australia in Australian Patent Application No. 2018394875 (4 pages).

Ren et al., "Synthesis of Galactosyl Compounds for Targeted Gene Delivery", Bioorganic & Medicinal Chemistry, 2001, 9(11), pp. 2969-2978.

Extended European Search Report issued on Mar. 27, 2023, by the European Patent Office in European Patent Application No. 19902173.4 (11 pages).

Li et al., "The silencing of ApoC3 suppresses oxidative stress and inflammatory responses in placenta cells from mice with preeclampsia via inhibition of the NF-B signaling pathway", Biomedicine & Pharmacotherapy, Aug. 31, 2018, vol. 107, pp. 1377-1384.

(56) References Cited

OTHER PUBLICATIONS

Notice of Reasons for Refusal issued on Jun. 1, 2023, by the Japanese Patent Office in Japanese Patent Application No. 2021-537877, with an English translation of the Notice (6 pages).
Kanasty et al., "Delivery materials for siRNA therapeutics", Nature Materials, Nov. 2023, vol. 12, pp. 967-977.
Notice of Reasons for Refusal issued on Jun. 6, 2023, by the Japanese Patent Office in Japanese Patent Application No. 2021-509880, with an English translation of the Notice (6 pages).
The First Office Action issued on Jan. 30, 2022, by the State Intellectual Property Office of the People's Republic of China in Chinese Patent Application No. 201880049520.8 and an English translation of the Action. (11 pages).
Decision of Rejection issued on Mar. 3, 2022, by the State Intellectual Property Office of the People's Republic of China in Chinese Patent Application No. 202010426194.7 and an English translation of the Action. (20 pages).
The Second Office Action issued on Mar. 16, 2022, by the State Intellectual Property Office of the People's Republic of China in Chinese Patent Application No. 201980046892.X and an English translation of the Action. (24 pages).
The Second Office Action issued on Mar. 21, 2022, by the State Intellectual Property Office of the People's Republic of China in Chinese Patent Application No. 201980046893.4 and an English translation of the Action. (19 pages).
The First Office Action issued on May 7, 2022, by the State Intellectual Property Office of the People's Republic of China in Chinese Patent Application No. 201980010095.6 and an English translation of the Action. (27 pages).
The First Office Action issued on May 7, 2022, by the State Intellectual Property Office of the People's Republic of China in Chinese Patent Application No. 201980010175.1 and an English translation of the Action. (30 pages).
The First Office Action issued on May 7, 2022, by the State Intellectual Property Office of the People's Republic of China in Chinese Patent Application No. 201880049190.2 and an English translation of the Action. (31 pages).
The First Office Action issued on May 7, 2022, by the State Intellectual Property Office of the People's Republic of China in Chinese Patent Application No. 201880049191.7 and an English translation of the Action. (30 pages).
The First Office Action issued on May 7, 2022, by the State Intellectual Property Office of the People's Republic of China in Chinese Patent Application No. 202080007282.1 and an English translation of the Action. (33 pages).
The First Office Action issued on May 7, 2022, by the State Intellectual Property Office of the People's Republic of China in Chinese Patent Application No. 201880049564.0 and an English translation of the Action. (29 pages).
The First Office Action issued on May 7, 2022, by the State Intellectual Property Office of the People's Republic of China in Chinese Patent Application No. 201880049586.7 and an English translation of the Action. (33 pages).
The First Office Action issued on May 7, 2022, by the State Intellectual Property Office of the People's Republic of China in Chinese Patent Application No. 201880048597.3 and an English translation of the Action. (34 pages).
The First Office Action issued on May 7, 2022, by the State Intellectual Property Office of the People's Republic of China in Chinese Patent Application No. 201880048600.1 and an English translation of the Action. (34 pages).
The First Office Action issued on May 7, 2022, by the State Intellectual Property Office of the People's Republic of China in Chinese Patent Application No. 202080009787.1 and an English translation of the Action. (50 pages).
The First Office Action issued on May 7, 2022, by the State Intellectual Property Office of the People's Republic of China in Chinese Patent Application No. 201880048949.5 and an English translation of the Action. (33 pages).
The First Office Action issued on May 20, 2021, by the State Intellectual Property Office of the People's Republic of China in Chinese Patent Application No. 202010426194.7 and an English translation of the Action. (20 pages).
The First Office Action issued on Jun. 23, 2021, by the State Intellectual Property Office of the People's Republic of China in Chinese Patent Application No. 201980046892.X and an English translation of the Action. (13 pages).
The First Office Action issued on Jun. 23, 2021, by the State Intellectual Property Office of the People's Republic of China in Chinese Patent Application No. 201980046893.4 and an English translation of the Action. (12 pages).
The First Office Action issued on Jun. 29, 2022, by the State Intellectual Property Office of the People's Republic of China in Chinese Patent Application No. 201980046892.X and an English translation of the Action. (8 pages).
The First Office Action issued on Jun. 29, 2022, by the State Intellectual Property Office of the People's Republic of China in Chinese Patent Application No. 201980046893.4 and an English translation of the Action. (8 pages).
The First Office Action issued on Oct. 25, 2021, by the State Intellectual Property Office of the People's Republic of China in Chinese Patent Application No. 202010426196.6 and an English translation of the Action. (16 pages).
The Second Office Action issued on Nov. 12, 2021, by the State Intellectual Property Office of the People's Republic of China in Chinese Patent Application No. 202010426194.7 and an English translation of the Action. (16 pages).
The Extended European Search Report issued on Jun. 9, 2022, by the European Patent Office in European Patent Application Publication No. 19851738.5. (64 pages).
The Extended European Search Report issued on Jul. 19, 2022, by the European Patent Office in European Patent Application No. 19867686.8. (12 pages).
The Extended European Search Report and Supplementary European Search Report issued on Aug. 9, 2021, by the European Patent Office in European Patent Application Publication No. 18883362.8. (9 pages).
The Extended European Search Report issued on Sep. 16, 2021, by the European Patent Office in European Patent Application No. 18883803.1. (10 pages).
Extended European Search Report dated Sep. 17, 2021, issued by the European Patent Office in corresponding European Application No. 18883982.3. (9 pages).
Extended European Search Report dated Sep. 29, 2021, issued by the European Patent Office in corresponding European Application No. 18884492.2. (45 pages).
The Extended European Search Report issued on Oct. 7, 2021, by the European Patent Office in European Patent Application Publication No. 18896766.5. (19 pages).
Invitation to remedy deficiencies pursuant to Rule 30(3) EPC / Rule 163(3) EPC issued on Feb. 22, 2022, by the European Patent Office in European Patent Application No. 20809029.0. (2 pages).
Communication pursuant to Rule 159 and Rule 58 EPC Invitation to remedy deficiencies in the application documents issued on Jan. 24, 2022, by the European Patent Office in European Patent Application No. 20815633.1 (2 pages).
Supplementary European Search Report issued on Jul. 27, 2021, by the European Patent Office in European Patent Office in European Patent Application No. 18883153. (7 pages).
Notification of Substantive Examination Result issued on Aug. 24, 2021, by the Intellectual Property Office of the Republic of Indonesia in Indonesian Patent Application No. P00202003131 and an English translation of the Notification. (6 pages).
Notification of Substantive Examination Result issued on Dec. 2, 2021, by the Intellectual Property Office of the Republic of Indonesia in Indonesian Patent Application No. P00202003125 and an English translation of the Notification. (6 pages).
Examination report under sections 12 & 13 of the Patents Act, 1970 and the Patents Rules, 2003 issued on Nov. 24, 2021, by the Intellectual Property Office of India in Indian Patent Application No. 202047017398 and English translation of the Report. (7 pages).

(56) References Cited

OTHER PUBLICATIONS

International Preliminary Report on Patentability issued on Jun. 11, 2020, by the International Bureau of WIPO in International Patent Application No. PCT/CN2018/118191. (7 pages).
International Preliminary Report on Patentability issued on Jul. 2, 2020, by the International Bureau of WIPO in International Patent Application No. PCT/CN2018/118232 and English translation of the Report. (14 pages).
International Preliminary Report on Patentability issued on Jul. 8, 2021, by the International Bureau of WIPO in International Patent Application No. PCT/CN2019/128686 and English translation of the Report. (17 pages).
International Preliminary Report on Patentability issued on Sep. 3, 2021, by the State Intellectual Property Office of the People's Republic of China in International Patent Application No. PCT/CN2020/091489 and English translation of the Report. (12 pages).
Written Opinion of the International Searching Authority and International Search Report issued on Feb. 20, 2019, by the State Intellectual Property Office of the People's Republic of China in International Patent Application No. PCT/CN2018/118107 and English translation. (22 pages).
Written Opinion of the International Searching Authority and International Search Report issued on Feb. 25, 2019, by the State Intellectual Property Office of the People's Republic of China in International Patent Application No. PCT/CN2018/118212 and English translation. (23 pages).
English translation of the Written Opinion of the International Searching Authority and International Search Report issued on Feb. 27, 2019, by the State Intellectual Property Office of the People's Republic of China in International Patent Application No. PCT/CN2018/118224. (13 pages).
Written Opinion of the International Searching Authority and International Search Report issued on Feb. 28, 2019, by the State Intellectual Property Office of the People's Republic of China in International Patent Application No. PCT/CN2018/118300 and English translation. (20 pages).
Written Opinion of the International Searching Authority and International Search Report issued on Mar. 6, 2019, by the State Intellectual Property Office of the People's Republic of China in International Patent Application No. PCT/CN2018/118106 and English translation. (20 pages).
Written Opinion of the International Searching Authority and International Search Report issued on Mar. 6, 2019, by the State Intellectual Property Office of the People's Republic of China in International Application No. PCT/CN2018/118191 and English translation. (17 pages).
Written Opinion of the International Searching Authority and International Search Report issued on Mar. 7, 2019, by the State Intellectual Property Office of the People's Republic of China in International Patent Application No. PCT/CN2018/118303 and English translation. (22 pages).
Written Opinion of the International Searching Authority and International Search Report issued on Mar. 7, 2019, by the State Intellectual Property Office of the People's Republic of China in International Patent Application No. PCT/CN2018/118232 and English translation. (24 pages).
Written Opinion of the International Searching Authority and International Search Report issued on Mar. 26, 2020, by the State Intellectual Property Office of the People's Republic of China in International Patent Application No. PCT/CN2019/129016 and English translation. (27 pages).
Written Opinion of the International Searching Authority and International Search Report issued on Mar. 26, 2020, by the State Intellectual Property Office of the People's Republic of China in International Patent Application No. PCT/CN2019/128686 and English translation. (27 pages).
Written Opinion of the International Searching Authority and International Search Report issued on Aug. 19, 2020, by the State Intellectual Property Office of the People's Republic of China in International Patent Application No. PCT/CN2020/091489 and English translation. (26 pages).
Written Opinion of the International Searching Authority and International Search Report issued on Aug. 21, 2020, by the State Intellectual Property Office of the People's Republic of China in International Patent Application No. PCT/CN2020/091484 and English translation. (29 pages).
Written Opinion of the International Searching Authority and International Search Report issued on Aug. 21, 2020, by the State Intellectual Property Office of the People's Republic of China in International Patent Application No. PCT/CN2020/091614 and English translation. (24 pages).
Written Opinion of the International Searching Authority and International Search Report issued on Aug. 24, 2020, by the State Intellectual Property Office of the People's Republic of China in International Patent Application No. PCT/CN2020/091624 and English translation. (26 pages).
Written Opinion of the International Searching Authority and International Search Report issued on Aug. 25, 2020, by the State Intellectual Property Office of the People's Republic of China in International Patent Application No. PCT/CN2020/091485 and English translation. (30 pages).
Written Opinion of the International Searching Authority and International Search Report issued on Aug. 28, 2020, by the State Intellectual Property Office of the People's Republic of China in International Patent Application No. PCT/CN2020/091649 and English translation. (25 pages).
Written Opinion of the International Searching Authority and International Search Report issued on Sep. 2, 2020, by the State Intellectual Property Office of the People's Republic of China in International Patent Application No. PCT/CN2020/091606 and English translation. (28 pages).
Written Opinion of the International Searching Authority and International Search Report issued on Nov. 21, 2019, by the State Intellectual Property Office of the People's Republic of China in International Patent Application No. PCT/CN2019/101653 and English translation. (23 pages).
Written Opinion of the International Searching Authority and International Search Report issued on Nov. 28, 2019, by the State Intellectual Property Office of the People's Republic of China in International Patent Application No. PCT/CN2019/101656 and English translation. (21 pages).
Written Opinion of the International Searching Authority and International Search Report issued on Apr. 17, 2020, by the State Intellectual Property Office of the People's Republic of China in International Patent Application No. PCT/CN2020/072813 and English translation. (32 pages).
Office Action issued on Mar. 9, 2022, by the Russian Agency for Patents and Trademarks in Russian Patent Application No. 2020118025/10(030488) and English translation of the Action. (14 pages).
Office Action issued on May 11, 2022, by the Russian Agency for Patents and Trademarks in Russian Patent Application No. 2020121741/04(037329) and English translation of the Action. (18 pages).
Office Action issued on Jan. 28, 2022, by the U.S. Patent and Trademark Office in U.S. Appl. No. 16/758,532. (28 pages).
Office Action issued on Mar. 11, 2022, by the U.S. Patent and Trademark Office in U.S. Appl. No. 16/758,720. (21 pages).
Notice of Allowance issued on Mar. 31, 2022, by the U.S. Patent and Trademark Office in U.S. Appl. No. 16/764,307. (7 pages).
Notice of Allowance issued on Apr. 5, 2022, by the U.S. Patent and Trademark Office in U.S. Appl. No. 16/763,058. (7 pages).
Office Action issued on May 27, 2022, by the U.S. Patent and Trademark Office in U.S. Appl. No. 16/758,532. (8 pages).
Notice of Allowance issued on Jul. 25, 2022, by the U.S. Patent and Trademark Office in U.S. Appl. No. 16/758,720. (5 pages).
Office Action issued on Aug. 24, 2022, by the U.S. Patent and Trademark Office in U.S. Appl. No. 16/758,532. (13 pages).
Office Action issued on Oct. 29, 2021, by the U.S. Patent and Trademark Office in U.S. Appl. No. 16/764,307. (17 pages).
Office Action issued on Nov. 16, 2021, by the U.S. Patent and Trademark Office in U.S. Appl. No. 16/763,058. (26 pages).

(56) References Cited

OTHER PUBLICATIONS

Office Action issued Aug. 14, 2020, by the Intellectual Property Office of Vietnam in Vietnamese Patent Application No. 1-2020-03065 and an English translation of the Action. (3 pages).
Office Action issued Aug. 28, 2020, by the Intellectual Property Office of Vietnam in Vietnamese Patent Application No. 1-2020-03777 and an English translation of the Action. (3 pages).
Payment and Certificate of Renewal issued on May 30, 2022 by the Patent Office of South Africa in South African Patent Application No. 2020/03833. (1 page).
Ahmad Dar et al., "siRNAmod: A database of experimentally validated chemically modified SiRNAs," Scientific Reports, Jan. 28, 2016, vol. 6, No. 1. (8 pages).
Beaucage et al., "Advances in the Synthesis of Oligonucleotides by the Phosphoramidite Approach", Tetrahedron, 1992, vol. 48, No. 12, pp. 2223-2311.
Behlke, Mark A., "Chemical Modification of siRNAs for in Vivo Use," Oligonucleotides, 2008, vol. 18, pp. 305-320.
Berthold et al., "Cellular Delivery and Antisense Effects of Peptide Nucleic Acid Conjugated to Polyethyleneimine via Disulfide Linkers," Bioconjugate Chemistry, 2010, vol. 21, No. 10, pp. 1933-1938.
Chen et al., "Research progress on factor XI as a novel target for antithrombotic therapy," Chinese Pharmacological Bulletin, Apr. 15, 2015, vol. 31, No. 5, with English abstract, pp. 619-622.
Dai et al., "A vital role for Angpll3 in the PAN-induced podocyte loss by affecting detachment and apoptosis in vitro," BMC Nephrology, 2015, vol. 16, No. 1. (10 pages).
Ding et al., "Limited role of kininogen in the host response during gram-negative pneumonia derived sepsis," American Journal of Physiology Lung Cellular and Molecular Physiology, Nov. 9, 2017. (33 pages).
Dong et al., "Lipopeptide nanoparticles for potent and selective siRNA delivery in rodents and nonhuman primates", Proceedings of the National Academy of Sciences, Feb. 2014, www.pnas.org/cgi/doi/10.1073/pnas.1322937111 (6 pages).
Dong et al., "A novel packaging system of recombinant AAV5/5 vector," Chinese Journal of Biotechnology, May 25, 2010, vol. 26, No. 5, pp. 679-686.
Common knowledge "RNAi technology," 2005, with English translation. (5 pages).
Foster et al., "Advanced siRNA Designs Further Improve in Vivo Performance of GalNAc-SiRNA Conjugates," Molecular Therapy, Mar. 2018, vol. 26, No. 3, pp. 708-717.
Greene et al., "Protection for the Hydroxyl Group, Including 1,2- and 1,3-DIOLS", Protective Groups in Organic Synthesis, Third Edition, 1999 John Wiley & Sons, Inc. pp. 17-245, (229 pages).
"*Homo sapiens* Kininogen 1 (KNG1), Transcript Variant 1, mRNA" GenBank, May 2, 2018, NM 00102416.2. (8 pages).
Khaitmetova et al., "Synthesis and Study of the Properties of Polymer Complexes of Ethacizin with Carboxymethylcellulose," Chemistry of Plant Raw Materials, 2017, No. 4, with English translation. (18 pages).
Khan et al., "High-Molecular-Weight Kininogen Fragments Stimulate the Secretion of Cytokines and Chemokines Through uPAR, Mac-1, and gC1qR in Monocytes," Arteriosclerosis, Thrombosis, and Vascular Biology, Oct. 2006, vol. 26, No. 10, pp. 2260-2266.
Khvorova et al., "The chemical evolution of oligonucleotide therapies of clinical utility", Nature Biotechnology Advance Online Publication, Feb. 27, 2017; doi:10.1038/nbt.3765, (11 pages).
Kim et al., "Bifunctional compounds for targeted hepatic gene delivery," Gene Therapy, 2007, vol. 14, pp. 704-708.
Liu et al., "Determination of Human Plasma Pre-Kallikrein," Journal of China Medical University, 1988, vol. 17, No. 6, with English abstract, pp. 432-436.
Liu et al., "Coagulation factor XI induces Ca2+ response and accelerates cell migration in vascular smooth muscle cells via proteinase-activated receptor 1," American Journal of Physiology, Cell Physiology, Mar. 1, 2019, vol. 316, No. 3, pp. C377-C392.
Love et al., "Lipid-like materials for low-dose, in vivo gene silencing", Proceedings of the National Academy of Sciences, Feb. 2, 2010, vol. 107, No. 5, pp. 1864-1869. (7 pages).
Matsuda et al., "siRNA Conjugates Carrying Sequentially Assembled Trivalent N-Acetylgalactosamine Linked Through Nucleosides Elicit Robust Gene Silencing in Vivo in Hepatocytes", ACS Chemical Biology, 2015, DOI: 10.1021/cb501028c. (7 pages).
Montagne et al., "Pericyte degeneration causes white matter dysfunction in the mouse CNS," Nature Medicine, 2018, vol. 24, vol. 3, pp. 326-337.
Nair et al., "Multivalent N-Acetylgalactosamine-Conjugated siRNA Localizes in Hepatocytes and Elicits Robust RNAi-Mediated Gene Silencing", Journal of the American Chemical Society, 2014, vol. 136, pp. 16958-16961.
Nakagawa et al., "The RNAi-Mediated Silencing of Xanthine Dehydrogenase Impairs Growth and Fertility and Accelerates Leaf Senescence in Transgenic *Arabidopsis* Plants," Plant & Cell Physiology, 2007, vol. 48, No. 10, pp. 1484-1495.
Nakamoto et al., "Enhanced Intercellular Delivery of cRGD-siRNA Conjugates by an Additional Oligospermine Modification," ACS Omega, 2018, vol. 3, pp. 8226-8232. (7 pages).
Norata et al., "Gene silencing approaches for the management of dyslipidaemia," Trends in Pharmacological Sciences, Apr. 13, 2013, vol. 34, No. 4, pp. 198-205.
Nordestgaard et al., "Advances in lipid-lowering therapy through gene-silencing technologies," Nature Reviews, Feb. 8, 2018, vol. 15. (12 pages).
Nothisen et al., "Cationic siRNAs Provide Carrier-Free Gene Silencing in Animal Cells," Journal of the American Chemical Society, 2009, vol. 131, No. 29, pp. 17730-17731. (2 pages).
Papulov, Yu. G., "Relationship between Properties of Compounds with Their Structures: Math Modeling," Advances in Modern Natural Sciences, 2006, with English translation, pp. 75-76.
Paris et al., "Conjugating Phosphospermines to siRNAs for Improved Stability in Serum, Intracellular Delivery and RNAi-Mediated Gene Silencing," Molecular Pharmaceutics, 2012, vol. 9, No. 12, pp. 3464-3475.
Peña-Altamira, et al., "Release of soluble and vesicular purine nucleoside phosphorylase from rat astrocytes and microglia induced by pro-inflammatory stimulation with extracellular ATP via P2X7 receptors," Neurochemistry International, May 31, 2018, vol. 115, pp. 37-49.
Pessentheiner et al., "ANGPTL3 targeting: The power of versatile lipid-lowering," Atherosclerosis, Jan. 2018, vol. 268, pp. 185-187.
Prakash et al., "Comprehensive Structure-Activity Relationship of Triantennary N-Acetylgalactosamine Conjugated Antisense Oligonucleotides for Targeted Delivery to Hepatocytes," Journal of Medicinal Chemistry, 2016, vol. 59, pp. 2718-2733.
Rajeev et al., "Hepatocyte-Specific Delivery of siRNAs Conjugated to Novel Non-nucleosidic Trivalent N-Acetylgalactosamine Elicits Robust Gene Silencing in Vivo" ChemBioChem, 2015, vol. 16, pp. 903-908.
Ren et al., "Synthesis of bifunctional cationic compound for gene delivery," Tetrahedron Letters, 2001, vol. 42, pp. 1007-1010.
Ren et al., "Gene Expression Profile of Transgenic Mouse Kidney Reveals Pathogenesis of Hepatitis B Virus Associated Nephropathy," Journal of Medical Virology, 2006, vol. 78, pp. 551-560.
Ren et al., "Stable Inhibition of Hepatitis B Virus Expression and Replication by Expressed SIRNA", Biochemical and Biophysical Research Communications, Oct. 7, 2005, vol. 335, No. 4, with English abstract, pp. 1051-1058.
Springer et al., "GalNAc-siRNA Conjugates: Leading the Way for Delivery of RNAi Therapeutics," Nucleic Acid Therapeutics, May 2018, vol. 28, No. 3, pp. 109-118.
Su et al., "Progress on the Inhibition of Hepatitis B virus by siRNA Strategy," China Biotechnology, 2014, vol. 34, No. 9, with English abstract, pp. 102-107.
Tangkijvanich et al., "Low pretreatment serum HBsAg level and viral mutations as predictors of response to PEG-interferon alpha-2b therapy in chronic hepatitis B," Journal of Clinical Virology, vol. 46, 2009, pp. 117-123.
Ui-Tei et al., "Functional dissection of siRNA sequence by systematic DNA substitution: modified siRNA with a DNA seed arm is a

(56) References Cited

OTHER PUBLICATIONS powerful tool for mammalian gene silencing with significantly reduced off-target effect", Nucleic Acids Research, 2008, vol. 36, No. 7, pp. 2136-2151.
Watts et al., "Chemically modified siRNA: tools and applications," Drug Discovery Today, Oct. 2008, vol. 13, Nos. 19/20, pp. 842-855.
Wooddell et al., "Hepatocyte-targeted RNAi Therapeutics for the Treatment of Chronic Hepatitis B Virus Infection," The American Society of Gene & Cell Therapy, 2013, doi:10.1038/mt.2013.31. (13 pages).
Wu et al., "Cleaved high molecular weight kininogen inhibits tube formation of endothelial progenitor cells via suppression of matrix metalloproteinase 2," Journal of Thrombosis and Haemostasis, 2010, vol. 8, pp. 185-193.
Wu et al., "Contact pathway of coagulation and inflammation," Thrombosis Journal, 2015, pp. 13-17.
Xu et al., "Role of angiopoielin-like 3 (ANGPTL3) in regulating plasma level of low-density lipoprotein cholesterol," Atherosclerosis, 2018, vol. 268, pp. 196-206.
Yang et al., "A critical role for plasma kallikrein in the pathogenesis of autoantibody-induced arthritis," Federation of American Societies for Experimental Biology, Nov. 2017, vol. 31, No. 12, pp. 5419-5431.
Yang et al., "An essential role of high-molecular-weight kininogen in endotoxemia," Journal of Experimental Medicine, Sep. 4, 2017, vol. 214, No. 9, pp. 2649-2670.
Fedin A.I. et al., "Review of clinical recommendations for treatment and prevention of ischemic stroke", S. S. Korsakov Journal of Neurology and Psychiatry, 2019, vol. 119, no. 8, pp. 91-96, doi: 10.17116/jnevro201911908291, with an English abstract. (6 pages) (Cited in Office Action issued on Mar. 6, 2024, in corresponding Russian Application No. 2021130601).
Meijers J.C. et al., "High levels of coagulation factor XI as a risk factor for venous thrombosis", N. Engl. J. Med., 2000, vol. 342, no. 10, pp. 696-701, doi: 10.1056/NEJM200003093421004. (6 pages) (Cited in Office Action issued on Mar. 6, 2024, in corresponding Russian Application No. 2021130601).
Soodabeh S. et al., "From in vitro Experiments to in vivo and Clinical Studies; Pros and Cons", Curr. Drug Discov. Technol., 2015, vol. 12, no. 4, pp. 218-224. (7 pages) (Cited in Office Action issued on Mar. 6, 2024, in corresponding Russian Application No. 2021130601).
Shafer A.I. et al., "Thrombotic Disorders Diagnosis and Treatment", Am. Soc. Hematol. Educ. Program, 2003, v. 1, pp. 520-539, doi 10.1182asheducation-2003.1.520. (20 pages) (Cited in Office Action issued on Mar. 6, 2024, in corresponding Russian Application No. 2021130601).
Sehgal, Alfica et al., "Liver as a target for oligonucleotide therapeutics", Journal of hepatology, 2013, vol. 59, pp. 1354-1359. (6 pages) (Cited in Office Action issued on Mar. 11, 2024, in corresponding Taiwanese Patent Application No. 109116935).
Diaz-Torné, Cesar et al., "New medications in development for the treatment of hyperuricemia of gout", Current opinion in rheumatology. 2015, vol. 27, no. 2, pp. 164-169. (6 pages) (Cited in Office Action issued on Mar. 11, 2024, in corresponding Taiwanese Patent Application No. 109116934).
Kojima, S. et al., "Tumour suppressors miR-1 and miR-133a target the oncogenic function of purine necleoside phosphorylase (PNP) in prostate cancer", Br. J. Cancer, 2012, vol. 106(2), pp. 405-413. (9 pages) Cited in Office Action issued on May 21, 2024, in corresponding Japanese Patent Application No. JP2021-569112).
Chen et al., "Proof-of-concept Studies for siRNA-mediated Gene Silencing for Coagulation Factors in Rat and Rabbit". Molecular Therapy—Nucleic Acids, Jan. 27, 2015, vol. 4, No. 1, p. e224.
Ferrone et al., "IONIS-PKK Rx a Novel Antisense Inhibitor of Prekallikrein and Bradykinin Production", Nucleic Acid Therapeutics, Apr. 1, 2019, vol. 29, No. 2, pp. 82-91.
Ghosh et al., "Effectiveness and Safety of Inclisiran, A Novel Long-Acting RNA Therapeutic Inhibitor of Proprotein Convertase Subtilisin/Kexin 9", American Journal of Cardiology, Cahners Publishing Co., Newton, MA, US, Jul. 3, 2018, vol. 122, No. 7, pp. 1272-1277.
Joshi et al., "siRNA: novel therapeutics from functional genomics", Biotechnology and Genetic Engineering Reviews, Jan. 2, 2014, vol. 30, No. 1, pp. 1-30.
Pawluczyk et al., "Kallikrein gene 'knock-down' by small interfering RNA transfection induces a profibrotic phenotype in rat mesangial cells", Journal of Hypertension, Lippincott Williams & Wilkens, Ltd., Jan. 1, 2008, vol. 26, No. 1, pp. 93-101.
Revenko et al., "Selective depletion of plasma prekallikrein or coagulation factor XII inhibits thrombosis in mice without increased risk of bleeding", Blood, American Society of Hematology, Nov. 10, 2011, vol. 118, No. 19, pp. 5302-5311.
Yamasaki et al., "Novel molecular targets regulated by tumor suppressors microRNA-1 and microRNA-133a in bladder cancer", International Journal of Oncology, Feb. 29, 2012, vol. 40, pp. 1821-1830.
Supplementary European Search Report issued on Jun. 14, 2023, by the European Patent Office in European Patent Application No. 20809702.2 (12 pages).
Supplementary European Search Report issued on Jun. 16, 2023, by the European Patent Office in European Patent Application No. 20814338.8 (10 pages).
Partial Supplementary European Search Report issued on Jul. 5, 2023, by the European Patent Office in European Patent Application No. 20810635.1 (13 pages).
Partial Supplementary European Search Report issued on Jul. 10, 2023, by the European Patent Office in European Patent Application No. 20815633.1 (17 pages).
Dana et al., "Molecular Mechanisms and Biological Functions of siRNA," International Journal of Biomedical Science, vol. 13, No. 2, pp. 48-57 (2017).
Elbashir et al., "Functional anatomy of siRNAs for mediatng efficient RNAi in *Drosophila melanogaster* embryo lysate," The EMBO Journal, vol. 20, No. 23, pp. 6877-6888 (2001).
Fakhr et al., "Precise and efficient siRNA design: a key point in competent gene silencing," Cancer Gene Therapy, vol. 23, pp. 73-82 (2016).
Girardet et al., "Urate Crystal Deposition Disease and Gout—New Therapies for an Old problem," Annual Reports in Medicinal Chemistry, vol. 49, pp. 151-164 (2014).
Kliuchnikov et al., "Improving the potency prediction for chemically modified siRNAs through insights from molecular modeing of indvidual sequence positions," Molecular Therapy: Nucleic Acids, vol. 36, pp. 1-14 (2025).
Lorenzer et al., "Going beyond the liver: Progress and Challenges of Targeted Delivery of siRNA Therapeutics," Journal of Controlled Release, vol. 203, pp. 1-15 (2015).
Willoughby et al., "Evaluation of GalNAc-siRNA Conjugate Activity in Pre-clinical Animal Models with Reduced Asialoglycoprotein Receptor Expression," Molecular Therapy, vol. 26, No. 1, pp. 105-114 (2018).

* cited by examiner

NUCLEIC ACID, PHARMACEUTICAL COMPOSITION, CONJUGATE, PREPARATION METHOD, AND USE

SEQUENCE LISTING

Incorporated by reference herein in its entirety is a computer-readable sequence listing submitted via EFS-Web and identified as follows: One (127,713 byte ASCII (Text)) file named “20220630 Amended Sequence Listing.txt” created on Jun. 30, 2022.

TECHNICAL FIELD

The present disclosure relates to a nucleic acid capable of inhibiting the expression of a Plasma Coagulation Factor XI (FXI) gene, and a pharmaceutical composition and an siRNA conjugate containing the nucleic acid. The present disclosure also relates to a preparation method and use of such nucleic acids, pharmaceutical compositions and siRNA conjugates.

BACKGROUND ART

Plasma Coagulation Factor XI (hereinafter referred to as “FXI”), an essential component of the contact activation pathway, is conducive to the production of thrombin, which in turn is an important component that is engaged in the fibrin formation and offers protection from fibrinolysis. High levels of FXI are one of the risk factors for venous thrombosis. By inhibiting the expression of the FXI gene, it is possible to prevent and treat thrombotic diseases (in particular venous thrombosis and ischemic stroke) at the cellular level.

Based on the mechanism of RNA interference (RNAi), small interfering RNA (siRNA) could inhibit or block the expression of any target gene of interest in a sequence-specific manner, thereby achieving the purpose of treating diseases.

One of the crucial technologies for developing siRNA drugs that inhibit the expression of FXI gene and treat thrombotic diseases is to find suitable siRNA and the modification and effective delivery system thereof.

SUMMARY OF THE INVENTION

Surprisingly, the inventors of the present disclosure have found that the following siRNAs and their modified sequences provided herein can specifically inhibit the expression of FXI gene, and pharmaceutical compositions or siRNA conjugates containing such siRNAs can specifically target the liver, thus making it possible to inhibit the expression of FXI gene in the liver to prevent or treat thrombotic diseases, thereby completing the present invention.

In some embodiments, the present disclosure provides a first siRNA capable of inhibiting the expression of the FXI gene, comprising a sense strand and an antisense strand, each nucleotide in the siRNA being independently a modified or unmodified nucleotide, wherein the sense strand comprises a nucleotide sequence I, and the antisense strand comprises a nucleotide sequence II; the nucleotide sequence I and the nucleotide sequence II are at least partly reverse complementary to form a double-stranded region; wherein the nucleotide sequence I has the same length as the nucleotide sequence as shown by SEQ ID NO: 1 with no more than 3 nucleotide differences therebetween, and the nucleotide sequence II has the same length as the nucleotide sequence as shown by SEQ ID NO: 2 with no more than 3 nucleotide differences therebetween:

(SEQ ID NO: 1)
5'-GGGUAUUCUUUCAAGCAA$Z_1$-3';

(SEQ ID NO: 2)
5'-$Z_2$UUGCUUGAAAGAAUACCC-3', wherein, $Z_1$ is U and $Z_2$ is A, and the nucleotide sequence I comprises a nucleotide $Z_3$ at the position corresponding to $Z_1$; the nucleotide sequence II comprises a nucleotide $Z_4$ at the position corresponding to $Z_2$, wherein $Z_4$ is the first nucleotide at 5' terminal of the antisense strand.

In some embodiments, the present disclosure provides a second siRNA capable of inhibiting the expression of the FXI gene, comprising a sense strand and an antisense strand, each nucleotide in the siRNA being independently a modified or unmodified nucleotide, wherein the sense strand comprises a nucleotide sequence I, and the antisense strand comprises a nucleotide sequence II; the nucleotide sequence I and the nucleotide sequence II are at least partly reverse complementary to form a double-stranded region; wherein the nucleotide sequence I has the same length as the nucleotide sequence as shown by SEQ ID NO: 61 with no more than 3 nucleotide differences therebetween, and the nucleotide sequence II has the same length as the nucleotide sequence as shown by SEQ ID NO: 62 with no more than 3 nucleotide differences therebetween:

(SEQ ID NO: 61)
5'-GGCAUAAACUAUAACAGC$Z_5$-3';

(SEQ ID NO: 62)
5'-$Z_6$GCUGUUAUAGUUUAUGCC-3', wherein, $Z_5$ is U and $Z_6$ is A, and the nucleotide sequence I comprises a nucleotide $Z_7$ at the position corresponding to $Z_5$; the nucleotide sequence II comprises a nucleotide $Z_8$ at the position corresponding to $Z_6$, wherein $Z_8$ is the first nucleotide at 5' terminal of the antisense strand.

In some embodiments, the present disclosure provides a third siRNA capable of inhibiting the expression of the FXI gene, comprising a sense strand and an antisense strand, each nucleotide in the siRNA being independently a modified or unmodified nucleotide, wherein the sense strand comprises a nucleotide sequence I, and the antisense strand comprises a nucleotide sequence II;

the nucleotide sequence I and the nucleotide sequence II are at least partly reverse complementary to form a double-stranded region; wherein the nucleotide sequence I has the same length as the nucleotide sequence as shown by SEQ ID NO: 121 with no more than 3 nucleotide differences therebetween, and the nucleotide sequence II has the same length as the nucleotide sequence as shown by SEQ ID NO: 122 with no more than 3 nucleotide differences therebetween:

(SEQ ID NO: 121)
5'-GCUCAAGAAUGCCAAGAA$Z_9$-3';

(SEQ ID NO: 122)
5'-$Z_{10}$UUCUUGGCAUUCUUGAGC-3', wherein, $Z_9$ is A and $Z_{10}$ is U, and the nucleotide sequence I comprises a nucleotide $Z_{11}$ at the position corresponding to $Z_9$; the nucleotide sequence II comprises a nucleotide $Z_{12}$ at the position corresponding to $Z_{10}$, wherein $Z_{12}$ is the first nucleotide at 5' terminal of the antisense strand.

In some embodiments, the present disclosure provides a fourth siRNA capable of inhibiting the expression of the FXI gene, comprising a sense strand and an antisense strand, each nucleotide in the siRNA being independently a modified or unmodified nucleotide, wherein the sense strand comprises a nucleotide sequence I, and the antisense strand comprises a nucleotide sequence II; the nucleotide sequence I and the nucleotide sequence II are at least partly reverse complementary to form a double-stranded region; wherein the nucleotide sequence I has the same length as the nucleotide sequence as shown by SEQ ID NO: 181 with no more than 3 nucleotide differences therebetween, and the nucleotide sequence II has the same length as the nucleotide sequence as shown by SEQ ID NO: 182 with no more than 3 nucleotide differences therebetween:

(SEQ ID NO: 181)
5'-GCAACAAAGACAUUUAUG$Z_{13}$-3';

(SEQ ID NO: 182)
5'-$Z_{14}$CAUAAAUGUCUUUGUUGC-3', wherein, $Z_{13}$ is U and $Z_{14}$ is A, and the nucleotide sequence I comprises a nucleotide $Z_{15}$ at the position corresponding to $Z_{13}$; the nucleotide sequence II comprises a nucleotide $Z_{16}$ at the position corresponding to $Z_{14}$, wherein $Z_{16}$ is the first nucleotide at 5' terminal of the antisense strand.

In some embodiments, the present disclosure provides a fifth siRNA capable of inhibiting the expression of the FXI gene, comprising a sense strand and an antisense strand, each nucleotide in the siRNA being independently a modified or unmodified nucleotide, wherein the sense strand comprises a nucleotide sequence I, and the antisense strand comprises a nucleotide sequence II; the nucleotide sequence I and the nucleotide sequence II are at least partly reverse complementary to form a double-stranded region; wherein the nucleotide sequence I has the same length as the nucleotide sequence as shown by SEQ ID NO: 241 with no more than 3 nucleotide differences therebetween, and the nucleotide sequence II has the same length as the nucleotide sequence as shown by SEQ ID NO: 242 with no more than 3 nucleotide differences therebetween:

(SEQ ID NO: 241)
5'-GAAUCUCAAAGAAAUCUU$Z_{17}$-3';

(SEQ ID NO: 242)
5'-$Z_{18}$AAGAUUUCUUUGAGAUUC-3', wherein, $Z_{17}$ is U and $Z_{18}$ is A, and the nucleotide sequence I comprises a nucleotide $Z_{19}$ at the position corresponding to $Z_{17}$; the nucleotide sequence II comprises a nucleotide $Z_{20}$ at the position corresponding to $Z_{18}$, wherein $Z_{20}$ is the first nucleotide at 5' terminal of the antisense strand.

In some embodiments, the present disclosure provides a sixth siRNA capable of inhibiting the expression of the FXI gene, comprising a sense strand and an antisense strand, each nucleotide in the siRNA being independently a modified or unmodified nucleotide, wherein the sense strand comprises a nucleotide sequence I, and the antisense strand comprises a nucleotide sequence II; the nucleotide sequence I and the nucleotide sequence II are at least partly reverse complementary to form a double-stranded region; wherein the nucleotide sequence I has the same length as the nucleotide sequence as shown by SEQ ID NO: 301 with no more than 3 nucleotide differences therebetween, and the nucleotide sequence II has the same length as the nucleotide sequence as shown by SEQ ID NO: 302 with no more than 3 nucleotide differences therebetween:

(SEQ ID NO: 301)
5'-GUACGUGGACUGGAUUCU$Z_{21}$-3';

(SEQ ID NO: 302)
5'-$Z_{22}$AGAAUCCAGUCCACGUAC-3', wherein, $Z_{21}$ is G and $Z_{22}$ is C, and the nucleotide sequence I comprises a nucleotide $Z_{23}$ at the position corresponding to $Z_{21}$; the nucleotide sequence II comprises a nucleotide $Z_{24}$ at the position corresponding to $Z_{22}$, wherein $Z_{24}$ is the first nucleotide at 5' terminal of the antisense strand.

In some embodiments, the present disclosure provides a seventh siRNA capable of inhibiting the expression of the FXI gene, comprising a sense strand and an antisense strand, each nucleotide in the siRNA being independently a modified or unmodified nucleotide, wherein the sense strand comprises a nucleotide sequence I, and the antisense strand comprises a nucleotide sequence II; the nucleotide sequence I and the nucleotide sequence II are at least partly reverse complementary to form a double-stranded region; wherein the nucleotide sequence I has the same length as the nucleotide sequence as shown by SEQ ID NO: 361 with no more than 3 nucleotide differences therebetween, and the nucleotide sequence II has the same length as the nucleotide sequence as shown by SEQ ID NO: 362 with no more than 3 nucleotide differences therebetween:

(SEQ ID NO: 361)
5'-AUUUCUGGGUAUUCUUUC$Z_{25}$-3';

(SEQ ID NO: 362)
5'-$Z_{26}$GAAAGAAUACCCAGAAAU-3', wherein, $Z_{25}$ is A and $Z_{26}$ is U, and the nucleotide sequence I comprises a nucleotide $Z_{27}$ at the position corresponding to $Z_{25}$; the nucleotide sequence II comprises a nucleotide $Z_{28}$ at the position corresponding to $Z_{26}$, wherein $Z_{28}$ is the first nucleotide at 5' terminal of the antisense strand.

In some embodiments, the present disclosure provides an eighth siRNA capable of inhibiting the expression of the FXI gene, comprising a sense strand and an antisense strand, each nucleotide in the siRNA being independently a modified or unmodified nucleotide, wherein the sense strand comprises a nucleotide sequence I, and the antisense strand comprises a nucleotide sequence II; the nucleotide sequence I and the nucleotide sequence II are at least partly reverse complementary to form a double-stranded region; wherein the nucleotide sequence I has the same length as the nucleotide sequence as shown by SEQ ID NO: 421 with no more than 3 nucleotide differences therebetween, and the nucleotide sequence II has the same length as the nucleotide sequence as shown by SEQ ID NO: 422 with no more than 3 nucleotide differences therebetween:

(SEQ ID NO: 421)
5'-CAUGAAGGGCAUAAACUA$Z_{29}$-3';

(SEQ ID NO: 422)
5'-$Z_{30}$UAGUUUAUGCCCUUCAUG-3', wherein, $Z_{29}$ is U and $Z_{30}$ is A, and the nucleotide sequence I comprises a nucleotide $Z_{31}$ at the position corresponding to $Z_{29}$; the nucleotide sequence II comprises a nucleotide $Z_{32}$ at the position corresponding to $Z_{30}$, wherein $Z_{32}$ is the first nucleotide at 5' terminal of the antisense strand.

In some embodiments, the present disclosure provides a ninth siRNA capable of inhibiting the expression of the FXI gene, comprising a sense strand and an antisense strand, each nucleotide in the siRNA being independently a modified or unmodified nucleotide, wherein the sense strand comprises a nucleotide sequence I, and the antisense strand comprises a nucleotide sequence II; the nucleotide sequence I and the nucleotide sequence II are at least partly reverse complementary to form a double-stranded region; wherein the nucleotide sequence I has the same length as the nucleotide sequence as shown by SEQ ID NO: 481 with no more than 3 nucleotide differences therebetween, and the nucleotide sequence II has the same length as the nucleotide sequence as shown by SEQ ID NO: 482 with no more than 3 nucleotide differences therebetween:

(SEQ ID NO: 481)
5'-GGAUUCUGGAGAAAACUC$Z_{33}$-3';

(SEQ ID NO: 482)
5'-$Z_{34}$GAGUUUUCUCCAGAAUCC-3', wherein, $Z_{33}$ is A and $Z_{34}$ is U, and the nucleotide sequence I comprises a nucleotide $Z_{35}$ at the position corresponding to $Z_{33}$; the nucleotide sequence II comprises a nucleotide $Z_{36}$ at the position corresponding to $Z_{34}$, wherein $Z_{36}$ is the first nucleotide at 5' terminal of the antisense strand.

In some embodiments, the present disclosure provides a pharmaceutical composition, comprising the siRNA of the present disclosure, and a pharmaceutically acceptable carrier.

In some embodiments, the present disclosure provides an siRNA conjugate, comprising the siRNA of the present disclosure and a conjugating group conjugated to the siRNA.

In some embodiments, the present disclosure provides use of the siRNA and/or the pharmaceutical composition and/or the siRNA conjugate of the present disclosure in the manufacture of a medicament for treating and/or preventing thrombotic diseases and/or ischemic stroke caused by abnormal expression of the FXI gene.

In some embodiments, the present disclosure provides a method for treating and/or preventing thrombotic diseases and/or ischemic stroke, comprising administering an effective amount of the siRNA, and/or the pharmaceutical composition, and/or the siRNA conjugate of the present disclosure to a subject suffering from thrombotic diseases and/or ischemic stroke.

In some embodiments, the present disclosure provides a method for inhibiting the expression of FXI gene in hepatocytes, comprising contacting an effective amount of the siRNA, and/or the pharmaceutical composition, and/or the siRNA conjugate of the present disclosure with the hepatocytes.

In some embodiments, the present disclosure provides a kit, comprising the siRNA, and/or the pharmaceutical composition, and/or the siRNA conjugate of the present disclosure.

Beneficial Effects

The siRNA, the pharmaceutical composition, and the siRNA conjugate of the present disclosure have good stability, high FXI mRNA inhibitory activity, low off-target effect and/or could significantly treat or alleviate symptoms of the thrombotic diseases and/or ischemic stroke.

In some embodiments, the siRNA, the pharmaceutical composition, or the siRNA conjugate of the present disclosure exhibits excellent inhibitory activity against the target gene in in vitro cell experiments. In some embodiments, the siRNA, the pharmaceutical composition, or the siRNA conjugate of the present disclosure shows an inhibition rate of at least 20%, 30%, 40%, 50%, 60%, 70%, 80%, 90% or 95% against expression of the target gene in hepatocytes. In some embodiments, the siRNA of the present disclosure shows inhibitory activity against FXI mRNA in the psiCHECK system, with the $IC_{50}$ against FXI mRNA ranging between 0.013 and 0.119 nM. In some embodiments, the siRNA of the present disclosure shows high inhibitory activity in HepG2 cells, with the $IC_{50}$ against FXI mRNA ranging between 1.49 and 11.1 nM. In some embodiments, the siRNA conjugate of the present disclosure shows high inhibitory activity in mouse primary hepatocytes, with the $IC_{50}$ against FXI mRNA ranging between 0.012 and 3.86 nM. In some embodiments, the siRNA of the present disclosure can inhibit the expression of FXI mRNA in HepG2 cells and exhibit an inhibition rate of up to 86.9% against FXI mRNA at a concentration of 50 nM.

In some embodiments, the siRNA, the pharmaceutical composition, or the siRNA conjugate of the present disclosure could exhibit much higher stability and/or activity in vivo. In some embodiments, the siRNA, the pharmaceutical composition, or the siRNA conjugate of the present disclosure shows an inhibition rate of at least 20%, 30%, 40%, 50%, 60%, 70%, 80%, 90% or 95% in vivo against expression of the target gene. In some embodiments, the siRNA, the pharmaceutical composition, or the siRNA conjugate of the present disclosure shows an inhibition rate of at least 20%, 30%, 40%, 50%, 60%, 70%, 80%, 90% or 95% in vivo against expression of the FXI gene. In some embodiments, the siRNA, the pharmaceutical composition, or the siRNA conjugate of the present disclosure shows an inhibition rate of at least 20%, 30%, 40%, 50%, 60%, 70%, 80%, 90% or 95% in vivo against expression of the FXI gene in liver. In some embodiments, the siRNA, the pharmaceutical composition, or the siRNA conjugate of the present disclosure shows an inhibition rate of at least 20%, 30%, 40%, 50%, 60%, 70%, 80%, 90% or 95% in vivo against expression of the FXI gene in liver in animal models. In some embodiments, the siRNA, the pharmaceutical composition, or the siRNA conjugate of the present disclosure shows an inhibition rate of at least 20%, 30%, 40%, 50%, 60%, 70%, 80%, 90% or 95% in vivo against expression of the FXI gene in liver in human subjects. In some embodiments, the siRNA conjugate of the present disclosure shows an inhibition rate of up to 95.0% in vivo against expression of FXI mRNA in mice at the siRNA concentration of 5 mg/kg. In some embodiments, the siRNA conjugate of the present disclosure shows an inhibition rate of up to 93.09% in vivo against expression of human FXI mRNA in humanized mice at the siRNA concentration of 3 mg/kg. Meanwhile, the siRNA conjugate can show a significant effect of inhibiting Plasma FXI protein concentration with an inhibition rate of up to about 99%. In some embodiments, the siRNA conjugate of the present disclosure can show a significant effect of prolonging the plasma APTT assay value in CD57 mice in vivo, for example, by 64.9%.

In some embodiments, the siRNA, the pharmaceutical composition, or the siRNA conjugate of the present disclosure exhibits no significant off-target effect. An off-target effect may be, for example, inhibition of normal expression of a gene which is not the target gene. It is considered that if the binding/inhibition of the expression of an off-target gene is 50%, 40%, 30%, 20%, or 10% lower than that of the target gene, then the off-target effect is not significant.

Therefore, the siRNA, the pharmaceutical composition and the siRNA conjugate of the present disclosure could inhibit the expression of FXI gene, effectively treat and/or prevent thrombotic diseases and/or ischemic stroke conditions caused by the overexpression of FXI gene, and thus show a promising prospect of application.

Additional features and advantages of the present disclosure will be detailedly illustrated in the following part "detailed description of the invention".

DETAILED DESCRIPTION OF THE INVENTION

The following is the detailed description of the specific embodiments of the present disclosure. It should be understood that the specific embodiments described herein are only used to illustrate and explain the present disclosure and are not intended to limit the present disclosure.

In the present disclosure, FXI mRNA refers to the mRNA having the sequence as shown in Genbank Accession No. NM000128.3. Further, unless otherwise specified, the term "target gene" used in the present disclosure refers to a gene transcribing the above FXI mRNA; and the term "target mRNA" refers to the above FXI mRNA.

Definitions

In the context of the present disclosure, unless otherwise specified, C, G, U, and A represent the base composition of a nucleotide; m represents that the nucleotide adjacent to the left side of the letter m is a methoxy modified nucleotide; f represents that the nucleotide adjacent to the left side of the letter f is a fluoro modified nucleotide; s represents the two nucleotides adjacent to both sides of the letter s are linked by a thiophosphate linkage; P1 represents that the nucleotide adjacent to the right side of P1 is a 5'-phosphate nucleotide or a 5'-phosphate analogue modified nucleotide; VP represents that the nucleotide adjacent to the right side of VP is a vinyl phosphate (5'-(E)-vinylphosphonate, E-VP) modified nucleotide; Ps represents that the nucleotide adjacent to the right side of Ps is a thiophosphate modified nucleotide; and P represents that the nucleotide adjacent to the right side of the letter P is a 5'-phosphate nucleotide.

In the context of the present disclosure, a "fluoro modified nucleotide" refers to a nucleotide formed by substituting 2'-hydroxy of the ribose group with a fluorine atom. A "non-fluoro modified nucleotide" refers to a nucleotide formed by substituting 2'-hydroxy of the ribose group with a non-fluoro group, or a nucleotide analogue. A "nucleotide analogue" refers to a group that can replace a nucleotide in a nucleic acid, while structurally differs from an adenine ribonucleotide, a guanine ribonucleotide, a cytosine ribonucleotide, a uracil ribonucleotide, or thymine deoxyribonucleotide, such as an isonucleotide, a bridged nucleotide (bridged nucleic acid, BNA) or an acyclic nucleotide. The "methoxy modified nucleotide" refers to a nucleotide formed by substituting 2'-hydroxy of the ribose group with a methoxy group.

In the context of the present disclosure, expressions "complementary" and "reverse complementary" can be interchangeably used, and have a well-known meaning in the art, namely, the bases in one strand are complementarily paired with those in the other strand in a double-stranded nucleic acid molecule. In DNAs, a purine base adenine (A) is always paired with a pyrimidine base thymine (T) (or a uracil (U) in RNAs); and a purine base guanine (G) is always paired with a pyrimidine base cytosine (C). Each base pair comprises a purine and a pyrimidine. While adenines in one strand are always paired with thymines (or uracils) in another strand, and guanines are always paired with cytosines, the two strands are considered as being complementary with each other; and the sequence of a strand may be deduced from the sequence of its complementary strand. Correspondingly, a "mispairing" means that the bases at corresponding positions are not present in a manner of complementary pairing in a double-stranded nucleic acid.

In the context of the present disclosure, unless otherwise specified, "basically reverse complementary" means that there are no more than 3 base mispairings between two nucleotide sequences. "Substantially reverse complementary" means that there is no more than 1 base mispairing between two nucleotide sequences. "Completely reverse complementary" means that there is no base mispairing between two nucleotide sequences.

In the context of the present disclosure, a "nucleotide difference" between a nucleotide sequence and another nucleotide sequence refers to a change in the type of the nucleotide base at the same position therebetween. For example, in case that a nucleotide base in the latter sequence is A while the nucleotide base at the same position in the former sequence is U, C, G, or T, it is considered that a nucleotide difference is located in this position between these two nucleotide sequences. In some embodiments, if a nucleotide at a position is replaced with an abasic nucleotide or a nucleotide analogue, it is also considered that there is a nucleotide difference at the position.

In the context of the present disclosure, particularly in the description of the method for preparing the siRNA, the composition comprising the siRNA, or the siRNA conjugate of the present disclosure, unless otherwise specified, the "nucleoside monomer" refers to, according to the type and sequence of the nucleotides in the siRNA or siRNA conjugate to be prepared, unmodified or modified RNA phosphoramidites (sometimes RNA phosphoramidites are referred to as nucleoside phosphoramidites) used in a phosphoramidite solid phase synthesis. The phosphoramidite solid phase synthesis is a well-known method for RNA synthesis by those skilled in the art. Nucleoside monomers used in the present disclosure are all commercially available.

In the context of the present disclosure, unless otherwise specified, "conjugation" means that two or more chemical moieties each having specific function are linked to each other via a covalent linkage. Correspondingly, a "conjugate" refers to a compound formed by covalent linkage of individual chemical moieties. Furthermore, a "siRNA conjugate" represents a compound formed by covalently linking one or more chemical moieties each with specific functions to an siRNA. In the following text, the siRNA conjugate of the present disclosure is sometimes abbreviated as "conjugate". According to the context of the present disclosure, the siRNA conjugate should be understood as the generic term of siRNA conjugates, the generic term of siRNA conjugates as shown by Formulae (305) and (307), or siRNA conjugates as shown by Formula (305), (307) or (308). In the context of the present disclosure, "conjugating molecules" should be interpreted as specific compounds capable of being conjugated to an siRNA via reactions, thereby finally forming the siRNA conjugates of the present disclosure.

As used herein, "optional" or "optionally" means that the subsequently described event or circumstance may or may not occur, and that the description includes instances in which the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically infeasible and/or inherently unstable.

As used herein, "alkyl" refers to straight chain and branched chain having the indicated number of carbon atoms, usually from 1 to 20 carbon atoms, for example 1 to 10 carbon atoms, such as 1 to 8 or 1 to 6 carbon atoms. For example, $C_1$-$C_6$ alkyl encompasses both straight and branched chain alkyl of from 1 to 6 carbon atoms. When an alkyl residue having a specific number of carbon atoms is mentioned, all branched and straight chain forms having that number of carbon atoms are intended to be encompassed; thus, for example, "butyl" is meant to encompass n-butyl, sec-butyl, isobutyl, and t-butyl; "propyl" includes n-propyl and isopropyl. Alkylene is a subset of alkyl, referring to the same residues as alkyl, but having two attachment points.

As used herein, "alkenyl" refers to an unsaturated branched or straight-chain alkyl group having at least one carbon-carbon double bond obtained by removing one hydrogen molecule from two adjacent carbon atoms of the parent alkyl. The group may be in either the cis or trans configuration of the double bond(s). Typical alkenyl groups include, but are not limited to, ethenyl; propenyl, such as prop-1-en-1-yl, prop-1-en-2-yl, prop-2-en-1-yl (allyl), prop-2-en-2-yl; butenyl, such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl; and the like. In certain embodiments, an alkenyl group has from 2 to 20 carbon atoms, and in other embodiments, from 2 to 10, 2 to 8, or 2 to 6 carbon atoms. Alkenylene is a subset of alkenyl, referring to the same residues as alkenyl, but having two attachment points.

As used herein, "alkynyl" refers to an unsaturated branched or straight-chain alkyl group having at least one carbon-carbon triple bond obtained by removing two hydrogen molecules from two adjacent carbon atoms of the parent alkyl. Typical alkynyl groups include, but are not limited to, ethynyl; propynyl, such as prop-1-yn-1-yl, prop-2-yn-1-yl; butynyl, such as but-1-yn-1-yl, but-1-yn-3-yl, but-3-yn-1-yl; and the like. In certain embodiments, an alkynyl group has from 2 to 20 carbon atoms, and in other embodiments, from 2 to 10, 2 to 8, or 2 to 6 carbon atoms. Alkynylene is a subset of alkynyl, referring to the same residues as alkynyl, but having two attachment points.

As used herein, "alkoxy" refers to an alkyl group of the indicated number of carbon atoms linked through an oxygen bridge, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy group usually has from 1 to 10, 1 to 8, 1 to 6, or 1 to 4 carbon atoms linked through oxygen bridge.

As used herein, "aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon, including from 6 to 18 carbon atoms, wherein at least one ring in the ring system is fully unsaturated, i.e., it contains a cyclic, delocalized $(4n+2)\pi$-electron system in accordance with the Mickel theory. Aryl groups include, but are not limited to, groups such as phenyl, fluorenyl, and naphthyl. Arylene is a subset of aryl, referring to the same residues as aryl, but having two attachment points.

As used herein, "halo substituent" or "halogen" refers to fluoro, chloro, bromo, and iodo, and the term "halogen" includes fluorine, chlorine, bromine, and iodine.

As used herein, "haloalkyl" refers to alkyl as defined above with the specified number of carbon atoms being substituted with one or more halogen atoms, up to the maximum allowable number of halogen atoms. Examples of haloalkyl include, but are not limited to, trifluoromethyl, difluoromethyl, 2-fluoroethyl, and penta-fluoroethyl.

"Heterocyclyl" refers to a stable 3- to 18-membered non-aromatic ring radical that comprises two to twelve carbon atoms and from one to six heteroatoms selected from nitrogen, oxygen or sulfur. Unless stated otherwise in the description, heterocyclyl is a monocyclic, bicyclic, tricyclic or tetracyclic ring system, which may include fused or bridged ring system(s). The heteroatom(s) in the heterocyclyl radical may be optionally oxidized. One or more nitrogen atoms, if present, are optionally quaternized. The heterocyclyl radical is partially or fully saturated. The heterocyclyl may be linked to the rest of the molecule through any atom of the ring(s). Examples of such heterocyclyl radicals include, but are not limited to, dioxolanyl, thienyl [1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxapyrimidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxa-thiomorpholinyl, and 1,1-dioxa-thiomorpholinyl.

"Heteroaryl" refers to a radical derived from a 3- to 18-membered aromatic ring radical that comprises two to seventeen carbon atoms and one to six heteroatoms selected from nitrogen, oxygen or sulfur. As used herein, heteroaryl radical may be a monocyclic, bicyclic, tricyclic or tetracyclic ring system, wherein at least one ring in the ring system is fully unsaturated, i.e., it contains a cyclic, delocalized $(4n+2)$ $\pi$-electron system in accordance with the Hückel theory. Heteroaryl includes fused or bridged ring system(s). The heteroatom(s) in the heteroaryl radical is optionally oxidized. One or more nitrogen atoms, if present, are optionally quaternized. The heteroaryl is linked to the rest of the molecule through any atom of the ring(s). Examples of heteroaryls include, but are not limited to, azepinyl, acridinyl, benzimidazolyl, benzindolyl, 1,3-benzodioxazolyl, benzofuranyl, benzoxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-di hydrobenzo[h]cinnolinyl, 6,7-dihydro-5H-benzo[6,7]cyclohepta[1,2-c]pyridazinyl, dibenzofuranyl, dibenzothienyl, furanyl, furanonyl, furo[3,2-c]pyridinyl, 5,6,7,8,9,10-hexahydrocyclohepta[d]pyrimidinyl, 5,6,7,8,9, 10-hexahydrocyclohepta[d]pyridazinyl, 5,6,7,8,9,10-hexahydrocycloocta[d]pyridinyl, isothiazolyl, imidazolyl, indazolyl, indolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a, 7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta [4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl/thienyl.

Various hydroxyl protecting groups may be used in the present disclosure. In general, protecting groups render chemical functional groups inert to specific reaction conditions, and may be appended to and removed from such functional groups in a molecule without substantially damaging the remainder of the molecule. Representative hydroxyl protecting groups are disclosed in Beaucage, et al., Tetrahedron 1992, 48, 2223-2311, and also in Greene and Wuts, Protective Groups in Organic Synthesis, Chapter 2, 2d ed, John Wiley & Sons, New York, 1991, each of which is hereby incorporated by reference in their entirety. In some embodiments, the protecting group is stable under basic conditions but may be removed under acidic conditions. In some embodiments, non-exclusive examples of the hydroxyl protecting groups that may be used herein include dimethoxytrityl (DMT), monomethoxytrityl, 9-phenylxanthen-9-yl (Pixyl) and 9-(p-methoxyphenyl)xanthen-9-yl (Mox). In some embodiments, non-exclusive examples of hydroxyl protecting groups that may be used herein comprises Tr (trityl), MMTr (4-methoxytrityl), DMTr (4,4'-dimethoxytrityl), and TMTr (4,4',4"-trimethoxytrityl).

The term "subject", as used herein, refers to any animal, e.g., a mammal or marsupial. Subject of the present disclosure includes but are not limited to human, non-human primate (e.g., rhesus or other kinds of macaque), mouse, pig, horse, donkey, cow, sheep, rat and fowl of any kind.

As used herein, "treating" refers to an approach for obtaining advantageous or desired results, including but not limited to, therapeutic benefit. By "therapeutic benefit" is meant eradication or improvement of potential disorder being treated. Also, a therapeutic benefit is achieved by eradication or amelioration of one or more of physiological symptoms associated with the potential disorder such that an improvement is observed in the subject, notwithstanding that the subject may still be afflicted with the potential disorder.

As used herein, "preventing" refers to an approach for obtaining advantageous or desired results, including but not limited to, a prophylactic benefit. For "prophylactic benefit", the siRNAs, siRNA conjugates or pharmaceutical compositions may be administered to a subject at risk of developing a particular disease, or to a subject reporting one or more of the physiological symptoms of the disease, even though the diagnosis of this disease may not have been made.

In one aspect, the present disclosure provides the first to ninth siRNAs capable of inhibiting the expression of FXI gene. They will be successively described in detail below.

The siRNA of the present disclosure comprises nucleotide groups as basic structural units. It is well known to those skilled in the art that the nucleotide group contains a phosphate group, a ribose group and a base. Detailed illustrations of these groups are omitted herein.

First siRNA

According to the present disclosure, the siRNA may be a first siRNA.

The first siRNA comprises a sense strand and an antisense strand; each nucleotide in the first siRNA being independently a modified or unmodified nucleotide; wherein the sense strand comprises a nucleotide sequence I, and the antisense strand comprises a nucleotide sequence II; the nucleotide sequence I and the nucleotide sequence II are at least partly reverse complementary to form a double-stranded region; wherein the nucleotide sequence I has the same length as the nucleotide sequence as shown by SEQ ID NO: 1 with no more than 3 nucleotide differences therebetween, and the nucleotide sequence II has the same length as the nucleotide sequence as shown by SEQ ID NO: 2 with no more than 3 nucleotide differences therebetween:

(SEQ ID NO: 1)
5'-GGGUAUUCUUUCAAGCAA$Z_1$-3';

(SEQ ID NO: 2)
5'-$Z_2$UUGCUUGAAAGAAUACCC-3', wherein, $Z_1$ is U and $Z_2$ is A, and the nucleotide sequence I comprises a nucleotide $Z_3$ at the position corresponding to $Z_1$; the nucleotide sequence II comprises a nucleotide $Z_4$ at the position corresponding to $Z_2$, wherein $Z_4$ is the first nucleotide at 5' terminal of the antisense strand.

In the context of the present disclosure, "corresponding position" refers to the same position in the nucleotide sequence by counting from the same terminal of the nucleotide sequence. For example, the first nucleotide at 3' terminal of the nucleotide sequence I is a nucleotide at the position corresponding to the first nucleotide at 3' terminal of SEQ ID NO: 1.

In some embodiments, the sense strand comprises only the nucleotide sequence I, and the antisense strand comprises only the nucleotide sequence II.

In some embodiments, there is no more than 1 nucleotide difference between the nucleotide sequence I and the nucleotide sequence as shown by SEQ ID NO: 1, and/or there is no more than 1 nucleotide difference between the nucleotide sequence II and the nucleotide sequence as shown by SEQ ID NO: 2.

In some embodiments, the nucleotide difference between the nucleotide sequence II and the nucleotide sequence as shown by SEQ ID NO: 2 includes a difference at the position $Z_4$, where $Z_4$ is selected from U, C or G. In some embodiments, the nucleotide difference is a difference at the position $Z_4$, wherein $Z_4$ is selected from U, C or G. In some embodiments, $Z_3$ is a nucleotide complementary to $Z_4$. The siRNAs having these nucleotide differences also exhibit high capacity to inhibit the target mRNA, and thus these siRNAs comprising the nucleotide differences are also within the protection scope of the present disclosure.

In some embodiments, the nucleotide sequence I and the nucleotide sequence II are basically reverse complementary, substantially reverse complementary, or completely reverse complementary to each other; the "basically reverse complementary" means that there is no more than 3 base mispairings between two nucleotide sequences; the "substantially reverse complementary" means that there is no more than 1 base mispairing between two nucleotide sequences; the "completely reverse complementary" means that there is no mispairing between two nucleotide sequences.

In some embodiments, the nucleotide sequence I is the nucleotide sequence as shown by SEQ ID NO: 3, and the nucleotide sequence II is the nucleotide sequence as shown by SEQ ID NO: 4:

(SEQ ID NO: 3)
5'-GGGUAUUCUUUCAAGCAA$Z_3$-3';

(SEQ ID NO: 4)
5'-$Z_4$UUGCUUGAAAGAAUACCC-3', wherein, $Z_4$ is the first nucleotide at 5' terminal of the antisense strand, $Z_3$ is selected from A, U, G, or C, and $Z_4$ is a nucleotide complementary to $Z_3$; in some embodiments, $Z_3$ is U, and $Z_4$ is A.

Moreover, the sense strand and the antisense strand have the same or different length, wherein the sense strand has a length of 19 to 23 nucleotides, and the antisense strand has a length of 19 to 26 nucleotides. As such, the length ratio of the sense strand to the antisense strand in the siRNA of the present disclosure may be 19/19, 19/20, 19/21, 19/22, 19/23, 19/24, 19/25, 19/26, 20/20, 20/21, 20/22, 20/23, 20/24, 20/25, 20/26, 21/20, 21/21, 21/22, 21/23, 21/24, 21/25, 21/26, 22/20, 22/21, 22/22, 22/23, 22/24, 22/25, 22/26, 23/20, 23/21, 23/22, 23/23, 23/24, 23/25, or 23/26. In some embodiments, the length ratio of the sense strand to the antisense strand in the siRNA of the present disclosure may be 19/21, 21/23 or 23/25.

In some embodiments, the sense strand further comprises a nucleotide sequence III, the antisense strand further comprises a nucleotide sequence IV, and the nucleotide sequence III and the nucleotide sequence IV independently of each other have a length of 1 to 4 nucleotides; the nucleotide sequence III and the nucleotide sequence IV have the same length and are substantially reverse complementary or completely reverse complementary to each other; the nucleotide sequence III is linked to the 5' terminal of the nucleotide sequence I; and the nucleotide sequence IV is linked to the 3' terminal of the nucleotide sequence II. In some embodiments, the nucleotide sequence IV is substantially reverse complementary, or completely reverse complementary to a second nucleotide sequence, which refers to a nucleotide sequence that is adjacent to the 5' terminal of the nucleotide sequence as shown by SEQ ID NO: 1 in the target mRNA and has the same length as the nucleotide sequence IV.

In some embodiments, the nucleotide sequence III and the nucleotide sequence IV both have a length of 1 nucleotide, and the base of the nucleotide sequence III is U, and the base of the nucleotide sequence IV is A; in this case, the length ratio of the sense strand and the antisense strand thereof is 20/20; or, the nucleotide sequence III and the nucleotide sequence IV both have a length of 2 nucleotides, and in the direction from 5' terminal to 3' terminal, the base composition of the nucleotide sequence III is CU, and the base composition of the nucleotide sequence IV is AG; in this case, the length ratio of the sense strand and the antisense strand thereof is 21/21; or, the nucleotide sequence III and the nucleotide sequence IV both have a length of 3 nucleotides, and in the direction from 5' terminal to 3' terminal, the base composition of the nucleotide sequence III is UCU, and the base composition of the nucleotide sequence IV is AGA; in this case, the length ratio of the sense strand and the antisense strand thereof is 22/22; or, the nucleotide sequence III and the nucleotide sequence IV both have a length of 4 nucleotides, and in the direction from 5' terminal to 3' terminal, the base composition of the nucleotide sequence III is UUCU, and the base composition of the nucleotide sequence IV is AGAA; in this case, the length ratio of the sense strand and the antisense strand thereof is 23/23. In some embodiments, the nucleotide sequence III and the nucleotide sequence IV have a length of 2 nucleotides, and in the direction from 5' terminal to 3' terminal, the base composition of the nucleotide sequence III is CU, and the base composition of the nucleotide sequence IV is AG; in this case, the length ratio of the sense strand and the antisense strand thereof is 21/21.

In some embodiments, the nucleotide sequence III and the nucleotide sequence IV are completely reverse complementary. Hence, where the base(s) of nucleotide sequence III is(are) provided, the base(s) of nucleotide sequence IV is(are) also determined.

Second siRNA

According to the present disclosure, the siRNA may be a second siRNA.

The second siRNA comprises a sense strand and an antisense strand; each nucleotide in the second siRNA being independently a modified or unmodified nucleotide; wherein the sense strand comprises a nucleotide sequence I, and the antisense strand comprises a nucleotide sequence II; the nucleotide sequence I and the nucleotide sequence II are at least partly reverse complementary to form a double-stranded region; wherein the nucleotide sequence I has the same length as the nucleotide sequence as shown by SEQ ID NO: 61 with no more than 3 nucleotide differences therebetween, and the nucleotide sequence II has the same length as the nucleotide sequence as shown by SEQ ID NO: 62 with no more than 3 nucleotide differences therebetween:

(SEQ ID NO: 61)
5'-GGCAUAAACUAUAACAGC$Z_5$-3';

(SEQ ID NO: 62)
5'-$Z_6$GCUGUUAUAGUUUAUGCC-3', wherein, $Z_5$ is U and $Z_6$ is A, and the nucleotide sequence I comprises a nucleotide $Z_7$ at the position corresponding to $Z_5$; the nucleotide sequence II comprises a nucleotide $Z_8$ at the position corresponding to $Z_6$, wherein $Z_8$ is the first nucleotide at 5' terminal of the antisense strand.

In some embodiments, the sense strand comprises only the nucleotide sequence I, and the antisense strand comprises only the nucleotide sequence II.

In some embodiments, there is no more than 1 nucleotide difference between the nucleotide sequence I and the nucleotide sequence as shown by SEQ ID NO: 61, and/or there is no more than 1 nucleotide difference between the nucleotide sequence II and the nucleotide sequence as shown by SEQ ID NO: 62.

In some embodiments, the nucleotide difference between the nucleotide sequence II and the nucleotide sequence as shown by SEQ ID NO: 62 includes a difference at the position $Z_8$, where $Z_8$ is selected from U, C or G. In some embodiments, the nucleotide difference is a difference at the position $Z_8$, wherein $Z_8$ is selected from U, C or G. In some embodiments, $Z_7$ is a nucleotide complementary to $Z_8$. The siRNAs having these nucleotide differences also exhibit high capacity to inhibit the target mRNA, and thus these siRNAs comprising the nucleotide differences are also within the protection scope of the present disclosure.

In some embodiments, the nucleotide sequence I and the nucleotide sequence II are basically reverse complementary, substantially reverse complementary, or completely reverse complementary to each other.

In some embodiments, the nucleotide sequence I is the nucleotide sequence as shown by SEQ ID NO: 63, and the nucleotide sequence II is the nucleotide sequence as shown by SEQ ID NO: 64:

(SEQ ID NO: 63)
5'-GGCAUAAACUAUAACAGCZ$_7$-3';

(SEQ ID NO: 64)
5'-Z$_8$GCUGUUAUAGUUUAUGCC-3', wherein, $Z_8$ is the first nucleotide at 5' terminal of the antisense strand, $Z_7$ is selected from A, U, G, or C, and $Z_8$ is a nucleotide complementary to $Z_7$; in some embodiments, $Z_7$ is U, and $Z_8$ is A.

Moreover, the sense strand and the antisense strand have the same or different length, wherein the sense strand has a length of 19 to 23 nucleotides, and the antisense strand has a length of 19 to 26 nucleotides.

In some embodiments, the sense strand further comprises a nucleotide sequence III, the antisense strand further comprises a nucleotide sequence IV, and the nucleotide sequence III and the nucleotide sequence IV independently of each other have a length of 1 to 4 nucleotides; the nucleotide sequence III and the nucleotide sequence IV have the same length and are substantially reverse complementary or completely reverse complementary to each other; the nucleotide sequence III is linked to the 5' terminal of the nucleotide sequence I, and the nucleotide sequence IV is linked to the 3' terminal of the nucleotide sequence II; the nucleotide sequence IV is substantially reverse complementary, or completely reverse complementary to a second nucleotide sequence, which refers to a nucleotide sequence that is adjacent to the 5' terminal of the nucleotide sequence as shown by SEQ ID NO: 61 in the target mRNA and has the same length as the nucleotide sequence IV.

In some embodiments, the nucleotide sequence III and the nucleotide sequence IV both have a length of 1 nucleotide, and the base of the nucleotide sequence III is G, and the base of the nucleotide sequence IV is C; in this case, the length ratio of the sense strand and the antisense strand thereof is 20/20; or, the nucleotide sequence III and the nucleotide sequence IV both have a length of 2 nucleotides, and in the direction from 5' terminal to 3' terminal, the base composition of the nucleotide sequence III is AG, and the base composition of the nucleotide sequence IV is CU; in this case, the length ratio of the sense strand and the antisense strand thereof is 21/21; or, the nucleotide sequence III and the nucleotide sequence IV both have a length of 3 nucleotides, and in the direction from 5' terminal to 3' terminal, the base composition of the nucleotide sequence III is AAG, and the base composition of the nucleotide sequence IV is CUU; in this case, the length ratio of the sense strand and the antisense strand thereof is 22/22; or, the nucleotide sequence III and the nucleotide sequence IV both have a length of 4 nucleotides, and in the direction from 5' terminal to 3' terminal, the base composition of the nucleotide sequence III is GAAG, and the base composition of the nucleotide sequence IV is CUUC; in this case, the length ratio of the sense strand and the antisense strand thereof is 23/23. In some embodiments, the nucleotide sequence III and the nucleotide sequence IV have a length of 2 nucleotides, and in the direction from 5' terminal to 3' terminal, the base composition of the nucleotide sequence III is AG, and the base composition of the nucleotide sequence IV is CU; in this case, the length ratio of the sense strand and the antisense strand thereof is 21/21.

In some embodiments, the nucleotide sequence III and the nucleotide sequence IV are completely reverse complementary. Hence, where the base(s) of nucleotide sequence III is(are) provided, the base(s) of nucleotide sequence IV is(are) also determined.

Third siRNA

According to the present disclosure, the siRNA may be a third siRNA.

The third siRNA comprises a sense strand and an antisense strand; each nucleotide in the third siRNA being independently a modified or unmodified nucleotide; wherein the sense strand comprises a nucleotide sequence I, and the antisense strand comprises a nucleotide sequence II; the nucleotide sequence I and the nucleotide sequence II are at least partly reverse complementary to form a double-stranded region; wherein the nucleotide sequence I has the same length as the nucleotide sequence as shown by SEQ ID NO: 121 with no more than 3 nucleotide differences therebetween, and the nucleotide sequence II has the same length as the nucleotide sequence as shown by SEQ ID NO: 122 with no more than 3 nucleotide differences therebetween:

(SEQ ID NO: 121)
5'-GCUCAAGAAUGCCAAGAAZ$_9$-3';

(SEQ ID NO: 122)
5'-Z$_{10}$UUCUUGGCAUUCUUGAGC-3', wherein, $Z_9$ is A and $Z_{10}$ is U, and the nucleotide sequence I comprises a nucleotide $Z_{11}$ at the position corresponding to $Z_9$; the nucleotide sequence II comprises a nucleotide $Z_{12}$ at the position corresponding to $Z_{10}$, wherein $Z_{12}$ is the first nucleotide at 5' terminal of the antisense strand.

In some embodiments, the sense strand comprises only the nucleotide sequence I, and the antisense strand comprises only the nucleotide sequence II.

In some embodiments, there is no more than 1 nucleotide difference between the nucleotide sequence I and the nucleotide sequence as shown by SEQ ID NO: 121, and/or there is no more than 1 nucleotide difference between the nucleotide sequence II and the nucleotide sequence as shown by SEQ ID NO: 122.

In some embodiments, the nucleotide difference between the nucleotide sequence II and the nucleotide sequence as shown by SEQ ID NO: 122 includes a difference at the position $Z_{12}$, where $Z_{12}$ is selected from A, C or G. In some embodiments, the nucleotide difference is a difference at the position $Z_{12}$, wherein $Z_{12}$ is selected from A, C or G. In some embodiments, $Z_{11}$ is a nucleotide complementary to $Z_{12}$. The siRNAs having these nucleotide differences also exhibit high capacity to inhibit the target mRNA, and thus these siRNAs comprising the nucleotide differences are also within the protection scope of the present disclosure.

In some embodiments, the nucleotide sequence I and the nucleotide sequence II are basically reverse complementary, substantially reverse complementary, or completely reverse complementary to each other.

In some embodiments, the nucleotide sequence I is the nucleotide sequence as shown by SEQ ID NO: 123, and the nucleotide sequence II is the nucleotide sequence as shown by SEQ ID NO: 124:

(SEQ ID NO: 123)
5'-GCUCAAGAAUGCCAAGAAZ$_{11}$-3';

(SEQ ID NO: 124)
5'-Z$_{12}$UUCUUGGCAUUCUUGAGC-3', wherein, $Z_{12}$ is the first nucleotide at 5' terminal of the antisense strand, $Z_{11}$ is selected from A, U, G, or C, and $Z_{12}$ is a nucleotide complementary to $Z_{11}$; in some embodiments, $Z_{11}$ is A, and $Z_{12}$ is U.

Moreover, the sense strand and the antisense strand have the same or different length, wherein the sense strand has a length of 19 to 23 nucleotides, and the antisense strand has a length of 19 to 26 nucleotides.

In some embodiments, the sense strand further comprises a nucleotide sequence III, the antisense strand further comprises a nucleotide sequence IV, and the nucleotide sequence III and the nucleotide sequence IV independently of each other have a length of 1 to 4 nucleotides; the nucleotide sequence III and the nucleotide sequence IV have the same length and are substantially reverse complementary or completely reverse complementary to each other; the nucleotide sequence III is linked to the 5' terminal of the nucleotide sequence I, and the nucleotide sequence IV is linked to the 3' terminal of the nucleotide sequence II; the nucleotide sequence IV is substantially reverse complementary, or completely reverse complementary to a second nucleotide sequence, which refers to a nucleotide sequence that is adjacent to the 5' terminal of the nucleotide sequence as shown by SEQ ID NO: 121 in the target mRNA and has the same length as the nucleotide sequence IV.

In some embodiments, in the direction from 5' terminal to 3' terminal, the nucleotide sequence III and the nucleotide sequence IV both have a length of 1 nucleotide, and the base of the nucleotide sequence III is U, and the base of the nucleotide sequence IV is A; in this case, the length ratio of the sense strand and the antisense strand thereof is 20/20; or, the nucleotide sequence III and the nucleotide sequence IV both have a length of 2 nucleotides, and in the direction from 5' terminal to 3' terminal, the base composition of the nucleotide sequence III is GU, and the base composition of the nucleotide sequence IV is AC; in this case, the length ratio of the sense strand and the antisense strand thereof is 21/21; or, the nucleotide sequence III and the nucleotide sequence IV both have a length of 3 nucleotides, and in the direction from 5' terminal to 3' terminal, the base composition of the nucleotide sequence III is AGU, and the base composition of the nucleotide sequence IV is ACU; in this case, the length ratio of the sense strand and the antisense strand thereof is 22/22; or, the nucleotide sequence III and the nucleotide sequence IV both have a length of 4 nucleotides, and in the direction from 5' terminal to 3' terminal, the base composition of the nucleotide sequence III is GAGU, and the base composition of the nucleotide sequence IV is ACUC; in this case, the length ratio of the sense strand and the antisense strand thereof is 23/23. In some embodiments, the nucleotide sequence III and the nucleotide sequence IV have a length of 2 nucleotides, and in the direction from 5' terminal to 3' terminal, the base composition of the nucleotide sequence III is GU, and the base composition of the nucleotide sequence IV is AC; in this case, the length ratio of the sense strand and the antisense strand thereof is 21/21.

In some embodiments, the nucleotide sequence III and the nucleotide sequence IV are completely reverse complementary. Hence, where the base(s) of nucleotide sequence III is(are) provided, the base(s) of nucleotide sequence IV is(are) also determined.

Fourth siRNA

According to the present disclosure, the siRNA may be a fourth siRNA.

The fourth siRNA comprises a sense strand and an antisense strand, each nucleotide in the siRNA being independently a modified or unmodified nucleotide, wherein the sense strand comprises a nucleotide sequence I, and the antisense strand comprises a nucleotide sequence II; the nucleotide sequence I and the nucleotide sequence II are at least partly reverse complementary to form a double-stranded region; wherein the nucleotide sequence I has the same length as the nucleotide sequence as shown by SEQ ID NO: 181 with no more than 3 nucleotide differences therebetween, and the nucleotide sequence II has the same length as the nucleotide sequence as shown by SEQ ID NO: 182 with no more than 3 nucleotide differences therebetween:

(SEQ ID NO: 181)
5'-GCAACAAAGACAUUUAUG$Z_{13}$-3';

(SEQ ID NO: 182)
5'-$Z_{14}$CAUAAAUGUCUUUGUUGC-3', wherein, $Z_{13}$ is U and $Z_{14}$ is A, and the nucleotide sequence I comprises a nucleotide $Z_{15}$ at the position corresponding to $Z_{13}$; the nucleotide sequence II comprises a nucleotide $Z_{16}$ at the position corresponding to $Z_{14}$, wherein $Z_{16}$ is the first nucleotide at 5' terminal of the antisense strand.

In some embodiments, the sense strand comprises only the nucleotide sequence I, and the antisense strand comprises only the nucleotide sequence II.

In some embodiments, there is no more than 1 nucleotide difference between the nucleotide sequence I and the nucleotide sequence as shown by SEQ ID NO: 181, and/or there is no more than 1 nucleotide difference between the nucleotide sequence II and the nucleotide sequence as shown by SEQ ID NO: 182.

In some embodiments, the nucleotide difference between the nucleotide sequence II and the nucleotide sequence as shown by SEQ ID NO: 182 includes a difference at the position $Z_{16}$, where $Z_{16}$ is selected from U, C or G. In some embodiments, the nucleotide difference is a difference at the position $Z_{16}$, wherein $Z_{16}$ is selected from U, C or G. In some embodiments, $Z_{15}$ is a nucleotide complementary to $Z_{16}$. The siRNAs having these nucleotide differences also exhibit high capacity to inhibit the target mRNA, and thus these siRNAs comprising the nucleotide differences are also within the protection scope of the present disclosure.

In some embodiments, the nucleotide sequence I and the nucleotide sequence II are basically reverse complementary, substantially reverse complementary, or completely reverse complementary to each other.

In some embodiments, the nucleotide sequence I is the nucleotide sequence as shown by SEQ ID NO: 183, and the nucleotide sequence II is the nucleotide sequence as shown by SEQ ID NO: 184:

(SEQ ID NO: 183)
5'-GCAACAAAGACAUUUAUG$Z_{15}$-3';

(SEQ ID NO: 184)
5'-$Z_{16}$CAUAAAUGUCUUUGUUGC-3', wherein, $Z_{16}$ is the first nucleotide at 5' terminal of the antisense strand, $Z_{15}$ is selected from A, U, G, or C, and $Z_{16}$ is a nucleotide complementary to $Z_{15}$; in some embodiments, $Z_{15}$ is U, and $Z_{16}$ is A.

Moreover, the sense strand and the antisense strand have the same or different length, wherein the sense strand has a length of 19 to 23 nucleotides, and the antisense strand has a length of 19 to 26 nucleotides.

In some embodiments, the sense strand further comprises a nucleotide sequence III, the antisense strand further comprises a nucleotide sequence IV, and the nucleotide sequence III and the nucleotide sequence IV independently of each other have a length of 1 to 4 nucleotides; the nucleotide sequence III and the nucleotide sequence IV have the same length and are substantially reverse complementary or completely reverse complementary to each other; the nucleotide sequence III is linked to the 5' terminal of the nucleotide sequence I and the nucleotide sequence IV is linked to the 3' terminal of the nucleotide sequence II; the nucleotide sequence IV is substantially reverse complementary, or completely reverse complementary to a second nucleotide sequence, which refers to a nucleotide sequence that is adjacent to the 5' terminal of the nucleotide sequence as shown by SEQ ID NO: 181 in the target mRNA and has the same length as the nucleotide sequence IV.

In some embodiments, in the direction from 5' terminal to 3' terminal, the nucleotide sequence III and the nucleotide sequence IV both have a length of 1 nucleotide, and the base of the nucleotide sequence III is U, and the base of the nucleotide sequence IV is A; in this case, the length ratio of the sense strand and the antisense strand thereof is 20/20; or, the nucleotide sequence III and the nucleotide sequence IV both have a length of 2 nucleotides, and in the direction from 5' terminal to 3' terminal, the base composition of the nucleotide sequence III is UU, and the base composition of the nucleotide sequence IV is AA; in this case, the length ratio of the sense strand and the antisense strand thereof is 21/21; or, the nucleotide sequence III and the nucleotide sequence IV both have a length of 3 nucleotides, and in the direction from 5' terminal to 3' terminal, the base composition of the nucleotide sequence III is CUU, and the base composition of the nucleotide sequence IV is AAG; in this case, the length ratio of the sense strand and the antisense strand thereof is 22/22; or, the nucleotide sequence III and the nucleotide sequence IV both have a length of 4 nucleotides, and in the direction from 5' terminal to 3' terminal, the base composition of the nucleotide sequence III is GCUU, and the base composition of the nucleotide sequence IV is AAGC; in this case, the length ratio of the sense strand and the antisense strand thereof is 23/23. In some embodiments, the nucleotide sequence III and the nucleotide sequence IV have a length of 2 nucleotides, and in the direction from 5' terminal to 3' terminal, the base composition of the nucleotide sequence III is UU, and the base composition of the nucleotide sequence IV is AA; in this case, the length ratio of the sense strand and the antisense strand thereof is 21/21.

In some embodiments, the nucleotide sequence III and the nucleotide sequence IV are completely reverse complementary. Hence, where the base(s) of nucleotide sequence III is(are) provided, the base(s) of nucleotide sequence IV is(are) also determined.

Fifth siRNA

According to the present disclosure, the siRNA may be a fifth siRNA.

The fifth siRNA comprises a sense strand and an antisense strand, each nucleotide in the siRNA being independently a modified or unmodified nucleotide, wherein the sense strand comprises a nucleotide sequence I, and the antisense strand comprises a nucleotide sequence II; the nucleotide sequence I and the nucleotide sequence II are at least partly reverse complementary to form a double-stranded region; wherein the nucleotide sequence I has the same length as the nucleotide sequence as shown by SEQ ID NO: 241 with no more than 3 nucleotide differences therebetween, and the nucleotide sequence II has the same length as the nucleotide sequence as shown by SEQ ID NO: 242 with no more than 3 nucleotide differences therebetween:

(SEQ ID NO: 241)
5'-GAAUCUCAAAGAAAUCUU$Z_{17}$-3';

(SEQ ID NO: 242)
5'-$Z_{18}$AAGAUUUCUUUGAGAUUC-3', wherein, $Z_{17}$ is U and $Z_{18}$ is A, and the nucleotide sequence I comprises a nucleotide $Z_{19}$ at the position corresponding to $Z_{17}$; the nucleotide sequence II comprises a nucleotide $Z_{20}$ at the position corresponding to $Z_{18}$, wherein $Z_{20}$ is the first nucleotide at 5' terminal of the antisense strand.

In some embodiments, the sense strand comprises only the nucleotide sequence I, and the antisense strand comprises only the nucleotide sequence II.

In some embodiments, there is no more than 1 nucleotide difference between the nucleotide sequence I and the nucleotide sequence as shown by SEQ ID NO: 241, and/or there is no more than 1 nucleotide difference between the nucleotide sequence II and the nucleotide sequence as shown by SEQ ID NO: 242.

In some embodiments, the nucleotide difference between the nucleotide sequence II and the nucleotide sequence as shown by SEQ ID NO: 242 includes a difference at the position $Z_{20}$, where $Z_{20}$ is selected from U, C or G. In some embodiments, the nucleotide difference is a difference at the position $Z_{20}$, wherein $Z_{20}$ is selected from U, C or G. In some embodiments, $Z_{19}$ is a nucleotide complementary to $Z_{20}$. The siRNAs having these nucleotide differences also exhibit high capacity to inhibit the target mRNA, and thus these siRNAs comprising the nucleotide differences are also within the protection scope of the present disclosure.

In some embodiments, the nucleotide sequence I and the nucleotide sequence II are basically reverse complementary, substantially reverse complementary, or completely reverse complementary to each other.

In some embodiments, the nucleotide sequence I is the nucleotide sequence as shown by SEQ ID NO: 243, and the nucleotide sequence II is the nucleotide sequence as shown by SEQ ID NO: 244:

(SEQ ID NO: 243)
5'-GAAUCUCAAAGAAAUCUU$Z_{19}$-3';

(SEQ ID NO: 244)
5'-$Z_{20}$AAGAUUUCUUUGAGAUUC-3', wherein, $Z_{20}$ is the first nucleotide at 5' terminal of the antisense strand, $Z_{19}$ is selected from A, U, G, or C, and $Z_{20}$ is a nucleotide complementary to $Z_{19}$; in some embodiments, $Z_{19}$ is U, and $Z_{20}$ is A.

Moreover, the sense strand and the antisense strand have the same or different length, wherein the sense strand has a length of 19 to 23 nucleotides, and the antisense strand has a length of 19 to 26 nucleotides.

In some embodiments, the sense strand further comprises a nucleotide sequence III, the antisense strand further comprises a nucleotide sequence IV, and the nucleotide sequence III and the nucleotide sequence IV independently of each other have a length of 1 to 4 nucleotides; the nucleotide sequence III and the nucleotide sequence IV have the same length and are substantially reverse complementary or completely reverse complementary to each other; the nucleotide sequence III is linked to the 5' terminal of the nucleotide sequence I, and the nucleotide sequence IV is linked to the 3' terminal of the nucleotide sequence II; the nucleotide sequence IV is substantially reverse complementary, or completely reverse complementary to a second nucleotide sequence, which refers to a nucleotide sequence that is adjacent to the 5' terminal of the nucleotide sequence as shown by SEQ ID NO: 241 in the target mRNA and has the same length as the nucleotide sequence IV.

In some embodiments, in the direction from 5' terminal to 3' terminal, the nucleotide sequence III and the nucleotide sequence IV both have a length of 1 nucleotide, and the base of the nucleotide sequence III is A, and the base of the nucleotide sequence IV is U; in this case, the length ratio of the sense strand and the antisense strand thereof is 20/20; or, the nucleotide sequence III and the nucleotide sequence IV both have a length of 2 nucleotides, and in the direction from 5' terminal to 3' terminal, the base composition of the nucleotide sequence III is AA, and the base composition of the nucleotide sequence IV is UU; in this case, the length ratio of the sense strand and the antisense strand thereof is 21/21; or, the nucleotide sequence III and the nucleotide sequence IV both have a length of 3 nucleotides, and in the direction from 5' terminal to 3' terminal, the base composition of the nucleotide sequence III is AAA, and the base composition of the nucleotide sequence IV is UUU; in this case, the length ratio of the sense strand and the antisense strand thereof is 22/22; or, the nucleotide sequence III and the nucleotide sequence IV both have a length of 4 nucleotides, and in the direction from 5' terminal to 3' terminal, the base composition of the nucleotide sequence III is CAAA, and the base composition of the nucleotide sequence IV is UUUG; in this case, the length ratio of the sense strand and the antisense strand thereof is 23/23. In some embodiments, the nucleotide sequence III and the nucleotide sequence IV have a length of 2 nucleotides, and in the direction from 5' terminal to 3' terminal, the base composition of the nucleotide sequence III is AA, and the base composition of the nucleotide sequence IV is UU; in this case, the length ratio of the sense strand and the antisense strand thereof is 21/21.

In some embodiments, the nucleotide sequence III and the nucleotide sequence IV are completely reverse complementary. Hence, where the base(s) of nucleotide sequence III is(are) provided, the base(s) of nucleotide sequence IV is(are) also determined.

Sixth siRNA

According to the present disclosure, the siRNA may be a sixth siRNA.

The sixth siRNA comprises a sense strand and an antisense strand, each nucleotide in the siRNA being independently a modified or unmodified nucleotide, wherein the sense strand comprises a nucleotide sequence I, and the antisense strand comprises a nucleotide sequence II; the nucleotide sequence I and the nucleotide sequence II are at least partly reverse complementary to form a double-stranded region; wherein the nucleotide sequence I has the same length as the nucleotide sequence as shown by SEQ ID NO: 301 with no more than 3 nucleotide differences therebetween, and the nucleotide sequence II has the same length as the nucleotide sequence as shown by SEQ ID NO: 302 with no more than 3 nucleotide differences therebetween:

(SEQ ID NO: 301)
5'-GUACGUGGACUGGAUUCU$Z_{21}$-3';

(SEQ ID NO: 302)
5'-$Z_{22}$AGAAUCCAGUCCACGUAC-3', wherein, $Z_{21}$ is G and $Z_{22}$ is C, and the nucleotide sequence I comprises a nucleotide $Z_{23}$ at the position corresponding to $Z_{21}$; the nucleotide sequence II comprises a nucleotide $Z_{24}$ at the position corresponding to $Z_{22}$, wherein $Z_{24}$ is the first nucleotide at 5' terminal of the antisense strand.

In some embodiments, the sense strand comprises only the nucleotide sequence I, and the antisense strand comprises only the nucleotide sequence II.

In some embodiments, there is no more than 1 nucleotide difference between the nucleotide sequence I and the nucleotide sequence as shown by SEQ ID NO: 301, and/or there is no more than 1 nucleotide difference between the nucleotide sequence II and the nucleotide sequence as shown by SEQ ID NO: 302.

In some embodiments, the nucleotide difference between the nucleotide sequence II and the nucleotide sequence as shown by SEQ ID NO: 302 includes a difference at the position $Z_{24}$, where $Z_{24}$ is selected from U, G or A. In some embodiments, the nucleotide difference is a difference at the position $Z_{24}$, wherein $Z_{24}$ is selected from U, G or A. In some embodiments, $Z_{23}$ is a nucleotide complementary to $Z_{24}$. The siRNAs having these nucleotide differences also exhibit high capacity to inhibit the target mRNA, and thus these siRNAs comprising the nucleotide differences are also within the protection scope of the present disclosure.

In some embodiments, the nucleotide sequence I and the nucleotide sequence II are basically reverse complementary, substantially reverse complementary, or completely reverse complementary to each other.

In some embodiments, the nucleotide sequence I is the nucleotide sequence as shown by SEQ ID NO: 303, and the nucleotide sequence II is the nucleotide sequence as shown by SEQ ID NO: 304:

(SEQ ID NO: 303)
5'-GUACGUGGACUGGAUUCU$Z_{23}$-3';

(SEQ ID NO: 304)
5'-$Z_{24}$AGAAUCCAGUCCACGUAC-3', wherein, $Z_{24}$ is the first nucleotide at 5' terminal of the antisense strand, $Z_{23}$ is selected from A, U, G, or C, and $Z_{24}$ is a nucleotide complementary to $Z_{23}$; in some embodiments, $Z_{23}$ is G, and $Z_{24}$ is C.

Moreover, the sense strand and the antisense strand have the same or different length, wherein the sense strand has a length of 19 to 23 nucleotides, and the antisense strand has a length of 19 to 26 nucleotides.

In some embodiments, the sense strand further comprises a nucleotide sequence III, the antisense strand further comprises a nucleotide sequence IV, and the nucleotide sequence III and the nucleotide sequence IV independently of each other have a length of 1 to 4 nucleotides; the nucleotide sequence III and the nucleotide sequence IV have the same length and are substantially reverse complementary or completely reverse complementary to each other; the nucleotide sequence III is linked to the 5' terminal of the nucleotide sequence I, and the nucleotide sequence IV is linked to the 3' terminal of the nucleotide sequence II; the nucleotide sequence IV is substantially reverse complementary, or completely reverse complementary to a second nucleotide sequence, which refers to a nucleotide sequence that is adjacent to the 5' terminal of the nucleotide sequence as shown by SEQ ID NO: 301 in the target mRNA and has the same length as the nucleotide sequence IV.

In some embodiments, in the direction from 5' terminal to 3' terminal, the nucleotide sequence III and the nucleotide sequence IV both have a length of 1 nucleotide, and the base of the nucleotide sequence III is A, and the base of the nucleotide sequence IV is U; in this case, the length ratio of the sense strand and the antisense strand thereof is 20/20; or, the nucleotide sequence III and the nucleotide sequence IV both have a length of 2 nucleotides, and in the direction from 5' terminal to 3' terminal, the base composition of the nucleotide sequence III is GA, and the base composition of the nucleotide sequence IV is UC; in this case, the length ratio of the sense strand and the antisense strand thereof is 21/21; or, the nucleotide sequence III and the nucleotide sequence IV both have a length of 3 nucleotides, and in the direction from 5' terminal to 3' terminal, the base composition of the nucleotide sequence III is CGA, and the base composition of the nucleotide sequence IV is UCG; in this case, the length ratio of the sense strand and the antisense strand thereof is 22/22; or, the nucleotide sequence III and the nucleotide sequence IV both have a length of 4 nucleotides, and in the direction from 5' terminal to 3' terminal, the base composition of the nucleotide sequence III is UCGA, and the base composition of the nucleotide sequence IV is UCGA; in this case, the length ratio of the sense strand and the antisense strand thereof is 23/23. In some embodiments, the nucleotide sequence III and the nucleotide sequence IV have a length of 2 nucleotides, and in the direction from 5' terminal to 3' terminal, the base composition of the nucleotide sequence III is GA, and the base composition of the nucleotide sequence IV is UC; in this case, the length ratio of the sense strand and the antisense strand thereof is 21/21.

In some embodiments, the nucleotide sequence III and the nucleotide sequence IV are completely reverse complementary. Hence, where the base(s) of nucleotide sequence III is(are) provided, the base(s) of nucleotide sequence IV is(are) also determined.

Seventh siRNA

According to the present disclosure, the siRNA may be a seventh siRNA.

The seventh siRNA comprises a sense strand and an antisense strand, each nucleotide in the siRNA being independently a modified or unmodified nucleotide, wherein the sense strand comprises a nucleotide sequence I, and the antisense strand comprises a nucleotide sequence II; the nucleotide sequence I and the nucleotide sequence II are at least partly reverse complementary to form a double-stranded region; wherein the nucleotide sequence I has the same length as the nucleotide sequence as shown by SEQ ID NO: 361 with no more than 3 nucleotide differences therebetween, and the nucleotide sequence II has the same length as the nucleotide sequence as shown by SEQ ID NO: 362 with no more than 3 nucleotide differences therebetween:

(SEQ ID NO: 361)
5'-AUUUCUGGGUAUUCUUUC$Z_{25}$-3';

(SEQ ID NO: 362)
5'-$Z_{26}$GAAAGAAUACCCAGAAAU-3', wherein, $Z_{25}$ is A and $Z_{26}$ is U, and the nucleotide sequence I comprises a nucleotide $Z_{27}$ at the position corresponding to $Z_{25}$; the nucleotide sequence II comprises a nucleotide $Z_{28}$ at the position corresponding to $Z_{26}$, wherein $Z_{28}$ is the first nucleotide at 5' terminal of the antisense strand.

In some embodiments, the sense strand comprises only the nucleotide sequence I, and the antisense strand comprises only the nucleotide sequence II.

In some embodiments, there is no more than 1 nucleotide difference between the nucleotide sequence I and the nucleotide sequence as shown by SEQ ID NO: 361, and/or there is no more than 1 nucleotide difference between the nucleotide sequence II and the nucleotide sequence as shown by SEQ ID NO: 362.

In some embodiments, the nucleotide difference between the nucleotide sequence II and the nucleotide sequence as shown by SEQ ID NO: 362 includes a difference at the position $Z_{28}$, where $Z_{28}$ is selected from A, C or G. In some embodiments, the nucleotide difference is a difference at the position $Z_{28}$, wherein $Z_{28}$ is selected from A, C or G. In some embodiments, $Z_{27}$ is a nucleotide complementary to $Z_{28}$. The siRNAs having these nucleotide differences also exhibit high capacity to inhibit the target mRNA, and thus these siRNAs comprising the nucleotide differences are also within the protection scope of the present disclosure.

In some embodiments, the nucleotide sequence I and the nucleotide sequence II are basically reverse complementary, substantially reverse complementary, or completely reverse complementary to each other.

In some embodiments, the nucleotide sequence I is the nucleotide sequence as shown by SEQ ID NO: 363, and the nucleotide sequence II is the nucleotide sequence as shown by SEQ ID NO: 364:

(SEQ ID NO: 363)
5'-AUUUCUGGGUAUUCUUUC$Z_{27}$-3';

(SEQ ID NO: 364)
5'-$Z_{28}$GAAAGAAUACCCAGAAAU-3', wherein, $Z_{28}$ is the first nucleotide at 5' terminal of the antisense strand, $Z_{27}$ is selected from A, U, G, or C, and $Z_{28}$ is a nucleotide complementary to $Z_{27}$; in some embodiments, $Z_{27}$ is A, and $Z_{28}$ is U.

Moreover, the sense strand and the antisense strand have the same or different length, wherein the sense strand has a length of 19 to 23 nucleotides, and the antisense strand has a length of 19 to 26 nucleotides.

In some embodiments, the sense strand further comprises a nucleotide sequence III, the antisense strand further comprises a nucleotide sequence IV, and the nucleotide sequence III and the nucleotide sequence IV independently of each other have a length of 1 to 4 nucleotides; the nucleotide sequence III and the nucleotide sequence IV have the same length and are substantially reverse complementary or completely reverse complementary to each other; the nucleotide sequence III is linked to the 5' terminal of the nucleotide sequence I; and the nucleotide sequence IV is linked to the 3' terminal of the nucleotide sequence II. In some embodiments, the nucleotide sequence IV is substantially reverse complementary, or completely reverse complementary to a second nucleotide sequence, which refers to a nucleotide sequence that is adjacent to the 5' terminal of the nucleotide sequence as shown by SEQ ID NO: 361 in the target mRNA and has the same length as the nucleotide sequence IV.

In some embodiments, in the direction from 5' terminal to 3' terminal, the nucleotide sequence III and the nucleotide sequence IV both have a length of 1 nucleotide, and the base of the nucleotide sequence III is G, and the base of the nucleotide sequence IV is C; in this case, the length ratio of the sense strand and the antisense strand thereof is 20/20; or, the nucleotide sequence III and the nucleotide sequence IV both have a length of 2 nucleotides, and in the direction from 5' terminal to 3' terminal, the base composition of the nucleotide sequence III is CG, and the base composition of the nucleotide sequence IV is CG; in this case, the length ratio of the sense strand and the antisense strand thereof is 21/21; or, the nucleotide sequence III and the nucleotide sequence IV both have a length of 3 nucleotides, and in the direction from 5' terminal to 3' terminal, the base composition of the nucleotide sequence III is GCG, and the base composition of the nucleotide sequence IV is CGC; in this case, the length ratio of the sense strand and the antisense strand thereof is 22/22; or, the nucleotide sequence III and the nucleotide sequence IV both have a length of 4 nucleotides, and in the direction from 5' terminal to 3' terminal, the base composition of the nucleotide sequence III is AGCG, and the base composition of the nucleotide sequence IV is CGCU; in this case, the length ratio of the sense strand and the antisense strand thereof is 23/23. In some embodiments, the nucleotide sequence III and the nucleotide sequence IV have a length of 2 nucleotides, and in the direction from 5' terminal to 3' terminal, the base composition of the nucleotide sequence III is CG, and the base composition of the nucleotide sequence IV is CG; in this case, the length ratio of the sense strand and the anti sense strand thereof is 21/21.

In some embodiments, the nucleotide sequence III and the nucleotide sequence IV are completely reverse complementary. Hence, where the base(s) of nucleotide sequence III is(are) provided, the base(s) of nucleotide sequence IV is(are) also determined.

Eighth siRNA

According to the present disclosure, the siRNA may be a eighth siRNA.

The eighth siRNA comprises a sense strand and an antisense strand, each nucleotide in the siRNA being independently a modified or unmodified nucleotide, wherein the sense strand comprises a nucleotide sequence I, and the antisense strand comprises a nucleotide sequence II; the nucleotide sequence I and the nucleotide sequence II are at least partly reverse complementary to form a double-stranded region; wherein the nucleotide sequence I has the same length as the nucleotide sequence as shown by SEQ ID NO: 421 with no more than 3 nucleotide differences therebetween, and the nucleotide sequence II has the same length as the nucleotide sequence as shown by SEQ ID NO: 422 with no more than 3 nucleotide differences therebetween:

(SEQ ID NO: 421)
5'-CAUGAAGGGCAUAAACUAZ$_{29}$-3';

(SEQ ID NO: 422)
5'-Z$_{30}$UAGUUUAUGCCCUUCAUG-3', wherein, $Z_{29}$ is U and $Z_{30}$ is A, and the nucleotide sequence I comprises a nucleotide $Z_{31}$ at the position corresponding to $Z_{29}$; the nucleotide sequence II comprises a nucleotide $Z_{32}$ at the position corresponding to $Z_{30}$, wherein $Z_{32}$ is the first nucleotide at 5' terminal of the antisense strand.

In some embodiments, the sense strand comprises only the nucleotide sequence I, and the antisense strand comprises only the nucleotide sequence II.

In some embodiments, there is no more than 1 nucleotide difference between the nucleotide sequence I and the nucleotide sequence as shown by SEQ ID NO: 421, and/or there is no more than 1 nucleotide difference between the nucleotide sequence II and the nucleotide sequence as shown by SEQ ID NO: 422.

In some embodiments, the nucleotide difference between the nucleotide sequence II and the nucleotide sequence as shown by SEQ ID NO: 422 includes a difference at the position $Z_{32}$, where $Z_{32}$ is selected from U, C or G. In some embodiments, the nucleotide difference is a difference at the position $Z_{32}$, wherein $Z_{32}$ is selected from U, C or G. In some embodiments, $Z_{31}$ is a nucleotide complementary to $Z_{32}$. The siRNAs having these nucleotide differences also exhibit high capacity to inhibit the target mRNA, and thus these siRNAs comprising the nucleotide differences are also within the protection scope of the present disclosure.

In some embodiments, the nucleotide sequence I and the nucleotide sequence II are basically reverse complementary, substantially reverse complementary, or completely reverse complementary to each other.

In some embodiments, the nucleotide sequence I is the nucleotide sequence as shown by SEQ ID NO: 423, and the nucleotide sequence II is the nucleotide sequence as shown by SEQ ID NO: 424:

(SEQ ID NO: 423)
5'-CAUGAAGGGCAUAAACUAZ$_{31}$-3';

(SEQ ID NO: 424)
5'-Z$_{32}$UAGUUUAUGCCCUUCAUG-3', wherein, $Z_{32}$ is the first nucleotide at 5' terminal of the antisense strand, $Z_{31}$ is selected from A, U, G, or C, and $Z_{32}$ is a nucleotide complementary to $Z_{31}$; in some embodiments, $Z_{31}$ is U, and $Z_{32}$ is A.

Moreover, the sense strand and the antisense strand have the same or different length, wherein the sense strand has a length of 19 to 23 nucleotides, and the antisense strand has a length of 19 to 26 nucleotides.

In some embodiments, the sense strand further comprises a nucleotide sequence III, the antisense strand further comprises a nucleotide sequence IV, and the nucleotide sequence III and the nucleotide sequence IV independently of each other have a length of 1 to 4 nucleotides; the nucleotide sequence III and the nucleotide sequence IV have the same length and are substantially reverse complementary or completely reverse complementary to each other; the nucleotide sequence III is linked to the 5' terminal of the nucleotide sequence I; and the nucleotide sequence IV is linked to the 3' terminal of the nucleotide sequence II. In some embodiments, the nucleotide sequence IV is substantially reverse complementary, or completely reverse complementary to a second nucleotide sequence, which refers to a nucleotide sequence that is adjacent to the 5' terminal of the nucleotide sequence as shown by SEQ ID NO: 421 in the target mRNA and has the same length as the nucleotide sequence IV.

In some embodiments, in the direction from 5' terminal to 3' terminal, the nucleotide sequence III and the nucleotide sequence IV both have a length of 1 nucleotide, and the base of the nucleotide sequence III is A, and the base of the nucleotide sequence IV is U; in this case, the length ratio of the sense strand and the antisense strand thereof is 20/20; or, the nucleotide sequence III and the nucleotide sequence IV both have a length of 2 nucleotides, and in the direction from 5' terminal to 3' terminal, the base composition of the nucleotide sequence III is GA, and the base composition of the nucleotide sequence IV is UC; in this case, the length ratio of the sense strand and the antisense strand thereof is 21/21; or, the nucleotide sequence III and the nucleotide sequence IV both have a length of 3 nucleotides, and in the direction from 5' terminal to 3' terminal, the base composition of the nucleotide sequence III is AGA, and the base composition of the nucleotide sequence IV is UCU; in this case, the length ratio of the sense strand and the antisense strand thereof is 22/22; or, the nucleotide sequence III and the nucleotide sequence IV both have a length of 4 nucleotides, and in the direction from 5' terminal to 3' terminal, the base composition of the nucleotide sequence III is UAGA, and the base composition of the nucleotide sequence IV is UCUA; in this case, the length ratio of the sense strand and the antisense strand thereof is 23/23. In some embodiments, the nucleotide sequence III and the nucleotide sequence IV have a length of 2 nucleotides, and in the direction from 5' terminal to 3' terminal, the base composition of the nucleotide sequence III is GA, and the base composition of the nucleotide sequence IV is UC; in this case, the length ratio of the sense strand and the anti sense strand thereof is 21/21.

In some embodiments, the nucleotide sequence III and the nucleotide sequence IV are completely reverse complementary. Hence, where the base(s) of nucleotide sequence III is(are) provided, the base(s) of nucleotide sequence IV is(are) also determined.

Ninth siRNA

According to the present disclosure, the siRNA may be a ninth siRNA.

The ninth siRNA comprises a sense strand and an antisense strand, each nucleotide in the siRNA being independently a modified or unmodified nucleotide, wherein the sense strand comprises a nucleotide sequence I, and the antisense strand comprises a nucleotide sequence II; the nucleotide sequence I and the nucleotide sequence II are at least partly reverse complementary to form a double-stranded region; wherein the nucleotide sequence I has the same length as the nucleotide sequence as shown by SEQ ID NO: 481 with no more than 3 nucleotide differences therebetween, and the nucleotide sequence II has the same length as the nucleotide sequence as shown by SEQ ID NO: 482 with no more than 3 nucleotide differences therebetween:

(SEQ ID NO: 481)
5'-GGAUUCUGGAGAAAACUCZ$_{33}$-3';

(SEQ ID NO: 482)
5'-Z$_{34}$GAGUUUUCUCCAGAAUCC-3', wherein, $Z_{33}$ is A and $Z_{34}$ is U, and the nucleotide sequence I comprises a nucleotide $Z_{35}$ at the position corresponding to $Z_{33}$; the nucleotide sequence II comprises a nucleotide $Z_{36}$ at the position corresponding to $Z_{34}$, wherein $Z_{36}$ is the first nucleotide at 5' terminal of the antisense strand.

In some embodiments, the sense strand comprises only the nucleotide sequence I, and the antisense strand comprises only the nucleotide sequence II.

In some embodiments, there is no more than 1 nucleotide difference between the nucleotide sequence I and the nucleotide sequence as shown by SEQ ID NO: 481, and/or there is no more than 1 nucleotide difference between the nucleotide sequence II and the nucleotide sequence as shown by SEQ ID NO: 482.

In some embodiments, the nucleotide difference between the nucleotide sequence II and the nucleotide sequence as shown by SEQ ID NO: 482 includes a difference at the position $Z_{36}$, where $Z_{36}$ is selected from A, C or G. In some embodiments, the nucleotide difference is a difference at the position $Z_{36}$, wherein $Z_{36}$ is selected from A, C or G. In some embodiments, $Z_{35}$ is a nucleotide complementary to $Z_{36}$. The siRNA having these nucleotide differences also exhibit high capacity to inhibit the target mRNA, and thus these siRNAs comprising the nucleotide differences are also within the protection scope of the present disclosure.

In some embodiments, the nucleotide sequence I and the nucleotide sequence II are basically reverse complementary, substantially reverse complementary, or completely reverse complementary to each other.

In some embodiments, the nucleotide sequence I is the nucleotide sequence as shown by SEQ ID NO: 483, and the nucleotide sequence II is the nucleotide sequence as shown by SEQ ID NO: 484:

(SEQ ID NO: 483)
5'-GGAUUCUGGAGAAAACUCZ$_{35}$-3';

(SEQ ID NO: 484)
5'-Z$_{36}$GAGUUUUCUCCAGAAUCC-3', wherein, $Z_{36}$ is the first nucleotide at 5' terminal of the antisense strand, $Z_{35}$ is selected from A, U, G, or C, and $Z_{36}$ is a nucleotide complementary to $Z_{35}$; in some embodiments, $Z_{35}$ is A, and $Z_{36}$ is U.

Moreover, the sense strand and the antisense strand have the same or different length, wherein the sense strand has a length of 19 to 23 nucleotides, and the antisense strand has a length of 19 to 26 nucleotides.

In some embodiments, the sense strand further comprises a nucleotide sequence III, the antisense strand further comprises a nucleotide sequence IV, and the nucleotide sequence III and the nucleotide sequence IV independently of each other have a length of 1 to 4 nucleotides; the nucleotide sequence III and the nucleotide sequence IV have the same length and are substantially reverse complementary or completely reverse complementary to each other; the nucleotide sequence III is linked to the 5' terminal of the nucleotide sequence I, and the nucleotide sequence IV is linked to the 3' terminal of the nucleotide sequence II. In some embodiments, the nucleotide sequence IV is substantially reverse complementary, or completely reverse complementary to a second nucleotide sequence, which refers to a nucleotide sequence that is adjacent to the 5' terminal of the nucleotide sequence as shown by SEQ ID NO: 481 in the target mRNA and has the same length as the nucleotide sequence IV.

In some embodiments, in the direction from 5' terminal to 3' terminal, the nucleotide sequence III and the nucleotide sequence IV both have a length of 1 nucleotide, and the base of the nucleotide sequence III is U, and the base of the nucleotide sequence IV is A; in this case, the length ratio of the sense strand and the antisense strand thereof is 20/20; or, the nucleotide sequence III and the nucleotide sequence IV both have a length of 2 nucleotides, and in the direction from 5' terminal to 3' terminal, the base composition of the nucleotide sequence III is CU, and the base composition of the nucleotide sequence IV is AG; in this case, the length ratio of the sense strand and the antisense strand thereof is 21/21; or, the nucleotide sequence III and the nucleotide sequence IV both have a length of 3 nucleotides, and in the direction from 5' terminal to 3' terminal, the base composition of the nucleotide sequence III is ACU, and the base composition of the nucleotide sequence IV is AGU; in this case, the length ratio of the sense strand and the antisense strand thereof is 22/22; or, the nucleotide sequence III and the nucleotide sequence IV both have a length of 4 nucleotides, and in the direction from 5' terminal to 3' terminal, the base composition of the nucleotide sequence III is GACU, and the base composition of the nucleotide sequence IV is AGUC; in this case, the length ratio of the sense strand and the antisense strand thereof is 23/23. In some embodiments, the nucleotide sequence III and the nucleotide sequence IV have a length of 2 nucleotides, and in the direction from 5' terminal to 3' terminal, the base composition of the nucleotide sequence III is CU, and the base composition of the nucleotide sequence IV is AG; in this case, the length ratio of the sense strand and the antisense strand thereof is 21/21.

In some embodiments, the nucleotide sequence III and the nucleotide sequence IV are completely reverse complementary. Hence, where the base(s) of nucleotide sequence III is(are) provided, the base(s) of nucleotide sequence IV is(are) also determined.

The following description regarding the nucleotide sequence V, the nucleic acid sequence, or the nucleotide modification and the modified sequence in the siRNA is applicable to any one of the above-mentioned first siRNA to the ninth siRNA. Namely, unless stated otherwise, the following description of the siRNA should be regarded as the description of the first, second, third, fourth, fifth, sixth, seventh, eighth, and ninth siRNAs one by one. For example, if no particular siRNA is specifically indicated, "the siRNA further comprises a nucleotide sequence V" means "the first siRNA, the second siRNA, the third siRNA, the fourth siRNA, the fifth siRNA, the sixth siRNA, the seventh siRNA, the eighth siRNA, or the ninth siRNA further comprises a nucleotide sequence V".

In some embodiments, the antisense strand further comprises a nucleotide sequence V. The nucleotide sequence V has a length of 1 to 3 nucleotides and is linked to 3' terminal of the antisense strand, thereby forming a 3' overhang of the antisense strand. In this case, the length ratio of the sense strand and the antisense strand of the siRNA of the present disclosure may be 19/20, 19/21, 19/22, 20/21, 20/22, 20/23, 21/22, 21/23, 21/24, 22/23, 22/24, 22/25, 23/24, 23/25, or 23/26. In some embodiments, the nucleotide sequence V has a length of 2 nucleotides. In this case, the length ratio of the sense strand and the antisense strand of the siRNA of the present disclosure may be 19/21, 21/23 or 23/25.

Each nucleotide in the nucleotide sequence V may be any nucleotide. In order to facilitate the synthesis and to save synthesis cost, the nucleotide sequence V is 2 consecutive thymine deoxyribonucleotides (dTdT) or 2 consecutive uracil ribonucleotides (UU); or, in order to enhance the affinity between the antisense strand of the siRNA and the target mRNA, the nucleotide sequence V is complementary to the nucleotides at the corresponding positions of the target mRNA. Thus, in some embodiments, the length ratio of the sense strand and the antisense strand of the siRNA of the present disclosure is 19/21 or 21/23. In this case, the siRNA of the present disclosure exhibits better activity for silencing the target mRNA.

The nucleotides at the corresponding positions of the target mRNA refer to the nucleotides or nucleotide sequence adjacent to 5' terminal of a segment of the nucleotide sequence of the target mRNA. This segment of the nucleotide sequence of the target mRNA refers to the segment of the nucleotide sequence which is substantially reverse complementary or completely reverse complementary to the nucleotide sequence II, or is substantially reverse complementary or completely reverse complementary to the nucleotide sequence consisting of the nucleotide sequence II and the nucleotide sequence IV.

In some embodiments, for the first siRNA, the sense strand of the siRNA comprises the nucleotide sequence as shown by SEQ ID NO: 5, and the antisense strand of the siRNA comprises the nucleotide sequence as shown by SEQ ID NO: 6:

(SEQ ID NO: 5)
5'-GGGUAUUCUUUCAAGCAA$Z_3$-3';

(SEQ ID NO: 6)
5'-$Z_4$UUGCUUGAAAGAAUACCCAG-3';

or, the sense strand of the siRNA comprises the nucleotide sequence as shown by SEQ ID NO: 7, and the antisense strand of the siRNA comprises the nucleotide sequence as shown by SEQ ID NO: 8:

(SEQ ID NO: 7)
5'-CUGGGUAUUCUUUCAAGCAA$Z_3$-3';

(SEQ ID NO: 8)
5'-$Z_4$UUGCUUGAAAGAAUACCCAGAA-3';

wherein, $Z_4$ is the first nucleotide at 5' terminal of the antisense strand; $Z_3$ is selected from A, U, G or C, and $Z_4$ is a nucleotide complementary to $Z_3$.

In some embodiments, for the second siRNA, the sense strand of the siRNA comprises the nucleotide sequence as shown by SEQ ID NO: 65, and the antisense strand of the siRNA comprises the nucleotide sequence as shown by SEQ ID NO: 66:

(SEQ ID NO: 65)
5'-GGCAUAAACUAUAACAGC$Z_7$-3';

(SEQ ID NO: 66)
5'-$Z_8$GCUGUUAUAGUUUAUGCCCU-3', or, the sense strand of the siRNA comprises the nucleotide sequence as shown by SEQ ID NO: 67, and the antisense strand of the siRNA comprises the nucleotide sequence as shown by SEQ ID NO: 68:

(SEQ ID NO: 67)
5'-AGGGCAUAAACUAUAACAGC$Z_7$-3';

(SEQ ID NO: 68)
5'-$Z_8$GCUGUUAUAGUUUAUGCCCUUC-3', wherein, $Z_8$ is the first nucleotide at 5' terminal of the antisense strand; $Z_7$ is selected from A, U, G or C, and $Z_8$ is a nucleotide complementary to $Z_7$.

In some embodiments, for the third siRNA, the sense strand of the siRNA comprises the nucleotide sequence as shown by SEQ ID NO: 125, and the antisense strand of the siRNA comprises the nucleotide sequence as shown by SEQ ID NO: 126:

(SEQ ID NO: 125)
5'-GCUCAAGAAUGCCAAGAA$Z_{11}$-3';

(SEQ ID NO: 126)
5'-$Z_{12}$UUCUUGGCAUUCUUGAGCAC-3', or, the sense strand of the siRNA comprises the nucleotide sequence as shown by SEQ ID NO: 127, and the antisense strand of the siRNA comprises the nucleotide sequence as shown by SEQ ID NO: 128:

(SEQ ID NO: 127)
5'-GUGCUCAAGAAUGCCAAGAA$Z_{11}$-3';

(SEQ ID NO: 128)
5'-$Z_{12}$UUCUUGGCAUUCUUGAGCACUC-3', wherein, $Z_{12}$ is the first nucleotide at 5' terminal of the antisense strand; $Z_{11}$ is selected from A, U, G or C, and $Z_{12}$ is a nucleotide complementary to $Z_{11}$.

In some embodiments, for the fourth siRNA, the sense strand of the siRNA comprises the nucleotide sequence as shown by SEQ ID NO: 185, and the antisense strand of the siRNA comprises the nucleotide sequence as shown by SEQ ID NO: 186:

(SEQ ID NO: 185)
5'-GCAACAAAGACAUUUAUGZ$_{15}$-3';

(SEQ ID NO: 186)
5'-Z$_{16}$CAUAAAUGUCUUUGUUGCAA-3', or, the sense strand of the siRNA comprises the nucleotide sequence as shown by SEQ ID NO: 187, and the antisense strand of the siRNA comprises the nucleotide sequence as shown by SEQ ID NO: 188:

(SEQ ID NO: 187)
5'-UUGCAACAAAGACAUUUAUGZ$_{15}$-3';

(SEQ ID NO: 188)
5'-Z$_{16}$CAUAAAUGUCUUUGUUGCAAGC-3', wherein, $Z_{16}$ is the first nucleotide at 5' terminal of the antisense strand; $Z_{15}$ is selected from A, U, G or C, and $Z_{16}$ is a nucleotide complementary to $Z_{15}$.

In some embodiments, for the fifth siRNA, the sense strand of the siRNA comprises the nucleotide sequence as shown by SEQ ID NO: 245, and the antisense strand of the siRNA comprises the nucleotide sequence as shown by SEQ ID NO: 246:

(SEQ ID NO: 245)
5'-GAAUCUCAAAGAAAUCUUZ$_{19}$-3';

(SEQ ID NO: 246)
5'-Z$_{20}$AAGAUUUCUUUGAGAUUCUU-3', or, the sense strand of the siRNA comprises the nucleotide sequence as shown by SEQ ID NO: 247, and the antisense strand of the siRNA comprises the nucleotide sequence as shown by SEQ ID NO: 248:

(SEQ ID NO: 247)
5'-AAGAAUCUCAAAGAAAUCUUZ$_{19}$-3';

(SEQ ID NO: 248)
5'-Z$_{20}$AAGAUUUCUUUGAGAUUCUUUG-3', wherein, $Z_{20}$ is the first nucleotide at 5' terminal of the antisense strand; $Z_{19}$ is selected from A, U, G or C, and $Z_{20}$ is a nucleotide complementary to $Z_{19}$.

In some embodiments, for the sixth siRNA, the sense strand of the siRNA comprises the nucleotide sequence as shown by SEQ ID NO: 305, and the antisense strand of the siRNA comprises the nucleotide sequence as shown by SEQ ID NO: 306:

(SEQ ID NO: 305)
5'-GUACGUGGACUGGAUUCUZ$_{23}$-3';

(SEQ ID NO: 306)
5'-Z$_{24}$AGAAUCCAGUCCACGUACUC-3', or, the sense strand of the siRNA comprises the nucleotide sequence as shown by SEQ ID NO: 307, and the antisense strand of the siRNA comprises the nucleotide sequence as shown by SEQ ID NO: 308:

(SEQ ID NO: 307)
5'-GAGUACGUGGACUGGAUUCUZ$_{23}$-3';

(SEQ ID NO: 308)
5'-Z$_{24}$AGAAUCCAGUCCACGUACUCGA-3', wherein, $Z_{24}$ is the first nucleotide at 5' terminal of the antisense strand; $Z_{23}$ is selected from A, U, G or C, and $Z_{24}$ is a nucleotide complementary to $Z_{23}$.

In some embodiments, for the seventh siRNA, the sense strand of the siRNA comprises the nucleotide sequence as shown by SEQ ID NO: 365, and the antisense strand of the siRNA comprises the nucleotide sequence as shown by SEQ ID NO: 366:

(SEQ ID NO: 365)
5'-AUUUCUGGGUAUUCUUUCZ$_{27}$-3';

(SEQ ID NO: 366)
5'-Z$_{28}$GAAAGAAUACCCAGAAAUCG-3', or, the sense strand of the siRNA comprises the nucleotide sequence as shown by SEQ ID NO: 367, and the antisense strand of the siRNA comprises the nucleotide sequence as shown by SEQ ID NO: 368:

(SEQ ID NO: 367)
5'-CGAUUUCUGGGUAUUCUUUCZ$_{27}$-3';

(SEQ ID NO: 368)
5'-Z$_{28}$GAAAGAAUACCCAGAAAUCGCU-3', wherein, $Z_{28}$ is the first nucleotide at 5' terminal of the antisense strand; $Z_{27}$ is selected from A, U, G or C, and $Z_{28}$ is a nucleotide complementary to $Z_{27}$.

In some embodiments, for the eighth siRNA, the sense strand of the siRNA comprises the nucleotide sequence as shown by SEQ ID NO: 425, and the antisense strand of the siRNA comprises the nucleotide sequence as shown by SEQ ID NO: 426:

(SEQ ID NO: 425)
5'-CAUGAAGGGCAUAAACUAZ$_{31}$-3';

(SEQ ID NO: 426)
5'-Z$_{32}$UAGUUUAUGCCCUUCAUGUC-3', or, the sense strand of the siRNA comprises the nucleotide sequence as shown by SEQ ID NO: 427, and the antisense strand of the siRNA comprises the nucleotide sequence as shown by SEQ ID NO: 428:

(SEQ ID NO: 427)
5'-GACAUGAAGGGCAUAAACUAZ$_{31}$-3';

(SEQ ID NO: 428)
5'-Z$_{32}$UAGUUUAUGCCCUUCAUGUCUA-3', wherein, $Z_{32}$ is the first nucleotide at 5' terminal of the antisense strand; $Z_{31}$ is selected from A, U, G or C, and $Z_{32}$ is a nucleotide complementary to $Z_{31}$.

In some embodiments, for the ninth siRNA, the sense strand of the siRNA comprises the nucleotide sequence as shown by SEQ ID NO: 485, and the antisense strand of the siRNA comprises the nucleotide sequence as shown by SEQ ID NO: 486:

(SEQ ID NO: 485)
5'-GGAUUCUGGAGAAAACUC$Z_{35}$-3';

(SEQ ID NO: 486)
5'-$Z_{36}$GAGUUUUCUCCAGAAUCCAG-3', or, the sense strand of the siRNA comprises the nucleotide sequence as shown by SEQ ID NO: 487, and the antisense strand of the siRNA comprises the nucleotide sequence as shown by SEQ ID NO: 488:

(SEQ ID NO: 487)
5'-CUGGAUUCUGGAGAAAACUC$Z_{35}$-3';

(SEQ ID NO: 488)
5'-$Z_{36}$GAGUUUUCUCCAGAAUCCAGUC-3', wherein, $Z_{36}$ is the first nucleotide at 5' terminal of the antisense strand; $Z_{35}$ is selected from A, U, G or C, and $Z_{36}$ is a nucleotide complementary to $Z_{35}$.

In some embodiments, the siRNA of the present disclosure is siFXIa1, siFXIa2, siFXIb1, siFXIb2, siFXIc1, siFXIc2, siFXId1, siFXId2, siFXIe1, siFXIe2, siFXIf1, siFXIf2, siFXIg1, siFXIg2, siFXIh1, siFXIh2, siFXIi1, or siFXIi2 as shown in Tables 1a to 1i.

As mentioned above, in the siRNA of the present disclosure, each nucleotide is independently a modified or unmodified nucleotide. In some embodiments, the nucleotide in the siRNA of the present disclosure is an unmodified nucleotide; in some embodiments, in the siRNA of the present disclosure, some or all of the nucleotides are modified nucleotides. These modifications on the nucleotide groups would not lead to significant decrease or loss of the functions of the siRNA conjugate of the present disclosure for inhibiting the expression of FXI gene.

In some embodiments, the siRNA of the present disclosure comprises at least 1 modified nucleotide. In the context of the present disclosure, the term "modified nucleotide" used refers to a nucleotide formed by substituting 2'-hydroxy of the ribose group thereof with other groups, or nucleotide analogue, or a nucleotide with a modified base. The modified nucleotide would not lead to significant impairment or loss of the functions of the siRNA for inhibiting gene expression. For example, the modified nucleotides disclosed in J. K. Watts, G. F. Deleavey and M. J. Damha, Chemically Modified siRNA: tools and applications. Drug Discov Today, 2008.13(19-20): p. 842-55 may be selected.

In some embodiments, at least one nucleotide in the sense strand or the antisense strand of the siRNA of the present disclosure is a modified nucleotide, and/or at least one phosphate group is a phosphate group with modified group(s). In other words, at least a portion of the phosphate and/or ribose groups in the phosphate-ribose backbone of at least one single strand in the sense strand and the antisense strand are phosphate groups with modified groups and/or ribose groups with modified groups.

In some embodiments, all the nucleotides in the sense strand and/or the antisense strand are modified nucleotides. In some embodiments, each nucleotide in the sense strand and the antisense strand of the siRNA of the present disclosure is independently a fluoro modified nucleotide or a non-fluoro modified nucleotide.

The inventors of the present disclosure have surprisingly found that the siRNAs of the present disclosure achieve high balance between plasma stability and gene silencing efficiency in animal experiments.

In some embodiments, the fluoro modified nucleotides are located in the nucleotide sequence I and the nucleotide sequence II. Moreover, in the direction from 5' terminal to 3' terminal, at least the nucleotides at positions 7, 8 and 9 of the nucleotide sequence I are fluoro modified nucleotides; and in the direction from 5' terminal to 3' terminal, at least the nucleotides at positions 2, 6, 14, and 16 of the nucleotide sequence II are fluoro modified nucleotides.

In some embodiments, the fluoro modified nucleotides are located in the nucleotide sequence I and the nucleotide sequence II; and the nucleotide sequence I comprises no more than 5 fluoro modified nucleotides. Moreover, in the direction from 5' terminal to 3' terminal, at least the nucleotides at positions 7, 8 and 9 of the nucleotide sequence I are fluoro modified nucleotides; the nucleotide sequence II comprises no more than 7 fluoro modified nucleotides; and al least the nucleotides at positions 2, 6, 14, and 16 of the nucleotide sequence II are fluoro modified nucleotides.

In some embodiments, in the direction from 5' terminal to 3' terminal, the nucleotides at positions 7, 8 and 9 or at positions 5, 7, 8 and 9 of the nucleotide sequence I in the sense strand are fluoro modified nucleotides, and the nucleotides at the other positions in the sense strand are non-fluoro modified nucleotides; in the direction from 5' terminal to 3' terminal, the nucleotides at positions 2, 6, 14, and 16 or at positions 2, 6, 8, 9, 14, and 16 of the nucleotide sequence II in the antisense strand are fluoro modified nucleotides, and the nucleotides at the other positions in the antisense strand are non-fluoro modified nucleotides.

In the context of the present disclosure, a "fluoro modified nucleotide" refers to a nucleotide formed by substituting 2'-hydroxy of the ribose group thereof with a fluorine atom, which has a structure as shown by the following Formula (7). A "non-fluoro modified nucleotide" refers to a nucleotide formed by substituting 2'-hydroxy of the ribose group thereof with a non-fluoro group, or a nucleotide analogue. In some embodiments, each non-fluoro modified nucleotide is independently selected from a nucleotide formed by substituting 2'-hydroxy of the ribose group thereof with a non-fluoro group, or a nucleotide analogue.

The nucleotides formed by substituting 2'-hydroxy of the ribose group with a non-fluoro group are well-known to those skilled in the art, and can be one selected from the group consisting of 2'-alkoxy modified nucleotides, 2'-substituted alkoxy modified nucleotides, 2'-alkyl modified nucleotides, 2'-substituted alkyl modified nucleotides, 2'-amino modified nucleotides, 2'-substituted amino modified nucleotides, and 2'-deoxy nucleotides.

In some embodiments, the 2'-alkoxy modified nucleotide is a 2'-methoxy (2'-OMe) modified nucleotide, as shown by Formula (8). In some embodiments, the 2'-substituted alkoxy modified nucleotide is for example a 2'-methoxyethyl (2'-MOE) modified nucleotide, as shown by Formula (9). In some embodiments, the 2'-amino (2'-$NH_2$) modified nucleotide is as shown by Formula (10). In some embodiments, the 2'-deoxy nucleotide (DNA) is as shown by Formula (11).

Formula (7)

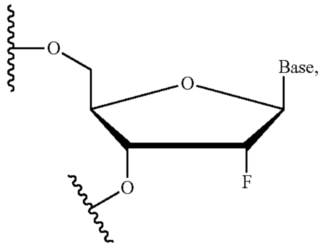

Formula (8)

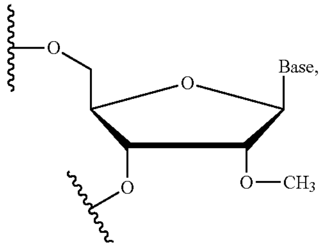

Formula (9)

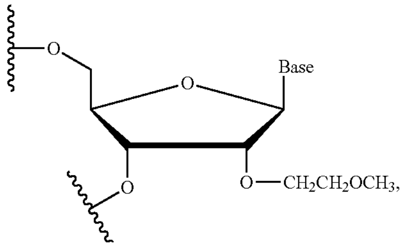

Formula (10)

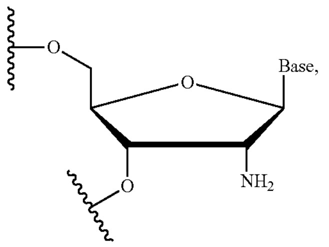

Formula (11)

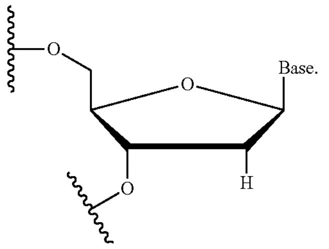

A nucleotide analogue refers to a group that can replace a nucleotide in a nucleic acid, while structurally differs from an adenine ribonucleotide, a guanine ribonucleotide, a cytosine ribonucleotide, a uracil ribonucleotide, or thymine deoxyribonucleotide. In some embodiments, the nucleotide analogue may be an isonucleotide, a bridged nucleotide or an acyclic nucleotide.

Abridged nucleic acid (BNA) refers to a constrained or inaccessible nucleotide. BNA can contain a 5-, 6-membered or a 7-membered ring bridged structure with a "fixed" C3'-endo sugar puckering. The bridge is typically incorporated at the 2'- and 4'-positions of the ribose to afford a 2', 4'-BNA nucleotide. In some embodiments, BNA may be LNA, ENA, cET BNA and so on, which are shown by Formulae (12), (13) and (14), respectively:

Formula (12)

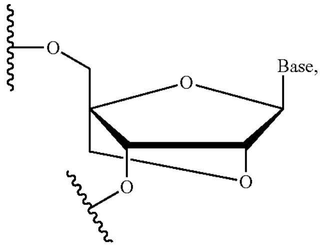

Formula (13)

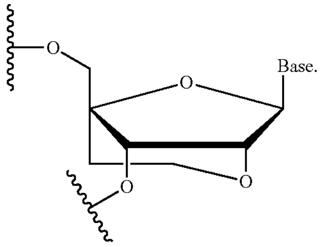

Formula (14)

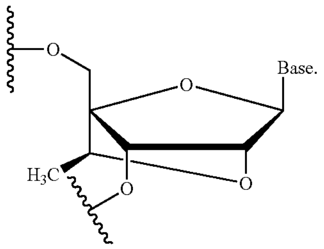

An acyclic nucleotide refers to a class of nucleotides in which the sugar ring is opened. In some embodiments, the acrylic nucleotide may be an unlocked nucleic acid (UNA) or a glycerol nucleic acid (GNA), which are as shown by Formulae (15) and (16), respectively:

Formula (15)

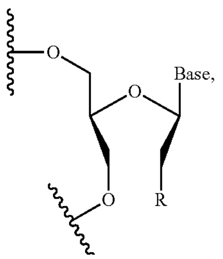

Formula (16)

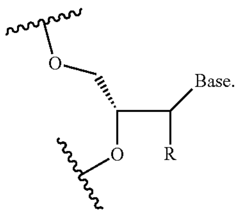

In the above Formulae (15) and (16), R is selected from H, OH or alkoxy (0-alkyl).

An isonucleotide is a compound formed by changing the position of the base on the ribose ring in the nucleotide. In some embodiments, the isonucleotide may be a compound formed by transposing the base from 1'-position to 2'-position or 3'-position on the ribose ring, as shown by Formula (17) or (18), respectively.

Formula (17)

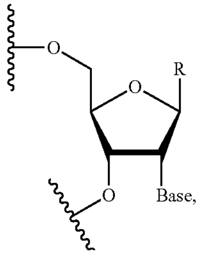

Formula (18)

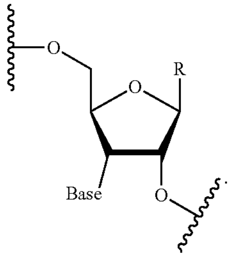

In the above compounds of Formulae (17)-(18), "Base" represents a base of a nucleic acid, such as A, U, G, C, or T; R is selected from H, OH, F, or the above non-fluoro group.

In some embodiments, a nucleotide analogue is one selected from the group consisting of isonucleotide, LNA, ENA, cET, UNA, and GNA. In some embodiments, each non-fluoro modified nucleotide is a methoxy modified nucleotide. In the context of the present disclosure, the methoxy modified nucleotide refers to a nucleotide formed by substituting 2'-hydroxy of the ribose group with a methoxy group.

In the context of the disclosure, a "fluoro modified nucleotide", a "2'-fluoro modified nucleotide", a "nucleotide in which 2'-hydroxy of a ribose group is substituted with a fluorine atom", and a "nucleotide with 2'-fluororibosyl" have the same meaning, referring to a compound in which 2'-hydroxy of the nucleotide is substituted with a flurorin atom, which has a structure as shown by Formula (7). A "methoxy modified nucleotide", a "2'-methoxy modified nucleotide", a "nucleotide in which 2'-hydroxy of a ribose group is substituted with a methoxy" and a "nucleotide with 2'-methoxyribosyl" have the same meaning, referring to a compound in which 2'-hydroxy of the ribose group in the nucleotide is substituted with a methoxy, which has a structure as shown by Formula (8).

In some embodiments, the siRNA of the present disclosure is an siRNA with the following modifications: in the direction from 5' terminal to 3' terminal, the nucleotides at positions 7, 8 and 9 or at positions 5, 7, 8 and 9 of the nucleotide sequence I in the sense strand are fluoro modified nucleotides, and the nucleotides at the other positions in the sense strand are methoxy modified nucleotides; the nucleotides at positions 2, 6, 14, and 16 or at positions 2, 6, 8, 9, 14, and 16 of the nucleotide sequence II in the antisense strand are fluoro modified nucleotides, and the nucleotides at the other positions in the antisense strand are methoxy modified nucleotides.

In some embodiments, the siRNA of the present disclosure is an siRNA with the following modifications: in the direction from 5' terminal to 3' terminal, the nucleotides at positions 5, 7, 8, and 9 of the nucleotide sequence I in the sense strand of the siRNA are fluoro modified nucleotides, and the nucleotides at the other positions of the sense strand of the siRNA are methoxy modified nucleotides; and in the direction from 5' terminal to 3' terminal, the nucleotides at positions 2, 6, 8, 9, 14, and 16 of the nucleotide sequence II in the antisense strand of the siRNA are fluoro modified nucleotides, and the nucleotides at the other positions in the antisense strand of the siRNA are methoxy modified nucleotides;

or, in the direction from 5' terminal to 3' terminal, the nucleotides at positions 5, 7, 8, and 9 of the nucleotide sequence I in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 14, and 16 of the nucleotide sequence II in the antisense strand of the siRNA are fluoro modified nucleotides, and the nucleotides at the other positions in the antisense strand of the siRNA are methoxy modified nucleotides;

or, in the direction from 5' terminal to 3' terminal, the nucleotides at positions 7, 8 and 9 of the nucleotide sequence I in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 14, and 16 of the nucleotide sequence II in the antisense strand of the siRNA are fluoro modified nucleotides, and the nucleotides at the other positions in the antisense strand of the siRNA are methoxy modified nucleotides.

In some embodiments, the siRNA of the present disclosure is any one of siFXIa1-M1, siFXIa1-M2, siFXIa1-M3, siFXIa2-M1, siFXIa2-M2, siFXIa2-M3, siFXIb1-M1, siFXIb1-M2, siFXIb1-M3, siFXIb2-M1, siFXIb2-M2, siFXIb2-M3, siFXIc1-M1, siFXIc1-M2, siFXIc1-M3, siFXIc2-M1, siFXIc2-M2, siFXIc2-M3, siFXId1-M1, siFXId1-M2, siFXId1-M3, siFXId2-M1, siFXId2-M2, siFXId2-M3, siFXIe1-M1, siFXIe1-M2, siFXIe1-M3, siFXIe2-M1, siFXIe2-M2, siFXIe2-M3, siFXIf1-M1, siFXIf1-M2, siFXIf1-M3, siFXIf2-M1, siFXIf2-M2, siFXIf2-M3, siFXIg1-M1, siFXIg1-M2, siFXIg1-M3, siFXIg2-M1, siFXIg2-M2, siFXIg2-M3, siFXIh1-M1, siFXIh1-M2, siFXIh1-M3, siFXIh2-M1, siFXIh2-M2, siFXIh2-M3, siFXIi1-M1, siFXIi1-M2, siFXIi1-M3, siFXIi2-M1, siFXIi2-M2, and siFXIi2-M3 as shown in Tables 1a to 1i.

The siRNAs with the above modifications not only have lower costs, but also allow the ribonucleases in the blood to be less liable to cleaving the nucleic acid, thereby increasing the stability of the nucleic acid and rendering the nucleic acid to have stronger resistance against nuclease hydrolysis. Moreover, the siRNAs with the above modifications exhibit higher inhibitory activity against the target mRNA.

In some embodiments, at least a portion of the phosphate groups in the phosphate-ribose backbone of at least one single strand in the sense strand and the antisense strand of the siRNA of the present disclosure are phosphate groups with modified groups. In some embodiments, the phosphate group with modified group(s) is a phosphorothioate group formed by substituting at least one oxygen atom in a phosphodiester bond in a phosphate group with a sulfur atom. In some embodiments, the phosphate group with modified group(s) is a phosphorothioate group having a structure as shown by Formula (1):

Formula (1)

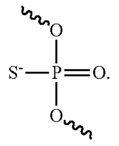

This modification can stabilize the double-stranded structure of the siRNA, thereby maintaining high specificity and high affinity of base pairing.

In some embodiments, in the siRNA of the present disclosure, the phosphorothioate linkage is located in at least one position selected from the group consisting of the following positions: the position between the first and the second nucleotides at either terminal of the sense or antisense strand, the position between the second and the third nucleotides at either terminal of the sense or antisense strand, or any combination thereof. In some embodiments, the phosphorothioate linkage is located in all the above positions except for 5' terminal of the sense strand. In some embodiments, the phosphorothioate linkage is located in all the above positions except for 3' terminal of the sense strand. In some embodiments, the phosphorothioate linkage is located in at least one of the following positions:

- the position between the first and second nucleotides at 5' terminal of the sense strand;
- the position between the second and third nucleotides at 5' terminal of the sense strand;
- the position between the first and second nucleotides at 3' terminal of the sense strand;
- the position between the second and third nucleotides at 3' terminal of the sense strand;
- the position between the first and second nucleotides at 5' terminal of the antisense strand;
- the position between the second and third nucleotides at 5' terminal of the antisense strand;
- the position between the first and second nucleotides at 3' terminal of the antisense strand; and
- the position between the second and third nucleotides at 3' terminal of the antisense strand.

In some embodiments, the siRNA of the present disclosure is any one of siFXIa1-M1S, siFXIa1-M2S, siFXIa1-M3S, siFXIa2-M1S, siFXIa2-M2S, siFXIa2-M3S, siFXIb1-M1S, siFXIb1-M2S, siFXIb1-M3S, siFXIb2-M1S, siFXIb2-M2S, siFXIb2-M3S, siFXIc1-M1S, siFXIc1-M2S, siFXIc1-M3S, siFXIc2-M1S, siFXIc2-M2S, siFXIc2-M3S, siFXId1-M1S, siFXId1-M2S, siFXId1-M3S, siFXId2-M1S, siFXId2-M2S, siFXId2-M3S, siFXIe1-M1S, siFXIe1-M2S, siFXIe1-M3S, siFXIe2-M1S, siFXIe2-M2S, siFXIe2-M3S, siFXIf1-M1S, siFXIf1-M2S, siFXIf1-M3S, siFXIf2-M1S, siFXIf2-M2S, siFXIf2-M3S, siFXIg1-M1S, siFXIg1-M2S, siFXIg1-M3S, siFXIg2-M1S, siFXIg2-M2S, siFXIg2-M3S, siFXIh1-M1S, siFXIh1-M2S, siFXIh1-M3S, siFXIh2-M1S, siFXIh2-M2S, siFXIh2-M3S, FXIi1-M1S, siFXIi1-M2S, siFXIi1-M3S, siFXIi2-M1S, siFXIi2-M2S, and siFXIi2-M3S as shown in Tables 1a to 1i.

In some embodiments, the nucleotide at 5'-terminal in the antisense strand of the siRNA is a 5'-phosphate nucleotide or a 5"-phosphate analogue modified nucleotide.

The commonly used 5'-phosphate nucleotides or 5'-phosphate analogue modified nucleotides are well known to those skilled in the art. For example, the 5'-phosphate nucleotides may have the following structure:

Formula (2)

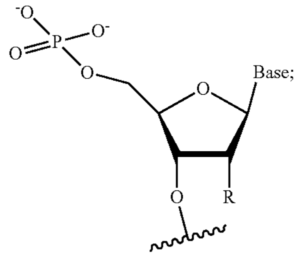

as another example, Anastasia Khvorova and Jonathan K. Watts, The chemical evolution of oligonucleotide therapies of clinical utility. Nature Biotechnology, 2017, 35(3): 238-48 discloses the following four 5'-phosphate analogue modified nucleotides:

Formula (3)

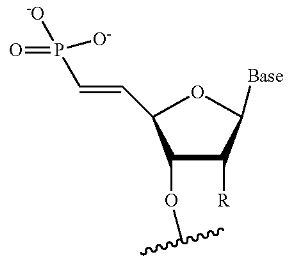

Formula (4)

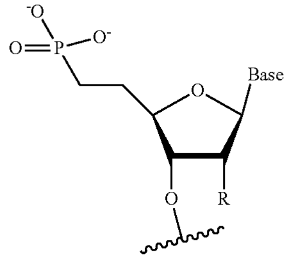

Formula (5)

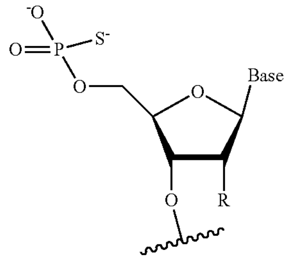

-continued

Formula (6)

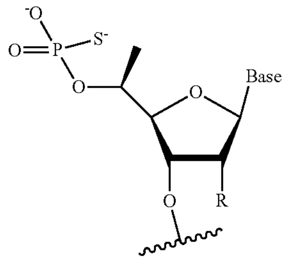

wherein R is selected from H, OH, methoxy, and F;

"Base" represents a nucleic acid base selected from A, U, C, G, or T.

In some embodiments, the 5'-phosphate nucleotide is a nucleotide with 5'-phosphate modification as shown by Formula (2); the 5'-phosphate analogue modified nucleotide is a nucleotide with vinylphosphonate modification as shown by Formula (3), or a phosphorothioate modified nucleotide as shown by Formula (5).

In some embodiments, the siRNA of the present disclosure is any one of siFXIa1-M1P1, siFXIa1-M2P1, siFXIa1-M3P1, siFXIa2-M1P1, siFXIa2-M2P1, siFXIa2-M3P1, siFXIa1-M1SP1, siFXIa1-M2SP1, siFXIa1-M3SP1, siFXIa2-M1SP1, siFXIa2-M2SP1, siFXIa2-M3SP1, siFXIb1-M1P1, siFXIb1-M2P1, siFXIb1-M3P1, siFXIb2-M1P1, siFXIb2-M2P1, siFXIb2-M3P1, siFXIb1-M1SP1, siFXIb1-M2SP1, siFXIb1-M3SP1, siFXIb2-M1SP1, siFXIb2-M2SP1, siFXIb2-M3SP1, siFXIc1-M1P1, siFXIc1-M2P1, siFXIc1-M3P1, siFXIc2-M1P1, siFXIc2-M2P1, siFXIc2-M3P1, siFXIc1-M1SP1, siFXIc1-M2SP1, siFXIc1-M3SP1, siFXIc2-M1SP1, siFXIc2-M2SP1, siFXIc2-M3SP1, siFXId1-M1P1, siFXId1-M2P1, siFXId1-M3P1, siFXId2-M1P1, siFXId2-M2P1, siFXId2-M3P1, siFXId1-M1SP1, siFXId1-M2SP1, siFXId1-M3SP1, siFXId2-M1SP1, siFXId2-M2SP1, siFXId2-M3SP1, siFXIe1-M1P1, siFXIe1-M2P1, siFXIe1-M3P1, siFXIe2-M1P1, siFXIe2-M2P1, siFXIe2-M3P1, siFXIe1-M1SP1, siFXIe1-M2SP1, siFXIe1-M3SP1, siFXIe2-M1SP1, siFXIe2-M2SP1, siFXIe2-M3SP1, siFXIf1-M1P1, siFXIf1-M2P1, siFXIf1-M3P1, siFXIf2-M1P1, siFXIf2-M2P1, siFXIf2-M3P1, siFXIf1-M1SP1, siFXIf1-M2SP1, siFXIf1-M3SP1, siFXIf2-M1SP1, siFXIf2-M2SP1, siFXIf2-M3SP1, siFXIg1-M1P1, siFXIg1-M2P1, siFXIg1-M3P1, siFXIg2-M1P1, siFXIg2-M2P1, siFXIg2-M3P1, siFXIg1-M1SP1, siFXIg1-M2SP1, siFXIg1-M3SP1, siFXIg2-M1SP1, siFXIg2-M2SP1, siFXIg2-M3SP1, siFXIh1-M1P1, siFXIh1-M2P1, siFXIh1-M3P1, siFXIh2-M1P1, siFXIh2-M2P1, siFXIh2-M3P1, siFXIh1-M1SP1, siFXIh1-M2SP1, siFXIh1-M3SP1, siFXIh2-M1SP1, siFXIh2-M2SP1, siFXIh2-M3SP1, FXIi1-M1P1, siFXIi1-M2P1, siFXIi1-M3P1, siFXIi2-M1P1, siFXIi2-M2P1, siFXIi2-M3P1, siFXIi1-M1SP1, siFXIi1-M2SP1, siFXIi1-M3SP1, siFXIi2-M1SP1, siFXIi2-M2SP1, and siFXIi2-M3SP1 as shown in Tables 1a to 1i.

The inventors of the present disclosure have surprisingly found that the above siRNAs of the present disclosure have significantly enhanced plasma and lysosomal stability, while displaying high target mRNA inhibitory activity.

The siRNAs of the present disclosure can be obtained by conventional methods for preparing siRNAs in the art, e.g., solid phase synthesis method and liquid phase synthesis method. Among them, commercial customization services have already been available for solid phase synthesis. A modified nucleotide group can be introduced into the siRNA of the present disclosure by using a nucleotide monomer having the corresponding modification. The method for preparing a nucleotide monomer having the corresponding modification and the method for introducing a modified nucleotide group into an siRNA are also well known to those skilled in the art.

Pharmaceutical Composition

The present disclosure provides a pharmaceutical composition, comprising the above siRNA as an active ingredient and a pharmaceutically acceptable carrier.

The pharmaceutically acceptable carrier may be a carrier conventionally used in the field of siRNA administration, for example, but not limited to, one or more of magnetic nanoparticles (such as $Fe_3O_4$ and $Fe_2O_3$-based nanoparticle), carbon nanotubes, mesoporous silicon, calcium phosphate nanoparticles, polyethylenimine (PEI), polyamidoamine (PAMAM) dendrimer, poly(L-lysine) (PLL), chitosan, 1,2-dioleoyl-3-trimethylammonium-propane (DOTAP), poly(D&L-lactic/glycolic acid) copolymer (PLGA), poly(2-aminoethyl ethylene phosphate) (PPEEA), poly(2-dimethylaminoethyl methacrylate) (PDMAEMA), and derivatives thereof.

In the pharmaceutical composition, there are no special requirements for the contents of the siRNA and the pharmaceutically acceptable carrier. They may be present in any amount conventionally used for each component. In some embodiments, the weight ratio of the siRNA to the pharmaceutically acceptable carrier may be 1:(1-500), and in some embodiments, the above weight ratio is 1:(1-50).

In some embodiments, the pharmaceutical composition may also contain other pharmaceutically acceptable excipients, which may be one or more of various formulations or compounds conventionally employed in the art. For example, said other pharmaceutically acceptable excipients may comprise at least one of a pH buffer, a protective agent and an osmotic pressure regulator.

The pH buffer may be a tris(hydroxymethyl) aminomethane hydrochloride buffer solution with a pH of 7.5-8.5, and/or a phosphate buffer solution with a pH of 5.5-8.5, such as a phosphate buffer solution with a pH of 5.5-8.5.

The protective agent may be at least one of inositol, sorbitol, sucrose, trehalose, mannose, maltose, lactose, and glucose. The content of the protective agent may be from 0.01 wt % to 30 wt % based on the total weight of the pharmaceutical composition.

The osmotic pressure regulator may be sodium chloride and/or potassium chloride. The content of the osmotic pressure regulator renders the osmotic pressure of the pharmaceutical composition to be 200-700 mOsm/kg. Depending on the desired osmotic pressure, those skilled in the art can readily determine the content of the osmotic pressure regulator.

In some embodiments, the pharmaceutical composition may be a liquid formulation, for example, an injection solution; or a lyophilized powder for injection, which will be mixed with a liquid excipient to form a liquid formulation upon administration. The liquid formulation may be administered by, but not limited to, subcutaneous, intramuscular or intravenous injection, and also may be administered to, but not limited to, lung by spray, or other organ tissues (such as liver) via lung by spray. In some embodiments, the pharmaceutical composition is administered by intravenous injection.

In some embodiments, the pharmaceutical composition may be in the form of a liposome formulation. In some embodiments, the pharmaceutically acceptable carrier used in the liposome formulation comprises an amine-containing transfection compound (hereinafter also referred to as an organic amine), a helper lipid and/or a PEGylated lipid. Therein, the organic amine, the helper lipid and the PEGylated lipid may be respectively selected from one or more of the amine-containing transfection compounds or the pharmaceutically acceptable salts or derivatives thereof, the helper lipids and the PEGylated lipids as described in CN103380113A, which is incorporated herein by reference in its entirety.

In some embodiments, the organic amine may be a compound as shown by Formula (201) or a pharmaceutically acceptable salt thereof as described in CN103380113A:

Formula (201)

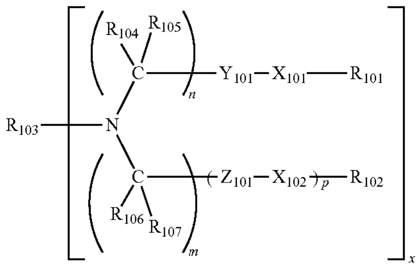

wherein, $X_{101}$ and $X_{102}$ independently of one another are selected from O, S, N-A or C-A, wherein A is hydrogen or a $C_1$-$C_{20}$ hydrocarbon chain;

$Y_{101}$ and $Z_{101}$ independently of one another are selected from C=O, C=S, S=O, CH—OH or $SO_2$;

$R_{101}$, $R_{102}$, $R_{103}$, $R_{104}$, $R_{105}$, $R_{106}$ and $R_{107}$ independently of one another are selected from hydrogen; a cyclic or an acyclic, substituted or unsubstituted, branched or linear aliphatic group;

a cyclic or an acyclic, substituted or unsubstituted, branched or linear heteroaliphatic group; a substituted or unsubstituted, branched or linear acyl group; a substituted or unsubstituted, branched or linear aryl group; and a substituted or unsubstituted, branched or linear heteroaryl group;

x is an integer of 1-10;

n is an integer of 1-3, m is an integer of 0-20, p is 0 or 1, wherein if m=p=0, then $R_{102}$ is hydrogen; and if at least one of n and m is 2, then $R_{103}$ and nitrogen in Formula (201) form a structure as shown by Formula (202) or (203):

Formula (202)

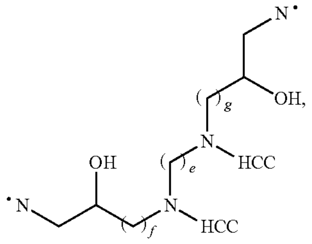

Formula (203)

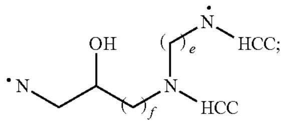

wherein g, e and f independently of one another are an integer of 1-6; "HCC" represents a hydrocarbon chain, and each *N represents a nitrogen atom shown in Formula (201).

In some embodiments, $R_{103}$ is a polyamine. In other embodiments, $R_{103}$ is a ketal. In some embodiments, $R_{101}$ and $R_{102}$ in the Formula (201) independently of one another are any substituted or unsubstituted, branched or linear alkyl or alkenyl, wherein the alkyl or alkenyl has 3 to about 20 carbon atoms (such as 8 to about 18 carbon atoms) and 0-4 double bonds (such as 0-2 double bonds).

In some embodiments, if n and m independently of one another are 1 or 3, $R_{103}$ may be any of the following Formulae (204)-(213):

Formula (204)

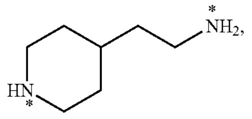

Formula (205)

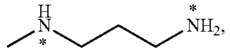

Formula (206)

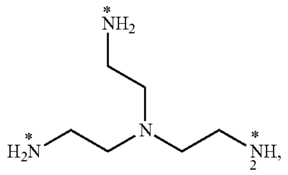

Formula (207)

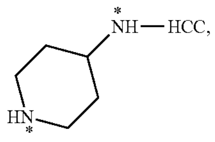

-continued

Formula (208)

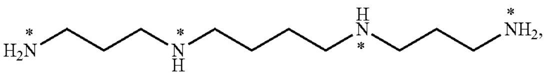

Formula (209)

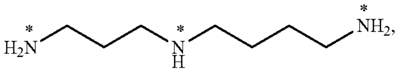

Formula (210)

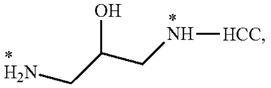

Formula (211)

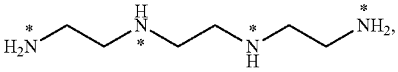

Formula (212)

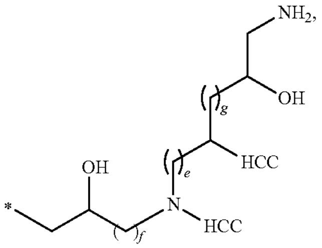

and

-continued

Formula (213)

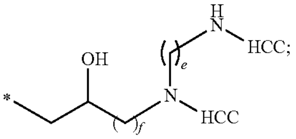

wherein, in Formulae (204)-(213), g, e and f independently of one another are an integer of 1-6, each "HCC" represents a hydrocarbon chain, and each * represents a potential attachment point of $R_{103}$ to the nitrogen atom in Formula (201), wherein each H at any *position can be replaced to achieve the attachment to the nitrogen atom in Formula (201).

The compound as shown by Formula (201) may be prepared according to the description of CN103380113A.

In some embodiments, the organic amine is an organic amine as shown by Formula (214) and/or an organic amine as shown by Formula (215):

Formula (214)

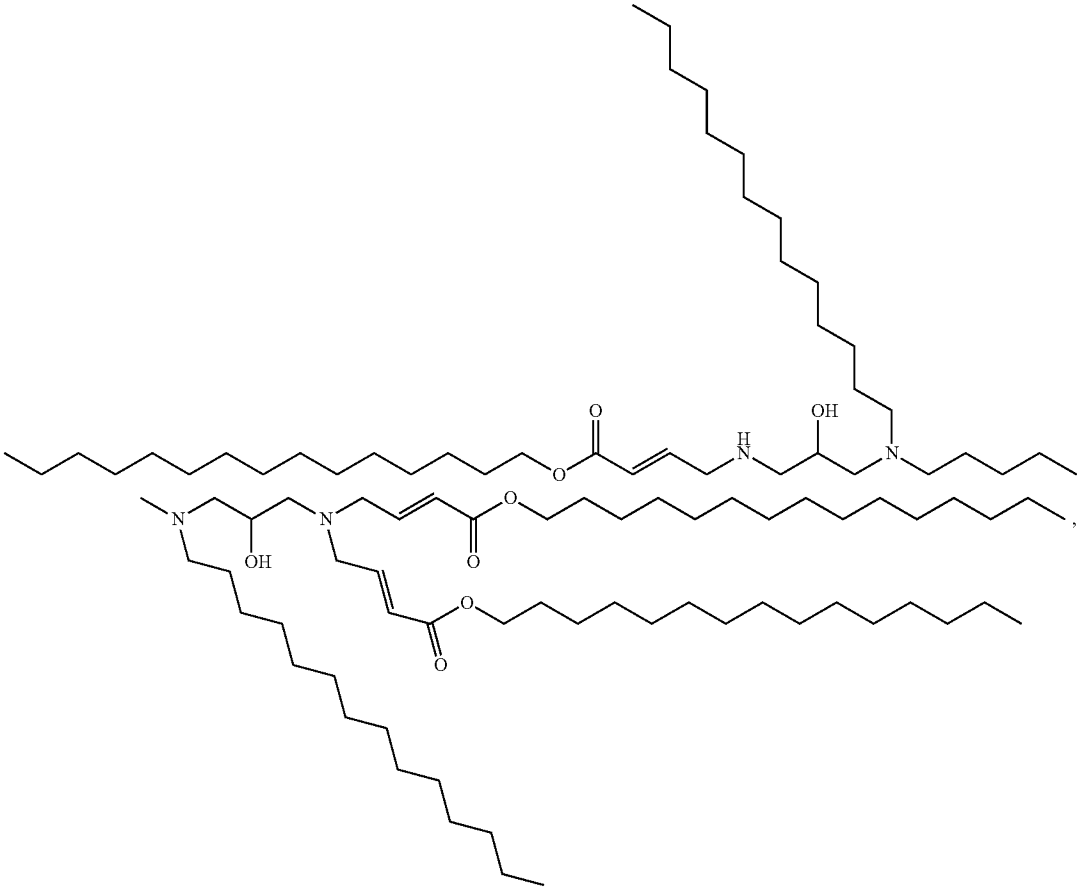

-continued

Formula (215)

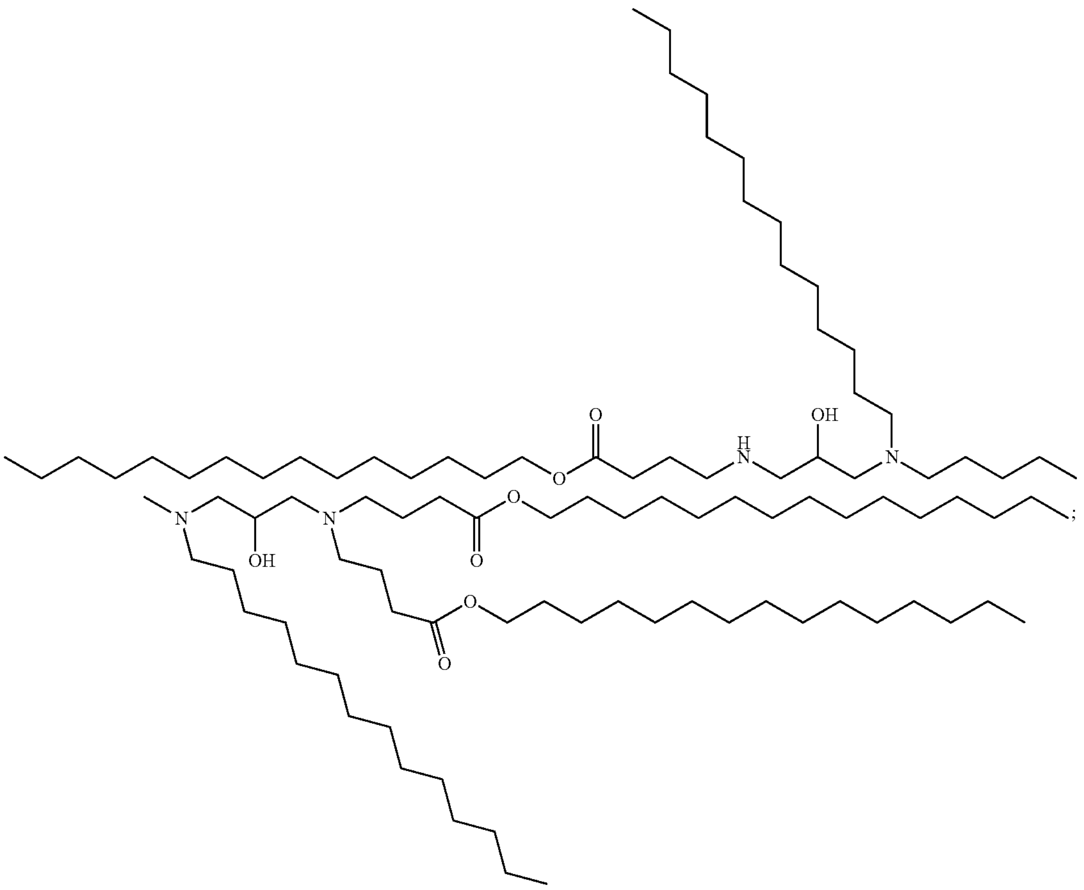

the helper lipid is cholesterol, cholesterol analogs and/or cholesterol derivatives, and the PEGylated lipid is 1,2-dipalmitoylamine-sn-glycero-3-phosphatidylethanolamine-N-[methoxy(polyethylene glycol)]-2000.

In some embodiments, the molar ratio among the organic amine, the helper lipid, and the PEGylated lipid in the pharmaceutical composition is (19.7-80):(19.7-80):(0.3-50), for example, the molar ratio may be (50-70):(20-40):(3-20).

In some embodiments, the pharmaceutical composition particles formed by the siRNA of the present disclosure and the above amine-containing transfection reagents have an average diameter from about 30 nm to about 200 nm, typically from about 40 nm to about 135 nm, and more typically, the average diameter of the liposome particles is from about 50 nm to about 120 nm, from about 50 nm to about 100 nm, from about 60 nm to about 90 nm, or from about 70 nm to about 90 nm; for example, the average diameter of the liposome particles is about 30, 40, 50, 60, 70, 75, 80, 85, 90, 100, 110, 120, 130, 140, 150 or 160 nm.

In some embodiments, in the pharmaceutical composition formed by the siRNA of the present disclosure and the above amine-containing transfection reagents, the weight ratio (weight/weight ratio) of the siRNA to total lipids, e.g., the organic amines, the helper lipids and/or the PEGylated lipids, ranges from about 1:1 to about 1:50, from about 1:1 to about 1:30, from about 1:3 to about 1:20, from about 1:4 to about 1:18, from about 1:5 to about 1:17, from about 1:5 to about 1:15, from about 1:5 to about 1:12, from about 1:6 to about 1:12, or from about 1:6 to about 1:10. For example, the weight ratio of the siRNA of the present disclosure to total lipids is about 1:5, 1:6, 1:7, 1:8, 1:9, 1:10, 1:11, 1:12, 1:13, 1:14, 1:15, 1:16, 1:17, or 1:18.

In some embodiments, the pharmaceutical composition may be marketed with each component being separate, and used in the form of a liquid formulation. In some embodiments, the pharmaceutical composition formed by the siRNA of the present disclosure and the above pharmaceutically acceptable carrier may be prepared by various known processes, except for replacing the existing siRNA with the siRNA of the present disclosure. In some specific embodiments, the pharmaceutical composition may be prepared according to the following process:

The organic amines, helper lipids and PEGylated lipids are suspended in alcohol at a molar ratio as described above and mixed homogeneously to yield a lipid solution; the alcohol is used in an amount such that the resultant lipid solution is present at a total mass concentration of 2 to 25 mg/mL (e.g., 8 to 18 mg/mL). The alcohol is a pharmaceutically acceptable alcohol, such as an alcohol that is in liquid form at about room temperature, for example, one or more of ethanol, propylene glycol, benzyl alcohol, glycerol, polyethylene glycol 200, polyethylene glycol 300, and polyethylene glycol 400, such as ethanol.

The siRNA of the present disclosure is dissolved in a buffered salt solution to produce an aqueous solution of the siRNA. The buffered salt solution has a concentration of 0.05 to 0.5 M, such as 0.1 to 0.2 M. The pH of the buffered salt solution is adjusted to 4.0 to 5.5, such as 5.0 to 5.2. The buffered salt solution is used in an amount such that the siRNA is present at a concentration of no more than 0.6 mg/ml, such as 0.2 to 0.4 mg/mL. The buffered salt may be one or more selected from the group consisting of soluble acetate and soluble citrate, such as sodium acetate and/or potassium acetate.

The lipid solution and the aqueous solution of the siRNA are mixed. The product obtained by mixing is incubated at a temperature of 40 to 60° C. for at least 2 minutes (e.g., 5 to 30 minutes) to produce an incubated liposome formulation. The volume ratio of the lipid solution to the aqueous solution of the siRNA is 1:(2-5) (such as 1:4).

The incubated liposome formulation is concentrated or diluted, and then subjected to impurity removal and sterilization to afford the pharmaceutical composition of the present disclosure, which has the following physicochemical parameters: a pH of 6.5 to 8, an encapsulation percentage of not lower than 80%, a particle size of 40 to 200 nm, a polydispersity index of no greater than 0.30, and an osmotic pressure of 250 to 400 mOsm/kg. For example, the physicochemical parameters may be as follows: a pH of 7.2 to 7.6, an encapsulation percentage of not lower than 90%, a particle size of 60 to 100 nm, a polydispersity index of no greater than 0.20, and an osmotic pressure of 300 to 400 mOsm/kg.

Therein, the concentration or dilution step may be performed before, after or simultaneously with removal of the impurities. The method for removing impurities may be any of various existing methods, for example, ultrafiltration under 100 kDa using a hollow fiber column, a phosphate buffer (PBS) at pH 7.4 as ultrafiltration exchange solution, and tangential flow system. The method for sterilization may be any of various existing methods, such as filtration sterilization on a 0.22 μm filter.

siRNA Conjugate

The present disclosure provides an siRNA conjugate comprising the above siRNA and a conjugation group conjugatively linked to the siRNA.

Generally speaking, the conjugation group comprises at least one pharmaceutically acceptable targeting group and an optional linker. Moreover, the siRNA, the linker and the targeting group are sequentially linked. In some embodiments, the number of the targeting groups is 1 to 6. In some embodiments, the number of target groups is 2 to 4. The siRNA molecule may be non-covalently or covalently conjugated to the conjugation group, for example the siRNA molecule may be covalently conjugated to the conjugation group. The conjugation site between the siRNA and the conjugation group can be at 3' terminal or 5' terminal of the sense strand of the siRNA, or at 5' terminal of the antisense strand of the siRNA, and can be within the internal sequence of the siRNA. In some embodiments, the conjugation site between the siRNA and the conjugation group is at 3' terminal of the sense strand of the siRNA.

In some embodiments, the conjugation group may be linked to the phosphate group, the 2'-hydroxy or the base of a nucleotide. In some embodiments, the conjugation group may also be linked to the 3'-hydroxy group when the nucleotides are linked via a 2'-5'-phosphodiester bond. When the conjugation group is linked to a terminal of the siRNA strand, the conjugation group is typically linked to the phosphate group of a nucleotide; when the conjugation group is linked to an internal sequence of the siRNA, the conjugation group is typically linked to a ribose ring or a base. For various linking modes, reference may be made to: Muthiah Manoharan et. al. siRNA conjugates carrying sequentially assembled trivalent N-acetylgalactosamine linked through nucleosides elicit robust gene silencing in vivo in hepatocytes. ACS Chemical biology, 2015, 10(5): 1181-7.

In some embodiments, the siRNA and the conjugation group can be linked by an acid-labile or reducible chemical bond, and these chemical bonds can be degraded under the acidic environment of cell endosomes, thereby making the siRNA to be in free state. For non-degradable conjugation modes, the conjugation group can be linked to the sense strand of the siRNA, thereby minimizing the effect of conjugation on the activity of the siRNA.

In some embodiments, the pharmaceutically acceptable targeting group may be a ligand conventionally used in the field of siRNA administration, for example, various ligands as described in WO2009082607A2, which is incorporated herein by reference in its entirety.

In some embodiments, the pharmaceutically acceptable targeting group may be selected from one or more of the ligands formed by the following targeting molecules or derivatives thereof: lipophilic molecules, such as cholesterol, bile acids, vitamins (such as vitamin E), lipid molecules with different chain lengths; polymers, such as polyethylene glycol; polypeptides, such as cell-penetrating peptide; aptamers; antibodies; quantum dots; saccharides, such as lactose, polylactose, mannose, galactose, N-acetylgalactosamine (GalNAc); folate; or receptor ligands expressed in hepatic parenchymal cells, such as asialoglycoprotein, asialo-sugar residue, lipoproteins (such as high density lipoprotein, low density lipoprotein and the like), glucagon, neurotransmitters (such as adrenaline), growth factors, transferrin and the like.

In some embodiments, each ligand is independently selected from a ligand capable of binding to a cell surface receptor. In some embodiments, at least one ligand is a ligand capable of binding to a surface receptor of a hepatocyte. In some embodiments, at least one ligand is a ligand capable of binding to a surface receptor of a mammalian hepatocyte. In some embodiments, at least one ligand is a ligand capable of binding to a surface receptor of a human hepatocyte. In some embodiments, at least one ligand is a ligand capable of binding to an asialoglycoprotein receptor (ASGPR) on the surface of hepatocytes. The types of these ligands are well-known to those skilled in the art and they typically serve the function of binding to specific receptor on the surface of the target cell, thereby mediating delivery of the siRNA linked to the ligand into the target cell.

In some embodiments, the pharmaceutically acceptable targeting group may be any ligand that has affinity to the asialoglycoprotein receptors (ASGPR) on the surface of mammalian hepatocytes. In some embodiments, each ligand is independently an asialoglycoprotein, such as asialoorosomucoid (ASOR) or asialofetuin (ASF). In some embodiments, the ligand is a saccharide or its derivatives.

In some embodiments, at least one ligand is a saccharide. In some embodiments, each ligand is a saccharide. In some embodiments, at least one ligand is a monosaccharide, polysaccharide, modified monosaccharide, modified polysaccharide, or saccharide derivative. In some embodiments, at least one ligand may be a monosaccharide, disaccharide or trisaccharide. In some embodiments, at least one ligand is a modified saccharide. In some embodiments, each ligand is a modified saccharide. In some embodiments, each ligand is independently selected from a polysaccharide, modified polysaccharide, monosaccharide, modified monosaccharide, polysaccharide derivative, and monosaccharide derivative. In some embodiments, each ligand or at least one ligand is selected from the group consisting of glucose and its derivatives, mannose and its derivatives, galactose and its derivatives, xylose and its derivatives, ribose and its derivatives, fucose and its derivatives, lactose and its derivatives, maltose and its derivatives, arabinose and its derivatives, fructose and its derivatives, and sialic acid.

In some embodiments, each ligand may be independently selected from the group consisting of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O—[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-β-D-glucopyranose, methyl 2,3,4-tris-O-acetyl-1-thio-6-O-trityl-α-D-glucopyranoside, 4-thio-β-D-galactopyranose, ethyl 3,4,6,7-tetra-0-acetyl-2-deoxy-1,5-dithio-α-D-glucoheptopyranoside, 2,5-anhydro-D-allononitrile, ribose, D-ribose, D-4-thioribose, L-ribose, L-4-thioribose. Other options of the ligand may be found, for example, in the disclosure of CN105378082A, which is incorporated herein by reference in its entirety.

In some embodiments, the pharmaceutically acceptable targeting group in the siRNA conjugate may be galactose or N-acetylgalactosamine, wherein the galactose or N-acetylgalactosamine molecules may be be mono-, bi-, tri-, or tetra-valent. It should be understood that the terms mono-, bi-, tri-, or tetra-valent described herein respectively mean that the molar ratio of the siRNA molecule to the galactose or N-acetylgalactosamine molecule in the siRNA conjugate is 1:1, 1:2, 1:3 or 1:4, wherein the siRNA conjugate is formed from the siRNA molecule and the conjugation group containing galactose or N-acetylgalactosamine molecule as the targeting group. In some embodiments, the pharmaceutically acceptable targeting group is N-acetylgalactosamine. In some embodiments, when the siRNA of the present disclosure is conjugated to a conjugation group containing N-acetylgalactosamine, the N-acetylgalactosamine molecule is trivalent or tetravalent. In some embodiments, when the siRNA of the present disclosure is conjugated to a conjugation group containing N-acetylgalactosamine, the N-acetylgalactosamine molecule is trivalent.

The targeting group can be linked to the siRNA molecule via an appropriate linker, and the appropriate linker can be selected by those skilled in the art according to the specific type of the targeting group. The types of these linkers and targeting groups and the linking modes with the siRNA may be found in the disclosure of WO2015006740A2, which is incorporated herein by reference in its entirety.

In some embodiments, when the targeting group is N-acetylgalactosamine, a suitable linker may have the following structure as shown by Formula (301):

Formula (301)

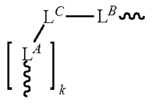

wherein, k is an integer of 1-3;

$L^A$ is an amide bond-comprising chain moiety that has a structure as shown by Formula (302), and each $L^A$ is respectively linked to the targeting group and the $L^C$ moiety through an ether bond at its two terminals:

Formula (302)

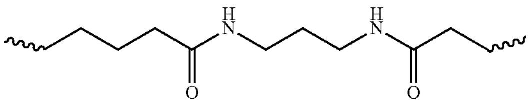

$L^B$ is a N-acylpyrrolidine-comprising chain moiety that has a structure as shown by Formula (303), wherein the chain moiety has a carbonyl group at its one terminal and is linked to the $L^C$ moiety through an amide bond, and has an oxy group at the other terminal and is linked to the siRNA via a phosphoester bond:

Formula (303)

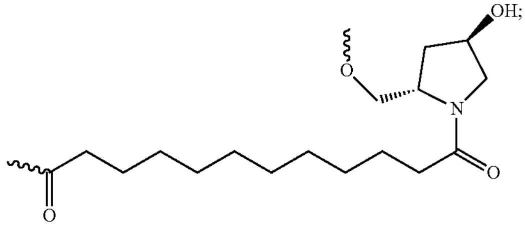

$L^C$ is a bivalent to tetravalent linking group based on hydroxymethyl aminomethane, dihydroxymethyl aminomethane or trihydroxymethyl aminomethane, and $L^C$ is linked to each $L^A$ moiety through an ether bond via an oxygen atom, and is linked to $L^B$ moiety through an amide bond via a nitrogen atom.

In some embodiments, when n=3 and $L^C$ is a tetravalent linking group based on trihydroxymethyl aminomethane, the siRNA conjugate formed by linking N-acetylgalactosamine molecules with an siRNA molecule via -$(L^A)_3$-trihydroxymethyl aminomethane-$L^B$- as a linker has a structure as shown by Formula (304):

Formula (304)

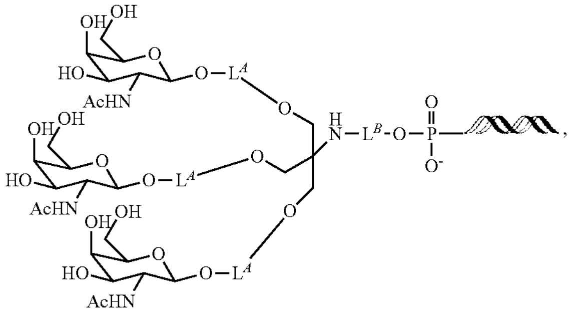

wherein the double helix structure represents the siRNA.

Likewise, the conjugation site between the siRNA and the conjugation group can be at 3'-terminal or 5'-terminal of the sense strand of the siRNA, or at 5'-terminal of the antisense strand, or within the internal sequence of the siRNA.

In some embodiments, the 3'-terminal of the sense strand of the siRNA of the present disclosure is covalently conjugated to three N-acetyl gal actosamine (GalNAc) molecules via a linker -$(L^A)_3$-trihydroxymethyl aminomethane-$L^B$-, to afford an siRNA conjugate in which the molar ratio of the siRNA molecule to the GalNAc molecule is 1:3 (hereinafter also referred to as (GalNAc)3-siRNA), and this siRNA conjugate has a structure as shown by Formula (305):

Formula (305)

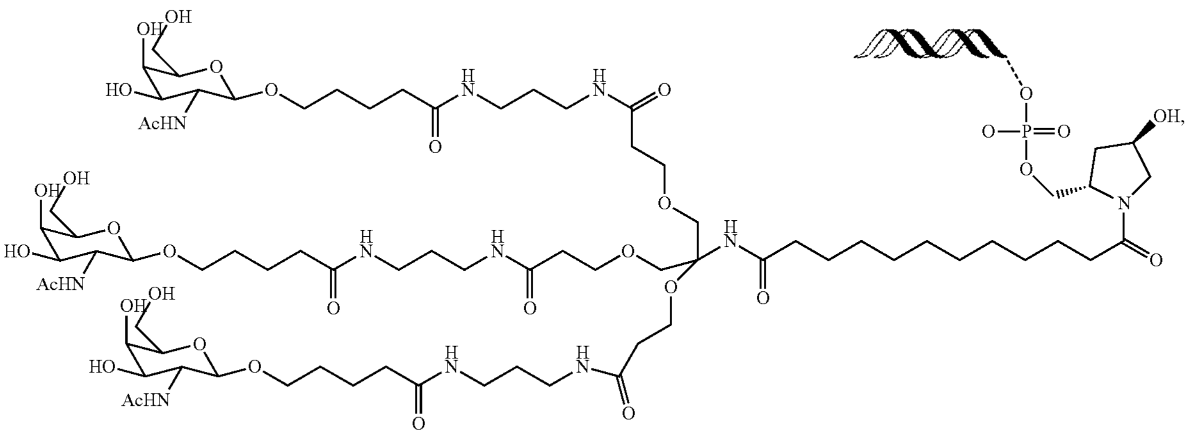

wherein the double helix structure represents the siRNA; and the linker is linked to 3'-terminal of the sense strand of the siRNA.

In some embodiments, when the targeting group is N-acetylgalactosamine, a suitable linker may has a structure as shown by Formula (306):

Formula (306)

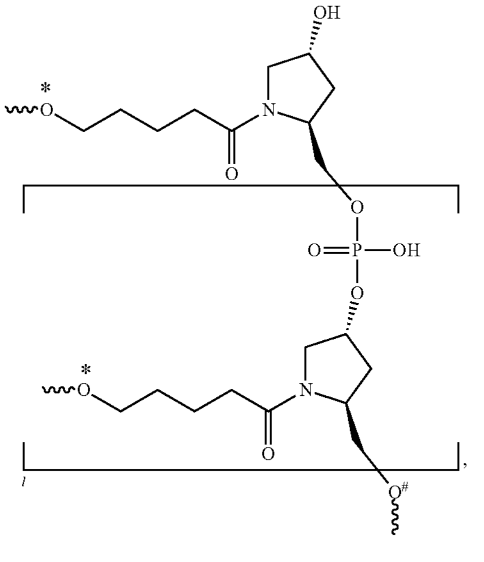

wherein, 1 is an integer of 0-3;

* represents a site on the linker linked to the targeting group via an ether bond; and # represents a site on the linker linked to the siRNA via a phosphoester bond.

In some embodiments, when 1=2, the siRNA conjugate has a structure as shown by Formula (307):

Formula (307)

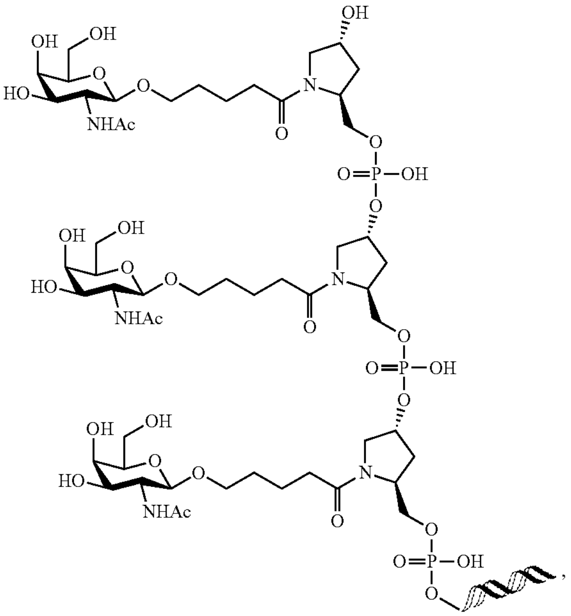

wherein, the double helix structure represents the siRNA; and the linker is linked to 3'-terminal of the sense strand of the siRNA.

The above conjugates can be synthesized according to the method described in detail in the prior art. For example, WO2015006740 A2 describes in detail the preparation methods of various conjugates. The siRNA conjugate of the present disclosure may be obtained by the methods well-known to those skilled in the art. For example, WO2014025805A1 describes the preparation method of the conjugate having the structure as shown by Formula (305). Rajeev et al., ChemBioChem 2015, 16, 903-908 describes the preparation method of the conjugate having the structure as shown by Formula (307).

In some embodiments, the siRNA conjugate has a structure as shown by Formula (308):

Formula (308)

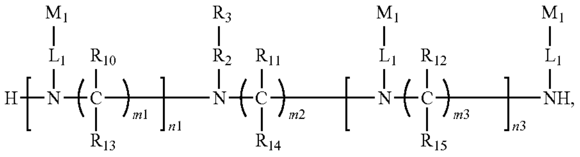

wherein, n1 is an integer of 1-3, and n3 is an integer of 0-4;

m1, m2, and m3 independently of one another are an integer of 2-10;

$R_{10}$, $R_{11}$, $R_{12}$, $R_{13}$, $R_{14}$, and $R_{15}$ independently of one another are H, or selected from the group consisting of $C_1$-$C_{10}$ alkyl, $C_1$-$C_{10}$ haloalkyl, and $C_1$-$C_{10}$ alkoxy, $R_3$ is a group having a structure as shown by Formula (A59):

Formula (A59)

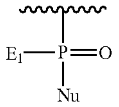

wherein $E_1$ is OH, SH or $BH_2$; and Nu is the siRNA of the present disclosure;

$R_2$ is a linear alkylene of 1 to 20 carbon atoms in length, wherein one or more carbon atoms are optionally replaced with any one or more groups selected from the group consisting of: C(O), NH, O, S, CH═N, $S(O)_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $R_2$ optionally has any one or more substituents selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —$OC_1$-$C_{10}$ alkyl, —$OC_1$-$C_{10}$ alkylphenyl, alkyl-OH, haloalkyl, —$SC_1$-$C_{10}$ alkyl, —$SC_1$-$C_{10}$ alkylphenyl, —$C_1$-$C_{10}$ alkyl-SH, —$SC_1$-$C_{10}$ haloalkyl, halo, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), —N($C_1$-$C_{10}$ alkyl)($C_1$-$C_{10}$ alkylphenyl), —NH($C_1$-$C_{10}$ alkylphenyl), cyano, nitro, —$CO_2$H, —C(O)O($C_1$-$C_{10}$) alkyl, —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2$NH($C_1$-$C_{10}$ alkyl), —$SO_2$NH(phenyl), —NHSO($C_1$-$C_{10}$ alkyl), —NHSO(phenyl), and —$NHSO_2$($C_1$-$C_{10}$ haloalkyl);

each $L_1$ is a linear alkylene of 1 to 70 carbon atoms in length, wherein one or more carbon atoms are optionally replaced with any one or more groups selected from the group consisting of: C(O), NH, O, S, CH═N, $S(O)_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $L_1$ optionally has any one or more substituents selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —$OC_1$-$C_{10}$ alkyl, —$OC_1$-$C_{10}$ alkylphenyl, —$C_1$-$C_{10}$ alkyl-OH, —$OC_1$-$C_{10}$ haloalkyl, —$SC_1$-$C_{10}$ alkyl, —$SC_1$-$C_{10}$ alkylphenyl, haloalkyl, halo, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), —N($C_1$-$C_{10}$ alkyl)($C_1$-$C_{10}$ alkylphenyl), —NH($C_1$-$C_{10}$ alkylphenyl), cyano, nitro, —$CO_2$H, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2$NH($C_1$-$C_{10}$ alkyl), —$SO_2$NH(phenyl), —NHSO($C_1$-$C_{10}$ alkyl), —NHSO(phenyl), and —$NHSO_2$($C_1$-$C_{10}$ haloalkyl).

In some embodiments, $L_1$ may be selected from the group consisting of the groups of Formulae (A1)-(A26) or any combination thereof, wherein the structures and definitions of A1-A26 are as follows:

(A1)

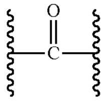, (A2)

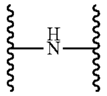, (A3)

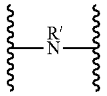, (A4)

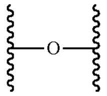, (A5)

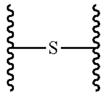, (A6)

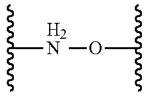, (A7)

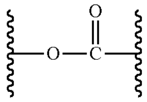

(A8)

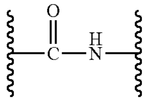, (A9)

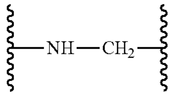, (A10)

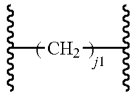,

-continued
(A11)
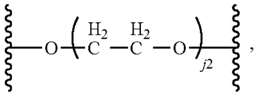
(A12)
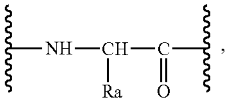
(A13)
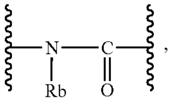
(A14)
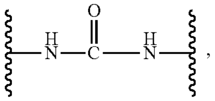
(A15)
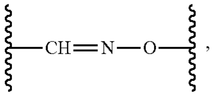
(A16)
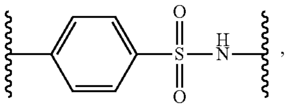
(A17)
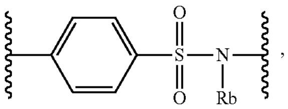
(A18)
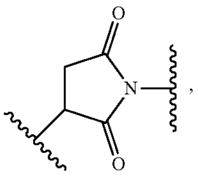
(A19)
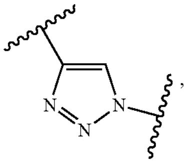
(A20)
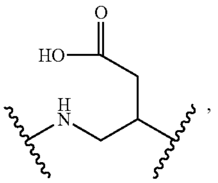
(A21)
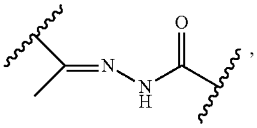
(A22)
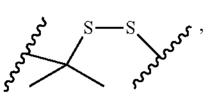
-continued
(A23)
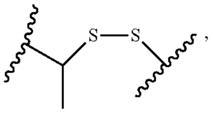
(A24)
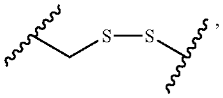
(A25)
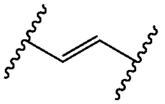
and
(A26)
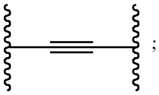
;
wherein j1 is an integer of 1-20;
j2 is an integer of 1-20;
R' is a $C_1$-$C_{10}$ alkyl;
Ra is selected from the group consisting of the groups of Formulae (A27)-(A45) or any combination thereof:
(A27)
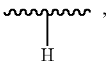
(A28)
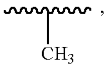
(A29)
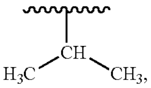
(A30)
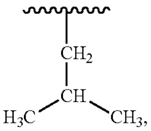
(A31)
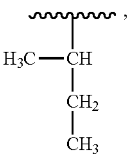
(A32)
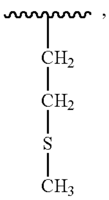

-continued (A33)

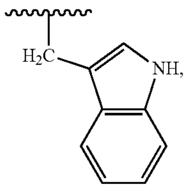

(A34)

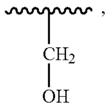

(A35)

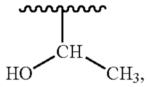

(A36)

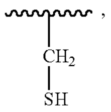

(A37)

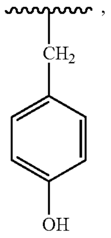

(A38)

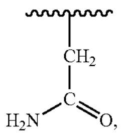

(A39)

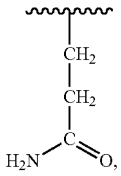

(A40)

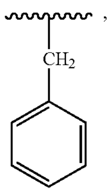

(A41)

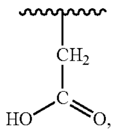

-continued (A42)

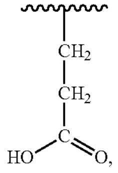

(A43)

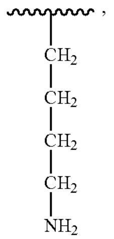

(A44)

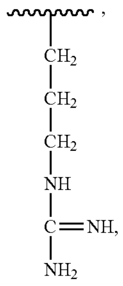

or (A45)

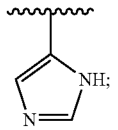

Rb is a $C_1$-$C_{10}$ alkyl; and represents the site at which a group is covalently linked.

Those skilled in the art would understand that, though $L_1$ is defined as a linear alkyl for convenience, but it may not be a linear group or be named differently, such as an amine or alkenyl produced by the above replacement and/or substitution. For the purpose of the present disclosure, the length of $L_1$ is the number of the atoms in the chain linking the two attachment points. For this purpose, a ring obtained by replacing a carbon atom in the linear alkylene, such as a heterocyclylene or heteroarylene, is counted as one atom.

$M_1$ represents a targeting group, of which the definitions and options are the same as those of the above targeting groups. In some embodiments, each $M_1$ is independently one selected from the ligands that have affinity to the asialoglycoprotein receptor on the surface of mammalian hepatocytes.

When $M_1$ is a ligand that has affinity to the asialoglycoprotein receptor on the surface of mammalian hepatocyte, in some embodiments, n1 may be an integer of 1-3, and n3 may be an integer of 0-4 to ensure that the number of the $M_1$ targeting group in the conjugate may be at least 2. In some embodiments, $n1+n3\geq 2$, such that the number of the $M_1$ targeting group is at least 3, thereby rendering the $M_1$ targeting group to more easily bind to the asialoglycoprotein receptor on the surface of hepatocytes, which may facilitates the endocytosis of the conjugate into cells. Experiments have shown that when the number of the $M_1$ targeting groups is greater than 3, the ease of the binding between the $M_1$ targeting groups and the asialoglycoprotein receptor on the surface of hepatocytes is not significantly increased. Therefore, in view of various aspects such as synthesis convenience, structure/process costs and delivery efficiency, in some embodiments, n1 is an integer of 1-2, n3 is an integer of 0-1, and n1+n3=2−3.

In some embodiments, when m1, m2, and m3 independently of one another are an integer selected from 2-10, the steric positions among many $M_1$ targeting groups may be suitable for the binding between the $M_1$ targeting groups and the asialoglycoprotein receptor on the surface of hepatocytes. In order to make the conjugate of the present disclosure have simpler structure, easier synthesis and/or reduced cost, in some embodiments, m1, m2 and m3 independently of one another are an integer of 2-5; in some embodiments, m1=m2=m3.

Those skilled in the art would understand that when $R_{10}$, $R_{11}$, $R_{12}$, $R_{13}$, $R_{14}$, or $R_{15}$ independently of one another is one selected from H, $C_1$-$C_{10}$ alkyl, $C_1$-$C_{10}$ haloalkyl, and $C_1$-$C_{10}$ alkoxy, they would not change the properties of the conjugate of the present disclosure and could all achieve the purpose of the present disclosure. In some embodiments, $R_{10}$, $R_{11}$, $R_{12}$, $R_{13}$, $R_{14}$, or $R_{15}$ independently of one another are selected from H, methyl and ethyl. In some embodiments, $R_{10}$, $R_{11}$, $R_{12}$, $R_{13}$, $R_{14}$, and $R_{15}$ are H.

$R_3$ is a group having the structure as shown by Formula A59, wherein $E_1$ is OH, SH or $BH_2$, and considering the easy availability of the starting materials, in some embodiments, $E_1$ is OH or SH.

$R_2$ is selected to achieve the linkage between the group as shown by Formula A59 and the N atom on a nitrogenous backbone. In the context of the present disclosure, a "nitrogenous backbone" refers to a chain structure in which the N atom are coadjacently linked to the carbon atoms to which $R_{10}$, $R_{11}$, $R_{12}$, $R_{13}$, $R_{14}$, and $R_{15}$ are attached. Therefore, $R_2$ may be any linking group capable of linking the group as shown by Formula (A59) to the N atom on the nitrogenous backbone by suitable means. In some embodiments, in the case where the siRNA conjugate as shown by Formula (308) is prepared by a solid phase synthesis process, $R_2$ group needs to have both a site linking to the N atom on the nitrogenous backbone and a site linking to the P atom in $R_3$. In some embodiments, in $R_2$, the site linking to the N atom on the nitrogenous backbone forms an amide bond with the N atom, and the site linking to the P atom in $R_3$ forms a phosphoester bond with the P atom. In some embodiments, $R_2$ may be B5, B6, B5', or B6':

(B5)

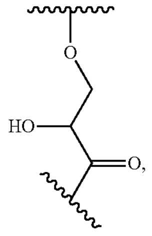

(B6)

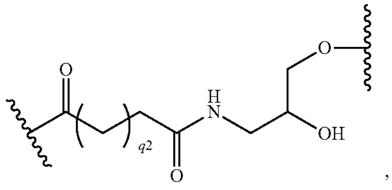

,

-continued (B5')

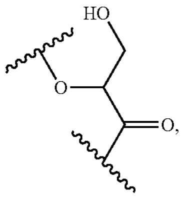

or (B6')

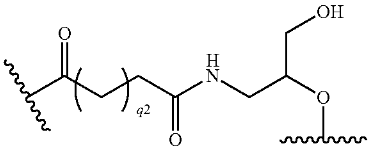

;

wherein represents the site where the group is covalently linked;

$q_2$ may be an integer of 1-10; in some embodiments, q2 is an integer of 1-5.

$L_1$ is used to link the $M_1$ targeting group to the N atom on the nitrogenous backbone, thereby providing liver targeting function for the siRNA conjugate as shown by Formula (308). In some embodiments, $L_1$ is selected from the connection combinations of one or more of the groups of Formulae (A1)-(A26). In some embodiments, $L_1$ is selected from the connection combinations of one or more of Formulae (A1), (A4), (A5), (A6), (A8), (A10), (A11), and (A13). In some embodiments, $L_1$ is selected from the connection combinations of at least two of Formulae (A1), (A4), (A8), (A10), and (A11). In some embodiments, $L_1$ is selected from the connection combinations of at least two of Formulae (A1), (A8) and (A10).

In some embodiments, $L_1$ may have a length of 3 to 25, 3 to 20, 4 to 15 or 5 to 12 atoms. In some embodiments, $L_1$ has a length of 3, 4, 5, 6, 7, 8, 9, 10, 11, 12, 13, 14, 15, 16, 17, 18, 19, 20, 21, 22, 23, 24, 25, 30, 35, 40, 45, 50, 55, or 60 atoms.

In some embodiments, $L_1$ is an integer of 2-10, and in some embodiments, j1 is an integer of 3-5. In some embodiments, j2 is an integer of 2-10, and in some embodiments, j2 is an integer of 3-5. R' is a $C_1$-$C_4$ alkyl, and in some embodiments, R' is one of methyl, ethyl and isopropyl. Ra is one of Formulae (A27), (A28), (A29), (A30), and (A31), and in some embodiments, Ra is Formula (A27) or (A28). Rb is a $C_1$-$C_5$ alkyl, and in some embodiments, is one of methyl, ethyl, isopropyl, and butyl. In some embodiments, j1, j2, R', Ra, and Rb in Formulae (A1)-(A26) are respectively selected to achieve the linkage between the $M_1$ targeting groups and the N atom on the nitrogenous backbone, and to make the steric position among the $M_1$ targeting groups more suitable for binding between the $M_1$ targeting groups and the asialoglycoprotein receptor on the surface of hepatocytes.

In some embodiments, the siRNA conjugate has a structure as shown by Formula (403), (404), (405), (406), (407), (408), (409), (410), (411), (412), (413), (414), (415), (416), (417), (418), (419), (420), (421) or (422):

Formula (403)
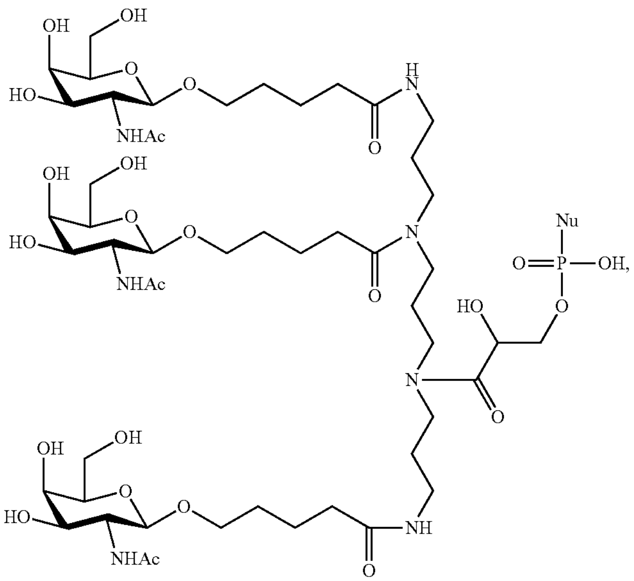
Formula (404)
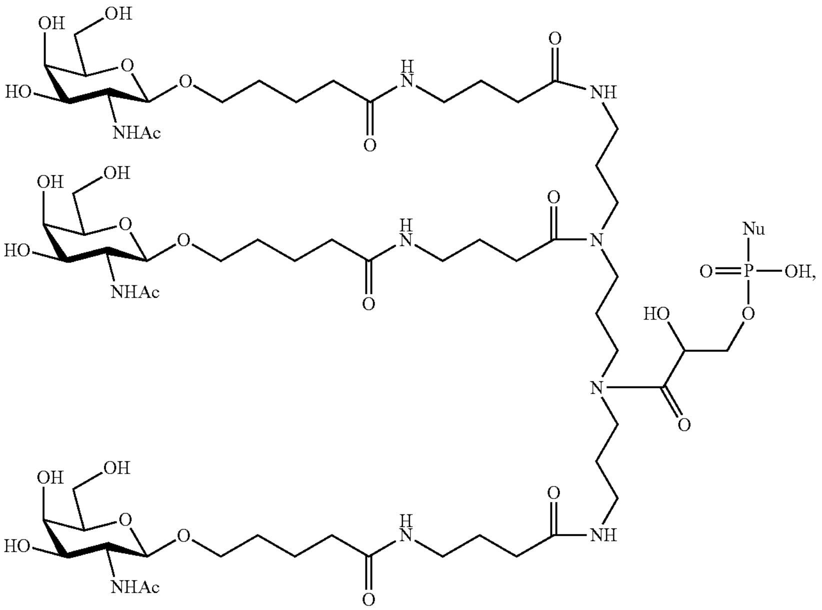

-continued
Formula (405)
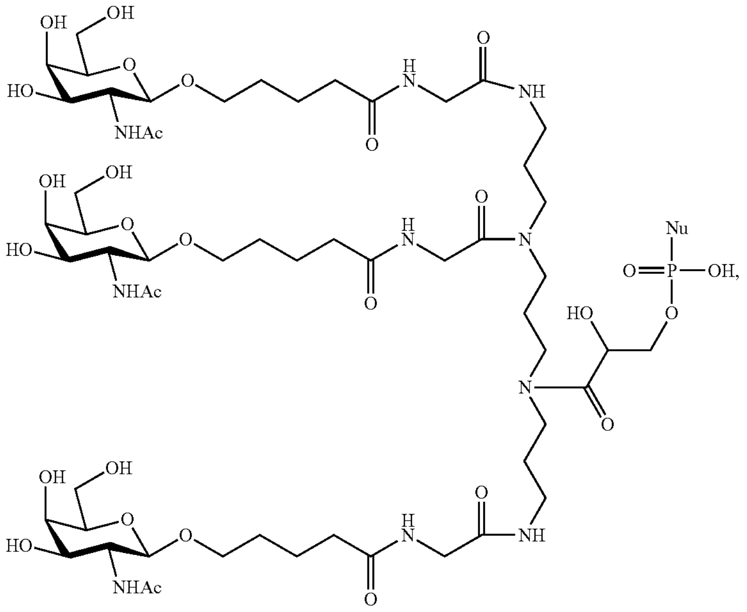
Formula (406)
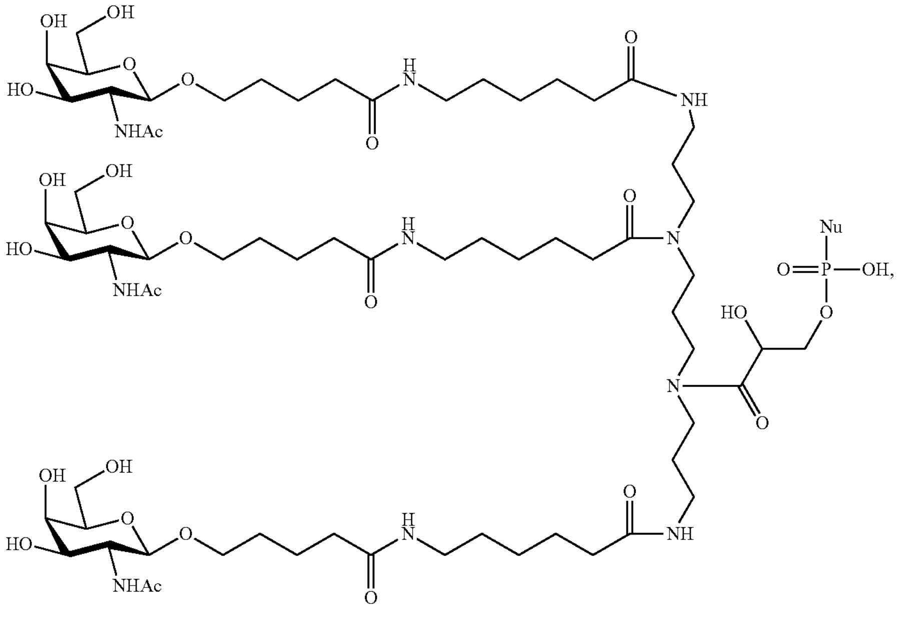

-continued
Formula (407)
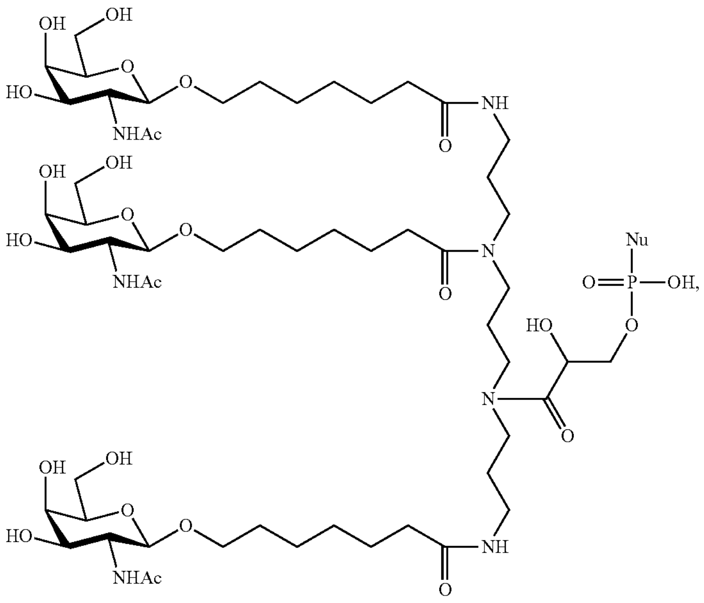
Formula (408)
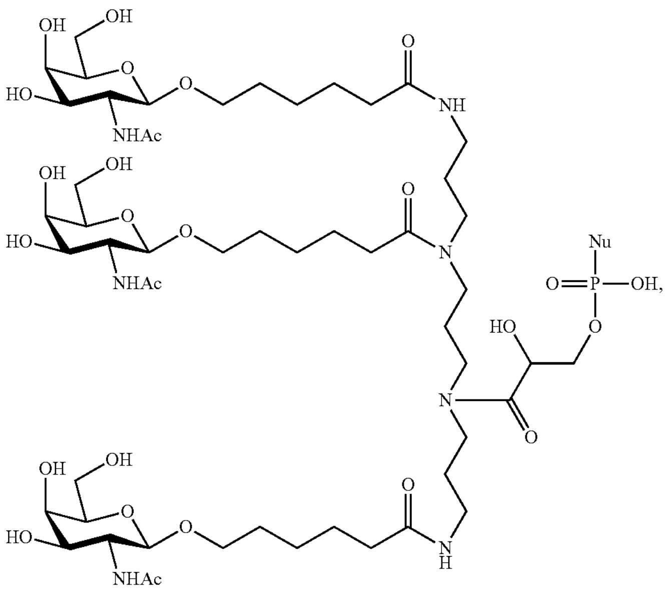

-continued
Formula (409)
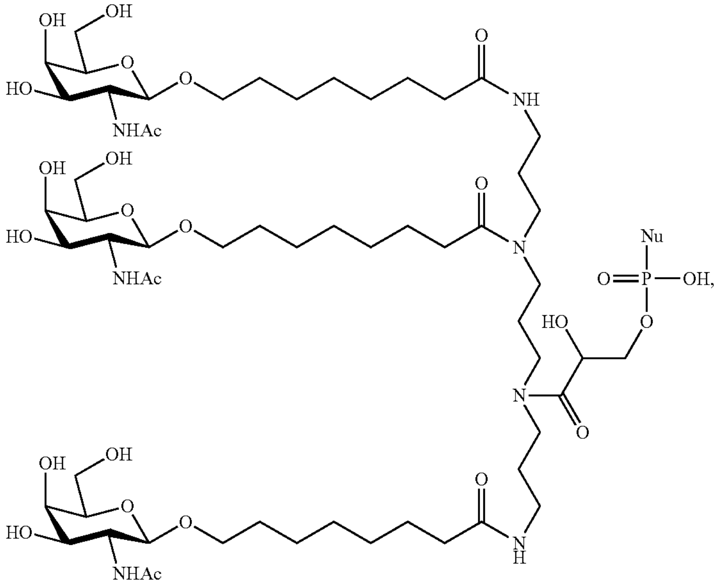
Formula (410)
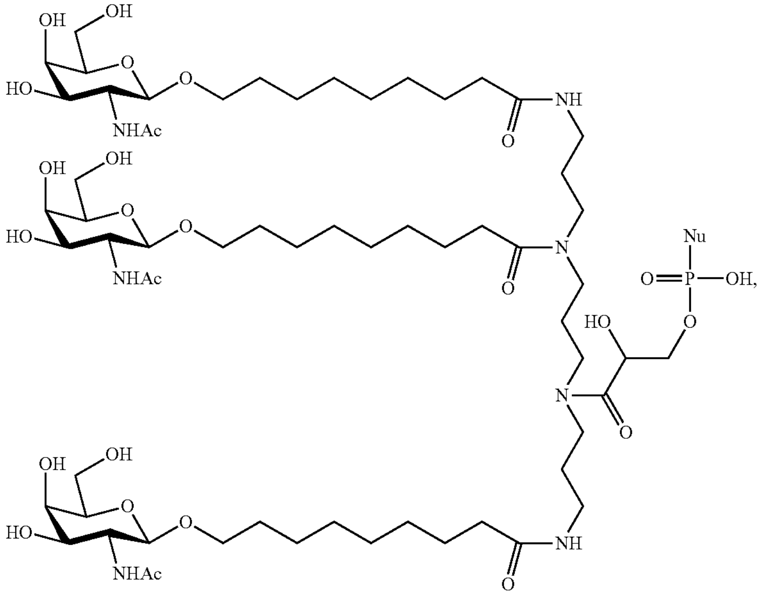

-continued
Formula (411)
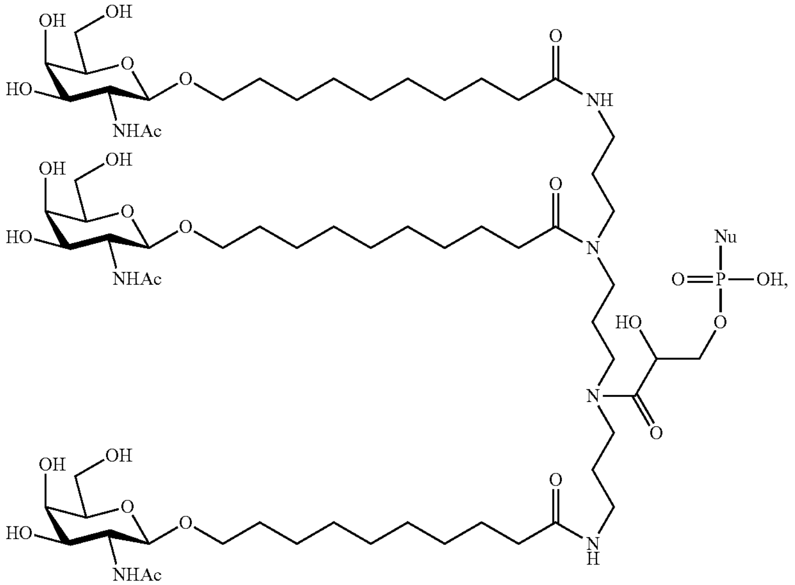
Formula (412)
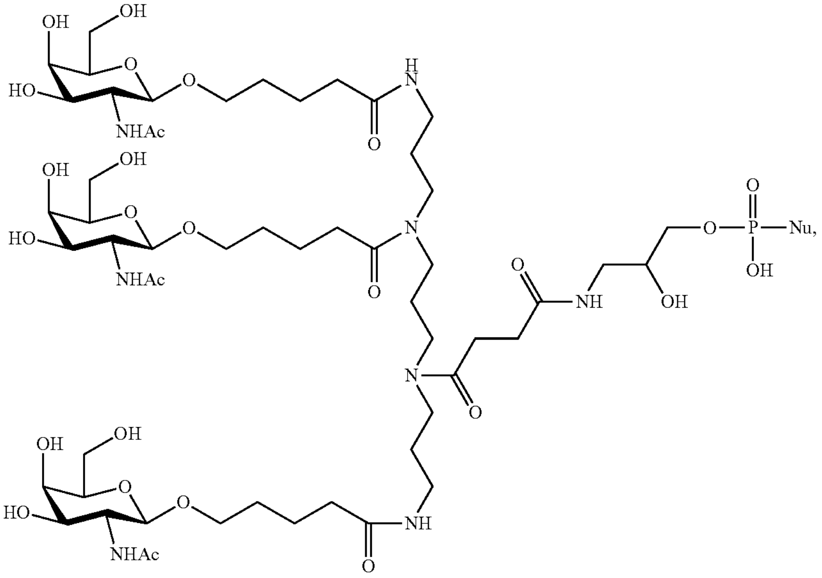

-continued
Formula (413)
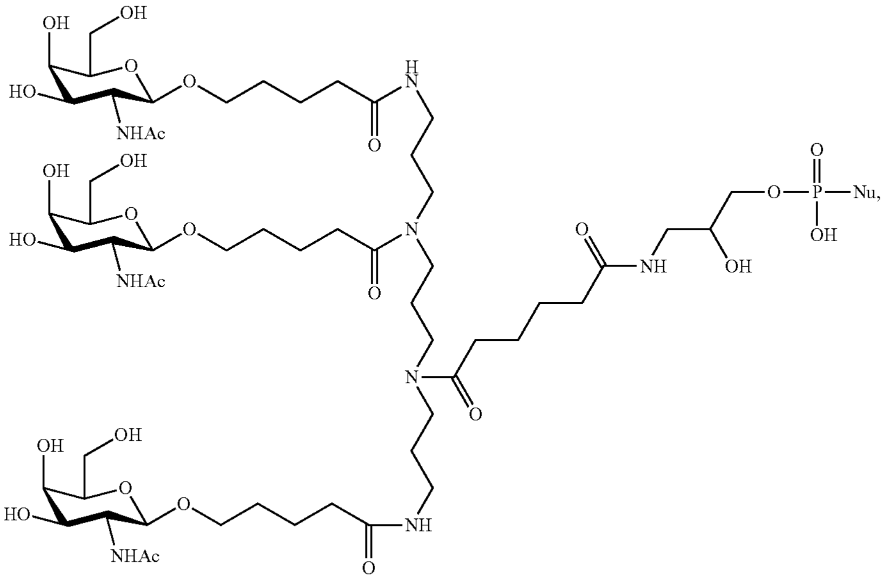
(Formula 414)
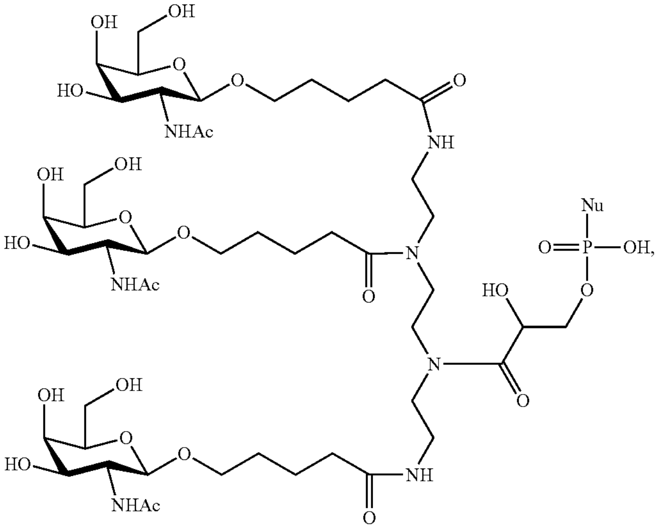

-continued
Formula (415)
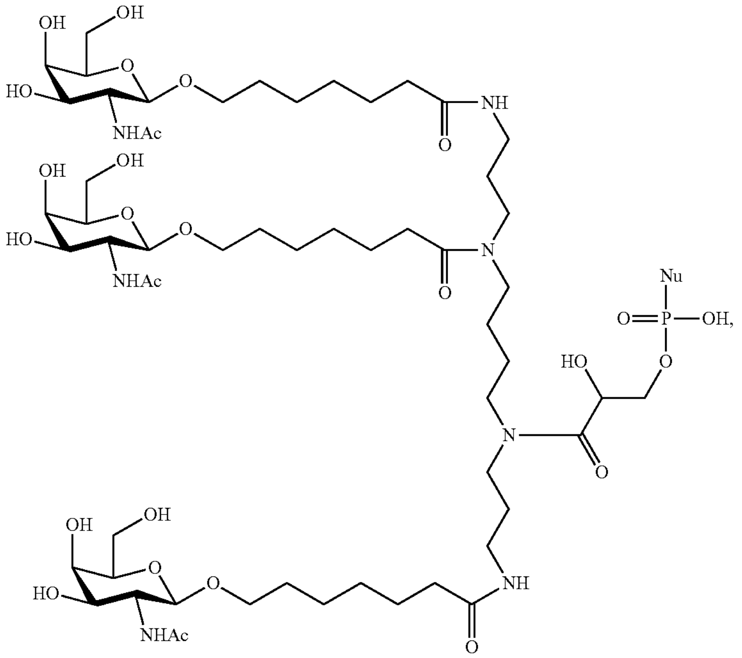
Formula (416)
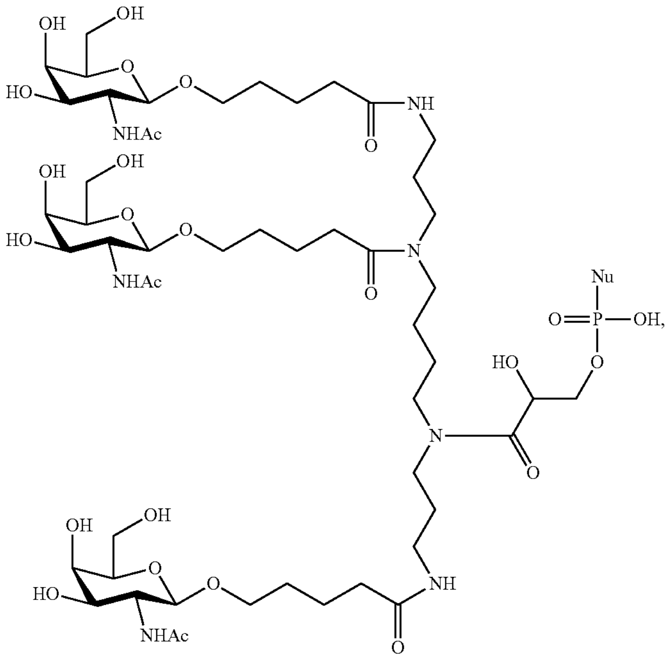

-continued
Formula (417)
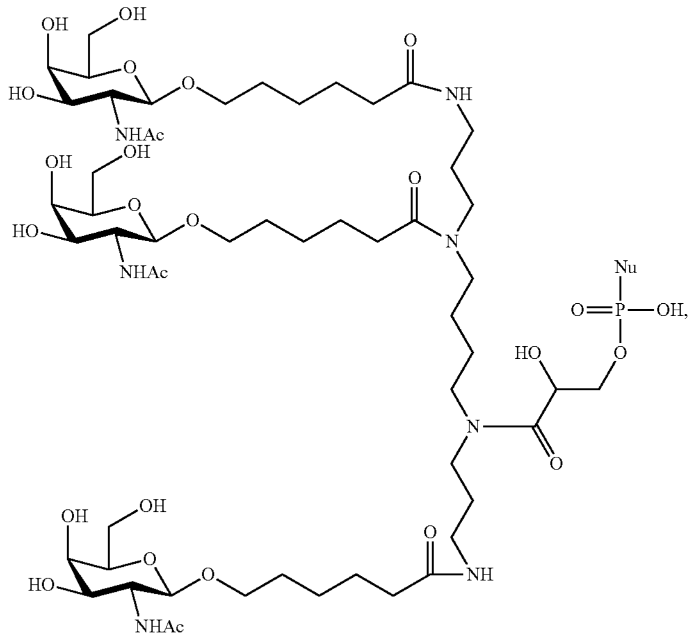
Formula (418)
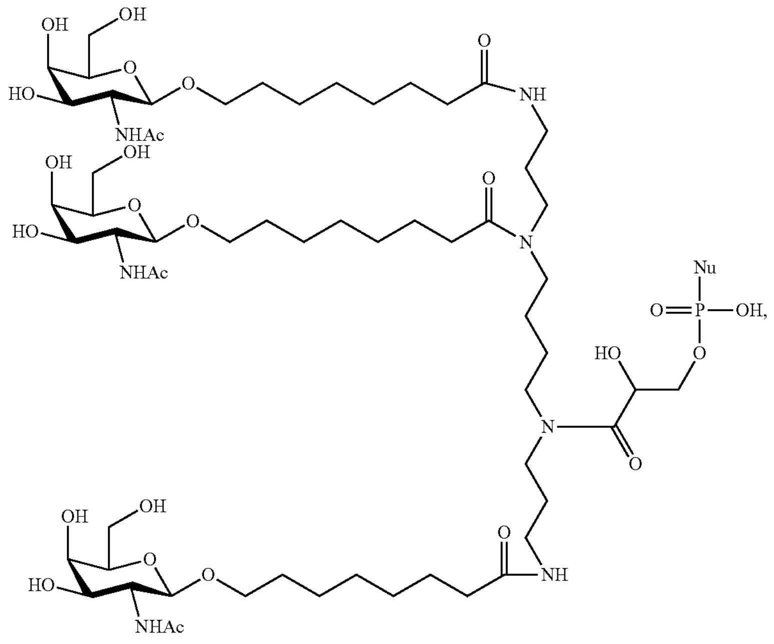

-continued
Formula (419)
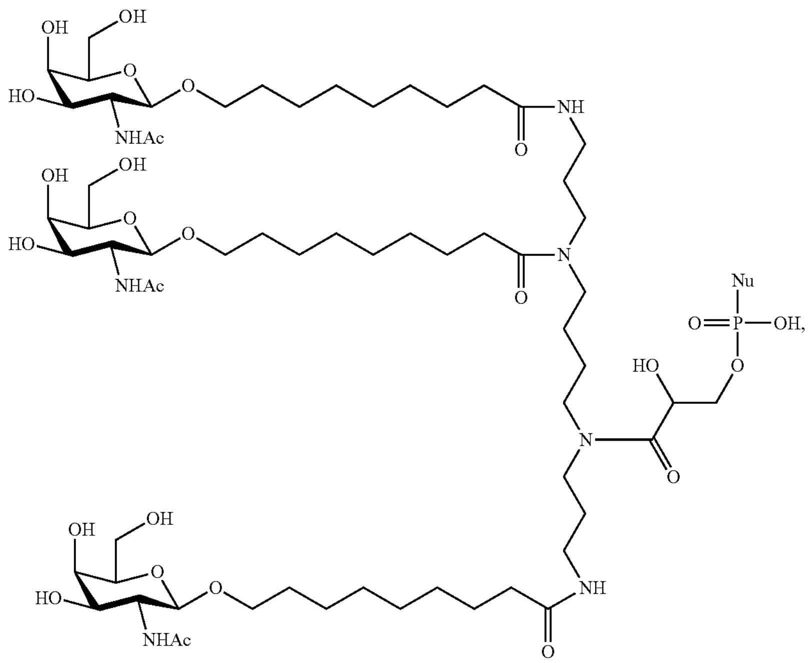
Formula (420)
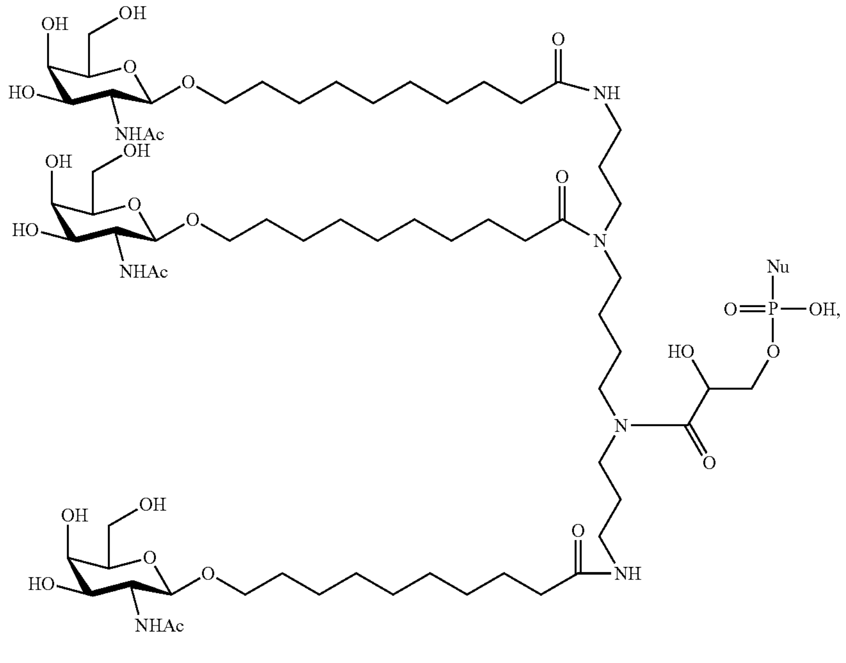

-continued
Formula (421)
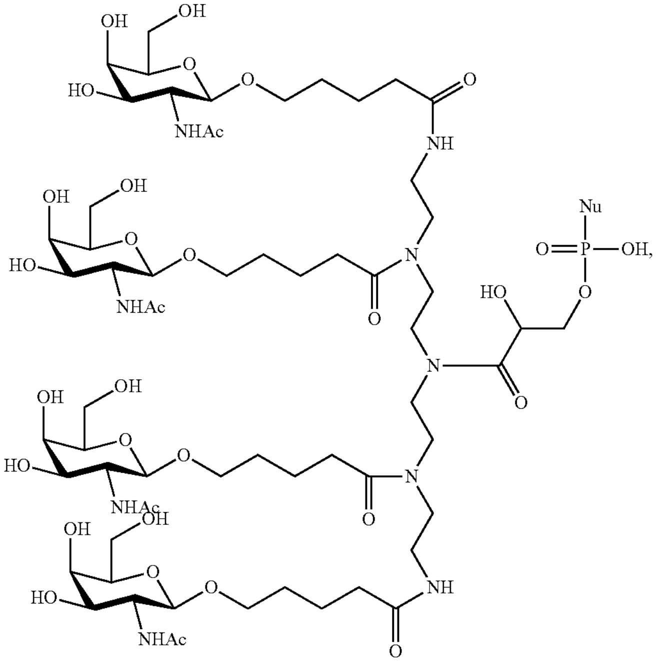
Formula (422)
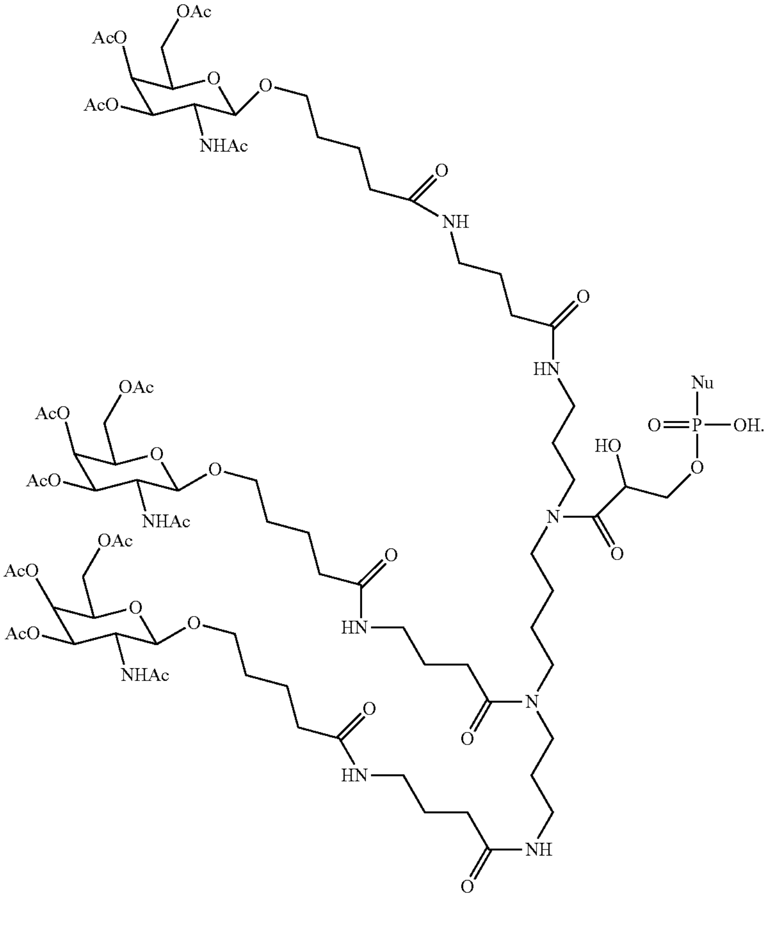
In some embodiments, the P atom in Formula (A59) may be linked to any possible position in the siRNA sequence. For example, the P atom in Formula (A59) may be linked to any nucleotide in the sense or antisense strand of the siRNA. In some embodiments, the P atom in Formula (A59) is linked to any nucleotide in the sense strand of the siRNA. In some embodiments, the P atom in Formula (A59) may be linked to a terminal region of the sense or antisense strand of the siRNA. In some embodiments, the P atom in Formula (A59) is linked to a terminal region of the sense strand of the siRNA. Said terminal region refers to the first 4 nucleotides counted from one terminal of the sense or antisense strand. In some embodiments, the P atom in Formula (A59) is linked to either terminal of the sense or antisense strand of the siRNA. In some embodiments, the P atom in Formula (A59) is linked to 3' terminal of the sense strand of the siRNA. In the case where the P atom in Formula (A59) is linked to the above position of the sense strand of the siRNA, after having entered into cells, the siRNA conjugate as shown by Formula (308) can release a separate antisense strand of the siRNA during unwinding, thereby blocking the translation of the FXI mRNA into a protein and inhibiting the expression of the FXI gene.

In some embodiments, the P atom in Formula (A59) may be linked to any possible position of a nucleotide in the siRNA, for example, position 5', position 2', position 3', or the base of the nucleotide. In some embodiments, the P atom in Formula (A59) may be linked to position 2', 3', or 5' of a nucleotide in the siRNA by forming a phosphodiester bond. In some embodiments, the P atom in Formula (A59) is linked to an oxygen atom formed by dehydrogenation of 3'-hydroxy of the nucleotide at 3' terminal of the sense strand of the siRNA (in this case, the P atom in Formula (A59) may be also regarded as the P atom in the phosphate group contained in the siRNA), or the P atom in Formula (A59) is linked to a nucleotide by substituting a hydrogen atom in 2'-hydroxy of a nucleotide of the sense strand of the siRNA, or the P atom in Formula (A59) is linked to a nucleotide by substituting a hydrogen atom in 5'-hydroxy of the nucleotide at 5' terminal of the sense strand of the siRNA.

The inventors of the present disclosure have surprisingly found that the siRNA conjugate of the present disclosure exhibits significantly improved stability in plasma and low off-target effect, and further shows higher silencing activity against FXI mRNA. In some embodiments, the siRNA of the present disclosure may be one of the siRNAs as shown in Tables 1a to 1i. The siRNA conjugates containing such siRNAs exhibit much higher silencing activity against FXI mRNA.

TABLE 1a

The sequences of first siRNAs of the present disclosure

| siRNA NO. | SEQ ID NO: | Sequence direction 5'-3' |
|---|---|---|
| siFXIa1 | 9 | GGGUAUUCUUUCAAGCAAU |
| | 10 | AUUGCUUGAAAGAAUACCCAG |
| siFXIa2 | 11 | CUGGGUAUUCUUUCAAGCAAU |
| | 12 | AUUGCUUGAAAGAAUACCCAGAA |
| siFXIa1-M1 | 13 | GmGmGmUmAmUmUfCfUfUmUmCmAmAmGmCmAmAmUm |
| | 14 | AmUfUmGmCmUfUmGmAmAmAmGmAmAfUmAfCmCmCmAmGm |
| siFXIa1-M2 | 15 | GmGmGmUmAfUmUfCfUfUmUmCmAmAmGmCmAmAmUm |
| | 16 | AmUfUmGmCmUfUmGfAfAmAmGmAmAfUmAfCmCmCmAmGm |
| siFXIa1-M3 | 17 | GmGmGmUmAfUmUfCfUfUmUmCmAmAmGmCmAmAmUm |
| | 18 | AmUfUmGmCmUfUmGmAmAmAmGmAmAfUmAfCmCmCmAmGm |
| siFXIa2-M1 | 19 | CmUmGmGmGmUmAmUmUfCfUfUmUmCmAmAmGmCmAmAmUm |
| | 20 | AmUfUmGmCmUfUmGmAmAmAmGmAmAfUmAfCmCmCmAmGmAmAm |
| siFXIa2-M2 | 21 | CmUmGmGmGmUmAfUmUfCfUfUmUmCmAmAmGmCmAmAmUm |
| | 22 | AmUfUmGmCmUfUmGfAfAmAmGmAmAfUmAfCmCmCmAmGmAmAm |
| siFXIa2-M3 | 23 | CmUmGmGmGmUmAfUmUfCfUfUmUmCmAmAmGmCmAmAmUm |
| | 24 | AmUfUmGmCmUfUmGmAmAmAmGmAmAfUmAfCmCmCmAmGmAmAm |
| siFXIa1-M1S | 25 | GmsGmsGmUmAmUmUfCfUfUmUmCmAmAmGmCmAmAmUm |
| | 26 | AmsUfsUmGmCmUfUmGmAmAmAmGmAmAfUmAfCmCmCmsAmsGm |
| siFXIa1-M2S | 27 | GmsGmsGmUmAfUmUfCfUfUmUmCmAmAmGmCmAmAmUm |
| | 28 | AmsUfsUmGmCmUfUmGfAfAmAmGmAmAfUmAfCmCmCmsAmsGm |
| siFXIa1-M3S | 29 | GmsGmsGmUmAfUmUfCfUfUmUmCmAmAmGmCmAmAmUm |
| | 30 | AmsUfsUmGmCmUfUmGmAmAmAmGmAmAfUmAfCmCmCmsAmsGm |
| siFXIa2-M1S | 31 | CmsUmsGmGmGmUmAmUmUfCfUfUmUmCmAmAmGmCmAmAmUm |

TABLE 1a-continued

The sequences of first siRNAs of the present disclosure

| siRNA NO. | SEQ ID NO: | Sequence direction 5'-3' |
|---|---|---|
| | 32 | AmsUfsUmGmCmUfUmGmAmAmAmGmAmAfUmAfCmCmCmAmGmsAmsAm |
| siFXIa2-M2S | 33 | CmsUmsGmGmGmUmAfUmUfCfUfUmUmCmAmAmGmCmAmAmUm |
| | 34 | AmsUfsUmGmCmUfUmGfAfAmAmGmAmAfUmAfCmCmCmAmGmsAmsAm |
| siFXIa2-M3S | 35 | CmsUmsGmGmGmUmAfUmUfCfUfUmUmCmAmAmGmCmAmAmUm |
| | 36 | AmsUfsUmGmCmUfUmGmAmAmAmGmAmAfUmAfCmCmCmAmGmsAmsAm |
| siFXIa1-M1P1 | 37 | GmGmGmUmAmUmUfCfUfUmUmCmAmAmGmCmAmAmUm |
| | 38 | P1AmUfUmGmCmUfUmGmAmAmAmGmAmAfUmAfCmCmCmAmGm |
| siFXIa1-M2P1 | 39 | GmGmGmUmAfUmUfCfUfUmUmCmAmAmGmCmAmAmUm |
| | 40 | P1AmUfUmGmCmUfUmGfAfAmAmGmAmAfUmAfCmCmCmAmGm |
| siFXIa1-M3P1 | 41 | GmGmGmUmAfUmUfCfUfUmUmCmAmAmGmCmAmAmUm |
| | 42 | P1AmUfUmGmCmUfUmGmAmAmAmGmAmAfUmAfCmCmCmAmGm |
| siFXIa2-M1P1 | 43 | CmUmGmGmGmUmAmUmUfCfUfUmUmCmAmAmGmCmAmAmUm |
| | 44 | P1AmUfUmGmCmUfUmGmAmAmAmGmAmAfUmAfCmCmCmAmGmAmAm |
| siFXIa2-M2P1 | 45 | CmUmGmGmGmUmAfUmUfCfUfUmUmCmAmAmGmCmAmAmUm |
| | 46 | P1AmUfUmGmCmUfUmGfAfAmAmGmAmAfUmAfCmCmCmAmGmAmAm |
| siFXIa2-M3P1 | 47 | CmUmGmGmGmUmAfUmUfCfUfUmUmCmAmAmGmCmAmAmUm |
| | 48 | P1AmUfUmGmCmUfUmGmAmAmAmGmAmAfUmAfCmCmCmAmGmAmAm |
| siFXIa1-M1SP1 | 49 | GmsGmsGmUmAmUmUfCfUfUmUmCmAmAmGmCmAmAmUm |
| | 50 | P1AmsUfsUmGmCmUfUmGmAmAmAmGmAmAfUmAfCmCmCmsAmsGm |
| siFXIa1-M2SP1 | 51 | GmsGmsGmUmAfUmUfCfUfUmUmCmAmAmGmCmAmAmUm |
| | 52 | P1AmsUfsUmGmCmUfUmGfAfAmAmGmAmAfUmAfCmCmCmsAmsGm |
| siFXIa1-M3SP1 | 53 | GmsGmsGmUmAfUmUfCfUfUmUmCmAmAmGmCmAmAmUm |
| | 54 | P1AmsUfsUmGmCmUfUmGmAmAmAmGmAmAfUmAfCmCmCmsAmsGm |
| siFXIa2-M1SP1 | 55 | CmsUmsGmGmGmUmAmUmUfCfUfUmUmCmAmAmGmCmAmAmUm |
| | 56 | P1AmsUfsUmGmCmUfUmGmAmAmAmGmAmAfUmAfCmCmCmAmGmsAmsAm |
| siFXIa2-M2SP1 | 57 | CmsUmsGmGmGmUmAfUmUfCfUfUmUmCmAmAmGmCmAmAmUm |
| | 58 | P1AmsUfsUmGmCmUfUmGfAfAmAmGmAmAfUmAfCmCmCmAmGmsAmsAm |
| siFXIa2-M3SP1 | 59 | CmsUmsGmGmGmUmAfUmUfCfUfUmUmCmAmAmGmCmAmAmUm |
| | 60 | P1AmsUfsUmGmCmUfUmGmAmAmAmGmAmAfUmAfCmCmCmAmGmsAmsAm |

TABLE 1b

The sequences of second siRNAs of the present disclosure

| siRNA NO. | SEQ ID NO: | Sequence direction 5'-3' |
|---|---|---|
| siFXIb1 | 69 | GGCAUAAACUAUAACAGCU |
| | 70 | AGCUGUUAUAGUUUAUGCCCU |
| siFXIb2 | 71 | AGGGCAUAAACUAUAACAGCU |
| | 72 | AGCUGUUAUAGUUUAUGCCCUUC |
| siFXIb1-M1 | 73 | GmGmCmAmUmAmAfAfCfUmAmUmAmAmCmAmGmCmUm |
| | 74 | AmGfCmUmGmUfUmAmUmAmGmUmUmUfAmUfGmCmCmCmUm |
| siFXIb1-M2 | 75 | GmGmCmAmUfAmAfAfCfUmAmUmAmAmCmAmGmCmUm |
| | 76 | AmGfCmUmGmUfUmAfUfAmGmUmUmUfAmUfGmCmCmCmUm |
| siFXIb1-M3 | 77 | GmGmCmAmUfAmAfAfCfUmAmUmAmAmCmAmGmCmUm |
| | 78 | AmGfCmUmGmUfUmAmUmAmGmUmUmUfAmUfGmCmCmCmUm |
| siFXIb2-M1 | 79 | AmGmGmGmCmAmUmAmAfAfCfUmAmUmAmAmCmAmGmCmUm |
| | 80 | AmGfCmUmGmUfUmAmUmAmGmUmUmUfAmUfGmCmCmCmUmUmCm |
| siFXIb2-M2 | 81 | AmGmGmGmCmAmUfAmAfAfCfUmAmUmAmAmCmAmGmCmUm |
| | 82 | AmGfCmUmGmUfUmAfUfAmGmUmUmUfAmUfGmCmCmCmUmUmCm |
| siFXIb2-M3 | 83 | AmGmGmGmCmAmUfAmAfAfCfUmAmUmAmAmCmAmGmCmUm |
| | 84 | AmGfCmUmGmUfUmAmUmAmGmUmUmUfAmUfGmCmCmCmUmUmCm |
| siFXIb1-M1S | 85 | GmsGmsCmAmUmAmAfAfCfUmAmUmAmAmCmAmGmCmUm |
| | 86 | AmsGfsCmUmGmUfUmAmUmAmGmUmUmUfAmUfGmCmCmsCmsUm |
| siFXIb1-M2S | 87 | GmsGmsCmAmUfAmAfAfCfUmAmUmAmAmCmAmGmCmUm |
| | 88 | AmsGfsCmUmGmUfUmAfUfAmGmUmUmUfAmUfGmCmCmsCmsUm |
| siFXIb1-M3S | 89 | GmsGmsCmAmUfAmAfAfCfUmAmUmAmAmCmAmGmCmUm |
| | 90 | AmsGfsCmUmGmUfUmAmUmAmGmUmUmUfAmUfGmCmCmsCmsUm |
| siFXIb2-M1S | 91 | AmsGmsGmGmCmAmUmAmAfAfCfUmAmUmAmAmCmAmGmCmUm |
| | 92 | AmsGfsCmUmGmUfUmAmUmAmGmUmUmUfAmUfGmCmCmCmUmsUmsCm |
| siFXIb2-M2S | 93 | GmsGmsCmAmUfAmAfAfCfUmAmUmAmAmCmAmGmCmUm |
| | 94 | AmsGfsCmUmGmUfUmAfUfAmGmUmUmUfAmUfGmCmCmCmUmsUmsCm |
| siFXIb2-M3S | 95 | AmsGmsGmGmCmAmUfAmAfAfCfUmAmUmAmAmCmAmGmCmUm |
| | 96 | AmsGfsCmUmGmUfUmAmUmAmGmUmUmUfAmUfGmCmCmCmUmsUmsCm |
| siFXIb1-M1P1 | 97 | GmGmCmAmUmAmAfAfCfUmAmUmAmAmCmAmGmCmUm |
| | 98 | P1AmGfCmUmGmUfUmAmUmAmGmUmUmUfAmUfGmCmCmCmUm |
| siFXIb1-M2P1 | 99 | GmGmCmAmUfAmAfAfCfUmAmUmAmAmCmAmGmCmUm |
| | 100 | P1AmGfCmUmGmUfUmAfUfAmGmUmUmUfAmUfGmCmCmCmUm |
| siFXIb1-M3P1 | 101 | GmGmCmAmUfAmAfAfCfUmAmUmAmAmCmAmGmCmUm |
| | 102 | P1AmGfCmUmGmUfUmAmUmAmGmUmUmUfAmUfGmCmCmCmUm |
| siFXIb2-M1P1 | 103 | AmGmGmGmCmAmUmAmAfAfCfUmAmUmAmAmCmAmGmCmUm |
| | 104 | P1AmGfCmUmGmUfUmAmUmAmGmUmUmUfAmUfGmCmCmCmUmUmCm |

TABLE 1b-continued

The sequences of second siRNAs of the present disclosure

| siRNA NO. | SEQ ID NO: | Sequence direction 5'-3' |
|---|---|---|
| siFXIb2-M2P1 | 105 | AmGmGmGmCmAmUfAmAfAfCfUmAmUmAmAmCmAmGmCm Um |
| | 106 | P1AmGfCmUmGmUfUmAfUfAmGmUmUmUfAmUfGmCmCmCm UmUmCm |
| siFXIb2-M3P1 | 107 | AmGmGmGmCmAmUfAmAfAfCfUmAmUmAmAmCmAmGmCm Um |
| | 108 | P1AmGfCmUmGmUfUmAmUmAmGmUmUmUfAmUfGmCmCmC mUmUmCm |
| siFXIb1-M1SP1 | 109 | GmsGmsCmAmUmAmAfAfCfUmAmUmAmAmCmAmGmCmUm |
| | 110 | P1AmsGfsCmUmGmUfUmAmUmAmGmUmUmUfAmUfGmCmCm sCmsUm |
| siFXIb1-M2SP1 | 111 | GmsGmsCmAmUfAmAfAfCfUmAmUmAmAmCmAmGmCmUm |
| | 112 | P1AmsGfsCmUmGmUfUmAfUfAmGmUmUmUfAmUfGmCmCmsC msUm |
| siFXIb1-M3SP1 | 113 | GmsGmsCmAmUfAmAfAfCfUmAmUmAmAmCmAmGmCmUm |
| | 114 | P1AmsGfsCmUmGmUfUmAmUmAmGmUmUmUfAmUfGmCmCm sCmsUm |
| siFXIb2-M1SP1 | 115 | AmsGmsGmGmCmAmUmAmAfAfCfUmAmUmAmAmCmAmGmC mUm |
| | 116 | P1AmsGfsCmUmGmUfUmAmUmAmGmUmUmUfAmUfGmCmCm CmUmsUmsCm |
| siFXIb2-M2SP1 | 117 | AmsGmsGmGmCmAmUfAmAfAfCfUmAmUmAmAmCmAmGmC mUm |
| | 118 | P1AmsGfsCmUmGmUfUmAfUfAmGmUmUmUfAmUfGmCmCmC mUmsUmsCm |
| siFXIb2-M3SP1 | 119 | AmsGmsGmGmCmAmUfAmAfAfCfUmAmUmAmAmCmAmGmC mUm |
| | 120 | P1AmsGfsCmUmGmUfUmAmUmAmGmUmUmUfAmUfGmCmCm CmUmsUmsCm |

TABLE 1c

The sequences of third siRNAs of the present disclosure

| siRNA NO. | SEQ ID NO: | Sequence direction 5'-3' |
|---|---|---|
| siFXIc1 | 129 | GCUCAAGAAUGCCAAGAAA |
| | 130 | UUUCUUGGCAUUCUUGAGCAC |
| siFXIc2 | 131 | GUGCUCAAGAAUGCCAAGAAA |
| | 132 | UUUCUUGGCAUUCUUGAGCACUC |
| siFXIc1-M1 | 133 | GmCmUmCmAmAmGfAfAfUmGmCmCmAmAmGmAmAmAm |
| | 134 | UmUfUmCmUmUfGmGmCmAmUmUmCmUfUmGfAmGmCmAmC m |
| siFXIc1-M2 | 135 | GmCmUmCmAfAmGfAfAfUmGmCmCmAmAmGmAmAmAm |
| | 136 | UmUfUmCmUmUfGmGfCfAmUmUmCmUfUmGfAmGmCmAmCm |
| siFXIc1-M3 | 137 | GmCmUmCmAfAmGfAfAfUmGmCmCmAmAmGmAmAmAm |
| | 138 | UmUfUmCmUmUfGmGmCmAmUmUmCmUfUmGfAmGmCmAmC m |
| siFXIc2-M1 | 139 | GmUmGmCmUmCmAmAmGfAfAfUmGmCmCmAmAmGmAmAm Am |
| | 140 | UmUfUmCmUmUfGmGmCmAmUmUmCmUfUmGfAmGmCmAmC mUmCm |

TABLE 1c-continued

| The sequences of third siRNAs of the present disclosure | | |
|---|---|---|
| siRNA NO. | SEQ ID NO: | Sequence direction 5'-3' |
| siFXIc2-M2 | 141 | GmUmGmCmUmCmAfAmGfAfAfUmGmCmCmAmAmGmAmAmAm |
| | 142 | UmUfUmCmUmUfGmGfCfAmUmUmCmUfUmGfAmGmCmAmCmUmCm |
| siFXIc2-M3 | 143 | GmUmGmCmUmCmAfAmGfAfAfUmGmCmCmAmAmGmAmAmAm |
| | 144 | UmUfUmCmUmUfGmGmCmAmUmUmCmUfUmGfAmGmCmAmCmUmCm |
| siFXIc1-M1S | 145 | GmsCmsUmCmAmAmGfAfAfUmGmCmCmAmAmGmAmAmAm |
| | 146 | UmsUfsUmCmUmUfGmGmCmAmUmUmCmUfUmGfAmGmCmsAmsCm |
| siFXIc1-M2S | 147 | GmsCmsUmCmAfAmGfAfAfUmGmCmCmAmAmGmAmAmAm |
| | 148 | UmsUfsUmCmUmUfGmGfCfAmUmUmCmUfUmGfAmGmCmsAmsCm |
| siFXIc1-M3S | 149 | GmsCmsUmCmAfAmGfAfAfUmGmCmCmAmAmGmAmAmAm |
| | 150 | UmsUfsUmCmUmUfGmGmCmAmUmUmCmUfUmGfAmGmCmsAmsCm |
| siFXIc2-M1S | 151 | GmsUmsGmCmUmCmAmAmGfAfAfUmGmCmCmAmAmGmAmAmAm |
| | 152 | UmsUfsUmCmUmUfGmGmCmAmUmUmCmUfUmGfAmGmCmAmCmsUmsCm |
| siFXIc2-M2S | 153 | GmsUmsGmCmUmCmAfAmGfAfAfUmGmCmCmAmAmGmAmAmAm |
| | 154 | UmsUfsUmCmUmUfGmGfCfAmUmUmCmUfUmGfAmGmCmAmCmsUmsCm |
| siFXIc2-M3S | 155 | GmsUmsGmCmUmCmAfAmGfAfAfUmGmCmCmAmAmGmAmAmAm |
| | 156 | UmsUfsUmCmUmUfGmGmCmAmUmUmCmUfUmGfAmGmCmAmCmsUmsCm |
| siFXIc1-M1P1 | 157 | GmCmUmCmAmAmGfAfAfUmGmCmCmAmAmGmAmAmAm |
| | 158 | P1UmUfUmCmUmUfGmGmCmAmUmUmCmUfUmGfAmGmCmAmCm |
| siFXIc1-M2P1 | 159 | GmCmUmCmAfAmGfAfAfUmGmCmCmAmAmGmAmAmAm |
| | 160 | P1UmUfUmCmUmUfGmGfCfAmUmUmCmUfUmGfAmGmCmAmCm |
| siFXIc1-M3P1 | 161 | GmCmUmCmAfAmGfAfAfUmGmCmCmAmAmGmAmAmAm |
| | 162 | P1UmUfUmCmUmUfGmGmCmAmUmUmCmUfUmGfAmGmCmAmCm |
| siFXIc2-M1P1 | 163 | GmUmGmCmUmCmAmAmGfAfAfUmGmCmCmAmAmGmAmAmAm |
| | 164 | P1UmUfUmCmUmUfGmGmCmAmUmUmCmUfUmGfAmGmCmAmCmUmCm |
| siFXIc2-M2P1 | 165 | GmUmGmCmUmCmAfAmGfAfAfUmGmCmCmAmAmGmAmAmAm |
| | 166 | P1UmUfUmCmUmUfGmGfCfAmUmUmCmUfUmGfAmGmCmAmCmUmCm |
| siFXIc2-M3P1 | 167 | GmUmGmCmUmCmAfAmGfAfAfUmGmCmCmAmAmGmAmAmAm |
| | 168 | P1UmUfUmCmUmUfGmGmCmAmUmUmCmUfUmGfAmGmCmAmCmUmCm |
| siFXIc1-M1SP1 | 169 | GmsCmsUmCmAmAmGfAfAfUmGmCmCmAmAmGmAmAmAm |
| | 170 | P1UmsUfsUmCmUmUfGmGmCmAmUmUmCmUfUmGfAmGmCmsAmsCm |
| siFXIc1-M2SP1 | 171 | GmsCmsUmCmAfAmGfAfAfUmGmCmCmAmAmGmAmAmAm |
| | 172 | P1UmsUfsUmCmUmUfGmGfCfAmUmUmCmUfUmGfAmGmCmsAmsCm |

TABLE 1c-continued

| The sequences of third siRNAs of the present disclosure | | |
|---|---|---|
| siRNA NO. | SEQ ID NO: | Sequence direction 5'-3' |
| siFXIc1-M3SP1 | 173 | GmsCmsUmCmAfAmGfAfAfUmGmCmCmAmAmGmAmAmAm |
| | 174 | P1UmsUfsUmCmUmUfGmGmCmAmUmUmCmUfUmGfAmGmCmsAmsCm |
| siFXIc2-M1SP1 | 175 | GmsUmsGmCmUmCmAmAmGfAfAfUmGmCmCmAmAmGmAmAmAm |
| | 176 | P1UmsUfsUmCmUmUfGmGmCmAmUmUmCmUfUmGfAmGmCmAmCmsUmsCm |
| siFXIc2-M2SP1 | 177 | GmsUmsGmCmUmCmAfAmGfAfAfUmGmCmCmAmAmGmAmAmAm |
| | 178 | P1UmsUfsUmCmUmUfGmGfCfAmUmUmCmUfUmGfAmGmCmAmCmsUmsCm |
| siFXIc2-M3SP1 | 179 | GmsUmsGmCmUmCmAfAmGfAfAfUmGmCmCmAmAmGmAmAmAm |
| | 180 | P1UmsUfsUmCmUmUfGmGmCmAmUmUmCmUfUmGfAmGmCmAmCmsUmsCm |

TABLE 1d

| The sequences of fourth siRNAs of the present disclosure | | |
|---|---|---|
| siRNA NO. | SEQ ID NO: | Sequence direction 5'-3' |
| siFXId1 | 189 | GCAACAAAGACAUUUAUGU |
| | 190 | ACAUAAAUGUCUUUGUUGCAA |
| siFXId2 | 191 | UUGCAACAAAGACAUUUAUGU |
| | 192 | ACAUAAAUGUCUUUGUUGCAAGC |
| siFXId1-M1 | 193 | GmCmAmAmCmAmAfAfGfAmCmAmUmUmUmAmUmGmUm |
| | 194 | AmCfAmUmAmAfAmUmGmUmCmUmUmUfGmUfUmGmCmAmAm |
| siFXId1-M2 | 195 | GmCmAmAmCfAmAfAfGfAmCmAmUmUmUmAmUmGmUm |
| | 196 | AmCfAmUmAmAfAmUfGfUmCmUmUmUfGmUfUmGmCmAmAm |
| siFXId1-M3 | 197 | GmCmAmAmCfAmAfAfGfAmCmAmUmUmUmAmUmGmUm |
| | 198 | AmCfAmUmAmAfAmUmGmUmCmUmUmUfGmUfUmGmCmAmAm |
| siFXId2-M1 | 199 | UmUmGmCmAmAmCmAmAfAfGfAmCmAmUmUmUmAmUmGmUm |
| | 200 | AmCfAmUmAmAfAmUmGmUmCmUmUmUfGmUfUmGmCmAmAmGmCm |
| siFXId2-M2 | 201 | UmUmGmCmAmAmCfAmAfAfGfAmCmAmUmUmUmAmUmGmUm |
| | 202 | AmCfAmUmAmAfAmUfGfUmCmUmUmUfGmUfUmGmCmAmAmGmCm |
| siFXId2-M3 | 203 | UmUmGmCmAmAmCfAmAfAfGfAmCmAmUmUmUmAmUmGmUm |
| | 204 | AmCfAmUmAmAfAmUmGmUmCmUmUmUfGmUfUmGmCmAmAmGmCm |
| siFXId1-M1S | 205 | GmsCmsAmAmCmAmAfAfGfAmCmAmUmUmUmAmUmGmUm |
| | 206 | AmsCfsAmUmAmAfAmUmGmUmCmUmUmUfGmUfUmGmCmsAmsAm |
| siFXId1-M2S | 207 | GmsCmsAmAmCfAmAfAfGfAmCmAmUmUmUmAmUmGmUm |
| | 208 | AmsCfsAmUmAmAfAmUfGfUmCmUmUmUfGmUfUmGmCmsAmsAm |
| siFXId1-M3S | 209 | GmsCmsAmAmCfAmAfAfGfAmCmAmUmUmUmAmUmGmUm |
| | 210 | AmsCfsAmUmAmAfAmUmGmUmCmUmUmUfGmUfUmGmCmsAmsAm |

TABLE 1d-continued

The sequences of fourth siRNAs of the present disclosure

| siRNA NO. | SEQ ID NO: | Sequence direction 5'-3' |
|---|---|---|
| siFXId2-M1S | 211 | UmsUmsGmCmAmAmCmAmAfAfGfAmCmAmUmUmUmAmUmG mUm |
| | 212 | AmsCfsAmUmAmAfAmUmGmUmCmUmUmUfGmUfUmGmCmA mAmsGmsCm |
| siFXId2-M2S | 213 | UmsUmsGmCmAmAmCfAmAfAfGfAmCmAmUmUmUmAmUmG mUm |
| | 214 | AmsCfsAmUmAmAfAmUfGfUmCmUmUmUfGmUfUmGmCmAmA msGmsCm |
| siFXId2-M3S | 215 | UmsUmsGmCmAmAmCfAmAfAfGfAmCmAmUmUmUmAmUmG mUm |
| | 216 | AmsCfsAmUmAmAfAmUmGmUmCmUmUmUfGmUfUmGmCmA mAmsGmsCm |
| siFXId1-M1P1 | 217 | GmCmAmAmCmAmAfAfGfAmCmAmUmUmUmAmUmGmUm |
| | 218 | P1AmCfAmUmAmAfAmUmGmUmCmUmUmUfGmUfUmGmCmA mAm |
| siFXId1-M2P1 | 219 | GmCmAmAmCfAmAfAfGfAmCmAmUmUmUmAmUmGmUm |
| | 220 | P1AmCfAmUmAmAfAmUfGfUmCmUmUmUfGmUfUmGmCmAm Am |
| siFXId1-M3P1 | 221 | GmCmAmAmCfAmAfAfGfAmCmAmUmUmUmAmUmGmUm |
| | 222 | P1AmCfAmUmAmAfAmUmGmUmCmUmUmUfGmUfUmGmCmA mAm |
| siFXId2-M1P1 | 223 | UmUmGmCmAmAmCmAmAfAfGfAmCmAmUmUmUmAmUmGm Um |
| | 224 | P1AmCfAmUmAmAfAmUmGmUmCmUmUmUfGmUfUmGmCmA mAmGmCm |
| siFXId2-M2P1 | 225 | UmUmGmCmAmAmCfAmAfAfGfAmCmAmUmUmUmAmUmGm Um |
| | 226 | P1AmCfAmUmAmAfAmUfGfUmCmUmUmUfGmUfUmGmCmAm AmGmCm |
| siFXId2-M3P1 | 227 | UmUmGmCmAmAmCfAmAfAfGfAmCmAmUmUmUmAmUmGm Um |
| | 228 | P1AmCfAmUmAmAfAmUmGmUmCmUmUmUfGmUfUmGmCmA mAmGmCm |
| siFXId1-M1SP1 | 229 | GmsCmsAmAmCmAmAfAfGfAmCmAmUmUmUmAmUmGmUm |
| | 230 | P1AmsCfsAmUmAmAfAmUmGmUmCmUmUmUfGmUfUmGmCm sAmsAm |
| siFXId1-M2SP1 | 231 | GmsCmsAmAmCfAmAfAfGfAmCmAmUmUmUmAmUmGmUm |
| | 232 | P1AmsCfsAmUmAmAfAmUfGfUmCmUmUmUfGmUfUmGmCmsA msAm |
| siFXId1-M3SP1 | 233 | GmsCmsAmAmCfAmAfAfGfAmCmAmUmUmUmAmUmGmUm |
| | 234 | P1AmsCfsAmUmAmAfAmUmGmUmCmUmUmUfGmUfUmGmCm sAmsAm |
| siFXId2-M1SP1 | 235 | UmsUmsGmCmAmAmCmAmAfAfGfAmCmAmUmUmUmAmUmG mUm |
| | 236 | P1AmsCfsAmUmAmAfAmUmGmUmCmUmUmUfGmUfUmGmCm AmAmsGmsCm |
| siFXId2-M2SP1 | 237 | UmsUmsGmCmAmAmCfAmAfAfGfAmCmAmUmUmUmAmUmG mUm |
| | 238 | P1AmsCfsAmUmAmAfAmUfGfUmCmUmUmUfGmUfUmGmCmA mAmsGmsCm |
| siFXId2-M3SP1 | 239 | UmsUmsGmCmAmAmCfAmAfAfGfAmCmAmUmUmUmAmUmG mUm |
| | 240 | P1AmsCfsAmUmAmAfAmUmGmUmCmUmUmUfGmUfUmGmCm AmAmsGmsCm |

TABLE 1e

The sequences of fifth siRNAs of the present disclosure

| siRNA NO. | SEQ ID NO: | Sequence direction 5'-3' |
|---|---|---|
| siFXIe1 | 249 | GAAUCUCAAAGAAAUCUUU |
| | 250 | AAAGAUUUCUUUGAGAUUCUU |
| siFXIe2 | 251 | AAGAAUCUCAAAGAAAUCUUU |
| | 252 | AAAGAUUUCUUUGAGAUUCUUUG |
| siFXIe1-M1 | 253 | GmAmAmUmCmUmCfAfAfAmGmAmAmAmUmCmUmUmUm |
| | 254 | AmAfAmGmAmUfUmUmCmUmUmUmGmAfGmAfUmUmCmUmUm |
| siFXIe1-M2 | 255 | GmAmAmUmCfUmCfAfAfAmGmAmAmAmUmCmUmUmUm |
| | 256 | AmAfAmGmAmUfUmUfCfUmUmUmGmAfGmAfUmUmCmUmUm |
| siFXIe1-M3 | 257 | GmAmAmUmCfUmCfAfAfAmGmAmAmAmUmCmUmUmUm |
| | 258 | AmAfAmGmAmUfUmUmCmUmUmUmGmAfGmAfUmUmCmUmUm |
| siFXIe2-M1 | 259 | AmAmGmAmAmUmCmUmCfAfAfAmGmAmAmAmUmCmUmUmUm |
| | 260 | AmAfAmGmAmUfUmUmCmUmUmUmGmAfGmAfUmUmCmUmUmUmGm |
| siFXIe2-M2 | 261 | AmAmGmAmAmUmCfUmCfAfAfAmGmAmAmAmUmCmUmUmUm |
| | 262 | AmAfAmGmAmUfUmUfCfUmUmUmGmAfGmAfUmUmCmUmUmUmGm |
| siFXIe2-M3 | 263 | AmAmGmAmAmUmCfUmCfAfAfAmGmAmAmAmUmCmUmUmUm |
| | 264 | AmAfAmGmAmUfUmUmCmUmUmUmGmAfGmAfUmUmCmUmUmUmGm |
| siFXIe1-M1S | 265 | GmsAmsAmUmCmUmCfAfAfAmGmAmAmAmUmCmUmUmUm |
| | 266 | AmsAfsAmGmAmUfUmUmCmUmUmUmGmAfGmAfUmUmCmsUmsUm |
| siFXIe1-M2S | 267 | GmsAmsAmUmCfUmCfAfAfAmGmAmAmAmUmCmUmUmUm |
| | 268 | AmsAfsAmGmAmUfUmUfCfUmUmUmGmAfGmAfUmUmCmsUmsUm |
| siFXIe1-M3S | 269 | GmsAmsAmUmCfUmCfAfAfAmGmAmAmAmUmCmUmUmUm |
| | 270 | AmsAfsAmGmAmUfUmUmCmUmUmUmGmAfGmAfUmUmCmsUmsUm |
| siFXIe2-M1S | 271 | AmsAmsGmAmAmUmCmUmCfAfAfAmGmAmAmAmUmCmUmUmUm |
| | 272 | AmsAfsAmGmAmUfUmUmCmUmUmUmGmAfGmAfUmUmCmUmUmsUmsGm |
| siFXIe2-M2S | 273 | AmsAmsGmAmAmUmCfUmCfAfAfAmGmAmAmAmUmCmUmUmUm |
| | 274 | AmsAfsAmGmAmUfUmUfCfUmUmUmGmAfGmAfUmUmCmUmUmsUmsGm |
| siFXIe2-M3S | 275 | AmsAmsGmAmAmUmCfUmCfAfAfAmGmAmAmAmUmCmUmUmUm |
| | 276 | AmsAfsAmGmAmUfUmUmCmUmUmUmGmAfGmAfUmUmCmUmUmsUmsGm |
| siFXIe1-M1P1 | 277 | GmAmAmUmCmUmCfAfAfAmGmAmAmAmUmCmUmUmUm |
| | 278 | P1AmAfAmGmAmUfUmUmCmUmUmUmGmAfGmAfUmUmCmUmUm |
| siFXIe1-M2P1 | 279 | GmAmAmUmCfUmCfAfAfAmGmAmAmAmUmCmUmUmUm |
| | 280 | P1AmAfAmGmAmUfUmUfCfUmUmUmGmAfGmAfUmUmCmUmUm |
| siFXIe1-M3P1 | 281 | GmAmAmUmCfUmCfAfAfAmGmAmAmAmUmCmUmUmUm |
| | 282 | P1AmAfAmGmAmUfUmUmCmUmUmUmGmAfGmAfUmUmCmUmUm |
| siFXIe2-M1P1 | 283 | AmAmGmAmAmUmCmUmCfAfAfAmGmAmAmAmUmCmUmUmUm |

TABLE 1e-continued

The sequences of fifth siRNAs of the present disclosure

| siRNA NO. | SEQ ID NO: | Sequence direction 5'-3' |
|---|---|---|
| | 284 | P1AmAfAmGmAmUfUmUmCmUmUmUmGmAfGmAfUmUmCmUmUmUmGm |
| siFXIe2-M2P1 | 285 | AmAmGmAmAmUmCfUmCfAfAfAmGmAmAmAmUmCmUmUmUm |
| | 286 | P1AmAfAmGmAmUfUmUfCfUmUmUmGmAfGmAfUmUmCmUmUmUmGm |
| siFXIe2-M3P1 | 287 | AmAmGmAmAmUmCfUmCfAfAfAmGmAmAmAmUmCmUmUmUm |
| | 288 | P1AmAfAmGmAmUfUmUmCmUmUmUmGmAfGmAfUmUmCmUmUmUmGm |
| siFXIe1-M1SP1 | 289 | GmsAmsAmUmCmUmCfAfAfAmGmAmAmAmUmCmUmUmUm |
| | 290 | P1AmsAfsAmGmAmUfUmUmCmUmUmUmGmAfGmAfUmUmCmsUmsUm |
| siFXIe1-M2SP1 | 291 | GmsAmsAmUmCfUmCfAfAfAmGmAmAmAmUmCmUmUmUm |
| | 292 | P1AmsAfsAmGmAmUfUmUfCfUmUmUmGmAfGmAfUmUmCmsUmsUm |
| siFXIe1-M3SP1 | 293 | GmsAmsAmUmCfUmCfAfAfAmGmAmAmAmUmCmUmUmUm |
| | 294 | P1AmsAfsAmGmAmUfUmUmCmUmUmUmGmAfGmAfUmUmCmsUmsUm |
| siFXIe2-M1SP1 | 295 | AmsAmsGmAmAmUmCmUmCfAfAfAmGmAmAmAmUmCmUmUmUm |
| | 296 | P1AmsAfsAmGmAmUfUmUmCmUmUmUmGmAfGmAfUmUmCmUmUmsUmsGm |
| siFXIe2-M2SP1 | 297 | AmsAmsGmAmAmUmCfUmCfAfAfAmGmAmAmAmUmCmUmUmUm |
| | 298 | P1AmsAfsAmGmAmUfUmUfCfUmUmUmGmAfGmAfUmUmCmUmUmsUmsGm |
| siFXIe2-M3SP1 | 299 | AmsAmsGmAmAmUmCfUmCfAfAfAmGmAmAmAmUmCmUmUmUm |
| | 300 | P1AmsAfsAmGmAmUfUmUmCmUmUmUmGmAfGmAfUmUmCmUmUmsUmsGm |

TABLE 1f

The sequences of sixth siRNAs of the present disclosure

| siRNA NO. | SEQ ID NO: | Sequence direction 5'-3' |
|---|---|---|
| siFXIf1 | 309 | GUACGUGGACUGGAUUCUG |
| | 310 | CAGAAUCCAGUCCACGUACUC |
| siFXIf2 | 311 | GAGUACGUGGACUGGAUUCUG |
| | 312 | CAGAAUCCAGUCCACGUACUCGA |
| siFXIf1-M1 | 313 | GmUmAmCmGmUmGfGfAfCmUmGmGmAmUmUmCmUmGm |
| | 314 | CmAfGmAmAmUfCmCmAmGmUmCmCmAfCmGfUmAmCmUmCm |
| siFXIf1-M2 | 315 | GmUmAmCmGfUmGfGfAfCmUmGmGmAmUmUmCmUmGm |
| | 316 | CmAfGmAmAmUfCmCfAfGmUmCmCmAfCmGfUmAmCmUmCm |
| siFXIf1-M3 | 317 | GmUmAmCmGfUmGfGfAfCmUmGmGmAmUmUmCmUmGm |
| | 318 | CmAfGmAmAmUfCmCmAmGmUmCmCmAfCmGfUmAmCmUmCm |
| siFXIf2-M1 | 319 | GmAmGmUmAmCmGmUmGfGfAfCmUmGmGmAmUmUmCmUmGm |
| | 320 | CmAfGmAmAmUfCmCmAmGmUmCmCmAfCmGfUmAmCmUmCmGmAm |

TABLE 1f-continued

The sequences of sixth siRNAs of the present disclosure

| siRNA NO. | SEQ ID NO: | Sequence direction 5'-3' |
|---|---|---|
| siFXIf2-M2 | 321 | GmAmGmUmAmCmGfUmGfGfAfCmUmGmGmAmUmUmCmUmGm |
| | 322 | CmAfGmAmAmUfCmCfAfGmUmCmCmAfCmGfUmAmCmUmCmGmAm |
| siFXIf2-M3 | 323 | GmAmGmUmAmCmGfUmGfGfAfCmUmGmGmAmUmUmCmUmGm |
| | 324 | CmAfGmAmAmUfCmCmAmGmUmCmCmAfCmGfUmAmCmUmCmGmAm |
| siFXIf1-M1S | 325 | GmsUmsAmCmGmUmGfGfAfCmUmGmGmAmUmUmCmUmGm |
| | 326 | CmsAfsGmAmAmUfCmCmAmGmUmCmCmAfCmGfUmAmCmsUmsCm |
| siFXIf1-M2S | 327 | GmsUmsAmCmGfUmGfGfAfCmUmGmGmAmUmUmCmUmGm |
| | 328 | CmsAfsGmAmAmUfCmCfAfGmUmCmCmAfCmGfUmAmCmsUmsCm |
| siFXIf1-M3S | 329 | GmsUmsAmCmGfUmGfGfAfCmUmGmGmAmUmUmCmUmGm |
| | 330 | CmsAfsGmAmAmUfCmCmAmGmUmCmCmAfCmGfUmAmCmsUmsCm |
| siFXIf2-M1S | 331 | GmsAmsGmUmAmCmGmUmGfGfAfCmUmGmGmAmUmUmCmUmGm |
| | 332 | CmsAfsGmAmAmUfCmCmAmGmUmCmCmAfCmGfUmAmCmUmCmsGmsAm |
| siFXIf2-M2S | 333 | GmsAmsGmUmAmCmGfUmGfGfAfCmUmGmGmAmUmUmCmUmGm |
| | 334 | CmsAfsGmAmAmUfCmCfAfGmUmCmCmAfCmGfUmAmCmUmCmsGmsAm |
| siFXIf2-M3S | 335 | GmsAmsGmUmAmCmGfUmGfGfAfCmUmGmGmAmUmUmCmUmGm |
| | 336 | CmsAfsGmAmAmUfCmCmAmGmUmCmCmAfCmGfUmAmCmUmCmsGmsAm |
| siFXIf1-M1P1 | 337 | GmUmAmCmGmUmGfGfAfCmUmGmGmAmUmUmCmUmGm |
| | 338 | P1CmAfGmAmAmUfCmCmAmGmUmCmCmAfCmGfUmAmCmUmCm |
| siFXIf1-M2P1 | 339 | GmUmAmCmGfUmGfGfAfCmUmGmGmAmUmUmCmUmGm |
| | 340 | P1CmAfGmAmAmUfCmCfAfGmUmCmCmAfCmGfUmAmCmUmCm |
| siFXIf1-M3P1 | 341 | GmUmAmCmGfUmGfGfAfCmUmGmGmAmUmUmCmUmGm |
| | 342 | P1CmAfGmAmAmUfCmCmAmGmUmCmCmAfCmGfUmAmCmUmCm |
| siFXIf2-M1P1 | 343 | GmAmGmUmAmCmGmUmGfGfAfCmUmGmGmAmUmUmCmUmGm |
| | 344 | P1CmAfGmAmAmUfCmCmAmGmUmCmCmAfCmGfUmAmCmUmCmGmAm |
| siFXIf2-M2P1 | 345 | GmAmGmUmAmCmGfUmGfGfAfCmUmGmGmAmUmUmCmUmGm |
| | 346 | P1CmAfGmAmAmUfCmCfAfGmUmCmCmAfCmGfUmAmCmUmCmGmAm |
| siFXIf2-M3P1 | 347 | GmAmGmUmAmCmGfUmGfGfAfCmUmGmGmAmUmUmCmUmGm |
| | 348 | P1CmAfGmAmAmUfCmCmAmGmUmCmCmAfCmGfUmAmCmUmCmGmAm |
| siFXIf1-M1SP1 | 349 | GmsUmsAmCmGmUmGfGfAfCmUmGmGmAmUmUmCmUmGm |
| | 350 | P1CmsAfsGmAmAmUfCmCmAmGmUmCmCmAfCmGfUmAmCmsUmsCm |
| siFXIf1-M2SP1 | 351 | GmsUmsAmCmGfUmGfGfAfCmUmGmGmAmUmUmCmUmGm |
| | 352 | P1CmsAfsGmAmAmUfCmCfAfGmUmCmCmAfCmGfUmAmCmsUmsCm |

TABLE 1f-continued

The sequences of sixth siRNAs of the present disclosure

| siRNA NO. | SEQ ID NO: | Sequence direction 5'-3' |
|---|---|---|
| siFXIf1-M3SP1 | 353 | GmsUmsAmCmGfUmGfGfAfCmUmGmGmAmUmUmCmUmGm |
| | 354 | P1CmsAfsGmAmAmUfCmCmAmGmUmCmCmAfCmGfUmAmCmsUmsCm |
| siFXIf2-M1SP1 | 355 | GmsAmsGmUmAmCmGmUmGfGfAfCmUmGmGmAmUmUmCmUmGm |
| | 356 | P1CmsAfsGmAmAmUfCmCmAmGmUmCmCmAfCmGfUmAmCmUmCmsGmsAm |
| siFXIf2-M2SP1 | 357 | GmsAmsGmUmAmCmGfUmGfGfAfCmUmGmGmAmUmUmCmUmGm |
| | 358 | P1CmsAfsGmAmAmUfCmCfAfGmUmCmCmAfCmGfUmAmCmUmCmsGmsAm |
| siFXIf2-M3SP1 | 359 | GmsAmsGmUmAmCmGfUmGfGfAfCmUmGmGmAmUmUmCmUmGm |
| | 360 | P1CmsAfsGmAmAmUfCmCmAmGmUmCmCmAfCmGfUmAmCmUmCmsGmsAm |

TABLE 1g

The sequences of seventh siRNAs of the present disclosure

| siRNA NO. | SEQ ID NO: | Sequence direction 5'-3' |
|---|---|---|
| siFXIg1 | 369 | AUUUCUGGGUAUUCUUUCA |
| | 370 | UGAAAGAAUACCCAGAAAUCG |
| siFXIg2 | 371 | CGAUUUCUGGGUAUUCUUUCA |
| | 372 | UGAAAGAAUACCCAGAAAUCGCU |
| siFXIg1-M1 | 373 | AmUmUmUmCmUmGfGfGfUmAmUmUmCmUmUmUmCmAm |
| | 374 | UmGfAmAmAmGfAmAmUmAmCmCmCmAfGmAfAmAmUmCmGm |
| siFXIg1-M2 | 375 | AmUmUmUmCfUmGfGfGfUmAmUmUmCmUmUmUmCmAm |
| | 376 | UmGfAmAmAmGfAmAfUfAmCmCmCmAfGmAfAmAmUmCmGm |
| siFXIg1-M3 | 377 | AmUmUmUmCfUmGfGfGfUmAmUmUmCmUmUmUmCmAm |
| | 378 | UmGfAmAmAmGfAmAmUmAmCmCmCmAfGmAfAmAmUmCmGm |
| siFXIg2-M1 | 379 | CmGmAmUmUmUmCmUmGfGfGfUmAmUmUmCmUmUmUmCmAm |
| | 380 | UmGfAmAmAmGfAmAmUmAmCmCmCmAfGmAfAmAmUmCmGmCmUm |
| siFXIg2-M2 | 381 | CmGmAmUmUmUmCfUmGfGfGfUmAmUmUmCmUmUmUmCmAm |
| | 382 | UmGfAmAmAmGfAmAfUfAmCmCmCmAfGmAfAmAmUmCmGmCmUm |
| siFXIg2-M3 | 383 | CmGmAmUmUmUmCfUmGfGfGfUmAmUmUmCmUmUmUmCmAm |
| | 384 | UmGfAmAmAmGfAmAmUmAmCmCmCmAfGmAfAmAmUmCmGmCmUm |
| siFXIg1-M1S | 385 | AmsUmsUmUmCmUmGfGfGfUmAmUmUmCmUmUmUmCmAm |
| | 386 | UmsGfsAmAmAmGfAmAmUmAmCmCmCmAfGmAfAmAmUmsCmsGm |
| siFXIg1-M2S | 387 | AmsUmsUmUmCfUmGfGfGfUmAmUmUmCmUmUmUmCmAm |
| | 388 | UmsGfsAmAmAmGfAmAfUfAmCmCmCmAfGmAfAmAmUmsCmsGm |
| siFXIg1-M3S | 389 | AmsUmsUmUmCfUmGfGfGfUmAmUmUmCmUmUmUmCmAm |
| | 390 | UmsGfsAmAmAmGfAmAmUmAmCmCmCmAfGmAfAmAmUmsCmsGm |

TABLE 1g-continued

| The sequences of seventh siRNAs of the present disclosure | | |
|---|---|---|
| siRNA NO. | SEQ ID NO: | Sequence direction 5'-3' |
| siFXIg2-M1S | 391 | CmsGmsAmUmUmUmCmUmGfGfGfUmAmUmUmCmUmUmUmCmAm |
| | 392 | UmsGfsAmAmAmGfAmAmUmAmCmCmCmAfGmAfAmAmUmCmGmsCmsUm |
| siFXIg2-M2S | 393 | CmsGmsAmUmUmUmCfUmGfGfGfUmAmUmUmCmUmUmUmCmAm |
| | 394 | UmsGfsAmAmAmGfAmAfUfAmCmCmCmAfGmAfAmAmUmCmGmsCmsUm |
| siFXIg2-M3S | 395 | CmsGmsAmUmUmUmCfUmGfGfGfUmAmUmUmCmUmUmUmCmAm |
| | 396 | UmsGfsAmAmAmGfAmAmUmAmCmCmCmAfGmAfAmAmUmCmGmsCmsUm |
| siFXIg1-M1P1 | 397 | AmUmUmUmCmUmGfGfGfUmAmUmUmCmUmUmUmCmAm |
| | 398 | P1UmGfAmAmAmGfAmAmUmAmCmCmCmAfGmAfAmAmUmCmGm |
| siFXIg1-M2P1 | 399 | AmUmUmUmCfUmGfGfGfUmAmUmUmCmUmUmUmCmAm |
| | 400 | P1UmGfAmAmAmGfAmAfUfAmCmCmCmAfGmAfAmAmUmCmGm |
| siFXIg1-M3P1 | 401 | AmUmUmUmCfUmGfGfGfUmAmUmUmCmUmUmUmCmAm |
| | 402 | P1UmGfAmAmAmGfAmAmUmAmCmCmCmAfGmAfAmAmUmCmGm |
| siFXIg2-M1P1 | 403 | CmGmAmUmUmUmCmUmGfGfGfUmAmUmUmCmUmUmUmCmAm |
| | 404 | P1UmGfAmAmAmGfAmAmUmAmCmCmCmAfGmAfAmAmUmCmGmCmUm |
| siFXIg2-M2P1 | 405 | CmGmAmUmUmUmCfUmGfGfGfUmAmUmUmCmUmUmUmCmAm |
| | 406 | P1UmGfAmAmAmGfAmAfUfAmCmCmCmAfGmAfAmAmUmCmGmCmUm |
| siFXIg2-M3P1 | 407 | CmGmAmUmUmUmCfUmGfGfGfUmAmUmUmCmUmUmUmCmAm |
| | 408 | P1UmGfAmAmAmGfAmAmUmAmCmCmCmAfGmAfAmAmUmCmGmCmUm |
| siFXIg1-M1SP1 | 409 | AmsUmsUmUmCmUmGfGfGfUmAmUmUmCmUmUmUmCmAm |
| | 410 | P1UmsGfsAmAmAmGfAmAmUmAmCmCmCmAfGmAfAmAmUmsCmsGm |
| siFXIg1-M2SP1 | 411 | AmsUmsUmUmCfUmGfGfGfUmAmUmUmCmUmUmUmCmAm |
| | 412 | P1UmsGfsAmAmAmGfAmAfUfAmCmCmCmAfGmAfAmAmUmsCmsGm |
| siFXIg1-M3SP1 | 413 | AmsUmsUmUmCfUmGfGfGfUmAmUmUmCmUmUmUmCmAm |
| | 414 | P1UmsGfsAmAmAmGfAmAmUmAmCmCmCmAfGmAfAmAmUmsCmsGm |
| siFXIg2-M1SP1 | 415 | CmsGmsAmUmUmUmCmUmGfGfGfUmAmUmUmCmUmUmUmCmAm |
| | 416 | P1UmsGfsAmAmAmGfAmAmUmAmCmCmCmAfGmAfAmAmUmCmGmsCmsUm |
| siFXIg2-M2SP1 | 417 | CmsGmsAmUmUmUmCfUmGfGfGfUmAmUmUmCmUmUmUmCmAm |
| | 418 | P1UmsGfsAmAmAmGfAmAfUfAmCmCmCmAfGmAfAmAmUmCmGmsCmsUm |
| siFXIg2-M3SP1 | 419 | CmsGmsAmUmUmUmCfUmGfGfGfUmAmUmUmCmUmUmUmCmAm |
| | 420 | P1UmsGfsAmAmAmGfAmAmUmAmCmCmCmAfGmAfAmAmUmCmGmsCmsUm |

TABLE 1h

The sequences of eighth siRNAs of the present disclosure

| siRNA NO. | SEQ ID NO: | Sequence direction 5'-3' |
|---|---|---|
| siFXIh1 | 429 | CAUGAAGGGCAUAAACUAU |
| | 430 | AUAGUUUAUGCCCUUCAUGUC |
| siFXIh2 | 431 | GACAUGAAGGGCAUAAACUAU |
| | 432 | AUAGUUUAUGCCCUUCAUGUCUA |
| siFXIh1-M1 | 433 | CmAmUmGmAmAmGfGfGfCmAmUmAmAmAmCmUmAmUm |
| | 434 | AmUfAmGmUmUfUmAmUmGmCmCmCmUfUmCfAmUmGmUmCm |
| siFXIh1-M2 | 435 | CmAmUmGmAfAmGfGfGfCmAmUmAmAmAmCmUmAmUm |
| | 436 | AmUfAmGmUmUfUmAfUfGmCmCmCmUfUmCfAmUmGmUmCm |
| siFXIh1-M3 | 437 | CmAmUmGmAfAmGfGfGfCmAmUmAmAmAmCmUmAmUm |
| | 438 | AmUfAmGmUmUfUmAmUmGmCmCmCmUfUmCfAmUmGmUmCm |
| siFXIh2-M1 | 439 | GmAmCmAmUmGmAmAmGfGfGfCmAmUmAmAmAmCmUmAmUm |
| | 440 | AmUfAmGmUmUfUmAmUmGmCmCmCmUfUmCfAmUmGmUmCmUmAm |
| siFXIh2-M2 | 441 | GmAmCmAmUmGmAfAmGfGfGfCmAmUmAmAmAmCmUmAmUm |
| | 442 | AmUfAmGmUmUfUmAfUfGmCmCmCmUfUmCfAmUmGmUmCmUmAm |
| siFXIh2-M3 | 443 | GmAmCmAmUmGmAfAmGfGfGfCmAmUmAmAmAmCmUmAmUm |
| | 444 | AmUfAmGmUmUfUmAmUmGmCmCmCmUfUmCfAmUmGmUmCmUmAm |
| siFXIh1-M1S | 445 | CmsAmsUmGmAmAmGfGfGfCmAmUmAmAmAmCmUmAmUm |
| | 446 | AmsUfsAmGmUmUfUmAmUmGmCmCmCmUfUmCfAmUmGmsUmsCm |
| siFXIh1-M2S | 447 | CmsAmsUmGmAfAmGfGfGfCmAmUmAmAmAmCmUmAmUm |
| | 448 | AmsUfsAmGmUmUfUmAfUfGmCmCmCmUfUmCfAmUmGmsUmsCm |
| siFXIh1-M3S | 449 | CmsAmsUmGmAfAmGfGfGfCmAmUmAmAmAmCmUmAmUm |
| | 450 | AmsUfsAmGmUmUfUmAmUmGmCmCmCmUfUmCfAmUmGmsUmsCm |
| siFXIh2-M1S | 451 | GmsAmsCmAmUmGmAmAmGfGfGfCmAmUmAmAmAmCmUmAmUm |
| | 452 | AmsUfsAmGmUmUfUmAmUmGmCmCmCmUfUmCfAmUmGmUmCmsUmsAm |
| siFXIh2-M2S | 453 | GmsAmsCmAmUmGmAfAmGfGfGfCmAmUmAmAmAmCmUmAmUm |
| | 454 | AmsUfsAmGmUmUfUmAfUfGmCmCmCmUfUmCfAmUmGmUmCmsUmsAm |
| siFXIh2-M3S | 455 | GmsAmsCmAmUmGmAfAmGfGfGfCmAmUmAmAmAmCmUmAmUm |
| | 456 | AmsUfsAmGmUmUfUmAmUmGmCmCmCmUfUmCfAmUmGmUmCmsUmsAm |
| siFXIh1-M1P1 | 457 | CmAmUmGmAmAmGfGfGfCmAmUmAmAmAmCmUmAmUm |
| | 458 | P1AmUfAmGmUmUfUmAmUmGmCmCmCmUfUmCfAmUmGmUmCm |
| siFXIh1-M2P1 | 459 | CmAmUmGmAfAmGfGfGfCmAmUmAmAmAmCmUmAmUm |
| | 460 | P1AmUfAmGmUmUfUmAfUfGmCmCmCmUfUmCfAmUmGmUmCm |
| siFXIh1-M3P1 | 461 | CmAmUmGmAfAmGfGfGfCmAmUmAmAmAmCmUmAmUm |
| | 462 | P1AmUfAmGmUmUfUmAmUmGmCmCmCmUfUmCfAmUmGmUmCm |

TABLE 1h-continued

The sequences of eighth siRNAs of the present disclosure

| siRNA NO. | SEQ ID NO: | Sequence direction 5'-3' |
|---|---|---|
| siFXIh2-M1P1 | 463 | GmAmCmAmUmGmAmAmGfGfGfCmAmUmAmAmAmCmUmAmUm |
| | 464 | P1AmUfAmGmUmUfUmAmUmGmCmCmCmUfUmCfAmUmGmUmCmUmAm |
| siFXIh2-M2P1 | 465 | GmAmCmAmUmGmAfAmGfGfGfCmAmUmAmAmAmCmUmAmUm |
| | 466 | P1AmUfAmGmUmUfUmAfUfGmCmCmCmUfUmCfAmUmGmUmCmUmAm |
| siFXIh2-M3P1 | 467 | GmAmCmAmUmGmAfAmGfGfGfCmAmUmAmAmAmCmUmAmUm |
| | 468 | P1AmUfAmGmUmUfUmAmUmGmCmCmCmUfUmCfAmUmGmUmCmUmAm |
| siFXIh1-M1SP1 | 469 | CmsAmsUmGmAmAmGfGfGfCmAmUmAmAmAmCmUmAmUm |
| | 470 | P1AmsUfsAmGmUmUfUmAmUmGmCmCmCmUfUmCfAmUmGmsUmsCm |
| siFXIh1-M2SP1 | 471 | CmsAmsUmGmAfAmGfGfGfCmAmUmAmAmAmCmUmAmUm |
| | 472 | P1AmsUfsAmGmUmUfUmAfUfGmCmCmCmUfUmCfAmUmGmsUmsCm |
| siFXIh1-M3SP1 | 473 | CmsAmsUmGmAfAmGfGfGfCmAmUmAmAmAmCmUmAmUm |
| | 474 | P1AmsUfsAmGmUmUfUmAmUmGmCmCmCmUfUmCfAmUmGmsUmsCm |
| siFXIh2-M1SP1 | 475 | GmsAmsCmAmUmGmAmAmGfGfGfCmAmUmAmAmAmCmUmAmUm |
| | 476 | P1AmsUfsAmGmUmUfUmAmUmGmCmCmCmUfUmCfAmUmGmUmCmsUmsAm |
| siFXIh2-M2SP1 | 477 | GmsAmsCmAmUmGmAfAmGfGfGfCmAmUmAmAmAmCmUmAmUm |
| | 478 | P1AmsUfsAmGmUmUfUmAfUfGmCmCmCmUfUmCfAmUmGmUmCmsUmsAm |
| siFXIh2-M3SP1 | 479 | GmsAmsCmAmUmGmAfAmGfGfGfCmAmUmAmAmAmCmUmAmUm |
| | 480 | P1AmsUfsAmGmUmUfUmAmUmGmCmCmCmUfUmCfAmUmGmUmCmsUmsAm |

TABLE 1i

The sequences of ninth siRNAs of the present disclosure

| siRNA NO. | SEQ ID NO: | Sequence direction 5'-3' |
|---|---|---|
| siFXIi1 | 489 | GGAUUCUGGAGAAAACUCA |
| | 490 | UGAGUUUUCUCCAGAAUCCAG |
| siFXIi2 | 491 | CUGGAUUCUGGAGAAAACUCA |
| | 492 | UGAGUUUUCUCCAGAAUCCAGUC |
| siFXIi1-M1 | 493 | GmGmAmUmUmCmUfGfGfAmGmAmAmAmAmCmUmCmAm |
| | 494 | UmGfAmGmUmUfUmUmCmUmCmCmAmGfAmAfUmCmCmAmGm |
| siFXIi1-M2 | 495 | GmGmAmUmUfCmUfGfGfAmGmAmAmAmAmCmUmCmAm |
| | 496 | UmGfAmGmUmUfUmUfCfUmCmCmAmGfAmAfUmCmCmAmGm |
| siFXIi1-M3 | 497 | GmGmAmUmUfCmUfGfGfAmGmAmAmAmAmCmUmCmAm |
| | 498 | UmGfAmGmUmUfUmUmCmUmCmCmAmGfAmAfUmCmCmAmGm |
| siFXIi2-M1 | 499 | CmUmGmGmAmUmUmCmUfGfGfAmGmAmAmAmAmCmUmCmAm |
| | 500 | UmGfAmGmUmUfUmUmCmUmCmCmAmGfAmAfUmCmCmAmGmUmCm |

TABLE 1i-continued

| The sequences of ninth siRNAs of the present disclosure | | |
|---|---|---|
| siRNA NO. | SEQ ID NO: | Sequence direction 5'-3' |
| siFXIi2-M2 | 501 | CmUmGmGmAmUmUfCmUfGfGfAmGmAmAmAmCmUmCmAm |
| | 502 | UmGfAmGmUmUfUmUfCfUmCmCmAmGfAmAfUmCmCmAmGmUmCm |
| siFXIi2-M3 | 503 | CmUmGmGmAmUmUfCmUfGfGfAmGmAmAmAmCmUmCmAm |
| | 504 | UmGfAmGmUmUfUmUmCmUmCmCmAmGfAmAfUmCmCmAmGmUmCm |
| siFXIi1-M1S | 505 | GmsGmsAmUmUmCmUfGfGfAmGmAmAmAmCmUmCmAm |
| | 506 | UmsGfsAmGmUmUfUmUmCmUmCmCmAmGfAmAfUmCmCmsAmsGm |
| siFXIi1-M2S | 507 | GmsGmsAmUmUfCmUfGfGfAmGmAmAmAmCmUmCmAm |
| | 508 | UmsGfsAmGmUmUfUmUfCfUmCmCmAmGfAmAfUmCmCmsAmsGm |
| siFXIi1-M3S | 509 | GmsGmsAmUmUfCmUfGfGfAmGmAmAmAmCmUmCmAm |
| | 510 | UmsGfsAmGmUmUfUmUmCmUmCmCmAmGfAmAfUmCmCmsAmsGm |
| siFXIi2-M1S | 511 | CmsUmsGmGmAmUmUmCmUfGfGfAmGmAmAmAmCmUmCmAm |
| | 512 | UmsGfsAmGmUmUfUmUmCmUmCmCmAmGfAmAfUmCmCmAmGmsUmsCm |
| siFXIi2-M2S | 513 | CmsUmsGmGmAmUmUfCmUfGfGfAmGmAmAmAmCmUmCmAm |
| | 514 | UmsGfsAmGmUmUfUmUfCfUmCmCmAmGfAmAfUmCmCmAmGmsUmsCm |
| siFXIi2-M3S | 515 | CmsUmsGmGmAmUmUfCmUfGfGfAmGmAmAmAmCmUmCmAm |
| | 516 | UmsGfsAmGmUmUfUmUmCmUmCmCmAmGfAmAfUmCmCmAmGmsUmsCm |
| siFXIi1-M1P1 | 517 | GmGmAmUmUmCmUfGfGfAmGmAmAmAmCmUmCmAm |
| | 518 | P1UmGfAmGmUmUfUmUmCmUmCmCmAmGfAmAfUmCmCmAmGm |
| siFXIi1-M2P1 | 519 | GmGmAmUmUfCmUfGfGfAmGmAmAmAmCmUmCmAm |
| | 520 | P1UmGfAmGmUmUfUmUfCfUmCmCmAmGfAmAfUmCmCmAmGm |
| siFXIi1-M3P1 | 521 | GmGmAmUmUfCmUfGfGfAmGmAmAmAmCmUmCmAm |
| | 522 | P1UmGfAmGmUmUfUmUmCmUmCmCmAmGfAmAfUmCmCmAmGm |
| siFXIi2-M1P1 | 523 | CmUmGmGmAmUmUmCmUfGfGfAmGmAmAmAmCmUmCmAm |
| | 524 | P1UmGfAmGmUmUfUmUmCmUmCmCmAmGfAmAfUmCmCmAmGmUmCm |
| siFXIi2-M2P1 | 525 | CmUmGmGmAmUmUfCmUfGfGfAmGmAmAmAmCmUmCmAm |
| | 526 | P1UmGfAmGmUmUfUmUfCfUmCmCmAmGfAmAfUmCmCmAmGmUmCm |
| siFXIi2-M3P1 | 527 | CmUmGmGmAmUmUfCmUfGfGfAmGmAmAmAmCmUmCmAm |
| | 528 | P1UmGfAmGmUmUfUmUmCmUmCmCmAmGfAmAfUmCmCmAmGmUmCm |
| siFXIi1-M1SP1 | 529 | GmsGmsAmUmUmCmUfGfGfAmGmAmAmAmCmUmCmAm |
| | 530 | P1UmsGfsAmGmUmUfUmUmCmUmCmCmAmGfAmAfUmCmCmsAmsGm |
| siFXIi1-M2SP1 | 531 | GmsGmsAmUmUfCmUfGfGfAmGmAmAmAmCmUmCmAm |
| | 532 | P1UmsGfsAmGmUmUfUmUfCfUmCmCmAmGfAmAfUmCmCmsAmsGm |

TABLE 1i-continued

The sequences of ninth siRNAs of the present disclosure

| siRNA NO. | SEQ ID NO: | Sequence direction 5'-3' |
|---|---|---|
| siFXIi1-M3SP1 | 533 | GmsGmsAmUmUfCmUfGfGfAmGmAmAmAmAmCmUmCmAm |
| | 534 | P1UmsGfsAmGmUmUfUmUmCmUmCmCmAmGfAmAfUmCmCmsAmsGm |
| siFXIi2-M1SP1 | 535 | CmsUmsGmGmAmUmUmCmUfGfGfAmGmAmAmAmAmCmUmCmAm |
| | 536 | P1UmsGfsAmGmUmUfUmUmCmUmCmCmAmGfAmAfUmCmCmAmGmsUmsCm |
| siFXIi2-M2SP1 | 537 | CmsUmsGmGmAmUmUfCmUfGfGfAmGmAmAmAmAmCmUmCmAm |
| | 538 | P1UmsGfsAmGmUmUfUmUfCfUmCmCmAmGfAmAfUmCmCmAmGmsUmsCm |
| siFXIi2-M3SP1 | 539 | CmsUmsGmGmAmUmUfCmUfGfGfAmGmAmAmAmAmCmUmCmAm |
| | 540 | P1UmsGfsAmGmUmUfUmUmCmUmCmCmAmGfAmAfUmCmCmAmGmsUmsCm |

wherein, C, G, U, and A represent the base composition of a nucleotide; m represents that the nucleotide adjacent to the left side of the letter m is a methoxy modified nucleotide; f represents that the nucleotide adjacent to the left side of the letter f is a fluoro modified nucleotide; s represents the two nucleotides adjacent to both sides of the letter s are linked by a thiophosphate linkage; P1 represents that the nucleotide adjacent to the right side of P1 is a 5'-phosphate nucleotide or a 5'-phosphate analogue modified nucleotide; in some embodiments, P1 represents the specific modified nucleotide VP, Ps or P, wherein VP represents that the nucleotide adjacent to the right side of VP is a vinyl phosphate modified nucleotide; Ps represents that the nucleotide adjacent to the right side of Ps is a thiophosphate modified nucleotide; and P represents that the nucleotide adjacent to the right side of the letter P is a 5'-phosphate nucleotide.

In the siRNA or siRNA conjugate of the present disclosure, each pair of adjacent nucleotides is linked via a phosphodiester bond or phosphorothioate diester bond. The non-bridging oxygen or sulfur atom in the phosphodiester bond or phosphorothioate diester bond has negative charges, and may be present in the form of hydroxy or sulfhydryl. Moreover, the hydrogen ion in the hydroxy or sulfhydryl may be partially or completely substituted with a cation. The cation may be any cation, such as one of a metal cation, an ammonium cation $NH_4^+$ or an organic ammonium cation. In order to increase solubility, in one embodiment, the cation is selected from one or more of an alkali metal cation, an ammonium cation formed by a tertiary amine and a quaternary ammonium cation. The alkali metal ion may be $K^+$ and/or $Na^+$, and the cation formed by a tertiary amine may be an ammonium cation formed by triethylamine and/or an ammonium cation formed by N,N-diisopropylethylamine. Thus, the siRNA and the siRNA conjugate of the present disclosure can be at least partially present in the form of salt. In one embodiment, the non-bridging oxygen atom or sulfur atom in the phosphodiester bond or phosphorothioate diester bond at least partly binds to sodium ion, and thus the siRNA and the siRNA conjugate of the present disclosure are present or partially present in the form of sodium salt.

Those skilled in the art clearly understand that a modified nucleotide group can be introduced into the siRNA of the present disclosure by a nucleoside monomer with a corresponding modification. The methods for preparing a nucleoside monomer having the corresponding modification and the methods for introducing a modified nucleotide group into an siRNA are also well-known to those skilled in the art. All modified nucleoside monomers may be either commercially available or prepared by known methods.

Preparation of the siRNA Conjugate as Shown by Formula (308)

The siRNA conjugate as shown by Formula (308) can be prepared by any appropriate synthetic routes.

In some embodiments, the siRNA conjugate as shown by Formula (308) can be prepared by the following method, comprising: sequentially linking nucleoside monomers in 3' to 5' direction according to the type and sequence of the nucleotides in the sense strand and antisense strands of the siRNA respectively, under the condition for phosphoramidite solid phase synthesis, wherein the step of linking each nucleoside monomer includes a four-step reaction of deprotection, coupling, capping, and oxidation or sulfurization; isolating the sense strand and the antisense strand of the siRNA; and annealing; wherein the siRNA is the above siRNA of the present disclosure.

Moreover, the method further comprises: contacting the compound as shown by Formula (321) with a nucleoside monomer or a nucleotide sequence attached to a solid phase support under coupling reaction condition and in the presence of a coupling agent, thereby linking the compound as shown by Formula (321) to the nucleotide sequence via a coupling reaction. Hereinafter, the compound as shown by Formula (321) is also referred to as a conjugation molecule.

Formula (321)

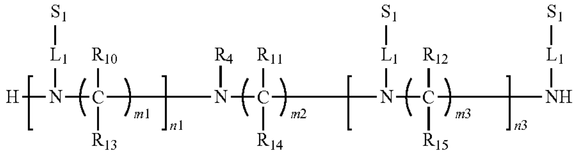

wherein, $R_4$ is a group capable of binding to the siRNA represented by Nu in the compound as shown by Formula (308). In some embodiments, $R_4$ is a group capable of binding to the siRNA represented by Nu via a covalent bond. In some embodiments, $R_4$ is a group capable of being conjugated to any functional group of the siRNA represented by Nu via a phosphodiester bond by a reaction;

Each $S_1$ is independently a group formed by substituting all active hydroxyls in $M_1$ with the group YCOO—, wherein each Y is independently one selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl; in some embodiments, Y is methyl.

The definitions and options of n1, n3, m1, m2, m3, $R_{10}$, $R_{11}$, $R_{12}$, $R_{13}$, $R_{14}$, $R_{15}$, $L_1$, and $M_1$ are respectively as described above.

$R_4$ is selected to achieve the linkage to the N atom on a nitrogenous backbone and to provide a suitable reaction site for synthesizing the siRNA conjugate as shown by Formula (308). In some embodiments, $R_4$ comprises a $R_2$ linking group or a protected $R_2$ linking group, and a functional group than can react with an siRNA to form a structure as shown by Formula (A59).

In some embodiments, $R_4$ comprises a first functional group that can react with a group on the siRNA represented by Nu or a nucleoside monomer to form a phosphite ester, and a second functional group that can react with a hydroxy group or an amino group to form a covalent bond, or comprises a solid phase support linked by the covalent bond. In some embodiments, the first functional group is a phosphoramidite, a hydroxy or a protected hydroxy. In some embodiments, the second functional group is a phosphoramidite, a carboxyl or a carboxylate salt. In some embodiments, the second functional group is a solid phase support linked to the rest of the molecule via a covalent bond which is formed by a hydroxy group or an amino group. In some embodiments, the solid phase support is linked via a phosphoester bond, a carboxylate ester bond or an amide bond. In some embodiments, the solid phase support is a resin.

In some embodiments, the first functional group comprises hydroxy, —$OR_k$ or a group as shown by Formula (C3); the second functional group has a structure as shown by Formula (C1), (C2), (C3), (C1'), or (C3'):

(C1)

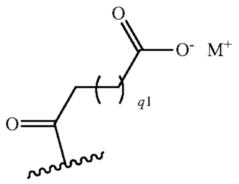

, (C2)

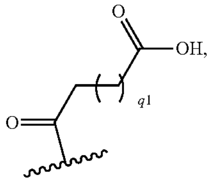

(C3)

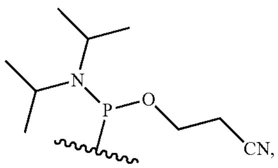

-continued (C1')

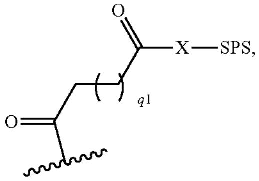

(C3')

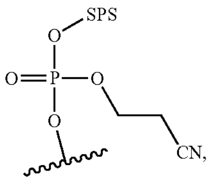

wherein $q_1$ is an integer of 1-4, X is O or NH, $M^+$ is a cation, $R_k$ is a hydroxy protection group, SPS represents a solid phase support, and 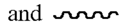 represents the site where a group is covalently linked.

In some embodiments, the first functional group comprises a phosphoramidite group, such as the group as shown by Formula (C3). The phosphoramidite group can form a phosphite ester with a hydroxy at any position (such as a 2'-hydroxy or 3'-hydroxy) on a nucleotide by a coupling reaction, and the phosphite ester can form a phosphodiester bond or phosphorothioate ester bond as shown by Formula (A59) via oxidation or sulfurization, so as to conjugate the conjugation molecule to an siRNA. Here, even if the second functional group does not exist, the compound as shown by Formula (321) could still be conjugated to the nucleotide, while not affecting the obtaining of the siRNA conjugate as shown by Formula (308). Under such circumstances, after obtaining a sense or antisense strand of the siRNA by a method such as phosphoramidite solid phase synthesis, the compound as shown by Formula (321) is reacted with a hydroxy on the nucleotide at the terminal of the nucleotide sequence, and a phosphodiester bond linkage or a phosphorothioate bond linkage is formed in the subsequent oxidation or sulfurization process, thereby conjugating the compound as shown by Formula (321) to the siRNA.

In some embodiments, the first functional group comprises a protected hydroxy. In some embodiments, the second functional group comprises a group that can react with a solid phase support to provide a conjugation molecule comprising a solid phase support. In some embodiments, the second functional group comprises a carboxyl, a carboxylate salt or a phosphoramidite, such as the functional group as shown by Formula (C1), (C2) or (C3). When the second functional group comprises a carboxyl or a carboxylate salt, the compound as shown by Formula (321) can react with a hydroxy or an amino group on a solid phase support (such as a resin) via esterification or amidation reaction, to form a conjugation molecule comprising a solid phase support linked via a carboxylate ester bond. When the second functional group comprises a phosphoramidite functional group, the compound as shown by Formula (321) can couple with a hydroxy group on a universal solid phase support (such as a resin), and form a conjugation molecule comprising a solid phase support linked via a phosphodiester bond by oxidation. Next, starting from the above product linked to a solid phase support, the nucleoside monomers are linked sequentially through a phosphoramidite solid phase synthesis method, so as to obtain a sense strand or an antisense strand of the siRNA linked to a conjugation group.

In the process of phosphoramidite solid phase synthesis, the first functional group is deprotected, and then coupled with a phosphoramidite group on a nucleoside monomer under coupling reaction condition.

In some embodiments, the first functional group comprises a hydroxy or a protected hydroxy group; the second functional group comprises a solid phase support linked via a carboxylate ester bond, an amide bond, or a phosphoester bond, as shown by Formula (C1') or (C3'). In this case, starting from the compound as shown by Formula (321) in place of a solid phase support, the nucleoside monomers are linked sequentially through a phosphoramidite solid phase synthesis method, so as to obtain a sense strand or an antisense strand of the siRNA linked to a conjugation group.

In some embodiments, the carboxylate may be expressed as —$COO^-M^+$, wherein $M^+$ is a cation such as one selected from a metal cation, an ammonium cation $NH_4^+$ and an organic ammonium cation. In one embodiment, the metal cation may be an alkali metal cation, such as $K^+$ or $Na^+$. In order to increase solubility and facilitate the reaction, in some embodiments, the organic ammonium cation is an ammonium cation formed by a tertiary amine or a quaternary ammonium cation, such as an ammonium cation formed by triethylamine or an ammonium cation formed by N,N-diisopropylethylamine. In some embodiments, the carboxylate is a triethylamine carboxylate or an N,N-diisopropylethylamine carboxylate.

In some embodiments, $R_4$ comprises the structure as shown by Formula (B9), (B10), (B9'), (B10'), (B11), (B12), (B11'), or B(12'):

(B9)

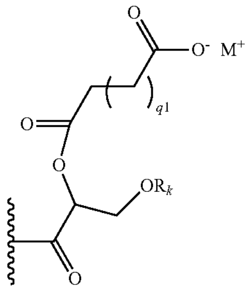

, (B10)

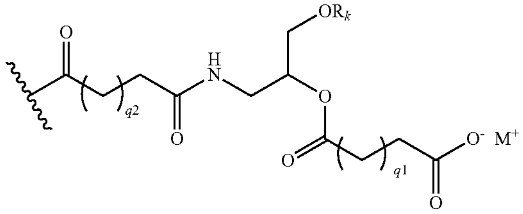

, (B9')

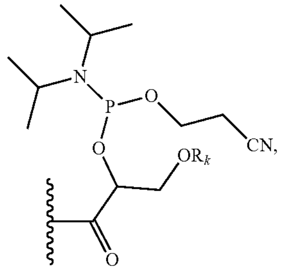

-continued (B10')

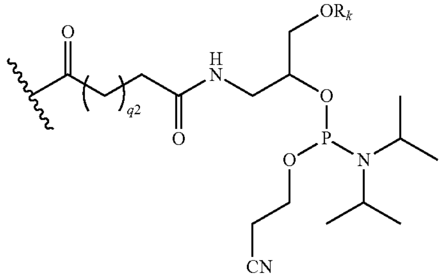

, (B11)

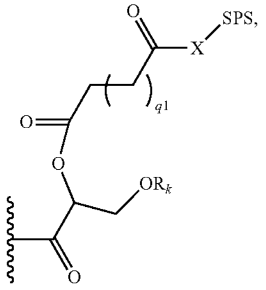

(B12)

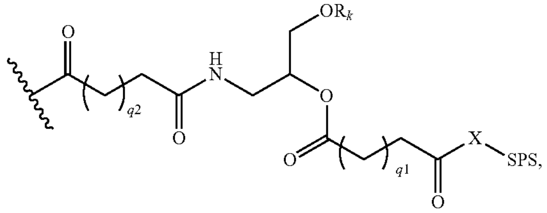

(B11')

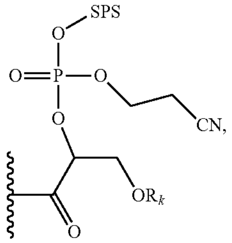

(B12')

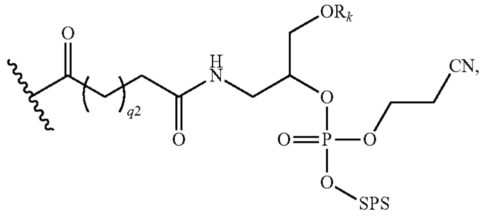

wherein $q_1$ is an integer of 1-4, $q_2$ is an integer of 1-10, X is O or NH, $M^+$ is a cation, $R_k$ is a hydroxy protection group, SPS represents a solid phase support, and ∿∿∿ represents the site where the group is covalently linked. In some embodiments, $q_1$ is 1 or 2. In some embodiments, $q_2$ is an integer of 1-5. In some embodiments, $R_4$ comprises a structure as shown by Formula (B9) or (B10). In some embodiments, $R_4$ comprises a structure as shown by Formula (B11) or (B12).

In some embodiments, $R_k$ is one or more of Tr (trityl), MMTr (4-methoxytrityl), DMTr (4,4'-dimethoxytrityl), and TMTr (4,4',4'-trimethoxytrityl). In some embodiments, $R_k$ may be DMTr, i.e., 4,4'-dimethoxytrityl.

The definition of $L_1$ is as described above.

In some embodiments, $L_1$ is used to link the $M_1$ targeting group to the N atom on the nitrogenous backbone, thereby providing liver targeting function for the siRNA conjugate as shown by Formula (308). In some embodiments, $L_1$ comprises any one of Formulae (A1)-(A26), or combination thereof.

According to the above description, those skilled in the art would easily understand that as compared with the well-known phosphoramidite solid phase synthesis method in the art, the siRNA conjugate as shown by Formula (308) in which the conjugation molecule is linked to any possible position of the nucleotide sequence can be obtained by using the above first functional group and an optional second functional group. For example, the conjugation molecule is linked to a terminal region of the nucleotide sequence, or to a terminal of the nucleotide sequence. Correspondingly, unless otherwise specified, in the following description regarding preparation of the conjugate and/or the conjugation molecule, when referring to the reactions such as "deprotection", "coupling", "capping", "oxidation", "sulfurization", it should be understood that the reaction conditions and agents involved in the well-known phosphoramidite solid phase synthesis method in the art would also apply to these reactions. Exemplary reaction conditions and agents will be described in detail hereinafter.

In some embodiments, each $S_1$ is independently a $M_1$. In some embodiments, each $S_1$ is independently a group formed by protecting at least one active hydroxyl group in $M_1$ with a hydroxyl protection group. In some embodiments, each $S_1$ is independently a group formed by protecting all existing active hydroxyl groups in $M_1$ with hydroxyl protection groups. In some embodiments, any hydroxyl protection group known to a skilled one may be used to protect the active hydroxyl group in $M_1$. In some embodiments, the protected hydroxy can be expressed as the Formula YCOO—, wherein each Y is independently selected from the group consisting of $C_1$-$C_{10}$ alkyl and $C_6$-$C_{10}$ aryl, which is optionally substituted with one or more substituents selected from the group consisting of halo and $C_1$-$C_6$ alkyl. In some embodiments, each Y is independently selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl, and $C_1$-$C_6$ alkylphenyl.

In some embodiments, each $S_1$ is independently selected from the group consisting of Formulae (A46)-(A54):

(A46)

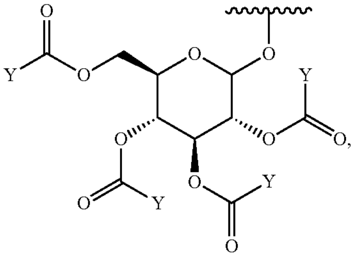

-continued (A47)

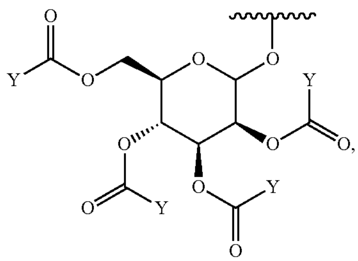

(A48)

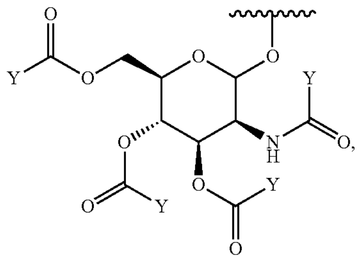

(A49)

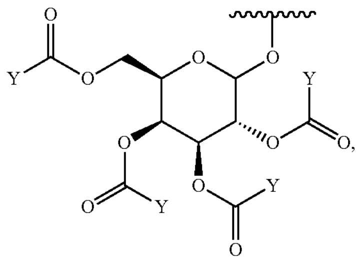

(A50)

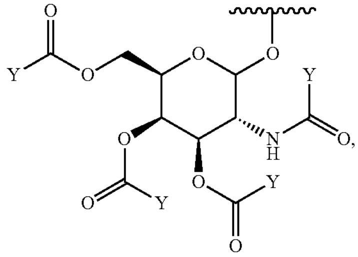

(A51)

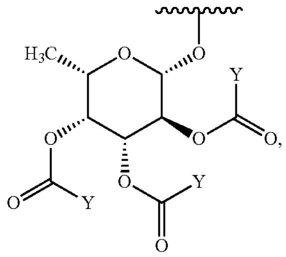

(A52)

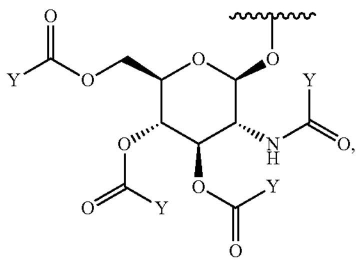

-continued (A53)

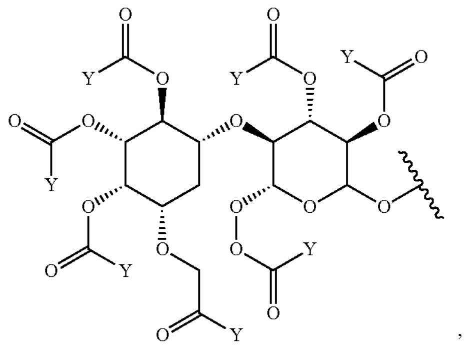

, (A54)

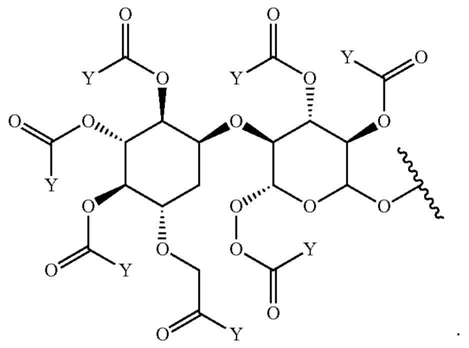

.

In some embodiments, $S_1$ is A49 or A50.

In some embodiments, each Y is independently selected from one of methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl. In some embodiments, Y is methyl.

As mentioned above, the method for preparing the siRNA conjugate as shown by Formula (308) further comprises the following steps: synthesizing the other strand of the siRNA (for example, when a sense strand of the siRNA linked to a conjugation molecule is synthesized in the above step, the method further comprises synthesizing an antisense strand of the siRNA according to the solid phase synthesis method, vice versa), isolating the sense strand and the antisense strand, and annealing. In particular, in the step of isolating, the solid phase support linked to the nucleotide sequence and/or the conjugation molecule is cleaved, and the necessary protection group is removed (in this case, each $S_1$ group in the compound of Formula (321) is converted to the corresponding $M_1$ targeting group), to afford a sense strand (or an antisense strand) of the siRNA linked to a conjugation molecule and the corresponding antisense strand (or sense strand). The sense strand and the antisense strand are annealed to form a double-strand RNA structure, thereby affording the siRNA conjugate as shown by Formula (308).

In some embodiments, the method for preparing the siRNA conjugate as shown by Formula (308) comprises the following steps: contacting the compound as shown by Formula (321) with the first nucleoside monomer at 3' terminal of the sense strand or the antisense strand under coupling reaction condition in the presence of a coupling agent, thereby linking the compound as shown by Formula (321) to the first nucleotide in the sequence; sequentially linking nucleoside monomers in 3' to 5' direction to synthesize a sense or antisense strand of the siRNA according to the type and sequence of the nucleotides in the desired sense or antisense strand under the condition for phosphoramidite solid phase synthesis, wherein the compound as shown by Formula (321) is a compound in which $R_4$ comprises a first functional group and a second functional group, wherein the first functional group comprises a protected hydroxyl and the second functional group has a structure as shown by Formula (C1') or (C3'), and the compound as shown by Formula (321) is deprotected before being linked to the first nucleoside monomer; and the linking of each nucleoside monomer comprises a four-step reaction of deprotection, coupling, capping, and oxidation or sulfurization; thus obtaining a sense or antisense strand of the nucleic acid linked to a conjugation group; sequentially linking nucleoside monomers in 3' to 5' direction to synthesize an antisense or sense strand of the nucleic acid according to the type and sequence of the nucleotides in the sense or antisense strand under the condition for phosphoramidite solid phase synthesis; wherein the linking of each nucleoside monomer includes a four-step reaction of deprotection, coupling, capping, and oxidation or sulfurization; removing the protection group and cleaving the solid phase support; isolating and purifying the sense strand and the antisense strand of the nucleic acid; and annealing.

In some embodiments, the method for preparing the siRNA conjugate as shown by Formula (308) comprises the following steps: according to the type and sequence of the nucleotides in the sense or antisense strand of the double-strand siRNA, sequentially linking nucleoside monomers in 3' to 5' direction to synthesize the antisense and sense strand; wherein the linking of each nucleoside monomer includes a four-step reaction of deprotection, coupling, capping, and oxidation or sulfurization, to obtain the sense strand linked to the solid phase support and the antisense strand linked to the solid phase support; contacting the compound as shown by Formula (321) with the sense strand linked to the solid phase support or the antisense strand linked to the solid phase support under coupling reaction condition in the presence of a coupling agent, thereby linking the compound as shown by Formula (321) to the sense strand or antisense strand; wherein the compound as shown by Formula (321) is a compound in which $R_4$ comprises a first functional group which is a phosphoramidite group; removing the protection group and cleaving the solid phase support; respectively isolating and purifying the sense strand or the antisense strand of the siRNA; and annealing, wherein the sense or antisense strand of the siRNA is linked to a conjugation group.

In some embodiments, the P atom in the Formula (A59) is linked to the 3' terminal of the sense strand of the siRNA, and the method for preparing the siRNA conjugate as shown by Formula (308) comprises:

(1) removing the hydroxyl protection group Pk in the compound as shown by Formula (321), wherein the compound as shown by Formula (321) is a compound in which $R_4$ comprises a first functional group comprising a protected hydroxyl $OR_k$, and a second functional group having a structure as shown by Formulas (C1') or (C3'); contacting the deprotected product with a nucleoside monomer to afford a nucleoside monomer linked to a solid phase support via a conjugation molecule under coupling reaction condition in the presence of a coupling agent;

(2) starting from the nucleoside monomer linked to a solid phase support via the conjugation molecule, synthesizing a sense strand of the siRNA in 3' to 5' direction by a phosphoramidite solid phase synthesis method;

(3) synthesizing an antisense strand of the siRNA by a phosphoramidite solid phase synthesis method; and (4) isolating the sense strand and the antisense strand of the siRNA and annealing the same to afford the siRNA conjugate as shown by Formula (308).

Therein, in step (1), the method for removing the protection group $R_k$ in the compound as shown by Formula (321) comprises contacting the compound as shown by Formula (321) with a deprotection agent under deprotection condition. The deprotection condition comprises a temperature of 0-50° C., and in some embodiments, 15-35° C., and a reaction time of 30-300 seconds, and in some embodiments, 50-150 seconds. The deprotection agent may be selected from one or more of trifluoroacetic acid, trichloroacetic acid, dichloroacetic acid, and monochloroacetic acid, and in some embodiments, dichloroacetic acid. The molar ratio of the deprotection agent to the compound as shown by Formula (321) is 10:1 to 1000:1, and in some embodiments, 50:1 to 500:1.

The coupling reaction condition and the coupling agent may be any condition and agent suitable for the above coupling reaction. In some embodiments, the same condition and agent as those of the coupling reaction in the solid phase synthesis method can be used.

In some embodiments, the coupling reaction condition comprises a reaction temperature of 0-50° C., and in some embodiments, 15-35° C. The molar ratio of the compound as shown by Formula (321) to the nucleoside monomer is 1:1 to 1:50, and in some embodiments, 1:2 to 1:5. The molar ratio of the compound as shown by Formula (321) to the coupling agent may be 1:1 to 1:50, and in some embodiments, 1:3 to 1:10. The reaction time is 200-3,000 seconds, and in some embodiments, 500-1,500 seconds. The coupling agent is selected from one or more of 1H-tetrazole, 5-ethylthio-1H-tetrazole and 5-benzylthio-1H-tetrazole, and in some embodiments, is 5-ethylthio-1H-tetrazole. The coupling reaction may be performed in an organic solvent. The organic solvent is selected from one or more of anhydrous acetonitrile, anhydrous DMF and anhydrous dichloromethane, and in some embodiments, is anhydrous acetonitrile. With respect to the compound as shown by Formula (321), the amount of the organic solvent is 3-50 L/mol, and in some embodiments, 5-20 L/mol.

In step (2), starting from the nucleoside monomer linked to a solid phase support via a conjugation molecule prepared in the above steps, a sense strand SS of the second siRNA conjugate is synthesized in 3' to 5' direction by the phosphoramidite solid phase synthesis method. In this case, the conjugation group is linked to 3' terminal of the resultant sense strand.

Other conditions for the solid phase synthesis in steps (2) and (3), including the deprotection condition for the nucleoside monomer, the type and amount of the deprotection agent, the coupling reaction condition, the type and amount of the coupling agent, the capping reaction condition, the type and amount of the capping agent, the oxidation reaction condition, the type and amount of the oxidation agent, the sulfurization reaction condition, and the type and amount of the sulfurization agent, adopt various agents, amounts, and conditions conventionally used in the art.

In some embodiments, for example, the solid phase synthesis in steps (2) and (3) can be performed by using the following conditions:

The deprotection condition for the nucleoside monomer comprises a reaction temperature of 0-50° C., and in some embodiments, 15-35° C., and a reaction time of 30-300 seconds, and in some embodiments, 50-150 seconds. The deprotection agent may be selected from one or more of trifluoroacetic acid, trichloroacetic acid, dichloroacetic acid, and monochloroacetic acid, and in some embodiments, is dichloroacetic acid. The molar ratio of the deprotection agent to the protection group 4,4'-dimethoxytrityl on the solid phase support is 2:1 to 100:1, and in some embodiments, 3:1 to 50:1.

The coupling reaction condition comprises a reaction temperature of 0-50° C., and in some embodiments, 15-35° C. The molar ratio of the nucleic acid sequence linked to the solid phase support to the nucleoside monomer is 1:1 to 1:50, and in some embodiments, 1:5 to 1:15. The molar ratio of the nucleic acid sequence linked to the solid phase support to the coupling agent is 1:1 to 1:100, and in some embodiments, 1:50 to 1:80. The selection of the reaction time and the coupling agent is the same as above.

The capping reaction condition comprises a reaction temperature of 0-50° C., and in some embodiments, 15-35° C., and a reaction time of 5-500 seconds, and in some embodiments, 10-100 seconds. The selection of the capping agent is the same as above. The molar ratio of the total amount of the capping agent to the nucleic acid sequence linked to the solid phase support is 1:100 to 100:1, and in some embodiments, is 1:10 to 10:1. In the case where equimolar acetic anhydride and N-methylimidazole are used as a capping agent, the molar ratio of acetic anhydride, N-methylimidazole, and the nucleic acid sequence linked to the solid phase support may be 1:1:10-10:10:1, and in some embodiments, is 1:1:2-2:2:1.

The oxidation reaction condition comprises a reaction temperature of 0-50° C., and in some embodiments, 15-35° C., and a reaction time of 1-100 seconds, and in some embodiments, 5-50 seconds. In some embodiments, the oxidation agent is iodine (in some embodiments provided as iodine water). The molar ratio of the oxidation agent to the nucleic acid sequence linked to the solid phase support in the coupling step may be 1:1 to 100:1, and in some embodiments, is 5:1 to 50:1. In some embodiments, the oxidation reaction is performed in a mixed solvent in which the ratio of tetrahydrofuran:water:pyridine is 3:1:1-1:1:3. The sulfurization reaction condition comprises a reaction temperature of 0-50° C., and in some embodiments, 15-35° C., and a reaction time of 50-2,000 seconds, and in some embodiments, 100-1,000 seconds. in some embodiments, the sulfurization agent is xanthane hydride. The molar ratio of the sulfurization agent to the nucleic acid sequence linked to the solid phase support in the coupling step is 10:1 to 1,000:1, and in some embodiments, is 10:1 to 500:1. In some embodiments, the sulfurization reaction is performed in a mixed solvent in which the ratio of acetonitrile:pyridine is 1:3-3:1.

The method further comprises isolating the sense strand and the antisense strand of the siRNA after linking all nucleoside monomers and before the annealing. Methods for isolation are well-known to those skilled in the art and generally comprise cleaving the synthesized nucleotide sequence from the solid phase support, removing the protection groups on the bases, phosphate groups and ligands, purifying, and desalting.

The synthesized nucleotide sequence may be cleaved from the solid phase support, and the protection groups on the bases, phosphate groups and ligands are removed, according to conventional cleavage and deprotection methods in the synthesis of siRNAs. For example, the resultant nucleotide sequence linked to the solid phase support is contacted with concentrated aqueous ammonia; during deprotection, the protection group YCOO— in groups A46-A54 is converted to a hydroxyl group, and thus the $S_1$ groups are converted to corresponding $M_1$ groups, providing the siRNA conjugate as shown by Formula (308); wherein the concentrated aqueous ammonia may be aqueous ammonia of a concentration of 25-30 wt %. With respect to the target siRNA sequence, the amount of the concentrated aqueous ammonia may be 0.2 ml/μmol-0.8 ml/μmol.

When there is at least one 2'-TBDMS protection on the synthesized nucleotide sequence, the method further comprises contacting the nucleotide sequence removed from the solid phase support with triethylamine trihydrofluoride to remove the 2'-TBDMS protection. Here, the corresponding nucleoside in the resultant target siRNA sequence has a free 2'-hydroxy. With respect to the target siRNA sequence, the amount of pure triethylamine trihydrofluoride may be 0.4 ml/μmol-1.0 ml/μmol. As such, the siRNA conjugate as shown by Formula (308) can be obtained.

Methods for purification and desalination are well-known to those skilled in the art. For example, nucleic acid purification may be performed using a preparative ion chromatography purification column with a gradient elution of NaBr or NaCl; after collection and combination of the product, the desalination may be performed using a reverse phase chromatography purification column.

In the resultant siRNA conjugate as shown by Formula (308), the non-bridging oxygen or sulfur atom in the phosphodiester bond or phosphorothioate diester bond between the nucleotides substantially binds to sodium ion, and the siRNA conjugate as shown by Formula (308) is substantially present in the form of a sodium salt. The well-known ion-exchange methods may be used, in which the sodium ion may be replaced with hydrogen ion and/or other cations, thereby providing other forms of siRNA conjugates as shown by Formula (308). The cations are as described above.

During synthesis, the purity and molecular weight of the nucleic acid sequence may be determined at any time, in order to better control the synthesis quality. Such determination methods are well-known to those skilled in the art. For example, the purity of the nucleic acid may be determined by ion exchange chromatography, and the molecular weight may be determined by liquid chromatography-mass spectrometry (LC-MS).

Methods for annealing are also well-known to those skilled in the art. For example, the synthesized sense strand (S strand) and the antisense strand (AS strand) may be simply mixed in water for injection at an equimolar ratio, heated to 70-95° C., and then cooled at room temperature to form a double-stranded structure via hydrogen bond. Hence, the siRNA conjugate as shown by Formula (308) can be obtained.

After having obtained the conjugate, in some embodiments, the synthesized siRNA conjugate as shown by Formula (308) can also be characterized by the means such as molecular weight detection using the methods such as liquid chromatography-mass spectrometry, to confirm that the synthesized siRNA conjugate is the siRNA conjugate as shown by Formula (308) as a designed target, and the synthesized siRNA sequence is the desired siRNA sequence, for example, is one of the sequences listed in Table 1.

The compound as shown by Formula (321) may be obtained by the following preparation method comprising: contacting a compound as shown by Formula (313) with a cyclic anhydride in an organic solvent under esterification reaction condition in the presence of a base and an esterification catalyst; ion exchanging and isolating the compound as shown by Formula (321):

Formula (313)

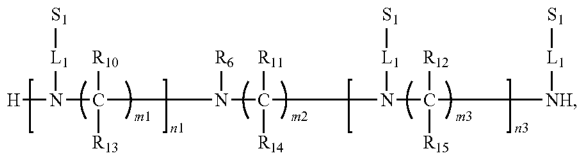

wherein the definitions and options of n1, n3, m1, m2, m3, $R_{10}$, $R_{11}$, $R_{12}$, $R_{13}$, $R_{14}$, $R_{15}$, $L_1$, and $S_1$ are respectively as described above;

$R_6$ is a group for providing $R_4$ of Formula (321); in some embodiments, $R_6$ has a structure as shown by Formula (A61):

(A61)

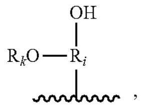

wherein $R_i$ is any group capable of linking to the N atom on the nitrogenous backbone, linking to $R_kO$ and linking to a free hydroxy group; $R_k$ is a hydroxy protection group. In this case, a compound as shown by Formula (321) is obtained, wherein $R_4$ comprises a first functional group as a hydroxy protection group and a second functional group which comprises a structure as shown by Formula (C1) or (C2).

The esterification reaction condition includes a reaction temperature of 0-100° C. and a reaction time of 8-48 hours. In some embodiments, the esterification reaction condition comprises a reaction temperature of 10-40° C. and a reaction time of 20-30 hours.

In some embodiments, the organic solvent comprises one or more of an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran, the ether solvent is diethyl ether and/or methyl tertbutyl ether, and the haloalkane solvent is one or more of dichloromethane, trichloromethane and 1,2-dichloroethane.

In some embodiments, the organic solvent is dichloromethane. With respect to the compound as shown by Formula (313), the amount of the organic solvent is 3-50 L/mol, and in some embodiments, 5-20 L/mol.

In some embodiments, the cyclic anhydride is one of succinic anhydride, glutaric anhydride, adipic anhydride or pimelic anhydride, and in some embodiments, the cyclic anhydride is succinic anhydride. The molar ratio of the cyclic anhydride to the compound as shown by Formula (313) is 1:1 to 10:1, and in some embodiments, 2:1 to 5:1.

The esterification catalyst may be any catalyst capable of catalyzing esterification, such as 4-dimethylaminopyridine. The molar ratio of the catalyst to the compound as shown by Formula (313) is 1:1 to 10:1, and in some embodiments, is 2:1 to 5:1.

In some embodiments, the base may be any inorganic base, organic base or combination thereof. Considering solubility and product stability, the base may be, for example, a tertiary amine. In some embodiments, the tertiary amine is triethylamine or N,N-diisopropylethylamine. The molar ratio of the tertiary amine to the compound as shown by Formula (313) is 1:1 to 20:1, and in some embodiments, 3:1 to 10:1.

The ion exchange serves the function of converting the compound as shown by Formula (321) into a desired form of carboxylic acid or carboxylic salt and the methods of ion exchange are well-known to those skilled in the art. The above conjugation molecule in which the cation is $M^+$ may be obtained by using suitable ion exchange solution and ion exchange condition, which are omitted herein. In some embodiments, the ion exchange reaction is performed using a triethylamine phosphate solution, and the concentration of the triethylamine phosphate solution is 0.2-0.8 M. In some embodiments, the concentration of the triethylamine phosphate solution is 0.4-0.6 M, and with respect to the compound as shown by Formula (313), the amount of the triethylamine phosphate solution is 3-6 L/mol, and in further embodiments, 4-5 L/mol.

The compound as shown by Formula (321) may be isolated from the reaction mixture using any suitable isolation methods. In some embodiments, the compound as shown by Formula (321) may be isolated by removal of solvent via evaporation followed by chromatography. For example, the following two chromatographic conditions can be used for isolation: (1) normal phase purification of silica gel: 200-300 mesh silica gel filler, with gradient elution of 1 wt % triethylamine-containing dichloromethane:methanol=100:18-100:20; or (2) reverse phase purification: C18 and C8 reverse phase filler, with gradient elution of methanol:acetonitrile=0.1:1-1:0.1. In some embodiments, the solvent may be directly removed to obtain a crude product of the compound as shown by Formula (321), which may be directly used in subsequent reactions.

In some embodiments, the method for preparing the compound as shown by Formula (321) further comprises: further contacting the product obtained by the above ion exchanging reaction with a solid phase support with amino or hydroxy groups in an organic solvent under condensation reaction condition in the presence of a condensation agent, a condensation catalyst and a tertiary amine. In this case, a compound as shown by Formula (321) is obtained, wherein $R_4$ comprises a first functional group which comprises a hydroxy protection group and a second functional group which comprises a structure as shown by Formula (C1').

The solid phase support is one of the supports used in solid phase synthesis of siRNA, some of which are well-known to those skilled in the art. For example, the solid phase support may be selected from the solid phase supports containing active hydroxy or amino functional group(s), and in some embodiments, is an amino or hydroxy resin. In some embodiments, the amino or hydroxy resin has the following parameters: particle size of 100-400 mesh, and surface amino or hydroxy loading of 0.2-0.5 mmol/g. The ratio of the compound as shown by Formula (321) to the solid phase support is 10-400 μmol compound per gram of the solid phase support (μmol/g). In some embodiments, the ratio of the compound as shown by Formula (321) to the solid phase support is 50 μmol/g to 200 μmol/g.

The organic solvent may be any suitable solvent or mixed solvent known to those skilled in the art. In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran; the ether solvent is diethyl ether and/or methyl tert-butyl ether; the haloalkane solvent is one or more of dichloromethane, trichloromethane and 1,2-dichloroethane. In some embodiments, the organic solvent is acetonitrile. With respect to the compound as shown by Formula (321), the amount of the organic solvent is 20-200 L/mol, and in some embodiments, 50-100 L/mol.

In some embodiments, the condensation agent may be benzotriazol-1-yl-oxytripyrrolidino phosphonium hexafluorophosphate (PyBop), 3-diethoxyphosphoryl-1,2,3-benzotrizin-4(3H)-one (DEPBT) and/or O-benzotriazol-tetramethyluronium hexafluorophosphate. In some embodiments, the condensation agent is O-benzotriazol-tetramethyluronium hexafluorophosphate. The molar ratio of the condensation agent to the compound as shown by Formula (321) is 1:1 to 20:1, and in some embodiments, 1:1 to 5:1.

In some embodiments, the tertiary amine is triethylamine and/or N,N-diisopropylethylamine, and in some embodiments, N,N-diisopropylethylamine. The molar ratio of the tertiary amine to the compound as shown by Formula (321) is 1:1 to 20:1, and in some embodiments, 1:1 to 5:1.

In some embodiments, the method for preparing the compound as shown by Formula (321) further comprises: contacting the resultant condensation product with a capping agent and an acylation catalyst in an organic solvent under capping reaction condition, and isolating the compound as shown by Formula (321). The capping reaction is used to remove any active functional group that does not completely react, so as to avoid producing unnecessary by-products in subsequent reactions. The capping reaction condition comprises a reaction temperature of 0-50° C., and in some embodiments, 15-35° C., and a reaction time of 1-10 hours, and in some embodiments, 3-6 hours. The capping agent may be the capping agent used in solid phase synthesis of siRNA, which are well-known to those skilled in the art.

In some embodiments, the capping agent is composed of a capping agent 1 (cap1) and a capping agent 2 (cap2). The cap1 is N-methylimidazole, and in some embodiments, provided as a mixed solution of N-methylimidazole in pyridine/acetonitrile, wherein the volume ratio of pyridine to acetonitrile is 1:10 to 1:1, and in some embodiments, 1:3 to 1:1. In some embodiments, the ratio of the total volume of pyridine and acetonitrile to the volume of N-methylimidazole is 1:1 to 10:1, and in some embodiments, 3:1 to 7:1. The cap2 is acetic anhydride, and in some embodiments, provided as a solution of acetic anhydride in acetonitrile, wherein the volume ratio of acetic anhydride to acetonitrile is 1:1 to 1:10, and in further embodiments, 1:2 to 1:6.

In some embodiments, the ratio of the volume of the mixed solution of N-methylimidazole in pyridine/acetonitrile to the mass of the compound as shown by Formula (321) is 5 ml/g-50 ml/g, and in some embodiments, 15 ml/g-30 ml/g. The ratio of the volume of the solution of acetic anhydride in acetonitrile to the weight of the compound as shown by Formula (321) is 0.5 ml/g-10 ml/g, and in some embodiments, 1 ml/g-5 ml/g.

In some embodiments, the capping agent comprises equimolar acetic anhydride and N-methylimidazole. In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the organic solvent is acetonitrile. With respect to the compound as shown by Formula (321), the amount of the organic solvent is 10-50 L/mol, and in some embodiments, 5-30 L/mol.

In some embodiments, the acylation catalyst may be selected from any catalyst that may be used for esterification condensation or amidation condensation, such as alkaline heterocyclic compounds. In some embodiments, the acylation catalyst is 4-dimethylaminopyridine. The mass ratio of the catalyst to the compound as shown by Formula (321) is 0.001:1 to 1:1, and in some embodiments, 0.01:1 to 0.1:1.

In some embodiments, the compound as shown by Formula (321) may be isolated from the reaction mixture by any suitable separation methods. In some embodiments, the compound as shown by Formula (321) may be obtained by thoroughly washing with an organic solvent and filtering to remove unreacted reactants, excess capping agent and other impurities, wherein the organic solvent is selected from acetonitrile, dichloromethane and methanol. In some embodiments, the organic solvent is acetonitrile.

In some embodiments, the preparation method of the conjugation molecule as shown by Formula (321) comprises contacting a compound as shown by Formula (313) with a phosphorodiamidite in an organic solvent under coupling reaction condition in the presence of a coupling agent, and isolating the compound as shown by Formula (321). In this case, a compound as shown by Formula (321) is obtained, wherein $R_4$ comprises a first functional group comprising a hydroxy protection group and a second functional group comprising a structure as shown by Formula (C3).

In some embodiments, the coupling reaction condition comprises: a reaction temperature of 0-50° C., such as 15-35° C.; the molar ratio of the compound as shown by Formula (313) to the phosphorodiamidite of 1:1 to 1:50, such as 1:5 to 1:15; the molar ratio of the compound as shown by Formula (313) to the coupling agent of 1:1 to 1:100, such as 1:50 to 1:80; and a reaction time of 200-3,000 seconds, such as 500-1,500 seconds. The phosphorodiamidite may be, for example, bis(diisopropylamino)(2-cyanoethoxy)phosphine, which may be commercially available or synthesized according to the methods well-known in the art. The coupling agent is selected from one or more of 1H-tetrazole, 5-ethylthio-1H-tetrazole and 5-benzylthio-1H-tetrazole, such as 5-ethylthio-1H-tetrazole. The coupling reaction may be performed in an organic solvent. The organic solvent is selected from one or more of anhydrous acetonitrile, anhydrous DMF and anhydrous dichloromethane, such as anhydrous acetonitrile. In some embodiments, with respect to the compound as shown by Formula (313), the amount of the organic solvent is 3-50 L/mol, such as 5-20 L/mol. By coupling reaction, the hydroxy group in the compound as shown by Formula (313) reacts with the phosphorodiamidite to form a phosphoramidite group. In some embodiments, the solvent may be directly removed to afford a crude product of the compound as shown by Formula (321), which may be directly used in subsequent reactions.

In some embodiments, the preparation method of the compound as shown by Formula (321) further comprises the following steps: further contacting the isolated product with a solid phase support with hydroxy groups in an organic solvent under coupling reaction condition in the presence of a coupling agent, followed by capping, oxidation, and isolation, to afford the compound as shown by Formula (321), wherein $R_4$ comprises a first functional group comprising a hydroxy protection group and a second functional group comprising a structure as shown by Formula (C3').

In some embodiments, the solid phase support is a solid support well-known in the art used in solid phase synthesis of nucleic acid, such as, a deprotected commercially available universal solid phase support (NittoPhase®HL UnyLinker™ 300 Oligonucleotide Synthesis Support, Kinovate Life Sciences, as shown by Formula B80):

(B80)

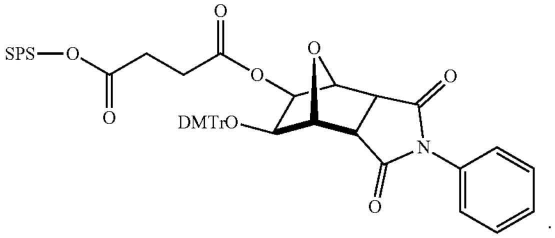

A deprotection reaction is well-known to those skilled in the art. In some embodiments, the deprotection condition comprises a temperature of 0-50° C., such as 15-35° C., and a reaction time of 30-300 seconds, such as 50-150 seconds. The deprotection agent may be selected from one or more of trifluoroacetic acid, trichloroacetic acid, dichloroacetic acid, and monochloroacetic acid. In some embodiments, the deprotection agent is dichloroacetic acid. The molar ratio of the deprotection agent to the protection group -DMTr (4,4'-dimethoxytrityl) on the solid phase support is 2:1 to 100:1, such as 3:1 to 50:1. Through such deprotection, reactive free hydroxy groups are obtained on the surface of the solid phase support, for facilitating the subsequent coupling reaction.

The coupling reaction condition and the coupling agent may be selected as above. Through the coupling reaction, the free hydroxy groups formed in the deprotection react with the phosphoramidite groups, so as to form a phosphite ester linkage.

In some embodiments, the capping reaction condition comprises a temperature of 0-50° C., such as 15-35° C., and a reaction time of 5-500 seconds, such as 10-100 seconds. The capping reaction is carried out in the presence of a capping agent. The selection and amount of the capping agent are as described above.

The oxidation reaction condition comprises a temperature of 0-50° C., such as 15-35° C., and a reaction time of 1-100 seconds, such as 5-50 seconds. The oxidation agent may be, for example, iodine (in some embodiments, provided as iodine water). In some embodiments, the molar ratio of the oxidation agent to the nucleic acid sequence linked to the solid phase support is 1:1 to 100:1, such as, may be 5:1 to 50:1. In some embodiments, the oxidation reaction is performed in a mixed solvent in which the ratio of tetrahydrofuran:water:pyridine=3:1:1-1:1:3.

In some embodiments, $R_6$ is one of the groups of Formula B7 or B8:

(B7)

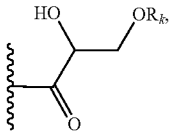

(B8)

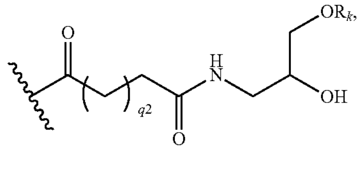

wherein the definition of q2 is as described above.

In this case, the compound as shown by Formula (313) may be obtained by the following preparation method, comprising: contacting the compound as shown by Formula (314) with a compound as shown by Formula (A-1) or (A-2) in an organic solvent under amidation reaction condition in the presence of a condensation agent for amidation reaction and a tertiary amine, followed by isolation:

Formula (314)

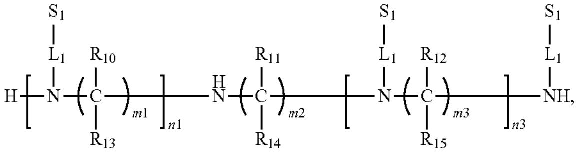

(A-1)

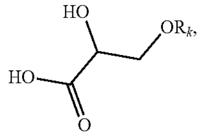

(A-2)

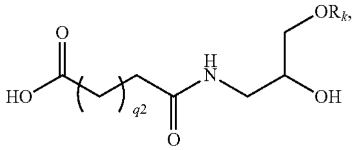

wherein the definitions and options of n1, n3, m1, m2, m3, $R_{10}$, $R_{11}$, $R_{12}$, $R_{13}$, $R_{14}$, $R_{15}$, $L_1$, $S_1$, $q_2$, and $R_k$ are respectively as described above.

The amidation reaction condition may comprise a reaction temperature of 0-100° C. and a reaction time of 1-48 hours. In some embodiments, the amidation reaction condition is a reaction temperature of 10-40° C. and a reaction time of 2-16 hours.

In some embodiments, the organic solvent is one or more of an alcohol solvent, an epoxy solvent, an ether solvent, an haloalkane solvent, dimethyl sulfoxide, N,N-dimethylformamide, and N,N-diisopropylethylamine. In some embodiments, the alcohol solvent is one or more of methanol, ethanol and propanol, and in some embodiments, ethanol. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is dichloromethane. With respect to the compound as shown by Formula (314), the amount of the organic solvent is 3-50 L/mol, and in some embodiments, 3-20 L/mol.

In some embodiments, the condensation agent for amidation reaction is benzotriazol-1-yl-oxytripyrrolidinophosphonium hexafluorophosphate, 3-diethoxyphosphoryl-1,2,3-benzotrizin-4(3H)-one, 4-(4,6-dimethoxytriazin-2-yl)-4-methylmorpholine hydrochloride, 2-ethoxy-1-ethoxycarbonyl-1,2-dihydroquinoline (EEDQ), or O-benzotriazol-tetramethyluronium hexafluorophosphate, and in further embodiments, 3-diethoxyphosphoryl-1,2,3-benzotrizin-4(3H)-one. The molar ratio of the condensation agent for amidation reaction to the compound as shown by Formula (314) may be 1:1 to 10:1, and in some embodiments, 2.5:1 to 5:1.

In some embodiments, the tertiary amine is triethylamine or N,N-diisopropylethylamine, and in some embodiments, N,N-diisopropylethylamine. The molar ratio of the tertiary amine to the compound as shown by Formula (314) is 3:1 to 20:1, and in some embodiments, 5:1 to 10:1.

The compounds as shown by Formula (A-1) and (A-2) may be prepared by any suitable means. For example, when $R_k$ is a DMTr group, the compound as shown by Formula (A-1) may be prepared by reacting calcium glycerate with DMTrCl. Similarly, the compound as shown by Formula (A-2) may be prepared by firstly contacting 3-amino-1,2-propanediol with a cyclic anhydride and then reacting with DMTrCl, wherein the cyclic anhydride may have 4-13 carbon atoms, and in some embodiments, 4-8 carbon atoms. Those skilled in the art would easily understand that the selections of different cyclic anhydrides correspond to different values for q2 in the compound as shown by Formula (A-2). For example, when the cyclic anhydride is succinic anhydride, q2=1; when the cyclic anhydride is glutaric anhydride, q2=2, and so on.

In some variations, the compound as shown by Formula (313) can also be prepared by sequentially reacting the compound as shown by Formula (314) with the cyclic anhydride, 3-amino-1,2-propanediol and DMTrCl. Those skilled in the art would easily understand that these variations would not affect the structure and function of the compound as shown by Formula (313), and these variations are readily realized by those skilled in the art on the basis of the above methods.

Similarly, the compound as shown by Formula (313) may be isolated from the reaction mixture by any suitable isolation methods. In some embodiments, the compound as shown by Formula (313) may be isolated by removal of solvent via evaporation followed by chromatography. For example, the following two chromatographic conditions may be used for isolation: (1) normal phase purification of silica gel: 200-300 mesh silica gel filler, with gradient elution of petroleum ether:ethyl acetate:dichloromethane:N,N-dimethylformamide=1:1:1:0.5-1:1:1:0.6; and (2) reverse phase purification: C18 and C8 reverse phase fillers, with gradient elution of methanol:acetonitrile=0.1:1-1:0.1. In some embodiments, the solvent may be directly removed to afford a crude product of the compound as shown by Formula (313), which may be directly used in subsequent reactions.

In some embodiments, the compound as shown by Formula (314) may be obtained by the following preparation method, comprising: contacting the compound as shown by Formula (320) with the compound as shown by Formula (316) in an organic solvent under condensation reaction condition in the presence of a condensation agent for amidation reaction and a tertiary amine, followed by isolation:

Formula (316)

$S_1$—$L_1$—OH

Formula (320)

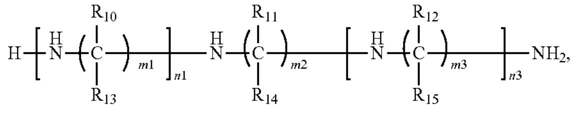

wherein the definitions and options of n1, n3, m1, m2, m3, $R_{10}$, $R_{11}$, $R_{12}$, $R_{13}$, $R_{14}$, and $R_{15}$ are respectively as described above.

The compound as shown by Formula (316) can be, such as, compound disclosed in J. Am. Chem. Soc. 2014, 136, 16958-16961. Alternatively, the compounds as shown by Formula (316) may be prepared by those skilled in the art via various methods. For example, some compounds as shown by Formula (316) may be prepared according to the method disclosed in Example 1 of the U.S. Pat. No. 8,106,022 B2, which is incorporated herein by reference in its entirety.

In some embodiments, the condensation reaction condition comprises a reaction temperature of 0-100° C. and a reaction time of 0.1-24 hours, and in some embodiments, a reaction temperature of 10-40° C. and a reaction time of 0.5-16 hours.

Considering the structure of the desired product compound as shown by Formula (314), the molar ratio of the compound as shown by Formula (316) to the compound as shown by Formula (320) should be determined based on the sum of n1 and n3 in Formula (320). In some embodiments, for example, when n1+n3=3, to ensure complete reaction without any excess, the molar ratio of the compound as shown by Formula (316) to the compound as shown by Formula (320) may be 3:1 to 3.5:1, and in some embodiments, 3.01:1 to 3.15:1.

In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is dichloromethane. With respect to the compound as shown by Formula (320), the amount of the organic solvent may be 3-50 L/mol, and in some embodiments, 5-20 L/mol.

In some embodiments, the condensing agent for amidation reaction is one or more of benzotriazol-1-yl-oxytripyrrolidinophosphonium hexafluorophosphate, 3-diethoxyphosphoryl oxy-1,2,3-benzotrizin-4(3H)-one (DEPBT), 0-benzotriazol-tetramethyluronium hexafluorophosphate, 4-(4,6-dimethoxytriazin-2-yl)-4-methylmorpholine hydrochloride, or 1-hydroxybenzotriazole, and in further embodiments, is a mixture of benzotriazol-1-yl-oxytripyrrolidinophosphonium hexafluorophosphate and 1-hydroxybenzotriazole, wherein benzotriazol-1-yl-oxytripyrrolidinophosphonium hexafluorophosphate and 1-hydroxybenzotriazole are used in equimolar amounts. The molar ratio of the total condensing agent for amidation reaction to the compound as shown by Formula (316) may be 1:1 to 3:1, and in some embodiments, 1.05:1 to 1.5:1.

The tertiary amine may be N-methylmorpholine, triethylamine or N,N-diisopropylethylamine, and in some embodiments, N-methylmorpholine. The molar ratio of the tertiary amine to the compound as shown by Formula (316) may be 2:1 to 10:1, and in some embodiments, 2:1 to 5:1.

Similarly, the compound as shown by Formula (314) may be isolated from the reaction mixture by any suitable isolation method. In some embodiments, the compound as shown by Formula (314) may be isolated by removal of solvent via evaporation followed by chromatography, for example, using the following two chromatographic conditions for isolation: (1) normal phase purification of silica gel: 200-300 mesh silica gel filler, with gradient elution of dichloromethane:methanol=100:5-100:7; and (2) reverse phase purification: $C_{18}$ and $C_8$ reverse phase fillers, with gradient elution of methanol:acetonitrile=0.1:1-1:0.1. In some embodiments, the solvent may be directly removed to afford a crude product of the compound as shown by Formula (314), which may be directly used in subsequent reactions.

The compound as shown by Formula (320) may be commercially available, or prepared by those skilled in the art via known methods. For example, in the case where m1=m2=m3=3, n1=1, n3=2, and $R_{10}$, $R_{11}$, $R_{12}$, $R_{13}$, $R_{14}$, and $R_{15}$ are all H, the compound as shown by Formula (320) may be commercially available from Alfa Aesar Inc.

The siRNA conjugate of the present disclosure may also be used in combination with other pharmaceutically acceptable excipients, which may be one or more of various formulations or compounds conventionally employed in the art. For details, please refer to the above description of the pharmaceutical compositions of the present disclosure.

Use of the siRNA, the Pharmaceutical Composition and the Conjugate Comprising the siRNA of the Present Disclosure In some embodiments, the present disclosure provides the use of the siRNA and/or the pharmaceutical composition and/or the siRNA conjugate of the present disclosure in the manufacture of a medicament for treating and/or preventing thrombotic diseases and/or ischemic stroke.

In some embodiments, the present disclosure provides a method for preventing and/or treating thrombotic diseases and/or ischemic stroke, comprising administering an effective amount of the siRNA and/or the pharmaceutical composition and/or the siRNA conjugate of the present disclosure to a subject in need thereof.

The purpose of preventing and/or treating thrombotic diseases and/or ischemic stroke may be achieved through the mechanism of RNA interference by administering the siRNA active ingredient of the present disclosure to a subject in need thereof. Therefore, the siRNA and/or the pharmaceutical composition and/or the siRNA conjugate of the present disclosure may be used for preventing and/or treating thrombotic diseases and/or ischemic stroke, or for preparing a medicament for preventing and/or treating thrombotic diseases and/or ischemic stroke.

As used herein, the term "administration/administer" refers to the placing the siRNA and/or the pharmaceutical composition and/or the siRNA conjugate of the present disclosure into a subject's body by a method or a route that at least partly the siRNA and/or the pharmaceutical composition and/or the siRNA conjugate of the present disclosure is located at a desired site to produce a desired effect. Suitable administration routes for the methods of the present disclosure include topical administration and systemic administration. In general, topical administration results in the delivery of more siRNA conjugate to a particular site as compared with the systemic circulation of the subject; whereas systemic administration results in the delivery of the siRNA and/or the pharmaceutical composition and/or the siRNA conjugate of the present disclosure to substantially systemic circulation of the subject. Considering that the present disclosure is intended to provide a means for preventing and/or treating thrombotic diseases and/or ischemic stroke, in some embodiments, an administration mode capable of delivering a medicament to the liver is employed.

The administration to a subject may be achieved by any suitable routes known in the art, including but not limited to, oral or parenteral routes, such as intravenous administration, intramuscular administration, subcutaneous administration, transdermal administration, intratracheal administration (aerosol), pulmonary administration, nasal administration, rectal administration, and topical administration (including buccal administration and sublingual administration). The frequency of administration may be once or more times daily, weekly, biweekly, triweekly, monthly, or yearly.

The used dosage of the siRNA or the pharmaceutical composition or the siRNA conjugate of the present disclosure may be a conventional dose in the art, which may be determined according to various parameters, especially age, weight and gender of a subject. Toxicity and efficacy may be determined in cell cultures or experimental animals by standard pharmaceutical procedures, for example, by determining $LD_{50}$ (the lethal dose that causes 50% population death) and $ED_{50}$ (the dose that can cause 50% of the maximum response intensity in a quantitative response, and that causes 50% of the experimental subjects to have a positive response in a qualitative response). The dose range for human use may be derived based on data obtained from cell culture analysis and animal studies.

When the siRNA, the pharmaceutical composition and/or the siRNA conjugate of the present disclosure is administered, for example, to male or female, 6 to 12 weeks old, C57BL/6N mice of 18 to 25 g body weight, based on the amount of the siRNA: (i) for the siRNA conjugate, the dosage of the siRNA thereof may be 0.001 to 100 mg/kg body weight, in some embodiments 0.01 to 50 mg/kg body weight, in some embodiments 0.05 to 20 mg/kg body weight, in further embodiments 0.1 to 15 mg/kg body weight, and in further embodiments 0.1 to 10 mg/kg body weight; (ii) for a pharmaceutical composition formed by the siRNA and the pharmaceutically acceptable carrier, the dosage of the siRNA thereof may be 0.001 to 50 mg/kg body weight, in some embodiments 0.01 to 10 mg/kg body weight, in some embodiments 0.05 to 5 mg/kg body weight, and in some embodiments 0.1 to 3 mg/kg body weight.

In some embodiments, the present disclosure provides a method of inhibiting the expression of FXI gene in hepatocytes, comprising contacting an effective amount of the siRNA and/or the pharmaceutical composition and/or the siRNA conjugate of the present disclosure with the hepatocytes, and introducing the siRNA and/or the pharmaceutical composition and/or the siRNA conjugate of the present disclosure into the hepatocytes, so as to realize the purpose of inhibiting the expression of FXI gene in hepatocytes through the mechanism of RNA interference. The hepatocytes may be selected from hepatoma cell lines (such as SMMC-7721, HepG2 and Huh7), or isolated liver primary cells. In some embodiments, the hepatocytes are HepG2 hepatoma cells.

In the case where the expression of FXI gene in a cell is inhibited by using the method of the present disclosure, the amount of the siRNA in the modified siRNA and/or the pharmaceutical composition and/or the siRNA conjugate of the present disclosure is generally such an amount that is sufficient to reduce the expression of the target gene and results in an extracellular concentration of 1 μM to 1 μM, or 0.01 nM to 100 nM, or 0.05 nM to 50 nM, or 0.05 nM to about 5 nM on the surface of the target cells. The amount required to achieve this topical concentration will vary with various factors, including the delivery method, the delivery site, the number of cell layers between the delivery site and the target cells or tissues, the delivery route (topical or systemic), etc. The concentration at the delivery site may be significantly higher than that on the surface of the target cells or tissues.

Kit

The present disclosure provides a kit comprising an effective amount of at least one of the modified siRNA, the pharmaceutical composition, and the siRNA conjugate of the present disclosure.

In some embodiments, the kit of the present disclosure may provide the modified siRNA in a container. In some embodiments, the kit of the present disclosure may comprise a container containing a pharmaceutically acceptable excipient. In some embodiments, the kit may further comprise other ingredients, such as stabilizers or preservatives. In some embodiments, the kit of the present disclosure may comprise at least one additional therapeutic agent in other container different from the container for providing the modified siRNA of the present disclosure. In some embodiments, the kit may comprise an instruction for mixing the modified siRNA with pharmaceutically acceptable carriers and/or excipients or other ingredients (if present).

In the kit of the present disclosure, the modified siRNA and the pharmaceutically acceptable carrier and/or excipient, as well as the modified siRNA, the pharmaceutical composition, and/or the siRNA conjugate and/or the conjugate, and/or the pharmaceutically acceptable excipient may be provided in any form, such as in a liquid form, a dry form or a lyophilized form. In some embodiments, the modified siRNA and the pharmaceutically acceptable carrier and/or excipient, and the pharmaceutical composition and/or conjugate and optional pharmaceutically acceptable excipient(s) are substantially pure and/or sterilized. In some embodiments, sterilized water may be provided in the kit of the present disclosure.

Hereinafter, the present disclosure will be further illustrated by way of examples, but will not be limited thereto in any respect.

EXAMPLES

Unless otherwise specified, the reagents and culture media used in following examples are all commercially available, and the procedures used such as nucleic acid electrophoresis and real-time PCR are all performed according to the methods described in Molecular Cloning (Cold Spring Harbor Laboratory Press (1989)).

When the siRNA or the siRNA conjugate against FXI gene synthesized in the present disclosure or the siRNA or the siRNA conjugate as negative control was used to transfect cells, Lipofectamine'2000 (Invitrogen) was used as a transfection reagent. The specific procedures could refer to the instruction provided by the manufacturer.

C57BL/6N mice: 6-8 weeks old, purchased from Beijing Vital River Laboratory Animal Technology Co., Ltd., and hereinafter referred to as C57 mice.

Heterozygous humanized mice: 6-8 weeks old, purchased from Cyagen Biosciences Inc.

Unless otherwise specified, ratios of reagents provided below are all calculated by volume ratio (v/v).

Unless otherwise specified, all the experimental data of the effects in vivo/in vitro are expressed as $\overline{X}$±SEM, and the data are analyzed with Graphpad prism 5.0 statistical analysis software.

Preparation Example 1: The Preparations of Conjugate L10-siFXIf1M1S

In this Preparation Example, Conjugate L10-siFXIf1M1S was synthesized. This conjugate was an siRNA conjugate formed by conjugating L-9 conjugation molecule to the siRNA No. siFXIf1M1S. The sequence of the siRNA conjugated in this conjugate may be found in Table 3.

(1-1) Synthesis of Compound L-10:
Compound L-10 was Synthesized according to the Following Method:
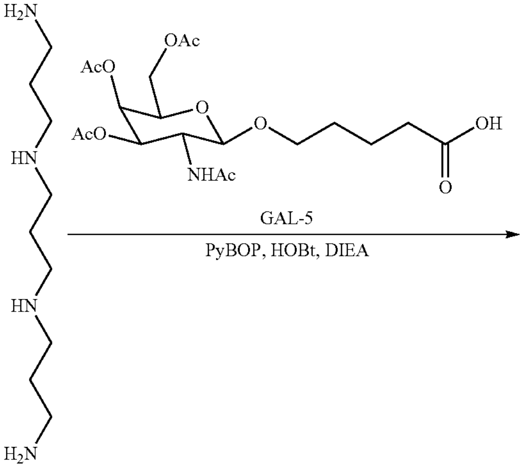
J-0
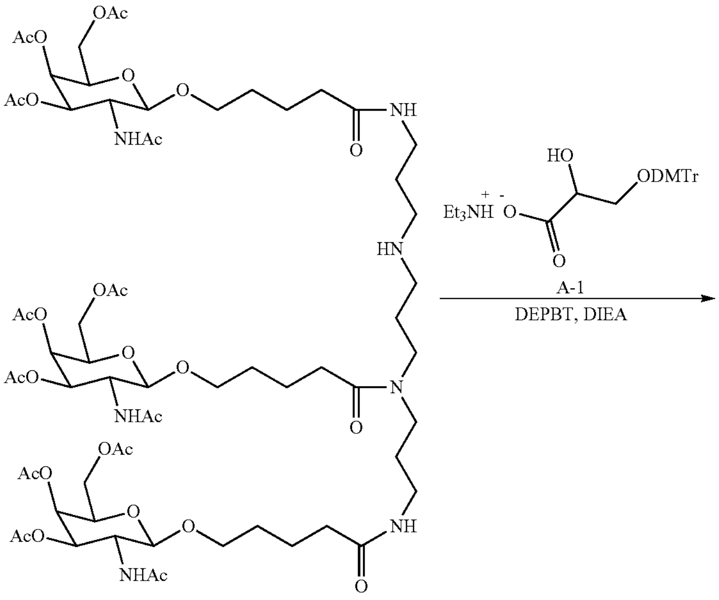
L-8

-continued
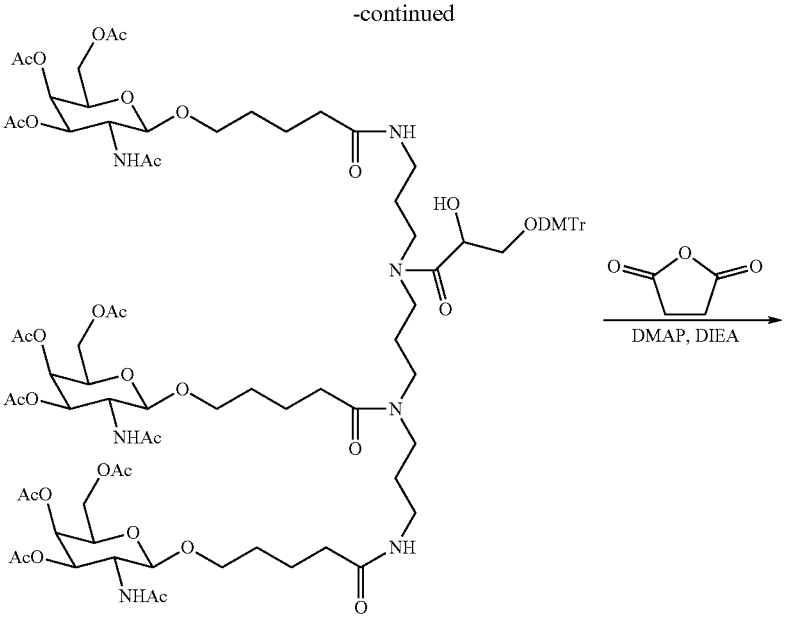
L-7
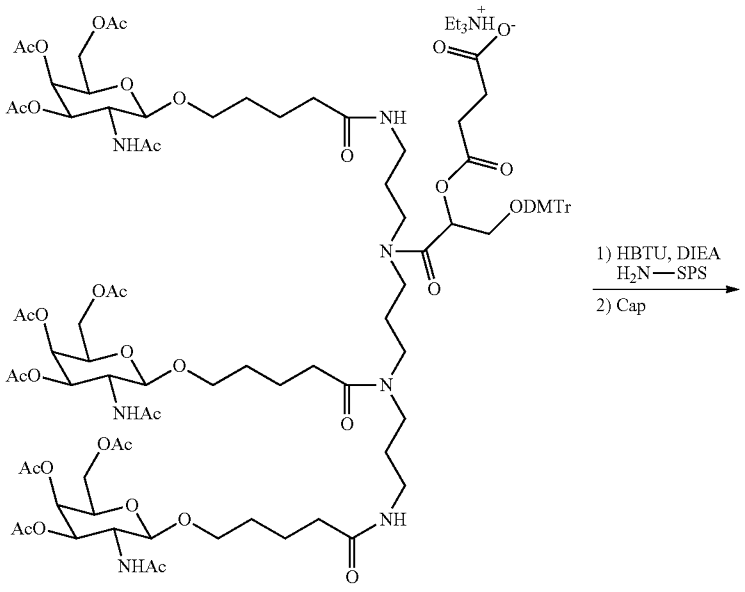
L-9

-continued

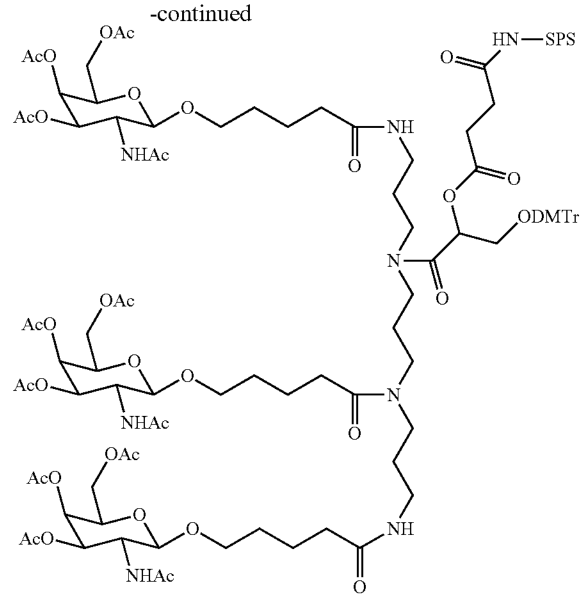

L-10

(1-1-1) Synthesis of the Conjugating Terminal Segment GAL-5

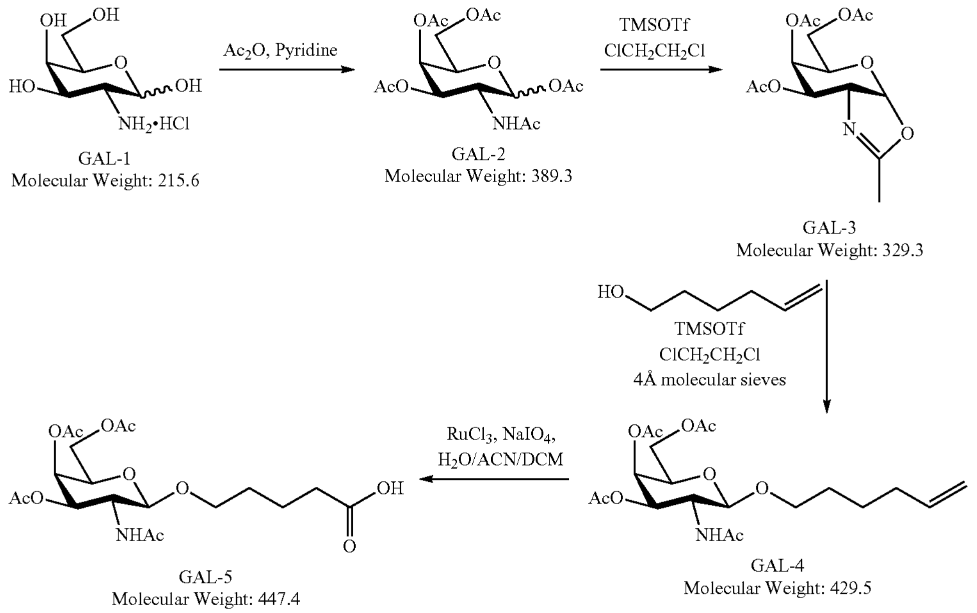

(1-1-1a) Synthesis of GAL-2

100.0 g of GAL-1 (N-acetyl-D-galactosamine hydrochloride, CAS No.: 1772-03-8, purchased from Ning Bo hongxiang bio-chem Co., Ltd., 463.8 mmol) was dissolved in 1000 ml of anhydrous pyridine, to which 540 ml of acetic anhydride (purchased from Enox Inc., 5565.6 mmol) was added in an ice water bath to react under stirring at room temperature for 1.5 hours. The resultant reaction solution was poured into 10 L of ice water and subjected to suction filtration under reduced pressure. The residue was washed with 2 L of ice water, and then added with a mixed solvent of acetonitrile/toluene (v/v ratio of acetonitrile:toluene=1:1) until completely dissolved. The solvent was evaporated to give 130.0 g of product GAL-2 as a white solid.

(1-1-1b) Synthesis of GAL-3

GAL-2 (35.1 g, 90.0 mmol) obtained in step (1-1-1a) was dissolved in 213 ml of anhydrous 1,2-dichloroethane, to which 24.0 g of TMSOTf (CAS No.: 27607-77-8, purchased from Macklin Inc., 108.0 mmol) was added in an ice water bath under nitrogen atmosphere to react at room temperature overnight.

The reaction solution was added with 400 ml dichloromethane for dilution, filtered with diatomite, and then added with 1 L saturated aqueous sodium bicarbonate solution and stirred evenly. An organic phase was isolated. The aqueous phase remained was extracted twice, each with 300 ml of dichloroethane. The organic phases were combined and washed with 300 ml of saturated aqueous sodium bicarbonate solution and 300 ml of saturated brine, respectively. The organic phase was isolated and dried with anhydrous sodium sulfate. The solvent was evaporated to dryness under reduced pressure to give 26.9 g of product GAL-3 as a light yellow viscous syrup.

(1-1-1c) Synthesis of GAL-4

GAL-3 (26.9 g, 81.7 mmol) obtained in step (1-1-1b) was dissolved in 136 ml of anhydrous 1,2-dichloroethane, added with 30 g of dry 4A molecular sieve powder followed by 9.0 g of 5-hexen-1-ol (CAS No.: 821-41-0, purchased from Adamas-beta Inc., 89.9 mmol), and stirred at room temperature for 30 minutes. 9.08 g of TMSOTf (40.9 mmol) was added in an ice bath under nitrogen atmosphere to react under stirring at room temperature overnight. The 4A molecular sieve powder was removed by filtration. The filtrate was added with 300 ml dichloroethane for dilution, filtered with diatomite, and then added with 500 ml of saturated aqueous sodium bicarbonate solution and stirred for 10 minutes for washing. An organic phase was isolated. The aqueous phase was extracted once with 300 ml of dichloroethane. The organic phases were combined and washed with 300 ml of saturated aqueous sodium bicarbonate solution and 300 ml of saturated brine, respectively. The organic phase was isolated and dried with anhydrous sodium sulfate. The solvent was evaporated to dryness under reduced pressure to give 41.3 g of product GAL-4 as a yellow syrup, which was directly used in the next oxidation reaction without purification.

(1-1-1d) Synthesis of GAL-5

GAL-4 (14.9 g, 34.7 mmol) obtained according to the method described in step (1-1-1c) was dissolved in a mixed solvent of 77 ml of dichloromethane and 77 ml of acetonitrile, added with 103 ml of deionized water and 29.7 g of sodium periodate (CAS No.: 7790-28-5, purchased from Aladdin Inc., 138.8 mmol) respectively, and stirred in an ice bath for 10 minutes. Ruthenium trichloride (CAS No.: 14898-67-0, available from Energy Chemical, 238 mg, 1.145 mmol) was added to react at room temperature overnight. The resultant reaction solution was diluted by adding 300 ml of water under stirring, and adjusted to a pH of about 7.5 by adding saturated sodium bicarbonate. The organic phase was isolated and discarded. The aqueous phase was extracted three times, each with 200 ml of dichloromethane, and the organic phase was discarded. The aqueous phase was adjusted to a pH of about 3 with citric acid solids and extracted three times, each with 200 ml of dichloromethane, and the resultant organic phases were combined and dried with anhydrous sodium sulfate. The solvent was evaporated to dryness under reduced pressure to give 6.85 g of product GAL-5 as a white foamy solid. $^1H$ NMR (400 MHz, DMSO) δ 12.01 (br, 1H), 7.83 (d, J=9.2 Hz, 1H), 5.21 (d, J=3.2 Hz, 1H), 4.96 (dd, J=11.2, 3.2 Hz, 1H), 4.49 (d, J=8.4 Hz, 1H), 4.07-3.95 (m, 3H), 3.92-3.85 (m, 1H), 3.74-3.67 (m, 1H), 3.48-3.39 (m, 1H), 2.20 (t, J=6.8 Hz, 2H), 2.11 (s, 3H), 2.00 (s, 3H), 1.90 (s, 3H), 1.77 (s, 3H), 1.55-1.45 (m, 4H).

(1-1-2) Synthesis of L-8

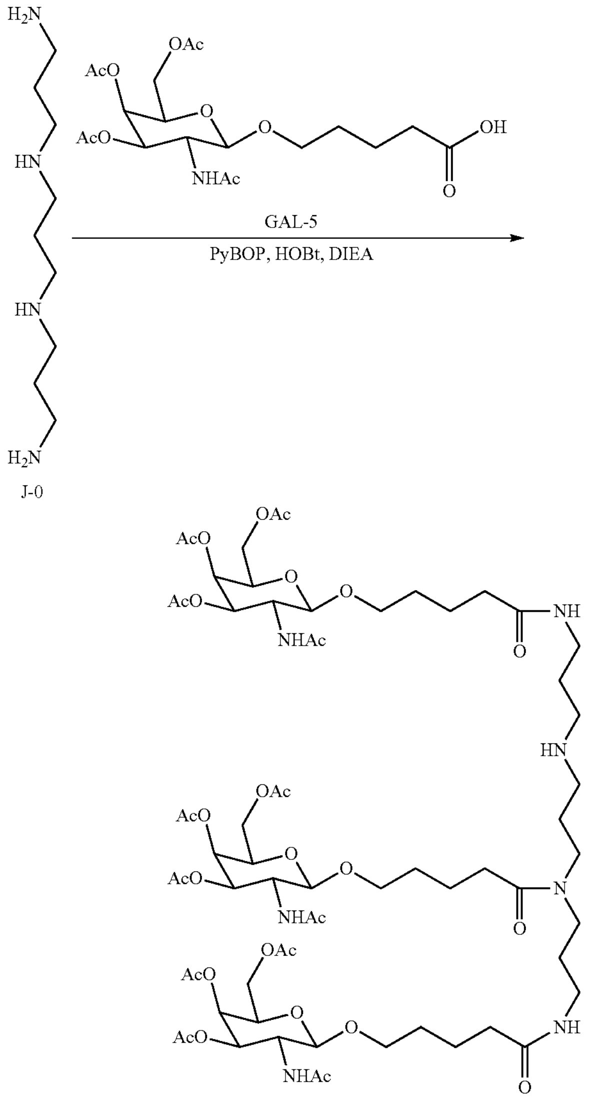

J-0

L-8

J-0 (9.886 g, 52.5 mmol, purchased from Alfa Aesar Inc.) and GAL-5 (72.819 g, 162.75 mmol, obtained by combining several batches of products) obtained in step (1-1-1) were dissolved in 525 ml of dichloromethane, and added with diisopropylethylamine (DIEA, 44.782 g, 346.50 mmol), benzotriazol-1-yl-oxytripyrrolidino phosphonium hexafluorophosphate (PyBOP, 90.158 g, 173.25 mmol) and hydroxybenzotriazole (HOBt, 23.410 g, 173.25 mmol) to react at room temperature for 4 hours. The resultant reaction solution was washed by adding 20 ml of saturated sodium bicarbonate solution and 200 ml of saturated brine. The aqueous phase was extracted twice, each with 100 ml of dichloromethane. The organic phases were combined, dried with anhydrous sodium sulfate, and filtered. Then the solvent was evaporated to dryness under reduced pressure to give a crude product. The crude product was purified by using a normal phase silica gel column (200-300 mesh). The column was added with 10 wt % triethylamine for neutralizing the acidity of silica gel, equilibrated with 1 wt ‰ triethylamine, and eluted with a gradient elution of dichloromethane:methanol=100:25-100:40. The eluate of product was collected, and the solvent was evaporated to dryness under reduced pressure to give 38.8 g of pure product L-8. $^1$H NMR (400 MHz, DMSO) δ 7.84 (d, J=9.0 Hz, 3H), 7.27-7.23 (m, 1H), 7.13-7.18 (m, 1H), 5.22 (d, J=3.1 Hz, 3H), 4.97 (dd, J=11.3, 3.1 Hz, 3H), 4.48 (d, J=8.4 Hz, 3H), 4.09-3.98 (m, 9H), 3.88 (dd, J=19.3, 9.3 Hz, 3H), 3.75-3.66 (m, 3H), 3.44-3.38 (m, 3H), 3.17-3.30 (m, 4H), 3.10-2.97 (m, 4H), 2.35-2.20 (m, 6H), 2.15-2.08 (m, 9H), 2.07-1.98 (m, 13H), 1.94-1.87 (m, 9H), 1.81-1.74 (m, 9H), 1.65-1.42 (m, 18H). MS m/z: $C_{85}H_{119}N_7O_{30}$, $[M+H]^+$, calculated: 1477.59, measured: 1477.23.

(1-1-3) Synthesis of L-7

(1-1-3a) Synthesis of A-1

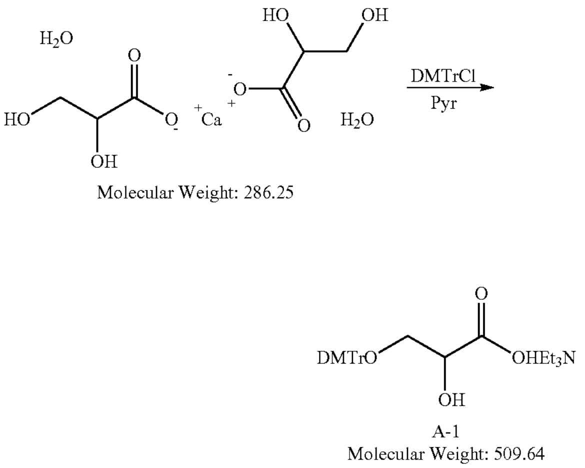

Molecular Weight: 286.25

A-1

Molecular Weight: 509.64

DMTrCl (4,4'-dimethoxytrityl chloride, 101.65 g, 300 mmol) was dissolved in 1000 ml of anhydrous pyridine, and added with calcium DL-glycerate hydrate (28.63 g, 100 mmol) to react at 45° C. for 20 hours. The resultant reaction solution was filtered. The residue was rinsed with 200 ml of DCM, and the filtrate was concentrated to dryness under reduced pressure. The residue was redissolved in 500 ml of dichloromethane and washed twice, each with 200 ml of 0.5 M triethylamine phosphate (pH=7-8). The aqueous phase was extracted twice, each with 200 ml of dichloromethane. The organic phases were combined, dried with anhydrous sodium sulfate, and filtered. The solvent was evaporated to dryness under reduced pressure, and the residue was purified by using a normal phase silica gel column (200-300 mesh). The column was eluted with a gradient elution of petroleum ether:ethyl acetate:dichloromethane:methanol=1:1:1:0.35-1:1:1:0.55. The eluate of product was collected, and the solvent was evaporated to dryness under reduced pressure. The residue was redissolved in 600 ml of dichloromethane, and washed once with 200 ml of 0.5 M triethylamine phosphate. The aqueous phase was extracted once with 200 ml of dichloromethane. The organic phases were combined, dried with anhydrous sodium sulfate, and filtered. The solvent was evaporated to dryness under reduced pressure, and the residue was subject to a reduced pressure with a vacuum oil pump overnight to give 50.7 g of product A-1 as a white solid. $^1$H NMR (400 MHz, DMSO-d6) δ 7.46 (ddd, J=6.5, 2.3, 1.1 Hz, 1H), 7.40-7.28 (m, 7H), 6.89-6.81 (m, 4H), 4.84 (d, J=5.0 Hz, 1H), 4.36-4.24 (m, 1H), 4.29 (s, 6H), 3.92 (dd, J=12.4, 7.0 Hz, 1H), 3.67 (dd, J=12.3, 7.0 Hz, 1H), 2.52 (q, J=6.3 Hz, 6H), 1.03 (t, J=6.3 Hz, 9H). MS m/z: $C_{24}H_{23}O_6$, $[M-H]^-$, calculated: 407.15, measured: 406.92.

(1-1-3b) Synthesis of L-7

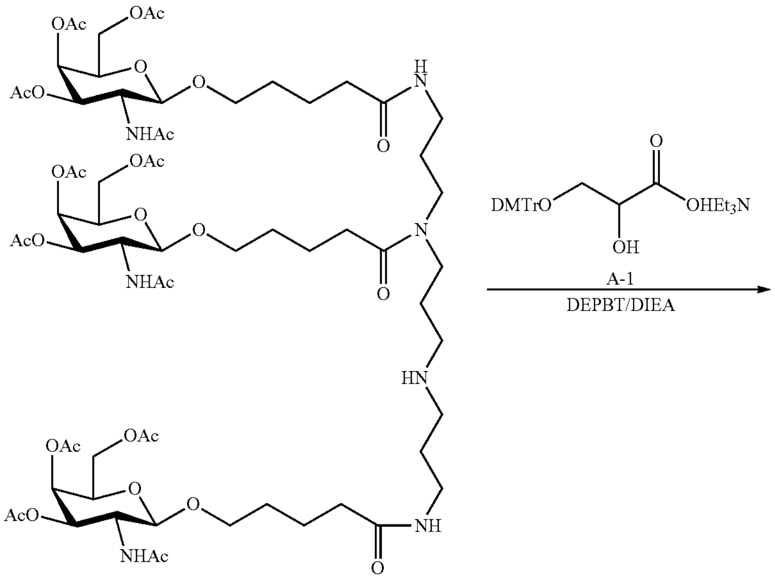

L-8

-continued

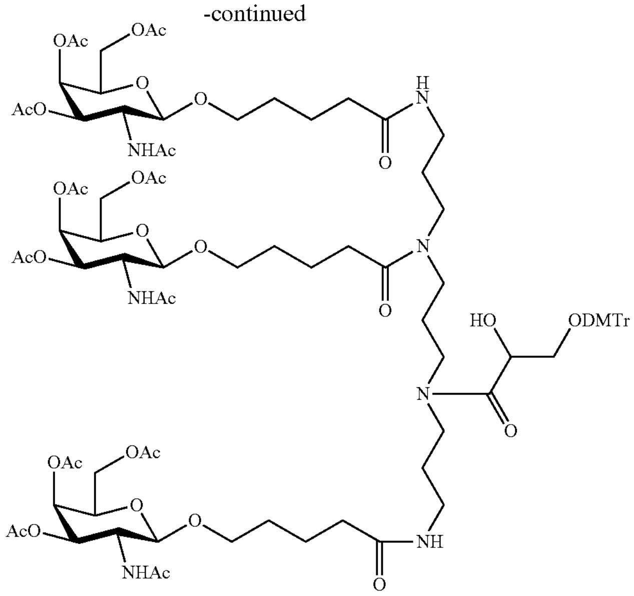

L-7

L-8 (40 g, 27.09 mmol, obtained by combining several batches of products) obtained in step (1-1-2) and A-1 (41.418 g, 81.27 mmol) obtained in step (1-1-3a) were mixed and dissolved in 271 ml of dichloromethane, added with 3-diethoxyphosphoryl-1,2,3-benzotrizin-4(3H)-one (DEPBT) (24.318 g, 81.37 mmol), and further added with diisopropylethylamine (21.007 g, 162.54 mmol) to react under stirring at 25° C. for 1.5 hours. The organic phase was washed with 800 ml of saturated sodium bicarbonate. The aqueous phase was extracted three times, each with 50 ml of dichloromethane. The organic phase was washed with 150 ml of saturated brine, and the aqueous phase was extracted once with 50 ml of dichloromethane, and the organic phases were combined, dried with anhydrous sodium sulfate and filtered. The solvent was evaporated to dryness under reduced pressure, and the residue was foam-dried with a vacuum oil pump overnight to give a crude product. The crude product was subjected to a column purification. The column was filled with 2 kg normal phase silica gel (200-300 mesh), added with 200 ml triethylamine for neutralizing the acidity of silica gel, equilibrated with petroleum ether containing 1 wt % triethylamine, and eluted with a gradient elution of petroleum ether:ethyl acetate:dichloromethane:N,N-dimethylformamide=1:1:1:0.5-1:1:1:0.6. The eluate of product was collected, and the solvent was evaporated to dryness under reduced pressure to give 40.4 g of pure product L-7. $^1$H NMR (400 MHz, DMSO) δ7.90-7.78 (m, 4H), 7.75-7.64 (m, 1H), 7.38-7.18 (m, 9H), 6.91-6.83 (m, 4H), 5.25-5.10 (m, 4H), 4.97 (dd, J=11.2, 3.2 Hz, 3H), 4.48-4.30 (m, 4H), 4.02 (s, 9H), 3.93-3.84 (m, 3H), 3.76-3.66 (m, 9H), 3.45-3.35 (m, 3H), 3.24-2.98 (m, 10H), 2.30-2.20 (m, 2H), 2.11-1.88 (m, 31H), 1.80-1.40 (m, 28H). MS m/z: $C_{90}H_{128}N_7O_{35}$, [M-DMT1]$^+$, calculated: 1564.65, measured: 1564.88.

(1-1-4) Synthesis of L-9

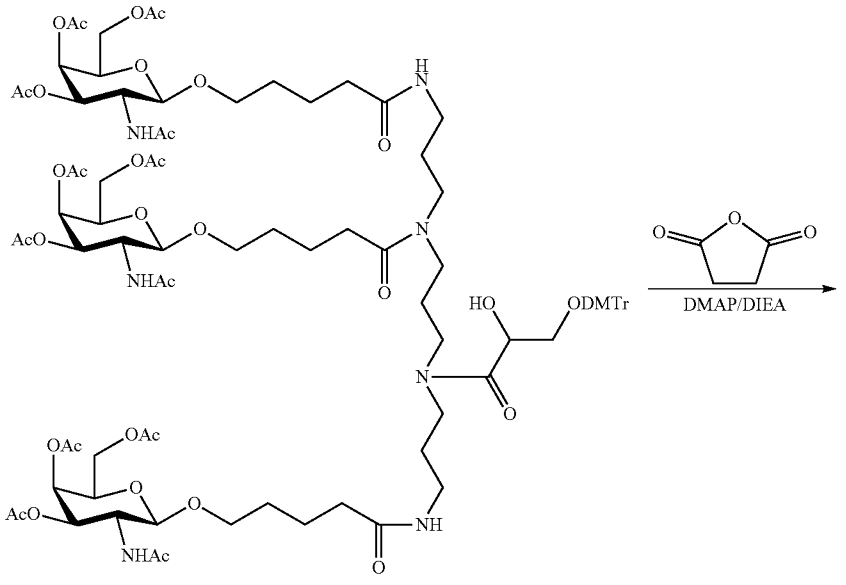

L-7

-continued

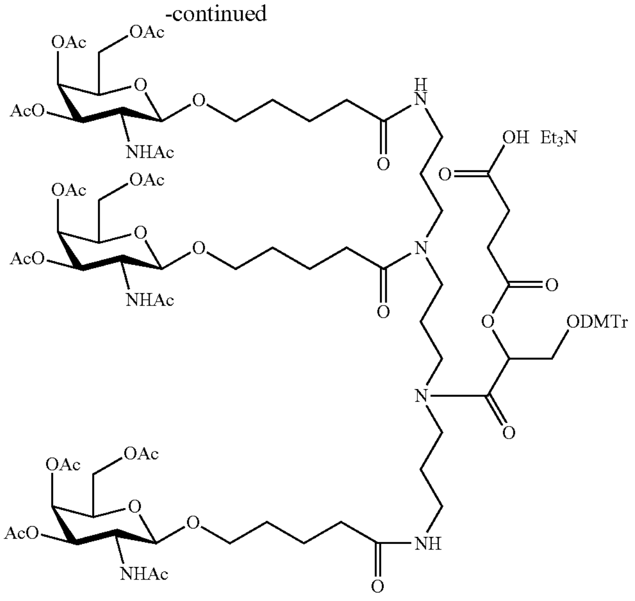

L-9

L-7 (40 g, 21.4247 mmol) obtained in step (1-1-3b), succinic anhydride (4.288 g, 42.8494 mmol) and 4-dimethylaminopyridine (DMAP, 5.235 g, 42.8494 mmol) were mixed and dissolved in 215 ml of dichloromethane, further added with diisopropylethylamine (DIEA, 13.845 g, 107.1235 mmol), and stirred at 25° C. for 24 hours. The resultant reaction solution was washed with 800 ml of 0.5 M triethylamine phosphate. The aqueous phase was extracted three times, each with 5 ml of dichloromethane. The organic phases were combined and evaporated to dryness under reduced pressure to give a crude product. The crude product was subjected to a column purification. The column was filled with 1 kg normal phase silica gel (200-300 mesh), added with 1 wt % triethylamine for neutralizing the acidity of silica gel, equilibrated with dichloromethane, and eluted with a gradient elution of 1 wt ‰ triethylamine-containing dichloromethane:methanol=100:18-100:20. The eluate of product was collected, and the solvent was evaporated to dryness under reduced pressure to give 31.0 g of pure product L-9 conjugation molecule. $^1$H NMR (400 MHz, DMSO) δ 8.58 (d, J=4.2 Hz, 1H), 7.94-7.82 (m, 3H), 7.41-7.29 (m, 5H), 7.22 (d, J=8.1 Hz, 5H), 6.89 (d, J=8.3 Hz, 4H), 5.49-5.37 (m, 1H), 5.21 (d, J=3.0 Hz, 3H), 4.97 (d, J=11.1 Hz, 3H), 4.49 (d, J=8.2 Hz, 3H), 4.02 (s, 9H), 3.88 (dd, J=19.4, 9.4 Hz, 3H), 3.77-3.65 (m, 9H), 3.50-3.39 (m, 6H), 3.11-2.90 (m, 5H), 2.61-2.54 (m, 4H), 2.47-2.41 (m, 2H), 2.26-2.17 (m, 2H), 2.15-1.95 (m, 22H), 1.92-1.84 (m, 9H), 1.80-1.70 (m, 10H), 1.65-1.35 (m, 17H), 1.31-1.19 (m, 4H), 0.96 (t, J=7.1 Hz, 9H). MS m/z: $C_{94}H_{132}N_7O_{38}$, $[M\text{-}DMTr]^+$, calculated: 1664.72, measured: 1665.03.

(1-1-5) Synthesis of Compound L-10

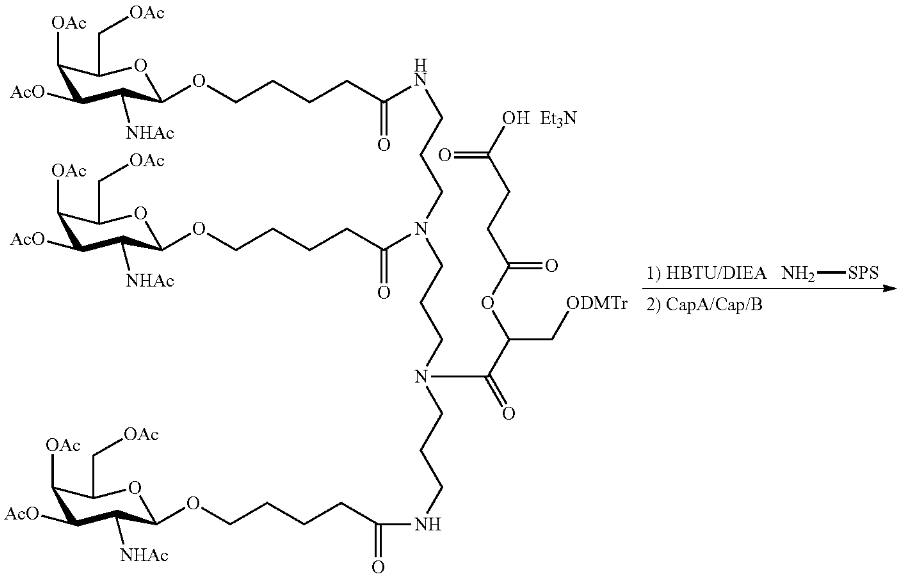

L-9

-continued

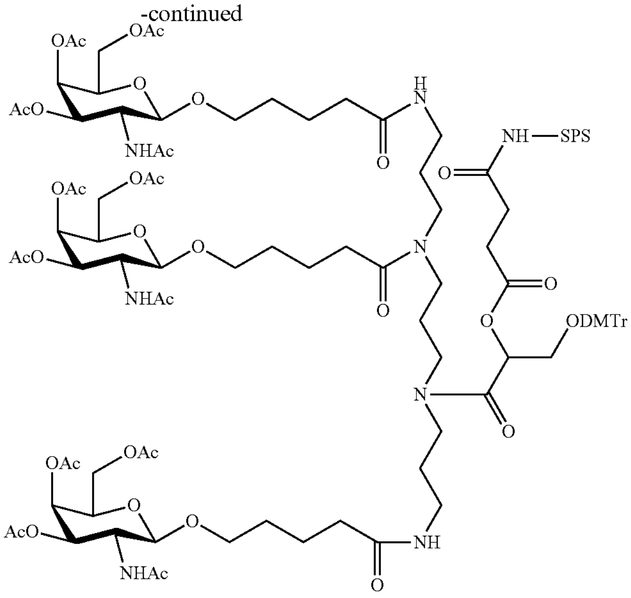

L-10

In this step, Compound L-10 was prepared by linking the L-9 conjugation molecule to a solid phase support.

The L-9 conjugation molecule (22.751 g, 11 mmol) obtained in step (1-1-4), O-benzotriazol-tetramethyluronium hexafluorophosphate (HBTU, 6.257 g, 16.5 mmol) and diisopropylethylamine (DIEA, 2.843 g, 22 mmol) were mixed and dissolved in 900 ml of acetonitrile, and stirred at room temperature for 5 minutes. The resultant reaction solution was added with Aminomethyl resin (88 g, 100-200 mesh, amino loading: 400 μmol/g, purchased from Tianjin Nankai HECHENG S&T Co., Ltd.). A reaction was performed on a shaker at 25° C. and at a rotation speed of 150 rpm/min for 18 hours, followed by filtration. The residue was rinsed twice (each with 300 ml of DCM) and three times (each with 300 ml of acetonitrile), and dried with a vacuum oil pump for 18 hours. Then starting materials (CapA, CapB, 4-dimethylaminopyridine (DMAP) and acetonitrile) were added according to the charge ratio as shown in Table 2 for a capping reaction. The reaction was performed on a shaker at 25° C. and at a rotation speed of 150 rpm/min for 5 hours. The reaction liquid was filtered. The residue was rinsed three times, each with 300 ml of acetonitrile. The solvent was evaporated to dryness under reduced pressure, and the residue was dried under reduced pressure with a vacuum oil pump overnight to give 102 g of Compound L-10 (i.e., the L-9 conjugation molecule linked to a solid phase support), with a loading of 90.8 μmol/g.

TABLE 2

The charge ratio of capping reaction

| Starting Materials | Amount | Specs | Lot No. | Manufacturer |
|---|---|---|---|---|
| CapA | 1980 ml | — | — | — |
| CapB | 220 ml | — | — | — |
| DMAP | 1.100 g | analytical pure | I1422139 | Aladdin |
| Acetonitrile | 220 ml | spectroscopic pure | O15161001 | CINC (Shanghai) Co., Ltd |

In the above table, Cap A and Cap B are solutions of capping agents. Cap A is a mixed solution of 20% by volume of N-methylimidazole in pyridine/acetonitrile, wherein the volume ratio of pyridine to acetonitrile is 3:5. Cap B is a solution of 20% by volume of acetic anhydride in acetonitrile.

(1-2) Synthesis of Sense Strand of Conjugate L10-siFXIf1M1S

Nucleoside monomers were linked one by one in 3' to 5' direction according to the arrangement sequences of nucleotides in the sense strand by the phosphoramidite solid phase synthesis method, starting the cycles from the Compound L-10 prepared in the above step. The linking of each nucleoside monomer included a four-step reaction of deprotection, coupling, capping, and oxidation or sulfurization. Therein, when two nucleotides are linked via a phosphoester linkage, a four-step reaction of deprotection, coupling, capping, and oxidation was included during linking of the later nucleoside monomer; and when two nucleotides is linked via a phosphorothioate linkage, a four-step reaction of deprotection, coupling, capping, and sulfurization was included during linking of the later nucleoside monomer. The synthesis conditions are given as follows.

The nucleoside monomers are provided in a 0.1 M acetonitrile solution. The condition for deprotection reaction in each step is identical, i.e., a temperature of 25° C., a reaction time of 70 seconds, a solution of dichloroacetic acid in dichloromethane (3% v/v) as a deprotection reagent, and a molar ratio of dichloroacetic acid to the protection group 4,4'-dimethoxytrityl on the solid phase support of 5:1.

The condition for coupling reaction in each step is identical, including a temperature of 25° C., a molar ratio of the nucleic acid sequence linked to the solid phase support to nucleoside monomers of 1:10, a molar ratio of the nucleic acid sequence linked to the solid phase support to a coupling reagent of 1:65, a reaction time of 600 seconds, and 0.5 M acetonitrile solution of 5-ethylthio-1H-tetrazole (ETT) as a coupling reagent.

The condition for capping reaction in each step is identical, including a temperature of 25° C., a reaction time of 15 seconds, a mixed solution of Cap A and Cap B in a molar ratio of 1:1 as a solution of capping agent, and a molar ratio of the capping agent to the nucleic acid sequence linked to the solid phase support of 1:1:1 (acetic anhydride:N-methylimidazole:the nucleic acid sequence linked to the solid phase support).

The condition for oxidation reaction in each step is identical, including a temperature of 25° C., a reaction time of 15 seconds, and 0.05 M iodine water as an oxidation reagent; and a molar ratio of iodine to the nucleic acid sequence linked to the solid phase support in the coupling step of 30:1. The reaction was carried out in a mixed solvent of tetrahydrofuran:water:pyridine=3:1:1.

The condition for sulfurization reaction in each step is identical, including a temperature of 25° C., a reaction time of 300 seconds, and xanthane hydride as a sulfurization reagent; and a molar ratio of the sulfurization reagent to the nucleic acid sequence linked to the solid phase support in the coupling step of 120:1. The reaction is carried out in a mixed solvent of acetonitrile:pyridine=1.1.

After the linking of the last nucleoside monomer was completed, the nucleic acid sequence linked to the solid phase support was cleaved, deprotected, purified, desalted in turn, and then lyophilized to obtain the sense strand, wherein:

The conditions for cleavage and deprotection are as follows: adding the synthesized nucleotide sequence linked to the support into 25 wt % aqueous ammonia to react at 55° C. for 16 hours, wherein the amount of the aqueous ammonia is 0.5 ml/μmol. The liquid was removed by filtration, and the supernatant was concentrated to dryness in vacuum.

The conditions for purification and desalination were as follows: purification of the nucleic acid was achieved by using a preparative ion chromatography purification column (Source 15Q) with a gradient elution of NaCl. Specifically, eluent A: 20 mM sodium phosphate (pH 8.1), solvent: water/acetonitrile=9:1 (v/v); eluent B: 1.5 M sodium chloride, 20 mM sodium phosphate (pH 8.1), solvent: water/acetonitrile=9:1 (v/v); elution gradient: the ratio of eluent A:eluent B=100:0-50:50. The eluate of product was collected, combined and desalted by using a reverse phase chromatography purification column. The specific condition includes: using a Sephadex column for desalination with Sephadex-G25 as the filler and eluting with deionized water.

The detection method is described as follows: the purity of the above sense strand was determined by ion exchange chromatography (IEX-HPLC); and the molecular weight was analyzed by Liquid Chromatography-Mass Spectrometry (LC-MS), with the calculated value being 7584.5 and the measured value being 7584.0. The result that the measured value was in conformity with the calculated value indicates that the sense strand SS conjugated with L-9 conjugation molecule at 3' terminal was synthesized.

(1-3) Synthesis of Antisense Strand of Conjugate L10-siFXIf1M1S

Antisense strand of Conjugate L10-siFXIf1M1S was synthesized by the phosphoramidite solid phase synthesis method, starting the cycles from a universal solid phase support (UnyLinker™ loaded NittoPhase®HL Solid Supports, Kinovate Life Sciences Inc.). The reaction conditions of deprotection, coupling, capping, oxidation or sulfurization, cleavage and deprotection, and purification and desalting in the solid phase synthesis method were the same as those used for the synthesis of the sense strand. The antisense strand AS was obtained by lyophilization.

The purity of the antisense strand was detected by ion exchange chromatography (IEX-HPLC); and the molecular weight of the antisense strand was analyzed by liquid chromatography-mass spectrometry (LC-MS). The result that the measured value was in conformity with the calculated value indicates that the antisense strand AS having the target sequence was synthesized.

(1-4) Synthesis of Conjugate L10-siFXIf1M1S

For Conjugate L10-siFXIf1M1S, the sense strand and antisense strand were respectively dissolved in water for injection to give a solution of 40 mg/mL. They were mixed in an equimolar ratio, heated at 50° C. for 15 min, cooled at room temperature to produce an annealed product, and then lyophilized to give a lyophilized powder. After the conjugate was diluted to a concentration of 0.2 mg/mL with ultra-pure water (Milli-Q ultra-pure water instrument, with resistivity of 18.2MΩ*cm (25° C.)), the molecular weight was determined by a liquid chromatography-mass spectrometry (LC-MS) (purchased from Waters Corp., model: LCT Premier). The result that the measured value was in conformity with the calculated value indicates that the synthesized siRNA conjugate was the designed target double-stranded nucleic acid sequence with the L-9 conjugation molecule. The siRNA conjugate has a structure as shown by Formula (403). The siRNA has the sequence corresponding to Conjugate L10-siFXIf1M1S as shown in Table 3.

TABLE 3 siRNA conjugates

| Preparation Example No. | Conjugate | | Sequence direction 5'-3' | SEQ ID NO |
|---|---|---|---|---|
| Preparation Example 1 | L10-siFXIf1M1S | Sense strand | GmsUmsAmCmGmUmGfGfAfCmUmGmGmAmUmUmCmUmGm | 541 |
| | | Antisense strand | CmsAfsGmAmAmUfCmCmAmGmUmCmCmAfCmGfUmAmCmsUmsUm | 542 |
| Preparation Example 2 | L10-siFXIa1M1SP | Sense strand | GmsGmsGmUmAmUmUfCfUfUmUmCmAmAmGmCmAmAmUm | 543 |
| | | Antisense strand | PAmsUfsUmGmCmUfUmGmAmAmAmGmAmAfUmAfCmCmCmsAmsGm | 544 |

TABLE 3-continued siRNA conjugates

| Preparation Example No. | Conjugate | | Sequence direction 5'-3' | SEQ ID NO |
|---|---|---|---|---|
| Preparation Example 3 | L10-siFXIb1M1SP | Sense strand | GmsGmsCmAmUmAmAfAfCfUmAmUmAmAmCmAmGmCmUm | 545 |
| | | Antisense strand | PAmsGfsCmUmGmUfUmAmUmAmGmUmUmUfAmUfGmCmCmsCmsUm | 546 |
| Preparation Example 4 | L10-siFXIc1M1SP | Sense strand | GmsCmsUmCmAmAmGfAfAfUmGmCmCmAmAmGmAmAmAm | 547 |
| | | Antisense strand | PUmsUfsUmCmUmUfGmGmCmAmUmUmCmUfUmGfAmGmCmsAmsCm | 548 |
| Preparation Example 5 | L10-siFXId1M1SP | Sense strand | GmsCmsAmAmCmAmAfAfGfAmCmAmUmUmUmAmUmGmUm | 549 |
| | | Antisense strand | PAmsCfsAmUmAmAfAmUmGmUmCmUmUmUfGmUfUmGmCmsAmsAm | 550 |
| Preparation Example 6 | L10-siFXIe1M1SP | Sense strand | GmsAmsAmUmCmUmCfAfAfAmGmAmAmAmUmCmUmUmUm | 551 |
| | | Antisense strand | PAmsAfsAmGmAmUfUmUmCmUmUmUmGmAfGmAfUmUmCmsUmsUm | 552 |
| Preparation Example 7 | L10-siFXIg1M1SP | Sense strand | AmsUmsUmUmCmUmGfGfGfUmAmUmUmCmUmUmUmCmAm | 553 |
| | | Antisense strand | PUmsGfsAmAmAmGfAmAmUmAmCmCmCmAfGmAfAmAmUmsCmsGm | 554 |
| Preparation Example 8 | L10-siFXIh1M1SP | Sense strand | CmsAmsUmGmAmAmGfGfGfCmAmUmAmAmAmCmUmAmUm | 555 |
| | | Antisense strand | PAmsUfsAmGmUmUfUmAmUmGmCmCmCmUfUmCfAmUmGmsUmsCm | 556 |
| Preparation Example 9 | L10-siFXIi1M1S | Sense strand | GmsGmsAmUmUmCmUfGfGfAmGmAmAmAmAmCmUmCmAm | 557 |
| | | Antisense strand | UmsGfsAmGmUmUfUmUmCmUmCmCmAmGfAmAfUmCmCmsAmsGm | 558 |
| Preparation Example 10 | L10-siFXIi1M1SP | Sense strand | GmsGmsAmUmUmCmUfGfGfAmGmAmAmAmAmCmUmCmAm | 559 |
| | | Antisense strand | PUmsGfsAmGmUmUfUmUmCmUmCmCmAmGfAmAfUmCmCmsAmsGm | 560 |

wherein, C, G, U, and A represent the base composition of a nucleotide; m represents that the nucleotide adjacent to the left side of the letter m is a methoxy modified nucleotide; f represents that the nucleotide adjacent to the left side of the letter f is a fluoro modified nucleotide; s represents the two nucleotides adjacent to both sides of the letter s are linked by a thiophosphate linkage; and P represents that the nucleotide adjacent to the right side of the letter P is a 5'-phosphate nucleotide.

Preparation Examples 2 to 10: Synthesis of the siRNA Conjugates of the Present Disclosure The siRNA conjugates of the present disclosure: L10-siFXIa1M1SP, L10-siFXIb1M1SP, L10-siFXIc1M1SP, L10-siFXId1M1SP, L10-siFXIe1M1SP, L10-siFXIg1M1SP, L10-siFXIh1M1SP, L10-siFXIi1M1S and L10-siFXIi1M1SP (which had the sequences corresponding to siFXIa1M1SP, siFXIb1M1SP, siFXIc1M1SP, siFXId1M1SP, siFXIe1M1SP, siFXIg1M1SP, siFXIh1M1SP, siFXIi1M1S and siFXIi1M1SP as shown in Table 3, respectively) were further synthesized respectively by the same methods as described in Preparation Example 1, except that (1) the sequences of the sense strand and antisense strand of Conjugate L10-siFXIf1M1S were replaced with those of the sense strands and antisense strands of the conjugates as shown in Table 3, respectively; and (2) as for Conjugates L10-siFXIa1M1SP, L10-siFXIb1M1SP, L10-siFXIc1M1SP, L10-siFXId1M1SP, L10-siFXIe1M1SP, L10-siFXIg1M1SP, L10-siFXIh1M1SP and L10-siFXIi1M1SP, the first nucleotide at the 5' terminal of their antisense strands was a 5'-phosphate nucleotide; correspondingly, during preparation of the antisense strands according to the phosphoramidite solid phase synthesis method, after the linking of the last nucleoside monomer, the monomer of Formula (CPR-I) (purchased from Suzhou GenePharma Inc. as Cat #13-2601-XX) was linked to the 5' terminal of the antisense strand by a four-step reaction of deprotection, coupling, capping, and oxidation, so as to form a 5'-phosphate nucleotide.

(CPR-I)

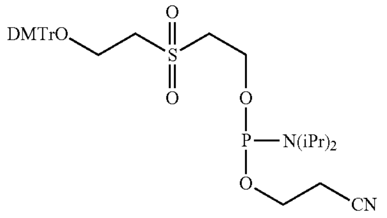

During the linking, the conditions of deprotection, coupling, capping and oxidation used were the same as those used in the synthesis of the sense strand. After having been completely linked, the sequence was further cleaved, deprotected, purified, desalted, and finally lyophilized to obtain the antisense strand AS.

After the conjugates had been prepared, their molecular weights were determined by the same method as in Preparation Example 1, respectively. The results showed that the measured values were in conformity with the calculated values, indicating that the synthesized siRNA conjugates were the designed target double-stranded nucleic acid sequences with the L-9 conjugation molecule and had the structure as shown by Formula (403). The siRNAs contained in these conjugates have the sequences corresponding to Conjugates L10-siFXIa1M1SP, L10-siFXIb1M1SP, L10-siFXIc1M1SP, L10-siFXId1M1SP, L10-siFXIe1M1SP, L10-siFXIg1M1SP, L10-siFXIh1M1SP, L10-siFXIi1M1S or L10-siFXIi1M1SP as shown in Table 3.

Preparation Examples 11 to 20: Synthesis of the siRNAs of the Present Disclosure The siRNA sequences as listed in Table 4 were synthesized by the solid phase synthesis method, respectively, and their molecular weights were determined. The sense strands and antisense strands, which were present in an equimolar ratio and complementary to one another as shown in Table 4, were dissolved in DEPC water, and then annealed to obtain the siRNAs of the present disclosure: siFXIa1M1SP, siFXIb1M1SP, siFXIc1M1SP, siFXId1M1SP, siFXIe1M1SP, siFXIf1M1SP, siFXIg1M1SP, siFXIh1M1SP, siFXIi1M1SP, and siFXIe1, as shown in Table 4.

During the preparation of the sequence siFXIe1, the target sequence comprises an unmodified nucleotide. In this case, under the cleavage and deprotection conditions, after treatment with aqueous ammonia, the product was dissolved in 0.4 ml/μmol of N-methylpyrrolidone, followed by addition of 0.3 ml/μmol of triethylamine and 0.6 ml/μmol of triethylamine trihydrofluoride, based on the amount of the single-strand nucleic acid, thereby removing the 2'-TBDMS protection on ribose.

Moreover, in the case where the first nucleotide at the 5' terminal of the antisense strand in the target sequence was a 5'-phosphate nucleotide, during preparation of the antisense strand according to the phosphoramidite solid phase synthesis method, after the linking of the last nucleoside monomer in the antisense strand, the monomer of Formula (CPR-I) (purchased from Suzhou GenePharma Inc. as Cat #13-2601-XX) was linked to the 5' terminal of the antisense strand by a four-step reaction of deprotection, coupling, capping, and oxidation, so as to form a 5'-phosphate nucleotide.

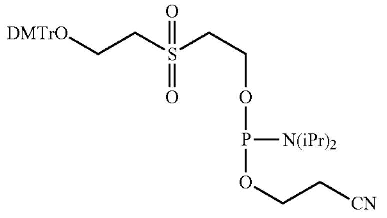

(CPR-I)

During the linking, the conditions of deprotection, coupling, capping and oxidation used were the same as those used in the synthesis of the sense strand. After having been completely linked, the sequence was further cleaved, deprotected, purified, desalted, and finally lyophilized to obtain the antisense strand AS.

Comparative Preparation Example 1: Synthesis of Comparative siRNA

The sense strand and anti sense strand of the siRNA numbered as NC in Table 4 were synthesized by the solid phase synthesis method, respectively, and their molecular weights were determined. The sense strand and antisense strand, which were present in an equimolar ratio, were dissolved in DEPC water and then annealed to obtain the comparative siRNA numbered as NC.

TABLE 4 siRNA sequences

| Preparation Example NO. | NO. | | Sequence direction 5'-3' | SEQ ID NO |
|---|---|---|---|---|
| Preparation Example 11 | siFXIa1 M1SP | Sense strand | GmsGmsGmUmAmUmUfCfUfUmUmCm AmAmGmCmAmAmUm | 543 |
| | | Antisense strand | PAmsUfsUmGmCmUfUmGmAmAmAmG mAmAfUmAfCmCmCmsAmsGm | 544 |
| Preparation Example 12 | siFXIb1 M1SP | Sense strand | GmsGmsCmAmUmAmAfAfCfUmAmUm AmAmCmAmGmCmUm | 545 |
| | | Antisense strand | PAmsGfsCmUmGmUfUmAmUmAmGmU mUmUfAmUfGmCmCmsCmsUm | 546 |
| Preparation Example 13 | siFXIc1 M1SP | Sense strand | GmsCmsUmCmAmAmGfAfAfUmGmCmC mAmAmGmAmAmAm | 547 |
| | | Antisense strand | PUmsUfsUmCmUmUfGmGmCmAmUmU mCmUfUmGfAmGmCmsAmsCm | 548 |
| Preparation Example 14 | siFXId1 M1SP | Sense strand | GmsCmsAmAmCmAmAfAfGfAmCmAmU mUmUmAmUmGmUm | 549 |
| | | Antisense strand | PAmsCfsAmUmAmAfAmUmGmUmCmU mUmUfGmUfUmGmCmsAmsAm | 550 |
| Preparation Example 15 | siFXIe1 M1SP | Sense strand | GmsAmsAmUmCmUmCfAfAfAmGmAm AmAmUmCmUmUmUm | 551 |

TABLE 4-continued siRNA sequences

| Preparation Example NO. | NO. | | Sequence direction 5'-3' | SEQ ID NO |
|---|---|---|---|---|
| | | Antisense strand | PAmsAfsAmGmAmUfUmUmCmUmUmUmGmAfGmAfUmUmCmsUmsUm | 552 |
| Preparation Example 16 | siFXIf1 M1SP | Sense strand | GmsUmsAmCmGmUmGfGfAfCmUmGmGmAmUmUmCmUmGm | 541 |
| | | Antisense strand | PCmsAfsGmAmAmUfCmCmAmGmUmCmCmAfCmGfUmAmCmsUmsUm | 542 |
| Preparation Example 17 | siFXIg1 M1SP | Sense strand | AmsUmsUmUmCmUmGfGfGfUmAmUmUmCmUmUmUmCmAm | 553 |
| | | Antisense strand | PUmsGfsAmAmAmGfAmAmUmAmCmCmCmAfGmAfAmAmUmsCmsGm | 554 |
| Preparation Example 18 | siFXIh1 M1SP | Sense strand | CmsAmsUmGmAmAmGfGfGfCmAmUmAmAmAmCmUmAmUm | 555 |
| | | Antisense strand | PAmsUfsAmGmUmUfUmAmUmGmCmCmCmUfUmCfAmUmGmsUmsCm | 556 |
| Preparation Example 19 | siFXIi1 M1SP | Sense strand | GmsGmsAmUmUmCmUfGfGfAmGmAmAmAmAmCmUmCmAm | 559 |
| | | Antisense strand | PUmsGfsAmGmUmUfUmUmCmUmCmCmAmGfAmAfUmCmCmsAmsGm | 560 |
| Preparation Example 20 | siFXIe1 | Sense strand | GAAUCUCAAAGAAAUCUUU | 561 |
| | | Antisense strand | AAAGAUUUCUUUGAGAUUC | 562 |
| Comparative Preparation Example 1 | NC | Sense strand | UmsUmsCmUmCmCmGfAfAfCmGmUmGmUmCmAmCmGmUm | 563 |
| | | Antisense strand | AmsCfsGmUmGmAfCmAmCmGmUmUmCmGfGmAfGmAmAmsCmsUm | 564 |

wherein, C, G, U, and A represent the base composition of a nucleotide; m represents that the nucleotide adjacent to the left side of the letter m is a methoxy modified nucleotide; f represents that the nucleotide adjacent to the left side of the letter f is a fluoro modified nucleotide; s represents the two nucleotides adjacent to both sides of the letter s are linked by a thiophosphate linkage; and P represents that the nucleotide adjacent to the right side of the letter P is a 5'-phosphate nucleotide.

After the above siRNAs or conjugates of the present disclosure having been completely prepared, they were lyophilized into solid powder and stored until use. When in use, they may be reconstituted with water for injection, normal saline (NS), phosphate buffer (PB) or phosphate salt buffer (PBS) to a solution at the desired concentration.

Experimental Example 1: Inhibitory Activity In Vitro of the siRNAs of the Present Disclosure HEK293A cells (purchased from Nanjing Cobioer Biosciences Co., LTD) were cultured in DMEM complete media (Hyclone company) containing 10% fetal bovine serum (FBS, Hyclone company), and 0.2 v % Penicillin-Streptomycin (Gibco, Invitrogen company) at 37° C. in an incubator containing 5% $CO_2$/95% air.

According to the method described by Kumico Ui-Tei et. al., Functional dissection of siRNA sequence by systematic DNA substitution: modified siRNA with a DNA seed arm is a powerful tool for mammalian gene silencing with significantly reduced off-target effect. Nucleic Acids Research, 2008.36(7), 2136-2151, plasmids for detection were constructed and co-transfected with the siRNA (siFXIe1) to be evaluated into HEK293A cells; and the inhibitory activities of the siRNAs were reflected by the expression levels of the dual luciferase reporter gene. The specific steps are as follows:

[1] Construction of Plasmid for Detection

The plasmid for detection was constructed using psiCHECK™-2 (Promega™) plasmid. This plasmid contains a target sequence, i.e., siRNA target sequence. The siRNAs to be detected have the target sequence shown below. In particular, the siFXIe1 (prepared from Preparation Example 20) has the following target sequence:

(SEQ ID NO: 565)
GAATCTCAAAGAAATCTTT.

The target sequence was cloned into the Xho I/Not I site of the psiCHECK™-2 plasmid.

[2] Transfection

HEK293A cells were inoculated in a 96-well plate at $8\times10^3$ cells/well. After 16 hours, the cell growth density reached 70 to 80%. At that time, the H-DMEM complete media in the culture wells were aspirated. An 80 μl Opti-MEM medium (GIBCO company) was added to each well and further cultured for 1.5 h.

The above plasmid for detection was diluted with DEPC-treated water to give a 200 ng/μl working solution with the plasmid for detection; the siFXIe1 was prepared with DEPC-treated water into siRNA working solutions at the concentrations of 10 nM and 3 nM (based on the amount of siRNA), respectively.

1A1 solution was prepared. Each portion of the 1A1 solution contains 1 μl of siRNA working solution at a concentration of 10 nM, 0.05 μl of the working solution with the plasmid for detection (containing 10 ng of plasmid for detection) and 10 μl of Opti-MEM medium.

1A2 solution was prepared. Each portion of the 1A2 solution contains 1 μl of siRNA working solution at a concentration of 3 nM, 0.05 μl of the working solution with the plasmid for detection (containing 10 ng of plasmid for detection) and 10 μl of Opti-MEM medium.

1B solution was prepared. Each portion of the 1B solution contains 0.2 μl of Lipofectamine™ 2000 and 10 μl of Opti-MEM medium.

1C solution was prepared. Each portion of the 1C solution contains 0.05 μl of the working solution with the plasmid for detection (containing 10 ng of plasmid for detection) and 10 μl of Opti-MEM medium One portion of the 1B solution was mixed with one portion of the 1A1 solution or one portion of the 1A2 solution, respectively. The mixed solution was incubated for 20 min at room temperature to form transfection complexes 1X1 and 1X2. One portion of the 1B solution was mixed with one portion of the 1C solution, and the mixed solution was incubated for 20 min at room temperature to form transfection complex 1X3.

The transfection complex 1X1 was added in an amount of 20 μl/well to three culture wells, respectively, and then mixed evenly to give a co-transfection mixture at a final siRNA concentration of 0.1 nM (recorded as test group 1).

The transfection complex 1X2 was added in an amount of 20 μl/well to three additional culture wells, respectively, and then mixed evenly to give a co-transfection mixture at a final siRNA concentration of 0.03 nM (recorded as test group 2).

The transfection complex 1X3 was added in an amount of 20 μl/well to three additional culture wells, respectively, to give an siRNA-free transfection mixture (recorded as the control group).

After the siRNA-containing co-transfection mixtures and the siRNA-free transfection mixture were co-transfected in the culture wells for 4 hours, each well was supplemented with 100 μl of H-DMEM complete medium containing 20% FBS. The 96-well plate was placed in a $CO_2$ incubator and further cultured for 24 hours.

[3] Detection

The media in the culture wells were aspirated. 150 μl of the mixed solution of Dual-Gb® Luciferase reagent and H-DMEM (in a volume ratio of 1:1) was added to each well, and thoroughly blended. After incubation for 10 minutes at room temperature, 120 μl of the mixed solution was transferred to a 96-well ELISA plate. The chemiluminescence value of Firefly (Fir) in each well of the ELISA plate was read using a Synergy II multimode microplate reader (BioTek company). Then, 60 μl of Dual-Gb® Stop & Glo® reagent was added to each well of the ELISA plate, and thoroughly blended. After incubation at room temperature for 10 minutes, the chemiluminescence value of Renilla (Ren) in each well of the ELISA plate was read using the microplate reader according to the arrangement for reading Fir.

The luminescence ratio (Ratio=Ren/Fir) of each well was calculated, and the luminescence ratio ((Ratio (test) or Ratio (control)) of each test group or control group was the mean value of the Ratios of the three culture wells. Using the luminescence ratio of the control group as the reference value, the luminescence ratio of each test group was normalized to obtain the ratio R of Ratio (test)/Ratio (control), which represents the expression level, i.e., the residual activity, of the reporter gene Renilla. The inhibition rate of siRNA was (1-R)×100%.

The inhibitory activity results of siFXIe1 at different concentrations against the target sequence were as shown in Table 5.

Comparative Experimental Example 1: Inhibitory Activity In Vitro of Comparative siRNA NC The inhibitory activity of the comparative siRNA NC in the psiCHECK system was investigated by the same method as described in Experimental Example 1 except that the siRNA to be tested was replaced with the comparative siRNA NC. The results were as shown in Table 5.

TABLE 5

Inhibition rate against the target sequence

| Preparation Example No. | NO. | Inhibition rate (%) against the target sequence 0.1 nM | 0.03 nM |
|---|---|---|---|
| Preparation Example 20 | siFXIe1 | 72.43 | 35.75 |
| Comparative Preparation Example 1 | NC | −3.64 | 8.91 |

The results indicated that siFXIe1 exhibited good concentration-dependent inhibitory activity in vitro against the target sequence at the respective concentration. In particular, the inhibition rate of siFXIe1 against the target sequence at the siRNA concentration of 0.1 nM was 72.43%, showing good effect of inhibiting the expression of FXI gene.

Experimental Example 2: Measuring $IC_{50}$ of siRNA Sequences Against FXI mRNA in the psiCHECK System In this experimental example, $IC_{50}$ values of siFXIa1M1SP, siFXIb1M1SP, siFXIc1M1SP, siFXId1M1SP, siFXIe1M1SP and siFXIi1M1SP in the psiCHECK system in vitro were investigated.

According to the method described by Kumico Ui-Tei et. al., Functional dissection of siRNA sequence by systematic DNA substitution: modified siRNA with a DNA seed arm is a powerful tool for mammalian gene silencing with significantly reduced off-target effect. Nucleic Acids Research, 2008.36(7), 2136-2151, the plasmids for detection were constructed and co-transfected with the siRNAs to be detected into HepG2 cells; and the on-target activities and off-target effects of the siRNAs were reflected by the expression levels of the dual luciferase reporter gene. The specific steps are as follows:

[1] Construction of Plasmid for Detection

The plasmid for detection was constructed using psiCHECK™-2 (Promega™) plasmid. This plasmid contains a target sequence, which was the sequence as shown in Genbank Accession No. NM_000128.3.

The target sequence was cloned into the Xho I/Not I site of the psiCHECK™-2 plasmid.

[2] Cell Culture and Transfection

HepG2 cells (purchased from GuangZhou Jennio Biotech Co., Ltd) were cultured in DMEM complete media (Hyclone company) containing 20% fetal bovine serum (FBS, Hyclone company), and 0.2 v % Penicillin-Streptomycin (Gibco, Invitrogen company) at 37° C. in an incubator containing 5% $CO_2$/95% air.

HepG2 cells were inoculated in a 96-well plate at $8\times10^3$ cells/well. After 16 hours, the cell growth density reached 70 to 80%. At that time, the H-DMEM complete media in the culture wells were aspirated. An 80 μl Opti-MEM medium (GIBCO company) was added to each well and further cultured for 1.5 h.

The above plasmid for detection was diluted with DEPC-treated water to give a 200 ng/μl working solution with the plasmid for detection; each of the following siRNAs was prepared with DEPC-treated water into siRNA working solutions at 10 different concentrations of 100 nM, 33.3 nM, 11.1 nM, 3.70 nM, 1.23 nM, 4.12 nM, 0.137 nM, 0.0457 nM, 0.0152 nM and 0.00508 nM, respectively. The siRNAs used are siFXIa1M1SP, siFXIb1M1SP, siFXIc1M1SP, siFXId1M1SP, siFXIe1M1SP and siFXIi1M1SP, respectively.

For each siRNA, 2A1 to 2A10 solutions were prepared, respectively. Each portion of the 2A1 to 2A10 solutions contains 1 μl of each of the siRNA working solutions at the above 10 concentrations, 0.05 μl of the working solution with the plasmid for detection (containing 10 ng of plasmid for detection) and 10 μl of Opti-MEM medium.

One portion of the 1B solution was mixed with one portion of the obtained 2A1 to 2A10 solutions for each siRNA, respectively. The mixed solution was incubated for 20 min at room temperature to form transfection complexes 2X1 to 2X10 for each siRNA.

The transfection complexes 2X1 to 2X10 for each siRNA were added in an amount of 20 μl/well to the culture wells, respectively, and then mixed evenly to give transfection complexes at final concentrations of about 1 nM, 0.333 nM, 0.111 nM, 0.0370 nM, 0.0123 nM, 0.00412 nM, 0.00137 nM, 0.000457 nM, 0.000152 nM, and 0.0000508 nM for each siRNA. The transfection complexes 2X1 to 2X10 for each siRNA were transfected respectively in three culture cells to give siRNA-containing co-transfection mixtures (recorded as the test groups).

The transfection complex 1X3 was added in an amount of 20 μl/well to three additional culture wells, respectively, to give an siRNA-free co-transfection mixture (recorded as the control group).

After the siRNA-containing co-transfection mixtures and the siRNA-free co-transfection mixture were transfected in the culture wells for 4 hours, each well was supplemented with 100 μl of H-DMEM complete medium containing 20% FBS. The 96-well plate was placed in a $CO_2$ incubator and further cultured for 24 hours.

[3] Detection

The media in the culture wells were aspirated. 150 μl of the mixed solution of Dual-Gb® Luciferase reagent and H-DMEM (in a volume ratio of 1:1) was added to each well, and thoroughly blended. After incubation for 10 minutes at room temperature, 120 μl of the mixed solution was transferred to a 96-well ELISA plate. The chemiluminescence value of Firefly (Fir) in each well of the ELISA plate was read using a Synergy II multimode microplate reader (BioTek company). Then, 60 μl of Dual-Gb® Stop & Glo® reagent was added to each well of the ELISA plate, and thoroughly blended. After incubation at room temperature for 10 minutes, the chemiluminescence value of Renilla (Ren) in each well of the ELISA plate was read using the microplate reader according to the arrangement for reading Fir.

The luminescence ratio (Ratio=Ren/Fir) of each well was calculated, and the luminescence ratio ((Ratio (test) or Ratio (control)) of each test group or control group was the mean value of the Ratios of the three culture wells. Using the luminescence ratio of the control group as the reference value, the luminescence ratio of each test group was normalized to obtain the ratio R of Ratio (test)/Ratio (control), which represents the expression level, i.e., the residual activity, of the reporter gene Renilla. The inhibition rate of siRNA was (1−R)×100%.

The dose-response curves were fitted using the function log(inhibitor) vs. response—Variable slope of Graphpad 5.0 software. The $IC_{50}$ values of the siRNA targeting GSCM were calculated based on the dose-response curve. In particular, the fitted dose-response curves complied with the formula below:

$$Y = Bot + \frac{\mathrm{Top} - Bot}{1 + 10^{(X' - X)\times HillSlope}}$$

wherein:

Y is the ratio R, i.e., the residual activity,

X is the logarithm of the concentration of transfected siRNAs,

Bot is the Y value at the bottom of the steady stage,

Top is the Y value at the top of the steady stage,

X' is the X value obtained by fitting at which Y is the median value between the bottom and the top, and Hill Slope is the slope of the curve by fitting at X'.

When Y=50% the corresponding X50 value was determined based on the dose-response curve and the corresponding calculation formula. The $IC_{50}$ value of each siRNA was calculated to be $10^{\wedge}X_{50}$.

The specific $IC_{50}$ values were summarized in Table 6.

TABLE 6

The $IC_{50}$ values of siRNAs

| Preparation Example No. | siRNA NO. | $IC_{50}$ |
|---|---|---|
| Preparation Example 11 | siFXIa1M1SP | 0.024 nM |
| Preparation Example 12 | siFXIb1M1SP | 0.078 nM |
| Preparation Example 13 | siFXIc1M1SP | 0.119 nM |
| Preparation Example 14 | siFXId1M1SP | 0.071 nM |
| Preparation Example 15 | siFXIe1M1SP | 0.013 nM |
| Preparation Example 19 | siFXIi1M1SP | 0.041 nM |

As can be seen from the results of Table 6 above, the siRNAs of the present disclosure exhibited very high inhibitory activity against the target sequence 1 in vitro in HepG2 cells, with the $IC_{50}$ value ranging between 0.013 and 0.119 nM.

Experimental Example 3: Measuring $IC_{50}$ of siRNAs Against FXI mRNA in HepG2 Cells HepG2 cells were inoculated in a 24-well plate at $7\times10^4$ cells/well. After 16 hours, the cell growth density reached 70 to 80%. At that time, the H-DMEM complete media in the culture wells were aspirated. A 500 μl Opti-MEM medium (GIBCO company) was added to each well and further cultured for 1.5 h.

Each of the following siRNAs was prepared with DEPC-treated water into siRNA working solutions at 7 different concentrations of 20 μM, 6.67 μM, 2.22 μM, 0.741 μM, 0.247 μM, 0.0823 μM and 0.0274 μM, respectively. The siRNAs used are siFXIa1M1SP, siFXIb1M1SP, siFXIc1M1SP or siFXId1M1SP, respectively.

For each siRNA, 3A1 to 3A7 solutions were prepared, respectively. Each portion of the 3A1 to 3A7 solutions contains, in turn, 3 μl of each of the siRNA working solutions at the above 7 concentrations and 50 μl of Opti-MEM medium.

3B solution was prepared. Each portion of the 3B solution contains 1 μl Lipofectamine™ 2000 and 50 μl of Opti-MEM medium.

One portion of the 3B solution was mixed with one portion of the obtained 3A1 to 3A7 solutions for each siRNA, respectively. The mixed solution was incubated for 20 min at room temperature to form transfection complexes 3X1 to 3X7 for each siRNA.

One portion of the 3B solution was mixed 50 μl of Opti-MEM medium. The mixed solution was incubated for 20 min at room temperature to form transfection complex 3X8.

The transfection complexes 3X1 to 3X7 for each siRNA were added in an amount of 100 μl/well to the culture wells, respectively, and then mixed evenly to give transfection mixtures at final concentrations of about 100 nM, 33.3 nM, 11.1 nM, 3.70 nM, 1.23 nM, 0.412 nM, and 0.137 nM for each siRNA. The transfection complexes 3X1 to 3X7 for each siRNA were transfected respectively in three culture cells to give siRNA-containing transfection mixtures (recorded as the test groups).

transcription reaction system was placed and incubated at 50° C. for 50 minutes, then incubated at 85° C. for 5 minutes, and finally incubated at 4° C. for 30 seconds; after the reaction was completed, 80 μl of DEPC water was added to each reverse transcription reaction system to obtain a cDNA-containing solution.

For each reverse transcription reaction system, 5 μl of the aforementioned cDNA-containing solution was taken as the template, and the reagent provided in the NovoStart® SYBR qPCR SuperMix Plus kit (purchased from Novoprotein Scientific Co., Ltd., Cat. No. E096-01B) was used to prepare 20 μl of a qPCR reaction system, wherein the sequences of PCR primers used for amplifying the target gene FXI and the internal reference gene GAPDH were as shown in Table 7, and the final concentration of each primer is 0.25 μM. Each qPCR reaction system was placed on an ABI StepOnePlus Real-Time PCR instrument, and was amplified using the three-step method. The amplification procedures was pre-denaturation at 95° C. for 10 minutes, followed by denaturation at 95° C. for 30 s, and annealing at 60° C. for 30 s, and extension at 72° C. for 30 s. After repeating the aforementioned process of denaturation, annealing, and extension 40 times, a product W containing the amplified target gene FXI and internal reference gene GAPDH was obtained. The product W was then incubated at 95° C. for 15 s, 60° C. for 1 min, and 95° C. for 15 s. The melting curves of the target gene FXI and the internal reference gene GAPDH in the product W were collected respectively using a real-time fluorescent qPCR instrument, and the Ct values of the target gene FXI and the internal reference gene GAPDH were obtained.

TABLE 7

The sequences of primers for detection

| Gene | Upstream Primers (in 5'-3' direction) | Downstream Primers (in 5'-3' direction) |
|---|---|---|
| Human FXI | TCACGGCGGAATCACCATC (SEQ ID NO: 566) | TGTCCTATTCACTCTTGGCAGT (SEQ ID NO: 567) |
| Human GAPDH | GGTCGGAGTCAACGGATTT (SEQ ID NO: 568) | CCAGCATCGCCCCACTTGA (SEQ ID NO: 569) |

The transfection complex 3X8 was added in an amount of 100 μl/well to three additional culture wells, respectively, to give an siRNA-free transfection mixture (recorded as the control group).

After the siRNA-containing transfection mixtures and the siRNA-free transfection mixture were transfected in the culture wells for 4 hours, each well was supplemented with 1 ml of H-DMEM complete medium containing 20% FBS. The 24-well plate was placed in a $CO_2$ incubator and further cultured for 24 hours.

Subsequently, the total RNA in the cells of each well was extracted by using RNAVzol (purchased from Vigorous Biotechnology Beijing Co., Ltd., Cat. No. N002) according to the detailed steps described in the instructions.

For the cells of each well, 1 μg of the total RNA was taken, and the reagent provided in the reverse transcription kit Goldenstar™ RT6 cDNA Synthesis Kit (purchased from Beijing Tsingke Biotechnology Co., Ltd., Cat. No. TSK301M), in which Goldenstar™ Oligo $(dT)_{17}$ was selected as the primer. 20 μl of a reverse transcription reaction system was prepared according to the precedures for reverse transcription in the kit instructions to reverse transcribe the total RNA of the cells in each well. Conditions for reverse transcription were as follows: each reverse Relative expression levels of the target gene FXI in each of the test groups and the control group were quantitatively calculated by the Comparative Ct (ΔΔCt) method. The calculation method was described as follows:

$$\Delta Ct\text{(the test group)}=Ct\text{ (target gene in the test group)}-Ct\text{ (internal reference gene in the test group)}$$

$$\Delta Ct\text{ (the control group)}=Ct\text{ (target gene in the control group)}-\Delta Ct\text{ (internal reference gene in the control group)}$$

$$\Delta\Delta Ct\text{ (the test group)}=\Delta Ct\text{ (the test group)}-\Delta Ct\text{ (mean value in the control group)}$$

$$\Delta\Delta Ct\text{ (the control group)}=\Delta Ct\text{ (the control group)}-\Delta Ct\text{ (mean value in the control group)}$$

wherein, the ΔCt (mean value in the control group) is the arithmetic mean value of the ΔCt (the control group) of each of the three culture wells in the control group. Thus, each culture well in either the test group or the control group corresponds to one ΔΔCt value.

The expression levels of FXI mRNA in the test groups were normalized based on that in the control group, wherein the expression level of FXI mRNA in the control group was defined as 100%;

Relative expression level of FXI mRNA in the test group=$2^{-\Delta\Delta Ct\ (the\ test\ group)}\times 100\%$.

For the siRNAs in the same test group, the mean value of the relative expression levels of FXI mRNA in the test group at each concentration was the arithmetic mean value of the relative expression levels of the three culture wells at that concentration.

The dose-response curves were fitted using the function log(inhibitor) vs. response—Variable slope of Graphpad 5.0 software. The $IC_{50}$ values of each siRNA against FXI mRNA were calculated based on the dose-response curve. In particular, the dose-response curves obtained by fitting complied with the formula below:

$$Y = Bot + \frac{\text{Top} - Bot}{1 + 10^{(X'-X)\times HillSlope}}$$

wherein:

Y is the relative expression level of FXI mRNA in each test group,

X is the logarithm of the final concentration of the siRNA used in the corresponding test group, Bot is the Y value at the bottom of the steady stage, Top is the Y value at the top of the steady stage, X' is the X value obtained by fitting at which Y is the median value between the bottom and the top, and HillSlope is the slope of the curve obtained by fitting at X'.

When Y=50% the corresponding $X_{50}$ value was determined based on the dose-response curve and the corresponding calculation formula. The $IC_{50}$ value of each siRNA was calculated to be $10^\wedge X_{50}$ (nM).

The $IC_{50}$ values of each siRNA against FXI mRNA were summarized in Table 8.

TABLE 8

$IC_{50}$ values of siRNAs against FXI mRNA

| Preparation Example No. | NO. | $IC_{50}$ |
|---|---|---|
| Preparation Example 2 | siFXIa1M1SP | 6.18 nM |
| Preparation Example 3 | siFXIb1M1SP | 7.54 nM |
| Preparation Example 4 | siFXIc1M1SP | 11.1 nM |
| Preparation Example 5 | siFXId1M1SP | 1.49 nM |

As can be seen from Table 8, the siRNAs of the present disclosure exhibited very high inhibitory activity against FXI mRNA in vitro in HepG2 cell lines, with the $IC_{50}$ value ranging between 1.49 and 11.1 nM.

Experimental Example 4: Measuring $IC_{50}$ of siRNAs Against FXI mRNA in Mouse Primary Hepatocytes Mouse primary hepatocytes were extracted from fresh liver tissues of normal C57BL/6N mice. The hepatocytes in an appropriate density were inoculated in Collagen Type I-coated glass, plastic coverslip or tissue culture dish, cultured in RPMI 1460 medium containing 1× dual antibody and 10% FBS, and further cultured in an incubator containing 5% $CO_2$/95% air at 37° C. for 30 min.

The inhibitory activity and $IC_{50}$ value of the siRNA against FXI mRNA were measured by the same methods as described in Experimental Example 3 except that the siRNA to be detected was siFXIf1M1SP; the cells used were mouse primary hepatocytes; and the final siRNA concentrations included totally 8 concentrations (100 nM, 25 nM, 6.25 nM, 1.56 nM, 0.391 nM, 0.098 nM, 0.0244 nM, and $6.1\times10^{-3}$ nM), respectively. The results were as shown in Table 9.

TABLE 9

$IC_{50}$ of siRNA against FXI mRNA

| Preparation Example No. | NO. | $IC_{50}$ |
|---|---|---|
| Preparation Example 7 | siFXIf1M1SP | 0.021 nM |

As can be seen from Table 9, the siFXIf1M1SP exhibited very high inhibitory activity against FXI mRNA in vitro in mice primary hepatocytes, with the $IC_{50}$ value being 0.021 nM.

Experimental Example 5: Detecting Inhibition Efficiency of siRNAs Against the Expression Levels of FXI mRNA in HepG2 Cells The inhibition rates of siRNAs against the expression levels of FXI mRNA were measured by the same method as described in Experimental Example 3 except that the siRNAs used were siFXIg1M1SP and siFXIh1M1SP; for each siRNA, the final siRNA concentrations included totally 3 concentrations (50 nM, 5 nM and 0.5 nM), respectively; and 2 culture wells were used at each concentration. The results were as shown in Table 10.

TABLE 10

Inhibition rates of siRNA at different concentrations against FXI mRNA

| | | Inhibition rate (%) against the expression level of FXI mRNA | | |
|---|---|---|---|---|
| Preparation Example No. | NO. | 50 nM | 5 nM | 0.5 nM |
| Preparation Example 8 | siFXIg1M1SP | 78.0 | 67.0 | 66.4 |
| Preparation Example 9 | siFXIh1M1SP | 83.0 | 75.0 | 64.6 |

As can be seen from Table 10, the siRNAs of the present disclosure exhibited very high inhibitory activity in vitro in HepG2 cells; and an inhibition rate against FXI mRNA of up to 83% could be achieved at the siRNA concentration of 50 nM.

Experimental Example 6: Detecting Inhibition Efficiency of Conjugates L10-siFXIf1M1S, L10-siFXIi1M1S and L10-siFXIi1M1SP Against the Expression Levels of FXI mRNA in Mice In Vivo C57BL/6N mice (all female) were randomly divided into groups (5 mice in each group) and numbered, respectively. The conjugate to be tested (i.e., L10-siFXIf1M1S, L10-siFXIi1M1S or L10-siFXIi1M1SP) was administered subcutaneously in two different doses of 5 mg/kg and 1 mg/kg (based on the amount of siRNA) to the mice in each group, respectively. Each siRNA conjugate was administered at the concentrations of 1 mg/mL and 0.2 mg/mL in the form of 0.9 wt % NaCl aqueous solution and the administration volume of 5 mL/kg.

One of the groups of mice was administered with 1×PBS in the administration volume of 5 mL/kg and recorded as the control group.

The mice were sacrificed on day 7 after administration. The liver tissue of each of the mice was collected and kept with RNA later (Sigma Aldrich company), and the liver tissue was homogenized with a tissue homogenizer. Then the total RNA was extracted and obtained by using Trizol according to the procedures as described in the instructions.

The expression levels of FXI mRNA were measured by fluorescent qPCR and the inhibition rates against FXI mRNA were calculated by the same methods as described in Experimental Example 3, except that the extracted total RNA was reverse transcribed into cDNA by using ImProm-II™ reverse transcription kit (Promega company) according to the instructions thereof, to give a cDNA-containing solution. Next, the expression level of FXI mRNA in the liver tissue was measured by using the fluorescent qPCR kit (Beijing ComWin Biotech Co., Ltd). In this fluorescent qPCR method, mouse GAPDH (mGAPDH) gene was used as an internal reference gene, the FXI and mouse GAPDH were detected by using primers for FXI and mouse GAPDH, respectively. The sequences of the primers for detection were as shown in Table 11.

In the course of measuring the expression levels of FXI mRNA and calculating the inhibition rate against FXI mRNA, the mice in the control group of this experiment were administered with PBS; and the mice in the test groups were administered with different siRNA conjugates, respectively. The expression level of FXI mRNA in the control group was recorded as 100%; and correspondingly, the inhibition rate against that expression level of FXI mRNA was recorded as 0%. The test results were normalized based on the expression level of FXI mRNA in the control group, as shown in Table 12.

TABLE 11

The sequences of primers for detection

| Gene name | Primer type | Nucleotide sequence (5'→3') | SEQ ID NO. |
|---|---|---|---|
| Mouse FXI | Upstream Primers | GCCCTGTTAAAACTGGAATCAGC | 574 |
| | Downstream Primers | CGTTTCTATCTCCTTTGGAAGGC | 575 |
| Mouse GAPDH | Upstream Primers | TGCACCACCAACTGCTTAG | 576 |
| | Downstream Primers | GGATGCAGGGATGATGTTC | 577 |

TABLE 12

Inhibition rates of siRNA conjugates at different concentrations against FXI mRNA

| Preparation Example No. | Conjugate | Inhibition rate (%) against FXI mRNA 1 mg/kg | 5 mg/kg |
|---|---|---|---|
| Preparation Example 1 | L10-siFXIf1M1S | 78.4 | 95.0 |
| Preparation Example 9 | L10-siFXIi1M1S | 67.1 | 90.2 |
| Preparation Example 10 | L10-siFXIi1M1SP | 56.8 | 92.1 |

As can be seen from Table 12, the siRNA conjugates of the present disclosure showed an inhibition rate ranging from 56.8 to 78.4% against FXI mRNA in an siRNA dose of 1 mg/kg; and an inhibition rate of up to 95.0% could be achieved at the siRNA concentration of 5 mg/kg, suggesting excellent inhibitory efficiency against FXI mRNA.

Experimental Example 7: Detecting the Inhibition of Conjugates L10-siFXIf1M1S and L10-siFXIi1M1SP Against the Expression of FXI mRNA and Prolongation of the Activated Partial Thromboplastin Time (APTT) at Different Time Points after Administration in Mice In Vivo C57BL/6N mice (all male) were randomly divided into 7 groups (5 mice in each group) and numbered, respectively. Conjugates L10-siFXIf1M1S and L10-siFXIi1M1SP were administered to every three groups of mice, respectively. The remaining group of mice was administered with saline as the control group. The administration route is subcutaneous injection. The conjugates were administered at the concentration of 1.8 mg/ml (based on siRNA) in the form of 0.9% NaCl aqueous solution and in the dosage of 9 mg/kg. The normal saline was 0.9% NaCl aqueous solution. The administration volume was 5 mL/kg. Plasma samples were collected on days 8, 15 and 29 after administration, respectively. The groups of mice administered with the conjugates were sacrificed on day 29 after administration; and the group of mice administered with NS were sacrificed on day 8 after administration. The liver tissue of each of the mice was collected and kept with RNA later (Sigma Aldrich company), and the liver tissue was homogenized with a tissue homogenizer. Then the total RNA was extracted and obtained by using Trizol according to the procedures as described in the instructions.

The expression levels of FXI mRNA were measured by fluorescent qPCR and the inhibition rates against FXI mRNA were calculated by the same methods as described in Experimental Example 3, except that the extracted total RNA was reverse transcribed into cDNA by using ImProm-II™ reverse transcription kit (Promega company) according to the instructions thereof, to give a cDNA-containing solution. Next, the expression level of FXI mRNA in the liver tissue was measured by using the fluorescent qPCR kit (Beijing ComWin Biotech Co., Ltd). In this fluorescent qPCR method, mouse GAPDH (mGAPDH) gene was used as an internal reference gene, the FXI and mouse GAPDH were detected by using primers for FXI and mouse GAPDH, respectively. The sequences of the primers for detection were as shown in Table 11.

In the course of measuring the expression levels of FXI mRNA and calculating the inhibition rates against FXI mRNA, the mice in the control group of this experiment were administered with saline; and the mice in the test groups were administered with different siRNA conjugates, respectively, with the samples being taken at different time points after administration. The expression level of FXI mRNA in the control group was recorded as 100%; and correspondingly, the inhibition rate against that expression level of FXI mRNA was recorded as 0%. The test results were normalized based on the expression level of FXI mRNA in the control group, as shown in Table 13. In this table, the inhibition rate against the expression level of FXI mRNA is the arithmetic mean value of the inhibition rates against the expression levels of FXI mRNA measured in 5 mice of the same group on the corresponding days after the administration of the corresponding siRNA conjugate.

TABLE 13

Inhibition rates of the siRNA conjugates against FXI mRNA at different time points after single administration

| | | Inhibition rate (%) against the expression level of FXI mRNA | | |
|---|---|---|---|---|
| Preparation Example No. | Conjugate | Day 8 | Day 15 | Day 29 |
| Preparation Example 1 | L10-siFXIf1M1S | 91.33 | 92.89 | 90.56 |
| Preparation Example 10 | L10-siFXIi1M1SP | 89.18 | 92.39 | 90.54 |

As can be seen from the results of Table 13, after single subcutaneous administration in mice, the siRNA conjugates of the present disclosure exhibited excellent inhibition rate against FXI mRNA in liver at different time points over a prolonged period, and showed an inhibition rate of at least 89.18% or even up to 92.89%.

Further, for the plasma samples as collected above, the APTT kit (Rayto company, Cat No. 20190402M) was used to measure the plasma APTT value of each mouse by turbidimetric assay in a semi-automatic coagulation analyzer (Rayto company, Model No. RT-2202). The specific detection method is carried out as described in the instructions of the APTT kit. By comparing the measured APTT values with that of the control group, the relative extension of APTT per mouse=(the measured value of APTT in the test group−the measured mean value of APTT in the control group)/(the measured mean value of APTT in the control group)×100%. The measured results were as shown in Table 14. In this table, the relative extension of APTT refers to the mean value of the relative extensions of APTT measured in 5 mice of the same group on the corresponding days after the administration of the corresponding siRNA conjugate.

TABLE 14

Relative extension of APTT at different time points after single administration of the siRNA conjugates

| | | Relative extension of APTT (%) | | |
|---|---|---|---|---|
| Preparation Example No. | Conjugate | Day 8 | Day 15 | Day 29 |
| Preparation Example 1 | L10-siFXIf1M1S | 64.9 | 62.1 | 18.2 |
| Preparation Example 10 | L10-siFXIi1M1SP | 42.5 | 42.5 | 51.2 |

As can be seen from the results of Table 14, the measured value of APTT was significantly extended in mice administered with the siRNA conjugates of the present disclosure over a prolonged period; and an extension of up to 64.9% could be achieved. Clearly, the siRNA conjugates of the present disclosure could effectively prolong the coagulation time of mice, suggesting that they have a promising prospect of application for the treatment and/or prevention of thrombotic disease and/or ischemic stroke.

Experimental Example 8: Measuring the Activities of the siRNA Conjugates of the Present Disclosure in Humanized Mice In Vivo The humanized mice used in this experiment were purchased from Cyagen Biosciences Inc. The mice were randomly divided into groups, with 4 mice (2 male mice and 2 female mice) in each group. Conjugates L10-siFXIf1M1S, L10-siFXIa1M1SP, L10-siFXIb1M1SP, L10-siFXIc1M1SP, L10-siFXId1M1SP, L10-siFXIe1M1SP, L10-siFXIg1M1SP, L10-siFXIh1M1SP and L10-siFXIi1M1S were individually administered to the mice in each group; and saline was used as the control. The drug dosages for all animals were calculated according to the body weight (single administration (subcutaneously). Each conjugate was administered at the concentrations of 0.3 mg/mL (based on siRNA) in the form of 0.9 wt % NaCl aqueous solution and the administration volume of 10 mL/kg, i.e., the dosage of each conjugate being 3 mg/kg (based on siRNA). The mice were sacrificed on day 8 after administration. The plasma samples were collected. 3.2 wt % (0.109 mol/L) of sodium citrate dihydrate aqueous solution was added at the volume ratio of anticoagulant to plasma of 1:9 (v/v) to prevent blood clotting; and the plasma samples were separated by centrifugation.

About 100 mg/mouse of the left lobe of the liver was taken and kept with RNA later (Sigma Aldrich). Subsequently, the liver tissue of each mouse was homogenized with a tissue homogenizer. Then the total RNA of liver tissue of each mice was extracted and obtained by using Trizol (Thermo Fisher company) according to the procedure as described in the instructions.

According to the same method as described in Experimental Example 6, the expression levels of FXI mRNA of liver tissue in mice administered with different siRNA conjugates of the present disclosure or in the mice in the control group were measured by real-time fluorescent qPCR method, except that the sequences of the primers for amplifying the human FXI and mouse GAPDH as the internal reference gene were as shown in Table 15.

TABLE 15

The sequences of primers for detection

| Gene name | Primer type | Nucleotide sequence (5'→3') | SEQ ID NO. |
|---|---|---|---|
| HumanFXI | Upstream Primers | TCACGGCGGAATCACCATC | 570 |
| | Downstream Primers | TGTCCTATTCACTCTTGGCAGT | 571 |
| Mouse | Upstream Primers | AACTTTGGCATTGTGGAAGGGCTC | 572 |
| GAPDH | Downstream Primers | TGGAAGAGTGGGAGTTGCTGTTGA | 573 |

The expression levels of FXI mRNA were measured and the inhibition rates against FXI mRNA were calculated by the same methods as described in Experimental Example 3. The expression level of FXI mRNA in the control group was recorded as 100%; and correspondingly, the inhibition rate against that expression level of FXI mRNA was recorded as 0%. The test results were normalized based on the expression level of FXI mRNA in the control group, as shown in Table 16. In this table, the inhibition rate against human FXI mRNA is the mean value of the inhibition rates against human FXI mRNA calculated in mice of the same group administered with the corresponding siRNA conjugate and the standard deviation thereof.

TABLE 16

The inhibition rates of the siRNA conjugates of the present disclosure against human FXI mRNA in humanized mice in vivo

| Preparation Example No. | Conjugate NO. | Inhibition rate against human FXI mRNA |
|---|---|---|
| Preparation Example 1 | L10-siFXIf1M1S | 76.03 ± 6.74 |
| Preparation Example 2 | L10-siFXIa1M1SP | 89.23 ± 3.25 |
| Preparation Example 3 | L10-siFXIb1M1SP | 81.75 ± 3.91 |
| Preparation Example 4 | L10-siFXIc1M1SP | 81.25 ± 3.61 |
| Preparation Example 5 | L10-siFXId1M1SP | 71.06 ± 9.62 |
| Preparation Example 6 | L10-siFXIe1M1SP | 85.26 ± 4.15 |
| Preparation Example 7 | L10-siFXIg1M1SP | 93.09 ± 1.96 |
| Preparation Example 8 | L10-siFXIh1M1SP | 76.78 ± 5.54 |
| Preparation Example 9 | L10-siFXIi1M1S | 74.25 ± 6.07 |

As can be seen from the results of Table 16, the siRNA conjugates of the present disclosure exhibited good inhibitory effects against human FXI mRNA in humanized heterozygous mouse liver, and showed an inhibition rate against FXI mRNA of up to about 71 to 93%.

Further, the above each group of mice (including the mice in the test groups administered with Conjugate L10-siFXIf1M1S, L10-siFXIa1M1SP, L10-siFXIb1M1SP, L10-siFXIc1M1SP, L10-siFXId1M1SP, L10-siFXIe1M1SP, L10-siFXIg1M1SP, L10-siFXIh1M1SP or L10-siFXIi1M1S, respectively and the mice in the control group administered with saline was tested using the Human Coagulation Factor X ELISA kit (Sigma company, Lot No.

0926F2350, Article No. RAB1385-1KT) to determine plasma FXI protein concentrations.

The sample diluent (labeled as ItemE2 in the kit) in the ELISA kit was 5-fold diluted with deionized water to obtain the diluted sample diluent.

For the plasma of mice administered with Conjugate L10-siFXIa1M1SP or L10-siFXIg1M1SP, 108 μL of the diluted sample diluent was added to 12 μL of plasma to form the sample solution to be tested, which was kept until use.

For the plasma of mice administered with other conjugates or saline, 108 μL of the diluted sample diluent was added to 12 μL of plasma to obtain 10-fold diluted plasma; 45 μL of the diluted sample diluent was added to 5 μL of the 10-fold diluted plasma to obtain 100-fold diluted plasma; and then 108 μL of the diluted sample diluent was added to 12 μL of the 100-fold diluted plasma to obtain a 1000-fold diluted sample diluent as the sample solution to be tested, which was kept until use.

The FXI antibody detection (labeled as ItemF in the kit) in the kit was dissolved with 100 μL of the diluted sample diluent into an antibody sample, and then 75 μL of the antibody sample was taken and added to 5925 μL of the diluted sample diluent to be 80-fold diluted to form the antibody detection solution.

The streptomycin concentrate (labeled as ItemG in the kit) in the kit was 250-fold diluted with the diluted sample diluent to form Streptomycin dilution solution.

The washing buffer (labeled as ItemB in the kit) in the kit was 20-fold diluted with deionized water to form the diluted washing solution.

Solutions with 8 standard concentration gradients were provided; one of the solutions was the diluted sample diluent (which could be regarded as the standard solution at the concentration of 0 pg/mL), and the other seven solutions were standard solutions of 7 concentrations of 2500 pg/mL, 1000 pg/mL, 400 pg/mL, 160 pg/mL, 64 pg/mL, 25.6 pg/mL and 10.24 pg/mL obtained by successively diluting the standard product (labeled as Item C in the kit) in the kit with the diluted sample diluent described above.

ELISA Assay

Human Coagulation Factor X ELISA kit (SIGMA company, Cat No. RAB1385-1KT) was used. The standard wells and sample wells were arranged according to the instruction manual for use. The solutions with different standard concentration gradients or the sample solutions to be tested were individually plated in an amount of 100 μL per well, and then incubated at room temperature for 2.5 hours. After removal of the solution therefrom, 300 μL of diluted washing solution was added per well to wash the wells for 1 minute, and then the washing solution was removed. 100 μL of antibody detection solution was added per well, and then incubated at room temperature for 1 hour. After removal of the solution therefrom, 300 μL of diluted washing solution was added per well to wash the wells for 1 minute, and then the washing solution was removed. This washing procedure was repeated for three times (i.e., washing for four times in total). 100 μL of Streptomycin dilution solution was added per well, and then incubated at room temperature for 45 minutes. After removal of the solution therefrom, 300 μL of diluted washing solution was added per well to wash the wells for 1 minute, and then the washing solution was removed. This washing procedure was repeated for three times (i.e., washing for four times in total). 100 μL of TMB (labeled as ItemH in the kit) was added per well, and then incubated for 30 minutes. 50 μL of a stop solution (provided in the kit) was added per well to stop the reaction. Absorbance at 450 nm was read immediately by using a fully-automatic microplate reader (BioTek company, Biotck SYNERGY MX). The results of each test group with a particular concentration of the siRNA conjugate were compared with the control group with saline.

According to the activity results measured in the solutions with standard concentration gradients, the dose-response standard curves were fitted using the function log(inhibitor) vs. response—Variable slope of Graphpad 6.0 software. The plasma protein concentration was calculated based on the dose-response curve, and the fitted curves complied with the calculation formula below:

$$Y = Bot + \frac{\text{Top} - Bot}{1 + 10^{(X'-X)\times HillSlope}}$$

wherein:

Y is the corresponding optical density value read at 450 nm,

X is the logarithm value (μg/mL) of the concentration in the standard curve,

Bot is the Y value at the bottom of the steady stage,

Top is the Y value at the top of the steady stage,

X' is the X value obtained by fitting at which Y is the median value between the bottom and the top, and Hill Slope is the slope of the curve at X'.

The logarithm value X of the corresponding concentration of each sample was obtained by placing the optical density value measured in each plasma sample in the formula based on the fitted standard curve; and the plasma FXI protein concentration value of each sample administered with different siRNA conjugate=^X (μg/mL) was calculated.

According to the plasma FXI protein concentration value, the inhibition rate against FXI protein=(the protein concentration in the control group−the protein concentration in the test group)/the protein concentration in the control group× 100% was calculated based on the protein concentration in the control group. The concentration results and inhibition rate data obtained were as shown in Table 17. In this table, the FXI protein concentration and the inhibition rate against FXI protein were the arithmetic mean value of the FXI protein concentrations and the inhibition rates against FXI protein in the same group of mice administered with the corresponding siRNA conjugate, respectively.

TABLE 17

Inhibitory effects of the siRNA conjugates of the present disclosure against the protein concentration in plasma

| Preparation Example No. | Conjugate NO. | FXI protein concentration (μg/mL) | Relative inhibition rate (%) against FXI protein |
|---|---|---|---|
| Control group | (Brine) | 0.2597 | 0 |
| Preparation Example 1 | L10-siFXIf1M1S | 0.0469 | 81.93 |
| Preparation Example 2 | L10-siFXIa1M1SP | 0.0026 | 99.02 |
| Preparation Example 3 | L10-siFXIb1M1SP | 0.0258 | 90.08 |
| Preparation Example 4 | L10-siFXIc1M1SP | 0.0205 | 92.09 |
| Preparation Example 5 | L10-siFXId1M1SP | 0.0417 | 83.94 |
| Preparation Example 6 | L10-siFXIe1M1SP | 0.0166 | 93.61 |
| Preparation Example 7 | L10-siFXIg1M1SP | 0.0017 | 99.34 |

TABLE 17-continued

Inhibitory effects of the siRNA conjugates of the present disclosure against the protein concentration in plasma

| Preparation Example No. | Conjugate NO. | FXI protein concentration (μg/mL) | Relative inhibition rate (%) against FXI protein |
|---|---|---|---|
| Preparation Example 8 | L10-siFXIh1M1SP | 0.0447 | 82.80 |
| Preparation Example 9 | L10-siFXIi1M1S | 0.0533 | 79.47 |

As can be seen from the results of Table 17, the siRNA conjugates of the present disclosure all exhibited excellent effects of inhibiting the expression of human FXI protein in plasma of humanized heterozygous mice; in particular, Conjugates L10-siFXIa1M1SP and L10-siFXIg1M1SP both showed high inhibition rate against FXI protein of up to about 99%.

Some embodiments of the present disclosure are described in detail above, but the present disclosure is not limited to the specific details of the above embodiments. Various simple variations to the technical solutions of the present disclosure can be made within the scope of the technical concept of the present disclosure, and these simple variations are also within the scope of the present disclosure.

It is to be noted that each of the specific technical features described in the above embodiments can be combined in any suitable manner provided that no contradiction is caused. In order to avoid unnecessary repetition, various possible combination manners are no longer described in the present disclosure.

In addition, various different embodiments of the present disclosure may also be carried out in any combination as long as it does not deviate from the idea of the present disclosure, which should also be regarded as the disclosure of the present disclosure.

INCORPORATION BY REFERENCE

All publications, patents and patent applications mentioned in this description are incorporated herein by reference to the extent as if each publication, patent and patent application were specifically and separately incorporated herein by reference.

The invention claimed is:

1. An siRNA conjugate, wherein the siRNA conjugate has a structure as shown by Formula (308):

Formula (308)

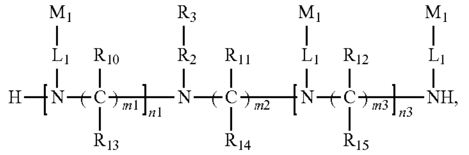

wherein, n1 is an integer of 1-2, and n3 is an integer of 0-1, and n1+n3=2-3:

m1, m2, and m3 independently of one another are an integer of 2-10;

$R_{10}$, $R_{11}$, $R_{12}$, $R_{13}$, $R_{14}$, and $R_{15}$ independently of one another are H, or selected from the group consisting of $C_1$-$C_{10}$ alkyl, $C_1$-$C_{10}$ haloalkyl, and $C_1$-$C_{10}$ alkoxy, $R_3$ is a group having a structure as shown by Formula (A59):

Formula (A59)

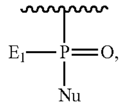

wherein $E_1$ is OH, SH or $BH_2$; and Nu is siRNA, wherein the siRNA comprises a sense strand and an antisense strand, each nucleotide in the siRNA being independently a modified or unmodified nucleotide, wherein the sense strand comprises a nucleotide sequence I, and the antisense strand comprises a nucleotide sequence II; the nucleotide sequence I and the nucleotide sequence II are at least partly reverse complementary to form a double-stranded region;

wherein the sense strand and the antisense strand have the same or different length, wherein the sense strand has a length of 19 to 23 nucleotides, and the antisense strand has a length of 19 to 26 nucleotides; and wherein the nucleotide sequence I and the nucleotide sequence II are selected from the sequences as shown in any of i) to ix):

i) the nucleotide sequence I has the same length as the nucleotide sequence as shown by SEQ ID NO: 1 with no more than 3 nucleotide differences therebetween, and the nucleotide sequence II has the same length as the nucleotide sequence as shown by SEQ ID NO: 2 with no more than 3 nucleotide differences therebetween:

(SEQ ID NO: 1)
5'-GGGUAUUCUUUCAAGCAA$Z_1$-3';

(SEQ ID NO: 2)
5'-$Z_2$UUGCUUGAAAGAAUACCC-3', wherein, $Z_1$ is U and $Z_2$ is A, and the nucleotide sequence I comprises a nucleotide $Z_3$ at the position corresponding to $Z_1$;

the nucleotide sequence II comprises a nucleotide $Z_4$ at the position corresponding to $Z_2$, wherein $Z_4$ is the first nucleotide at 5' terminal of the antisense strand;

ii) the nucleotide sequence I has the same length as the nucleotide sequence as shown by SEQ ID NO: 61 with no more than 3 nucleotide differences therebetween, and the nucleotide sequence II has the same length as the nucleotide sequence as shown by SEQ ID NO: 62 with no more than 3 nucleotide differences therebetween:

(SEQ ID NO: 61)
5'-GGCAUAAACUAUAACAGC$Z_5$-3';

(SEQ ID NO: 62)
5'-$Z_6$GCUGUUAUAGUUUAUGCC-3', wherein, $Z_5$ is U and $Z_6$ is A, and the nucleotide sequence I comprises a nucleotide $Z_7$ at the position corresponding to $Z_5$;

the nucleotide sequence II comprises a nucleotide $Z_8$ at the position corresponding to $Z_6$, wherein $Z_8$ is the first nucleotide at 5' terminal of the antisense strand;

iii) the nucleotide sequence I has the same length as the nucleotide sequence as shown by SEQ ID NO: 121 with no more than 3 nucleotide differences therebetween, and the nucleotide sequence II has the same length as the nucleotide sequence as shown by SEQ ID NO: 122 with no more than 3 nucleotide differences therebetween:

(SEQ ID NO: 121)
5'-GCUCAAGAAUGCCAAGAA$Z_9$-3';

(SEQ ID NO: 122)
5'-$Z_{10}$UUCUUGGCAUUCUUGAGC-3', wherein, $Z_9$ is A and $Z_{10}$ is U, and the nucleotide sequence I comprises a nucleotide $Z_{11}$ at the position corresponding to $Z_9$; the nucleotide sequence II comprises a nucleotide $Z_{12}$ at the position corresponding to $Z_{10}$, wherein $Z_{12}$ is the first nucleotide at 5' terminal of the antisense strand;

iv) the nucleotide sequence I has the same length as the nucleotide sequence as shown by SEQ ID NO: 181 with no more than 3 nucleotide differences therebetween, and the nucleotide sequence II has the same length as the nucleotide sequence as shown by SEQ ID NO: 182 with no more than 3 nucleotide differences therebetween:

(SEQ ID NO: 181)
5'-GCAACAAAGACAUUUAUG$Z_{13}$-3';

(SEQ ID NO: 182)
5'-$Z_{14}$CAUAAAUGUCUUUGUUGC-3', wherein, $Z_{13}$ is U and $Z_{14}$ is A, and the nucleotide sequence I comprises a nucleotide $Z_{15}$ at the position corresponding to $Z_{13}$; the nucleotide sequence II comprises a nucleotide $Z_{16}$ at the position corresponding to $Z_{14}$, wherein $Z_{16}$ is the first nucleotide at 5' terminal of the antisense strand;

v) the nucleotide sequence I has the same length as the nucleotide sequence as shown by SEQ ID NO: 241 with no more than 3 nucleotide differences therebetween, and the nucleotide sequence II has the same length as the nucleotide sequence as shown by SEQ ID NO: 242 with no more than 3 nucleotide differences therebetween:

(SEQ ID NO: 241)
5'-GAAUCUCAAAGAAAUCUUZ$_{17}$-3';

(SEQ ID NO: 242)
5'-Z$_{18}$AAGAUUUCUUUGAGAUUC-3', wherein, $Z_1$ is U and $Z_{18}$ is A, and the nucleotide sequence I comprises a nucleotide $Z_{19}$ at the position corresponding to $Z_{17}$; the nucleotide sequence II comprises a nucleotide $Z_{20}$ at the position corresponding to $Z_{18}$, wherein $Z_{20}$ is the first nucleotide at 5' terminal of the antisense strand;

vi) the nucleotide sequence I has the same length as the nucleotide sequence as shown by SEQ ID NO: 301 with no more than 3 nucleotide differences therebetween, and the nucleotide sequence II has the same length as the nucleotide sequence as shown by SEQ ID NO: 302 with no more than 3 nucleotide differences therebetween:

(SEQ ID NO: 301)
5'-GUACGUGGACUGGAUUCUZ$_{21}$-3';

(SEQ ID NO: 302)
5'-Z$_{22}$AGAAUCCAGUCCACGUAC-3', wherein, $Z_{21}$ is G and $Z_{22}$ is C, and the nucleotide sequence I comprises a nucleotide $Z_{23}$ at the position corresponding to $Z_{21}$; the nucleotide sequence II comprises a nucleotide $Z_{24}$ at the position corresponding to $Z_{22}$, wherein $Z_{24}$ is the first nucleotide at 5' terminal of the antisense strand;

vii) the nucleotide sequence I has the same length as the nucleotide sequence as shown by SEQ ID NO: 361 with no more than 3 nucleotide differences therebetween, and the nucleotide sequence II has the same length as the nucleotide sequence as shown by SEQ ID NO: 362 with no more than 3 nucleotide differences therebetween:

(SEQ ID NO: 361)
5'-AUUUCUGGGUAUUCUUUCZ$_{25}$-3';

(SEQ ID NO: 362)
5'-Z$_{26}$GAAAGAAUACCCAGAAAU-3', wherein, $Z_{25}$ is A and $Z_{26}$ is U, and the nucleotide sequence I comprises a nucleotide $Z_{27}$ at the position corresponding to $Z_{25}$; the nucleotide sequence II comprises a nucleotide $Z_{28}$ at the position corresponding to $Z_{26}$, wherein $Z_{28}$ is the first nucleotide at 5' terminal of the antisense strand;

viii) the nucleotide sequence I has the same length as the nucleotide sequence as shown by SEQ ID NO: 421 with no more than 3 nucleotide differences therebetween, and the nucleotide sequence II has the same length as the nucleotide sequence as shown by SEQ ID NO: 422 with no more than 3 nucleotide differences therebetween:

(SEQ ID NO: 421)
5'-CAUGAAGGGCAUAAACUAZ$_{29}$-3';

(SEQ ID NO: 422)
5'-Z$_{30}$UAGUUUAUGCCCUUCAUG-3', wherein, $Z_{29}$ is U and $Z_{30}$ is A, and the nucleotide sequence I comprises a nucleotide $Z_{31}$ at the position corresponding to $Z_{29}$; the nucleotide sequence II comprises a nucleotide $Z_{32}$ at the position corresponding to $Z_{30}$, wherein $Z_{32}$ is the first nucleotide at 5' terminal of the antisense strand;

ix) the nucleotide sequence I has the same length as the nucleotide sequence as shown by SEQ ID NO: 481 with no more than 3 nucleotide differences therebetween, and the nucleotide sequence II has the same length as the nucleotide sequence as shown by SEQ ID NO: 482 with no more than 3 nucleotide differences therebetween:

(SEQ ID NO: 481)
5'-GGAUUCUGGAGAAAACUCZ$_{33}$-3';

(SEQ ID NO: 482)
5'-Z$_{34}$GAGUUUUCUCCAGAAUCC-3', wherein, $Z_{33}$ is A and $Z_{34}$ is U, and the nucleotide sequence I comprises a nucleotide $Z_{35}$ at the position corresponding to $Z_{33}$; the nucleotide sequence II comprises a nucleotide $Z_{36}$ at the position corresponding to $Z_{34}$, wherein $Z_{36}$ is the first nucleotide at 5' terminal of the antisense strand_;

"corresponding position" refers to a same position in the nucleotide sequence by counting from a same terminal of the nucleotide sequence:

$R_2$ is a linear alkylene of 1 to 20 carbon atoms in length, wherein one or more carbon atoms are optionally replaced with any one or more groups selected from the group consisting of: C(O), NH, O, S, CH═N, $S(O)_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $R_2$ optionally has any one or more substituents selected from the group consisting of: $C_1$-$C_{10}$ alkyl, $C_6$-$C_{10}$ aryl, $C_5$-$C_{10}$ heteroaryl, $C_1$-$C_{10}$ haloalkyl, $OC_1$-$C_{10}$ alkyl, $OC_1$-$C_{10}$ alkylphenyl, —$C_1$-$C_{10}$ alkylOH, $OC_1$-$C_{10}$ haloalkyl, $SC_1$-$C_{10}$ alkyl, $SC_1$-$C_{10}$ alkylphenyl, —$C_1$-$C_{10}$ alkylSH, $SC_1$-$C_{10}$ haloalkyl, halo, OH, —SH, $NH_2$, $C_1$-$C_{10}$ alkyl$NH_2$, N($C_1$-$C_{10}$ alkyl)($C_1$-$C_{10}$ alkyl), NH($C_1$-$C_{10}$ alkyl), N($C_1$-$C_{10}$ alkyl)($C_1$-$C_{10}$ alkylphenyl), NH($C_1$-$C_{10}$ alkylphenyl), cyano, nitro, $CO_2H$, C(O)O($C_1$-$C_{10}$ alkyl), CON($C_1$-$C_{10}$ alkyl)($C_1$-$C_{10}$ alkyl), CONH($C_1$-$C_{10}$ alkyl), $CONH_2$, NHC(O)($C_1$-$C_{10}$ alkyl), NHC(O)(phenyl), N($C_1$-$C_{10}$ alkyl)C(O)($C_1$-$C_{10}$ alkyl), N($C_1$-$C_{10}$ alkyl)C(O)(phenyl), C(O)$C_1$-$C_{10}$ alkyl, C(O)$C_1$-$C_{10}$ alkylphenyl, C(O)$C_1$-$C_{10}$ haloalkyl, OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, $SO_2NH$($C_1$-$C_{10}$ alkyl), $SO_2NH$(phenyl), —$NHSO_2$($C_1$-$C_{10}$ alkyl), —$NHSO_2$(phenyl), and $NHSO_2$($C_1$-$C_{10}$ haloalkyl);

each $L_1$ is a linear alkylene of 1 to 70 carbon atoms in length, wherein one or more carbon atoms are optionally replaced with any one or more groups selected from the group consisting of: C(O), NH, O, S, CH═N, $S(O)_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $L_1$ optionally has any one or more substituents selected from the group consisting of: $C_1$-$C_{10}$ alkyl, $C_6$-$C_{10}$ aryl, $C_5$-$C_{10}$ heteroaryl, $C_1$-$C_{10}$ haloalkyl, $OC_1$-$C_{10}$ alkyl, $OC_1$-$C_{10}$ alkylphenyl, —$C_1$-$C_{10}$ alkylOH, $OC_1$-$C_{10}$ haloalkyl, $SC_1$-$C_{10}$ alkyl, $SC_1$-$C_{10}$ alkylphenyl, —$C_1$-$C_{10}$ alkylSH, $SC_1$-$C_{10}$ haloalkyl, halo, OH, —SH, $NH_2$, $C_1$-$C_{10}$ alkyl$NH_2$, N($C_1$-$C_{10}$ alkyl)($C_1$-$C_{10}$ alkyl), NH($C_1$-$C_{10}$ alkyl), $N(C_1-C_{10}$ alkyl)$(C_1-C_{10}$ alkylphenyl), $NH(C_1-C_{10}$ alkylphenyl), cyano, nitro, $CO_2H$, $C(O)O(C_1-C_{10}$ alkyl), $CON(C_1-C_{10}$ alkyl)$(C_1-C_{10}$ alkyl), $CONH(C_1-C_{10}$ alkyl), $CONH_2$, $NHC(O)(C_1-C_{10}$ alkyl), NHC(O)(phenyl), $N(C_1-C_{10}$ alkyl)$C(O)(C_1-C_{10}$ alkyl), $N(C_1-C_{10}$ alkyl)C(O)(phenyl), $C(O)C_1-C_{10}$ alkyl, $C(O)C_1-C_{10}$ alkylphenyl, $C(O)C_1-C_{10}$ haloalkyl, $OC(O)C_1-C_{10}$ alkyl, $—SO_2(C_1-C_{10}$ alkyl), $—SO_2$(phenyl), $—SO_2(C_1-C_{10}$ haloalkyl), $—SO_2NH_2$, $SO_2NH(C_1-C_{10}$ alkyl), $SO_2NH$(phenyl), $—NHSO_2(C_1-C_{10}$ alkyl), $—NHSO_2$(phenyl), and $NHSO_2(C_1-C_{10}$ haloalkyl);

represents the site where the group is covalently linked;

$M_1$ represents a targeting group, wherein each of the targeting groups is independently a ligand that has affinity to asialoglycoprotein receptors on a surface of mammalian hepatocytes.

2. The siRNA conjugate according to claim 1, wherein the sense strand further comprises a nucleotide sequence III, the antisense strand further comprises a nucleotide sequence IV, and the nucleotide sequence III and the nucleotide sequence IV independently of each other have a length of 1 to 4 nucleotides; the nucleotide sequence III is linked to the 5' terminal of the nucleotide sequence I; and the nucleotide sequence IV is linked to the 3' terminal of the nucleotide sequence II; the nucleotide sequence III and the nucleotide sequence IV have the same length and are reverse complementary to each other.

3. The siRNA conjugate according to claim 2, wherein the nucleotide sequence I has the same length as the nucleotide sequence as shown by SEQ ID NO: 1 with no more than 3 nucleotide differences therebetween; and the nucleotide sequence III and the nucleotide sequence IV both have a length of 1 nucleotide, and the base of the nucleotide sequence III is U; or the nucleotide sequence III and the nucleotide sequence IV both have a length of 2 nucleotides, and in the direction from 5' terminal to 3' terminal, the base composition of the nucleotide sequence III is CU; or the nucleotide sequence III and the nucleotide sequence IV both have a length of 3 nucleotides, and in the direction from 5' terminal to 3' terminal, the base composition of the nucleotide sequence III is UCU; or the nucleotide sequence III and the nucleotide sequence IV both have a length of 4 nucleotides, and in the direction from 5' terminal to 3' terminal, the base composition of the nucleotide sequence III is UUCU; or the nucleotide sequence I has the same length as the nucleotide sequence as shown by SEQ ID NO: 61 with no more than 3 nucleotide differences therebetween; and the nucleotide sequence III and the nucleotide sequence IV both have a length of 1 nucleotide, and the base of the nucleotide sequence III is G; or the nucleotide sequence III and the nucleotide sequence IV both have a length of 2 nucleotides, and in the direction from 5' terminal to 3' terminal, the base composition of the nucleotide sequence III is AG; or the nucleotide sequence III and the nucleotide sequence IV both have a length of 3 nucleotides, and in the direction from 5' terminal to 3' terminal, the base composition of the nucleotide sequence III is AAG; or the nucleotide sequence III and the nucleotide sequence IV both have a length of 4 nucleotides, and in the direction from 5' terminal to 3' terminal, the base composition of the nucleotide sequence III is GAAG; or the nucleotide sequence I has the same length as the nucleotide sequence as shown by SEQ ID NO: 121 with no more than 3 nucleotide differences therebetween; and the nucleotide sequence III and the nucleotide sequence IV both have a length of 1 nucleotide, and the base of the nucleotide sequence III is U; or the nucleotide sequence III and the nucleotide sequence IV both have a length of 2 nucleotides, and in the direction from 5' terminal to 3' terminal, the base composition of the nucleotide sequence III is GU; or the nucleotide sequence III and the nucleotide sequence IV both have a length of 3 nucleotides, and in the direction from 5' terminal to 3' terminal, the base composition of the nucleotide sequence III is AGU; or the nucleotide sequence III and the nucleotide sequence IV both have a length of 4 nucleotides, and in the direction from 5' terminal to 3' terminal, the base composition of the nucleotide sequence III is GAGU; or the nucleotide sequence I has the same length as the nucleotide sequence as shown by SEQ ID NO: 181 with no more than 3 nucleotide differences therebetween; and the nucleotide sequence III and the nucleotide sequence IV both have a length of 1 nucleotide, and the base of the nucleotide sequence III is U; or the nucleotide sequence III and the nucleotide sequence IV both have a length of 2 nucleotides, and in the direction from 5' terminal to 3' terminal, the base composition of the nucleotide sequence III is UU; or the nucleotide sequence III and the nucleotide sequence IV both have a length of 3 nucleotides, and in the direction from 5' terminal to 3' terminal, the base composition of the nucleotide sequence III is CUU; or the nucleotide sequence III and the nucleotide sequence IV both have a length of 4 nucleotides, and in the direction from 5' terminal to 3' terminal, the base composition of the nucleotide sequence III is GCUU; or the nucleotide sequence I has the same length as the nucleotide sequence as shown by SEQ ID NO: 241 with no more than 3 nucleotide differences therebetween; and the nucleotide sequence III and the nucleotide sequence IV both have a length of 1 nucleotide, and the base of the nucleotide sequence III is A; or the nucleotide sequence III and the nucleotide sequence IV both have a length of 2 nucleotides, and in the direction from 5' terminal to 3' terminal, the base composition of the nucleotide sequence III is AA; or the nucleotide sequence III and the nucleotide sequence IV both have a length of 3 nucleotides, and in the direction from 5' terminal to 3' terminal, the base composition of the nucleotide sequence III is AAA; or the nucleotide sequence III and the nucleotide sequence IV both have a length of 4 nucleotides, and in the direction from 5' terminal to 3' terminal, the base composition of the nucleotide sequence III is CAAA; or the nucleotide sequence I has the same length as the nucleotide sequence as shown by SEQ ID NO: 301 with no more than 3 nucleotide differences therebetween; and the nucleotide sequence III and the nucleotide sequence IV both have a length of 1 nucleotide, and the base of the nucleotide sequence III is A; or the nucleotide sequence III and the nucleotide sequence IV both have a length of 2 nucleotides, and in the direction from 5' terminal to 3' terminal, the base composition of the nucleotide sequence III is GA; or the nucleotide sequence III and the nucleotide sequence IV both have a length of 3 nucleotides, and in the direction from 5' terminal to 3' terminal, the base composition of the nucleotide sequence III is CGA; or the nucleotide sequence III and the nucleotide sequence IV both have a length of 4 nucleotides, and in the direction from 5' terminal to 3' terminal, the base composition of the nucleotide sequence III is UCGA; or the nucleotide sequence I has the same length as the nucleotide sequence as shown by SEQ ID NO: 361 with no more than 3 nucleotide differences therebetween; and the nucleotide sequence III and the nucleotide sequence IV both have a length of 1 nucleotide, and the base of the nucleotide sequence III is G; or the nucleotide sequence III and the nucleotide sequence IV both have a length of 2 nucleotides, and in the direction from 5' terminal to 3' terminal, the base composition of the nucleotide sequence III is CG; or the nucleotide sequence III and the nucleotide sequence IV both have a length of 3 nucleotides, and in the direction from 5' terminal to 3' terminal, the base composition of the nucleotide sequence III is GCG; or the nucleotide sequence III and the nucleotide sequence IV both have a length of 4 nucleotides, and in the direction from 5' terminal to 3' terminal, the base composition of the nucleotide sequence III is AGCG; or the nucleotide sequence I has the same length as the nucleotide sequence as shown by SEQ ID NO: 421 with no more than 3 nucleotide differences therebetween; and the nucleotide sequence III and the nucleotide sequence IV both have a length of 1 nucleotide, and the base of the nucleotide sequence III is A; or the nucleotide sequence III and the nucleotide sequence IV both have a length of 2 nucleotides, and in the direction from 5' terminal to 3' terminal, the base composition of the nucleotide sequence III is GA; or the nucleotide sequence III and the nucleotide sequence IV both have a length of 3 nucleotides, and in the direction from 5' terminal to 3' terminal, the base composition of the nucleotide sequence III is AGA; or the nucleotide sequence III and the nucleotide sequence IV both have a length of 4 nucleotides, and in the direction from 5' terminal to 3' terminal, the base composition of the nucleotide sequence III is UAGA; or the nucleotide sequence I has the same length as the nucleotide sequence as shown by SEQ ID NO: 481 with no more than 3 nucleotide differences therebetween; and the nucleotide sequence III and the nucleotide sequence IV both have a length of 1 nucleotide, and the base of the nucleotide sequence III is U; or the nucleotide sequence III and the nucleotide sequence IV both have a length of 2 nucleotides, and in the direction from 5' terminal to 3' terminal, the base composition of the nucleotide sequence III is CU; or the nucleotide sequence III and the nucleotide sequence IV both have a length of 3 nucleotides, and in the direction from 5' terminal to 3' terminal, the base composition of the nucleotide sequence III is ACU; or the nucleotide sequence III and the nucleotide sequence IV both have a length of 4 nucleotides, and in the direction from 5' terminal to 3' terminal, the base composition of the nucleotide sequence III is GACU.

4. The siRNA conjugate according to claim 1, wherein the antisense strand further comprises a nucleotide sequence V; the nucleotide sequence V has a length of 1 to 3 nucleotides and is linked to 3' terminal of the antisense strand, thereby forming a 3' overhang of the antisense strand.

5. The siRNA conjugate according to claim 4, wherein the nucleotide sequence V has a length of 2 nucleotides;

the nucleotide sequence V is 2 consecutive thymine deoxyribonucleotides or 2 consecutive uracil ribonucleotides; or the nucleotide sequence V is complementary to the nucleotides at the corresponding positions of the target mRNA.

6. The siRNA conjugate according to claim 1, wherein the sense strand of the siRNA comprises the nucleotide sequence as shown by SEQ ID NO: 5, and the antisense strand of the siRNA comprises the nucleotide sequence as shown by SEQ ID NO: 6:

(SEQ ID NO: 5)
5'-GGGUAUUCUUUCAAGCAAZ$_3$-3';

(SEQ ID NO: 6)
5'-Z$_4$UUGCUUGAAAGAAUACCCAG-3';

or, the sense strand of the siRNA comprises the nucleotide sequence as shown by SEQ ID NO: 7, and the antisense strand of the siRNA comprises the nucleotide sequence as shown by SEQ ID NO: 8:

(SEQ ID NO: 7)
5'-CUGGGUAUUCUUUCAAGCAAZ$_3$-3';

(SEQ ID NO: 8)
5'-Z$_4$UUGCUUGAAAGAAUACCCAGAA-3';

wherein, $Z_4$ is the first nucleotide at 5' terminal of the antisense strand; $Z_3$ is selected from A, U, G or C, and $Z_4$ is a nucleotide complementary to $Z_3$;

or, the sense strand of the siRNA comprises the nucleotide sequence as shown by SEQ ID NO: 65, and the antisense strand of the siRNA comprises the nucleotide sequence as shown by SEQ ID NO: 66:

(SEQ ID NO: 65)
5'-GGCAUAAACUAUAACAGCZ$_7$-3';

(SEQ ID NO: 66)
5'-Z$_8$GCUGUUAUAGUUUAUGCCCU-3';

or, the sense strand of the siRNA comprises the nucleotide sequence as shown by SEQ ID NO: 67, and the antisense strand of the siRNA comprises the nucleotide sequence as shown by SEQ ID NO: 68:

(SEQ ID NO: 67)
5'-AGGGCAUAAACUAUAACAGCZ$_7$-3';

(SEQ ID NO: 68)
5'-Z$_8$GCUGUUAUAGUUUAUGCCCUUC-3', wherein, $Z_8$ is the first nucleotide at 5' terminal of the antisense strand; $Z_7$ is selected from A, U, G or C, and $Z_8$ is a nucleotide complementary to $Z_7$;

or, the sense strand of the siRNA comprises the nucleotide sequence as shown by SEQ ID NO: 125, and the antisense strand of the siRNA comprises the nucleotide sequence as shown by SEQ ID NO: 126:

(SEQ ID NO: 125)
5'-GCUCAAGAAUGCCAAGAA$Z_{11}$-3';

(SEQ ID NO: 126)
5'-$Z_{12}$UUCUUGGCAUUCUUGAGCAC-3', or, the sense strand of the siRNA comprises the nucleotide sequence as shown by SEQ ID NO: 127, and the antisense strand of the siRNA comprises the nucleotide sequence as shown by SEQ ID NO: 128:

(SEQ ID NO: 127)
5'-GUGCUCAAGAAUGCCAAGAA$Z_{11}$-3';

(SEQ ID NO: 128)
5'-$Z_{12}$UUCUUGGCAUUCUUGAGCACUC-3', wherein, $Z_{12}$ is the first nucleotide at 5' terminal of the antisense strand; $Z_{11}$ is selected from A, U, G or C, and $Z_{12}$ is a nucleotide complementary to $Z_{11}$;

or, the sense strand of the siRNA comprises the nucleotide sequence as shown by SEQ ID NO: 185, and the antisense strand of the siRNA comprises the nucleotide sequence as shown by SEQ ID NO: 186:

(SEQ ID NO: 185)
5'-GCAACAAAGACAUUUAUG$Z_{15}$-3';

(SEQ ID NO: 186)
5'-$Z_{16}$CAUAAAUGUCUUUGUUGCAA-3', or, the sense strand of the siRNA comprises the nucleotide sequence as shown by SEQ ID NO: 187, and the antisense strand of the siRNA comprises the nucleotide sequence as shown by SEQ ID NO: 188:

(SEQ ID NO: 187)
5'-UUGCAACAAAGACAUUUAUG$Z_{15}$-3';

(SEQ ID NO: 188)
5'-$Z_{16}$CAUAAAUGUCUUUGUUGCAAGC-3', wherein, $Z_{16}$ is the first nucleotide at 5' terminal of the antisense strand; $Z_{15}$ is selected from A, U, G or C, and $Z_{16}$ is a nucleotide complementary to $Z_{15}$;

or, the sense strand of the siRNA comprises the nucleotide sequence as shown by SEQ ID NO: 245, and the antisense strand of the siRNA comprises the nucleotide sequence as shown by SEQ ID NO: 246:

(SEQ ID NO: 245)
5'-GAAUCUCAAAGAAAUCUU$Z_{19}$-3';

(SEQ ID NO: 246)
5'-$Z_{20}$AAGAUUUCUUUGAGAUUCUU-3', or, the sense strand of the siRNA comprises the nucleotide sequence as shown by SEQ ID NO: 247, and the antisense strand of the siRNA comprises the nucleotide sequence as shown by SEQ ID NO: 248:

(SEQ ID NO: 247)
5'-AAGAAUCUCAAAGAAAUCUU$Z_{19}$-3';

(SEQ ID NO: 248)
5'-$Z_{20}$AAGAUUUCUUUGAGAUUCUUUG-3', wherein, $Z_{20}$ is the first nucleotide at 5' terminal of the antisense strand; $Z_{19}$ is selected from A, U, G or C, and $Z_{20}$ is a nucleotide complementary to $Z_{19}$;

or, the sense strand of the siRNA comprises the nucleotide sequence as shown by SEQ ID NO: 305, and the antisense strand of the siRNA comprises the nucleotide sequence as shown by SEQ ID NO: 306:

(SEQ ID NO: 305)
5'-GUACGUGGACUGGAUUCU$Z_{23}$-3';

(SEQ ID NO: 306)
5'-$Z_{24}$AGAAUCCAGUCCACGUACUC-3', or, the sense strand of the siRNA comprises the nucleotide sequence as shown by SEQ ID NO: 307, and the antisense strand of the siRNA comprises the nucleotide sequence as shown by SEQ ID NO: 308:

(SEQ ID NO: 307)
5'-GAGUACGUGGACUGGAUUCU$Z_{23}$-3';

(SEQ ID NO: 308)
5'-$Z_{24}$AGAAUCCAGUCCACGUACUCGA-3', wherein, $Z_{24}$ is the first nucleotide at 5' terminal of the antisense strand; $Z_{23}$ is selected from A, U, G or C, and $Z_{24}$ is a nucleotide complementary to $Z_{23}$;

or, the sense strand of the siRNA comprises the nucleotide sequence as shown by SEQ ID NO: 365, and the antisense strand of the siRNA comprises the nucleotide sequence as shown by SEQ ID NO: 366:

(SEQ ID NO: 365)
5'-AUUUCUGGGUAUUCUUUC$Z_{27}$-3';

(SEQ ID NO: 366)
5'-$Z_{28}$GAAAGAAUACCCAGAAAUCG-3';

or, the sense strand of the siRNA comprises the nucleotide sequence as shown by SEQ ID NO: 367, and the antisense strand of the siRNA comprises the nucleotide sequence as shown by SEQ ID NO: 368:

(SEQ ID NO: 367)
5'-CGAUUUCUGGGUAUUCUUUC$Z_{27}$-3';

(SEQ ID NO: 368)
5'-$Z_{28}$GAAAGAAUACCCAGAAAUCGCU-3';

wherein, $Z_{28}$ is the first nucleotide at 5' terminal of the antisense strand; $Z_{27}$ is selected from A, U, G or C, and $Z_{28}$ is a nucleotide complementary to $Z_{27}$;

or, the sense strand of the siRNA comprises the nucleotide sequence as shown by SEQ ID NO: 425, and the antisense strand of the siRNA comprises the nucleotide sequence as shown by SEQ ID NO: 426:

(SEQ ID NO: 425)
5'-CAUGAAGGGCAUAAACUA$Z_{31}$-3';

(SEQ ID NO: 426)
5'-$Z_{32}$UAGUUUAUGCCCUUCAUGUC-3', or, the sense strand of the siRNA comprises the nucleotide sequence as shown by SEQ ID NO: 427, and the antisense strand of the siRNA comprises the nucleotide sequence as shown by SEQ ID NO: 428:

(SEQ ID NO: 427)
5'-GACAUGAAGGGCAUAAACUA$Z_{31}$-3';

(SEQ ID NO: 428)
5'-$Z_{32}$UAGUUUAUGCCCUUCAUGUCUA-3', wherein, $Z_{32}$ is the first nucleotide at 5' terminal of the antisense strand; $Z_{31}$ is selected from A, U, G or C, and $Z_{32}$ is a nucleotide complementary to $Z_{31}$;

or, the sense strand of the siRNA comprises the nucleotide sequence as shown by SEQ ID NO: 485, and the antisense strand of the siRNA comprises the nucleotide sequence as shown by SEQ ID NO: 486:

(SEQ ID NO: 485)
5'-GGAUUCUGGAGAAAACUC$Z_{35}$-3';

(SEQ ID NO: 486)
5'-$Z_{36}$GAGUUUUCUCCAGAAUCCAG-3', or, the sense strand of the siRNA comprises the nucleotide sequence as shown by SEQ ID NO: 487, and the antisense strand of the siRNA comprises the nucleotide sequence as shown by SEQ ID NO: 488:

(SEQ ID NO: 487)
5'-CUGGAUUCUGGAGAAAACUC$Z_{35}$-3';

(SEQ ID NO: 488)
5'-$Z_{36}$GAGUUUUCUCCAGAAUCCAGUC-3', wherein, $Z_{36}$ is the first nucleotide at 5' terminal of the antisense strand; $Z_{35}$ is selected from A, U, G or C, and $Z_{36}$ is a nucleotide complementary to $Z_{35}$.

7. The siRNA conjugate according to claim 1, wherein the siRNA is any one of siFXIa1, siFXIa2, siFXIb1, siFXIb2, siFXIc1, siFXIc2, siFXId1, siFXId2, siFXIe1, siFXIe2, siFXIf1, siFXIf2, siFXIg1, siFXIg2, siFXIh1, siFXIh2, siFXIi1, and siFXIi2.

8. The siRNA conjugate according to claim 1, wherein each nucleotide in the sense strand and the antisense strand is independently a fluoro modified nucleotide or a non-fluoro modified nucleotide;

wherein the fluoro modified nucleotides are located in the nucleotide sequence I; and in the direction from 5' terminal to 3' terminal, at least the nucleotides at positions 7, 8 and 9 of the nucleotide sequence I are fluoro modified nucleotides; and in the direction from 5' terminal to 3' terminal, at least the nucleotides at positions 2, 6, 14, and 16 of the nucleotide sequence II are fluoro modified nucleotides.

9. The siRNA conjugate according to claim 8, wherein each non-fluoro modified nucleotide is a methoxy modified nucleotide; and the methoxy modified nucleotide refers to a nucleotide formed by substituting 2'-hydroxy of the ribose group with a methoxy group.

10. The siRNA conjugate according to claim 9, wherein, in the direction from 5' terminal to 3' terminal, the nucleotides at positions 5, 7, 8 and 9 of the nucleotide sequence I in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 8, 9, 14, and 16 of the nucleotide sequence II in the antisense strand of the siRNA are fluoro modified nucleotides, and the nucleotides at the other positions in the antisense strand of the siRNA are methoxy modified nucleotides; or in the direction from 5' terminal to 3' terminal, the nucleotides at positions 5, 7, 8 and 9 of the nucleotide sequence I in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 14, and 16 of the nucleotide sequence II in the antisense strand of the siRNA are fluoro modified nucleotides, and the nucleotides at the other positions in the antisense strand of the siRNA are methoxy modified nucleotides; or in the direction from 5' terminal to 3' terminal, the nucleotides at positions 7, 8 and 9 of the nucleotide sequence I in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 14, and 16 of the nucleotide sequence II in the antisense strand of the siRNA are fluoro modified nucleotides, and the nucleotides at the other positions in the antisense strand of the siRNA are methoxy modified nucleotides.

11. The siRNA conjugate according to claim 8, wherein each non-fluoro modified nucleotide is independently selected from a nucleotide formed by substituting 2'-hydroxy of the ribose group thereof with a non-fluoro group, or a nucleotide analogue;

wherein the nucleotide formed by replacing 2'-hydroxy of the ribose group with a non-fluoro group is one selected from the group consisting of 2'-alkoxy modified nucleotides, 2'-substituted alkoxy modified nucleotides, 2'-alkyl modified nucleotides, 2'-substituted alkyl modified nucleotides, 2'-amino modified nucleotides, 2'-substituted amino modified nucleotides, and 2'-deoxy nucleotides; and the nucleotide analogue is one selected from the group consisting of isonucleotide, LNA, ENA, cET, UNA, and GNA, wherein LNA, ENA, cET, UNA, and GNA are shown by Formulae (12), (13), (14), (15), and (16) respectively:

Formula (12)

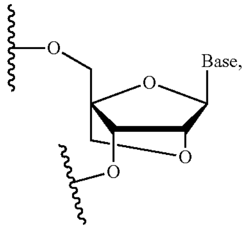

Formula (13)

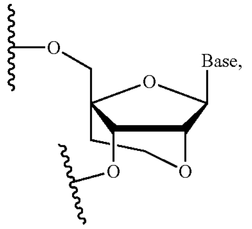

-continued

Formula (14)

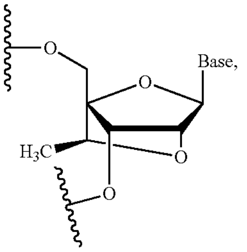

Formula (15)

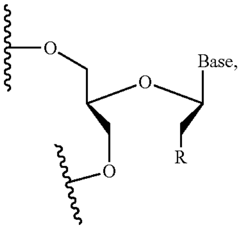

Formula (16)

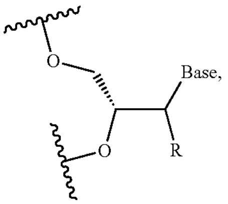

12. The siRNA conjugate according to claim 1, wherein the siRNA is any one of siFXIa1-M1, siFXIa1-M2, siFXIa1-M3, siFXIa2-M1, siFXIa2-M2, siFXIa2-M3, siFXIb1-M1, siFXIb1-M2, siFXIb1-M3, siFXIb2-M1, siFXIb2-M2, siFXIb2-M3, siFXIc1-M1, siFXIc1-M2, siFXIc1-M3, siFXIc2-M1, siFXIc2-M2, siFXIc2-M3, siFXId1-M1, siFXId1-M2, siFXId1-M3, siFXId2-M1, siFXId2-M2, siFXId2-M3, siFXIe1-M1, siFXIe1-M2, siFXIe1-M3, siFXIe2-M1, siFXIe2-M2, siFXIe2-M3, siFXIf1-M1, siFXIf1-M2, siFXIf1-M3, siFXIf2-M1, siFXIf2-M2, siFXIf2-M3, siFXIg1-M1, siFXIg1-M2, siFXIg1-M3, siFXIg2-M1, siFXIg2-M2, siFXIg2-M3, siFXIh1-M1, siFXIh1-M2, siFXIh1-M3, siFXIh2-M1, siFXIh2-M2, siFXIh2-M3, siFXIi1-M1, siFXIi1-M2, siFXIi1-M3, siFXIi2-M1, siFXIi2-M2, and siFXIi2-M3; or the siRNA is any one of siFXIa1-M1S, siFXIa1-M2S, siFXIa1-M3S, siFXIa2-M1S, siFXIa2-M2S, siFXIa2-M3S, siFXIb1-M1S, siFXIb1-M2S, siFXIb1-M3S, siFXIb2-M1S, siFXIb2-M2S, siFXIb2-M3S, siFXIc1-M1S, siFXIc1-M2S, siFXIc1-M3S, siFXIc2-M1S, siFXIc2-M2S, siFXIc2-M3S, siFXId1-M1S, siFXId1-M2S, siFXId1-M3S, siFXId2-M1S, siFXId2-M2S, siFXId2-M3S, siFXIe1-M1 S, siFXIe1-M2S, siFXIe1-M3S, siFXIe2-M1S, siFXIe2-M2S, siFXIe2-M3S, siFXIf1-M1S, siFXIf1-M2S, siFXIf1-M3S, siFXIf2-M1S, siFXIf2-M2S, siFXIf2-M3S, siFXIg1-M1S, siFXIg1-M2S, siFXIg1-M3S, siFXIg2-M1S, siFXIg2-M2S, siFXIg2-M3S, siFXIh1-M1 S, siFXIh1-M2S, siFXIh1-M3S, siFXIh2-M1S, siFXIh2-M2S, siFXIh2-M3S, FXIi1-M1S, siFXIi1-M2S, siFXIi1-M3S, siFXIi2-M1S, siFXIi2-M2S, and siFXIi2-M3S; or the siRNA is any one of siFXIa1-M1P1, siFXIa1-M2P1, siFXIa1-M3P1, siFXIa2-M1P1, siFXIa2-M2P1, siFXIa2-M3P1, siFXIa1-M1SP1, siFXIa1-M2SP1, siFXIa1-M3SP1, siFXIa2-M1SP1, siFXIa2-M2SP1, siFXIa2-M3SP1, siFXIb1-M1P1, siFXIb1-M2P1, siFXIb1-M3P1, siFXIb2-M1P1, siFXIb2-M2P1, siFXIb2-M3P1, siFXIb1-M1SP1, siFXIb1-M2SP1, siFXIb1-M3SP1, siFXIb2-M1SP1, siFXIb2-M2SP1, siFXIb2-M3SP1, siFXIc1-M1P1, siFXIc1-M2P1, siFXIc1-M3P1, siFXIc2-M1P1, siFXIc2-M2P1, siFXIc2-M3P1, siFXIc1-M1SP1, siFXIc1-M2SP1, siFXIc1-M3SP1, siFXIc2-M1SP1, siFXIc2-M2SP1, siFXIc2-M3SP1, siFXId1-M1P1, siFXId1-M2P1, siFXId1-M3P1, siFXId2-M1P1, siFXId2-M2P1, siFXId2-M3P1, siFXId1-M1SP1, siFXId1-M2SP1, siFXId1-M3SP1, siFXId2-M1SP1, siFXId2-M2SP1, siFXId2-M3SP1, siFXIe1-M1P1, siFXIe1-M2P1, siFXIe1-M3P1, siFXIe2-M1P1, siFXIe2-M2P1, siFXIe2-M3P1, siFXIe1-M1SP1, siFXIe1-M2SP1, siFXIe1-M3SP1, siFXIe2-M1SP1, siFXIe2-M2SP1, siFXIe2-M3SP1, siFXIf1-M1P1, siFXIf1-M2P1, siFXIf1-M3P1, siFXIf2-M1P1, siFXIf2-M2P1, siFXIf2-M3P1, siFXIf1-M1SP1, siFXIf1-M2SP1, siFXIf1-M3SP1, siFXIf2-M1SP1, siFXIf2-M2SP1, siFXIf2-M3SP1, siFXIg1-M1P1, siFXIg1-M2P1, siFXIg1-M3P1, siFXIg2-M1P1, siFXIg2-M2P1, siFXIg2-M3P1, siFXIg1-M1SP1, siFXIg1-M2SP1, siFXIg1-M3SP1, siFXIg2-M1SP1, siFXIg2-M2SP1, siFXIg2-M3SP1, siFXIh1-M1P1, siFXIh1-M2P1, siFXIh1-M3P1, siFXIh2-M1P1, siFXIh2-M2P1, siFXIh2-M3P1, siFXIh1-M1SP1, siFXIh1-M2SP1, siFXIh1-M3SP1, siFXIh2-M1SP1, siFXIh2-M2SP1, siFXIh2-M3SP1, siFXIi1-M1P1, siFXIi1-M2P1, siFXIi1-M3P1, siFXIi2-M1P1, siFXIi2-M2P1, siFXIi2-M3P1, siFXIi1-M1SP1, siFXIi1-M2SP1, siFXIi1-M3SP1, siFXIi2-M1SP1, siFXIi2-M2SP1, and siFXIi2-M3SP1.

13. The siRNA conjugate according to claim 1, wherein in the siRNA, at least one phosphate group is a phosphorothioate group, and the phosphorothioate linkage is located in at least one of the group consisting of the following positions:

the position between the first and second nucleotides at 5' terminal of the sense strand;

the position between the second and third nucleotides at 5' terminal of the sense strand;

the position between the first and second nucleotides at 3' terminal of the sense strand;

the position between the second and third nucleotides at 3' terminal of the sense strand;

the position between the first and second nucleotides at 5' terminal of the antisense strand;

the position between the second and third nucleotides at 5' terminal of the antisense strand;

the position between the first and second nucleotides at 3' terminal of the antisense strand; and the position between the second and third nucleotides at 3' terminal of the antisense strand.

14. The siRNA conjugate according to claim 1, wherein each $L_1$ is independently selected from the group consisting of the groups of Formulae (A1)-(A26) and any combination thereof:

(A1)

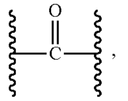

-continued
(A2)
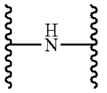,
(A3)
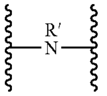,
(A4)
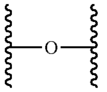,
(A5)
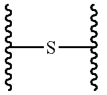,
(A6)
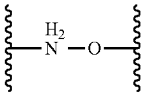,
(A7)
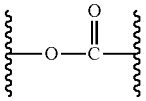
(A8)
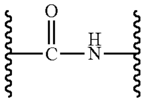,
(A9)
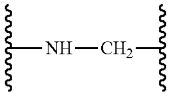,
(A10)
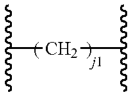,
(A11)
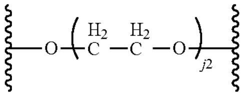,
(A12)
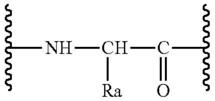,
(A13)
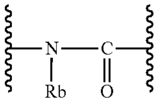,
(A14)
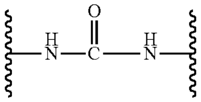,
(A15)
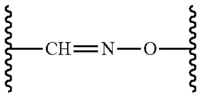,
-continued
(A16)
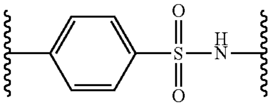,
(A17)
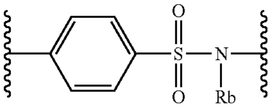,
(A18)
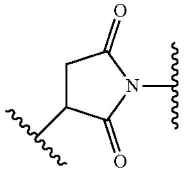,
(A19)
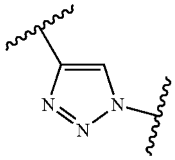,
(A20)
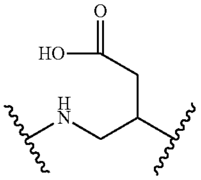,
(A21)
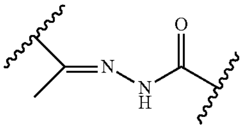,
(A22)
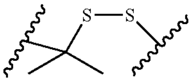,
(A23)
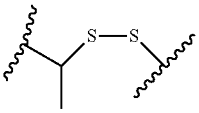,
(A24)
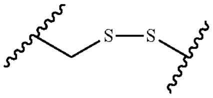,
(A25)
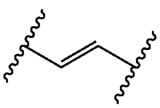
and
(A26)
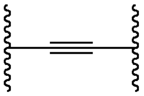;

wherein each j1 is independently an integer of 1-20;
each j2 is independently an integer of 1-20;
each R' is independently a $C_1$-$C_{10}$ alkyl;
each Ra is selected from the group consisting of the groups of Formulae (A27)-(A45) and any combination thereof:
(A27)
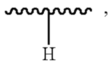
(A28)
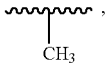
(A29)
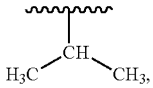
(A30)
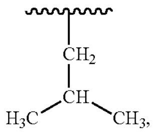
(A31)
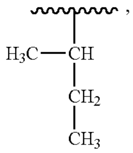
(A32)
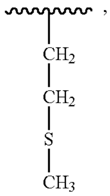
(A33)
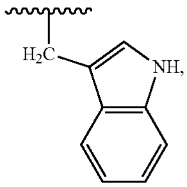
(A34)
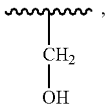
(A35)
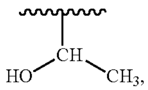
(A36)
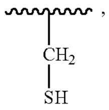
-continued
(A37)
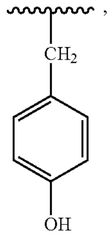
(A38)
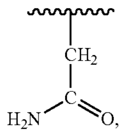
(A39)
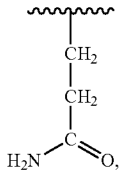
(A40)
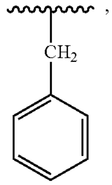
(A41)
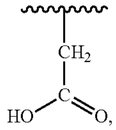
(A42)
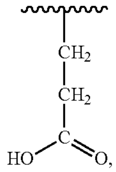
(A43)
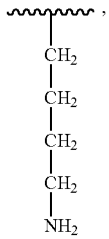

-continued (A44)

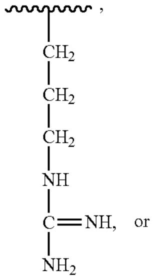

(A45)

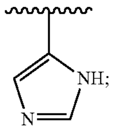

each Rb is independently a $C_1$-$C_{10}$ alkyl; and represents the site where a group is covalently linked.

15. The siRNA conjugate according to claim 14, wherein $L_1$ is selected from the group consisting of groups of Formulae (A1), (A4), (A5), (A6), (A8), (A10), (A11), and (A13) and connection combinations thereof; or $L_1$ is a connection combination of at least two of groups of Formulae (A1), (A4), (A8), (A10), and (A11).

16. The siRNA conjugate according to claim 1, wherein $L_1$ has a length of 3 to 25 atoms; or $L_1$ has a length of 4 to 15 atoms.

17. The siRNA conjugate according to claim 1, wherein each m1, m2 and m3 independently of one another are an integer of 2-5; or wherein m1=m2=m3.

18. The siRNA conjugate according to claim 1, wherein each of the targeting groups is independently selected from the group consisting of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O—[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-β-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2-deoxy-1,5-dithio-α-D-glucoheptopyranoside, 2,5-anhydro-D-allononitrile, ribose, D-ribose, D-4-thioribose, L-ribose and L-4-thioribose.

19. The siRNA conjugate according to claim 1, wherein the $R_2$ group has both a site linking to the N atom on the nitrogenous backbone and a site linking to the P atom in $R_3$; and in $R_2$, the site linking to the N atom on the nitrogenous backbone forms an amide bond with the N atom, and the site linking to the P atom in $R_3$ forms a phosphoester bond with the P atom; or;

$R_2$ is selected from B5, B6, B5', or B6':

(B5)

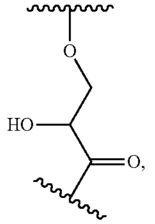

(B6)

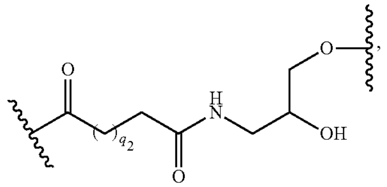

(B5')

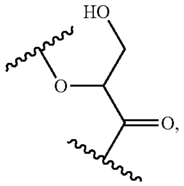

or (B6')

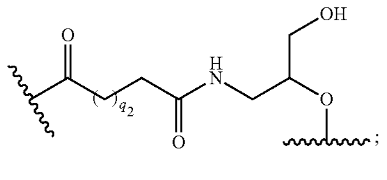

wherein  represents the site where the group is covalently linked;

q2 is an integer of 1-10.

20. The siRNA conjugate according to claim 1, wherein the siRNA conjugate has a structure as shown by Formula (403), (404), (405), (406), (407), (408), (409), (410), (411), (412), (413), (414), (415), (416), (417), (418), (419), (420), (421) or (422):

Formula (403)
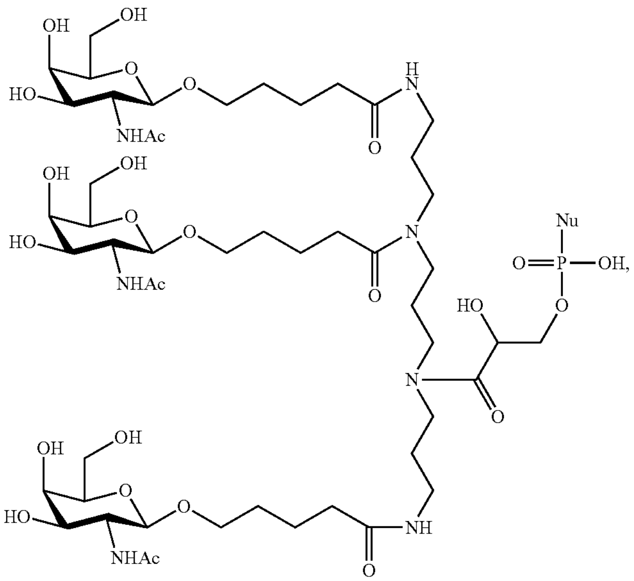
Formula (404)
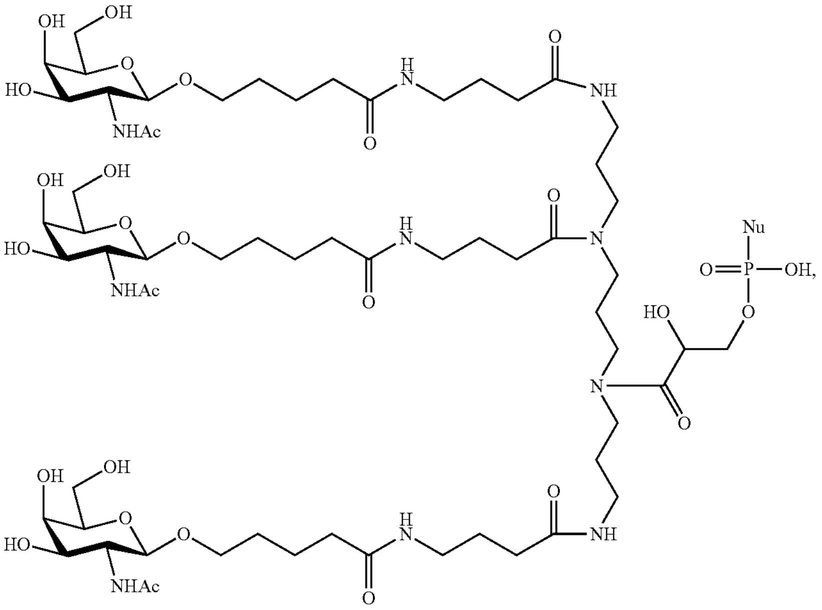

-continued
Formula (405)
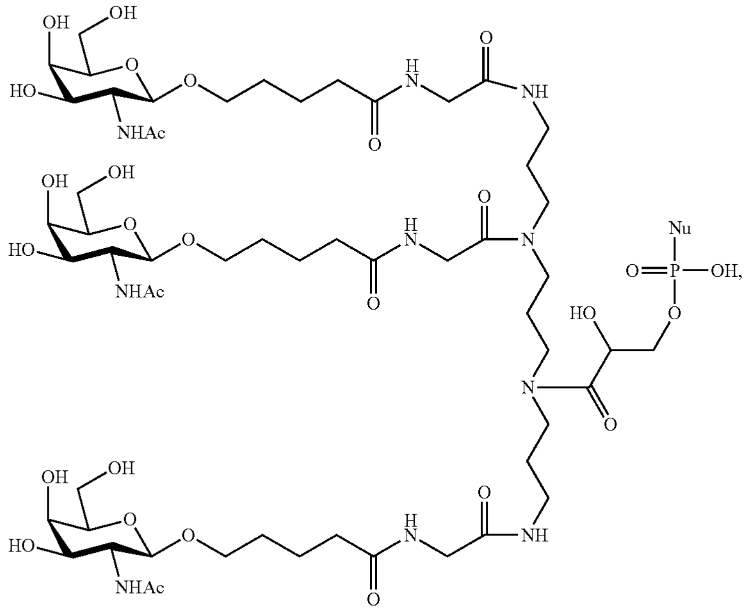
Formula (406)
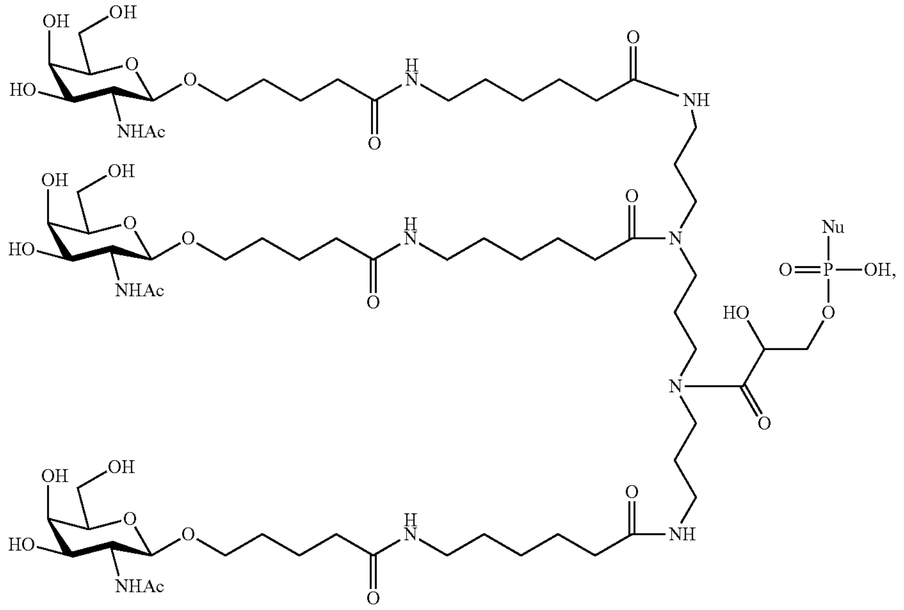

-continued
Formula (407)
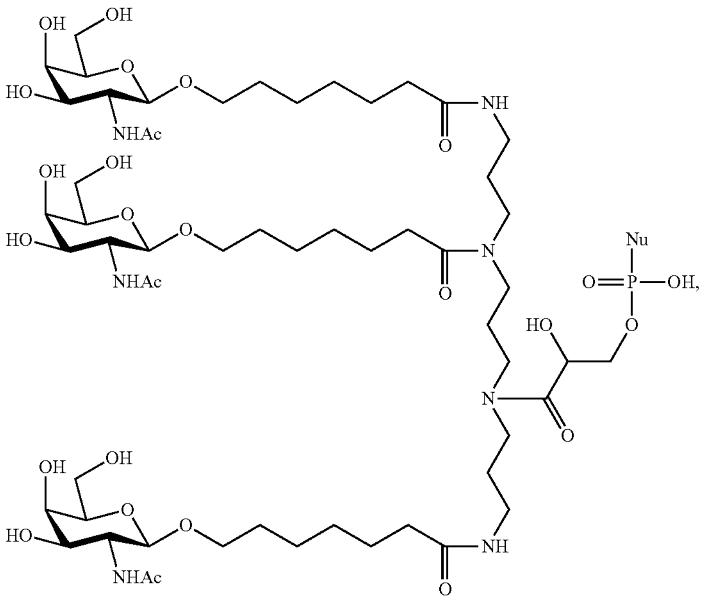
Formula (408)
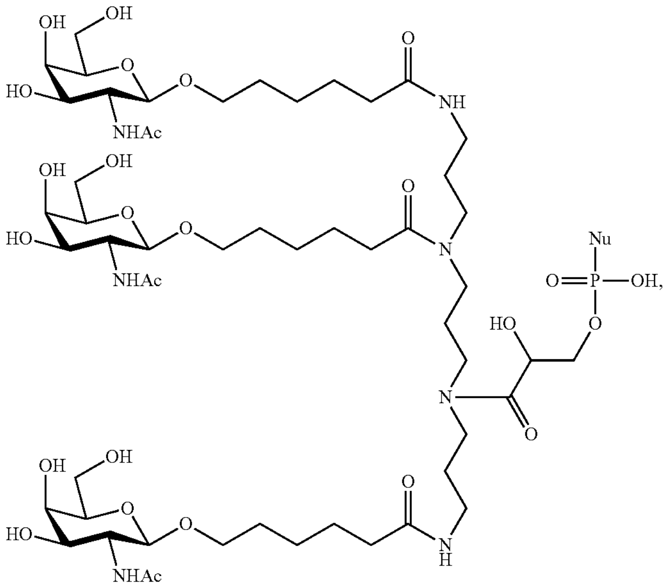

-continued
Formula (409)
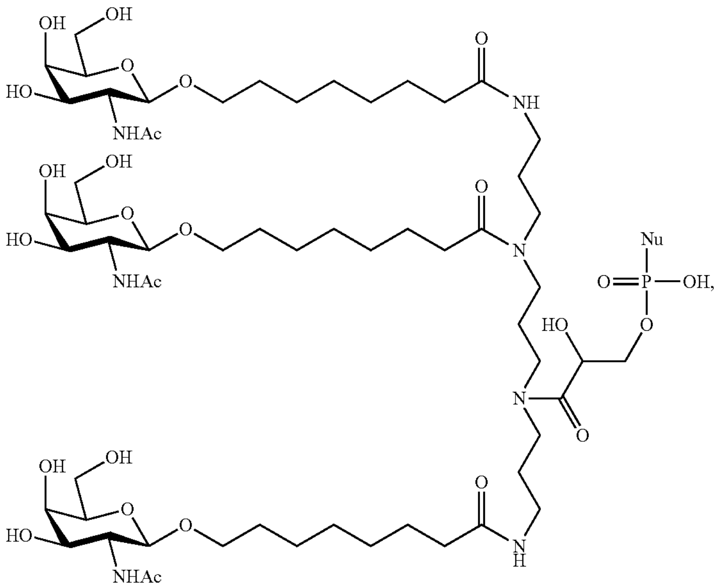
Formula (410)
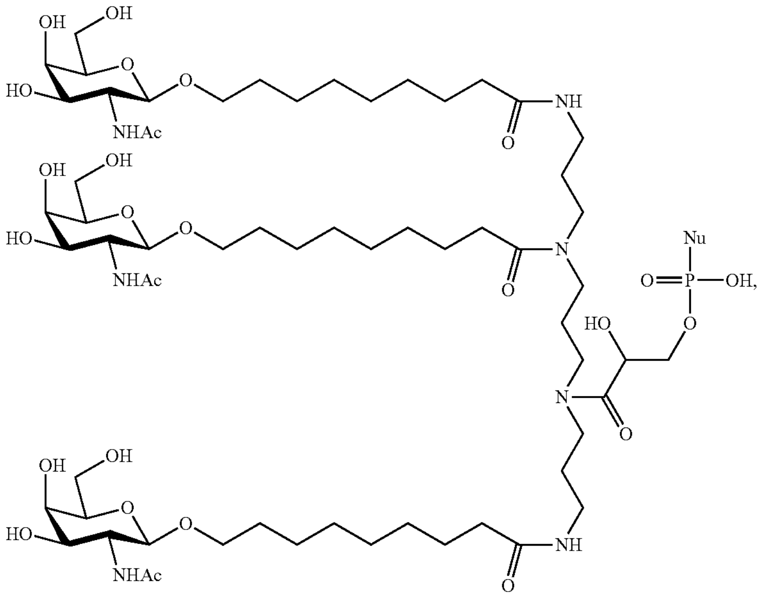

-continued
Formula (411)
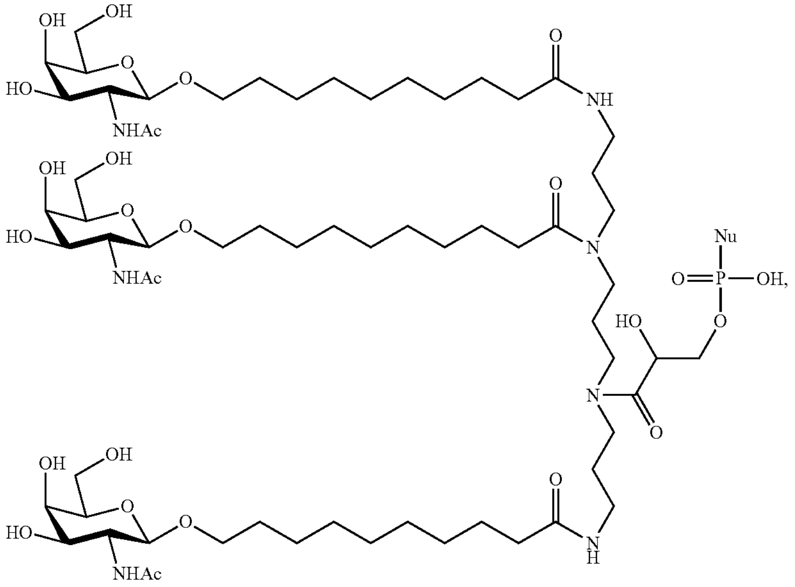
Formula (412)
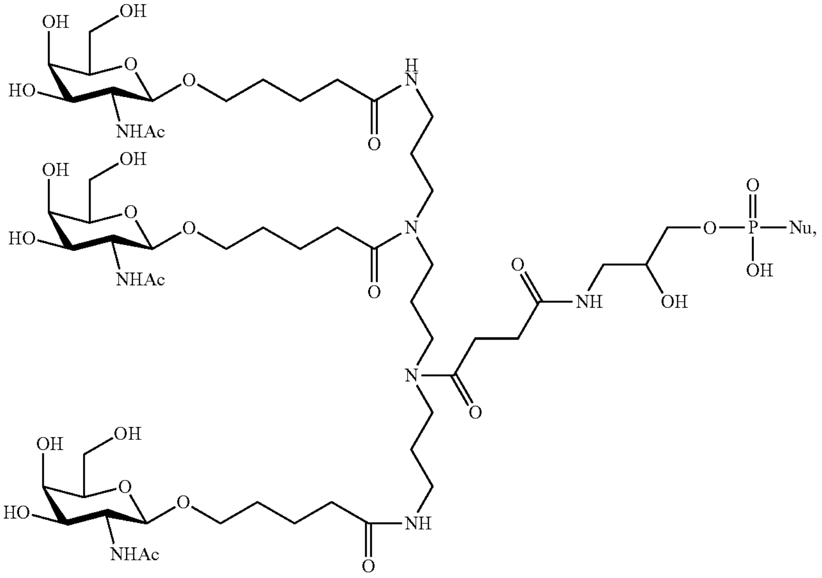

-continued
Formula (413)
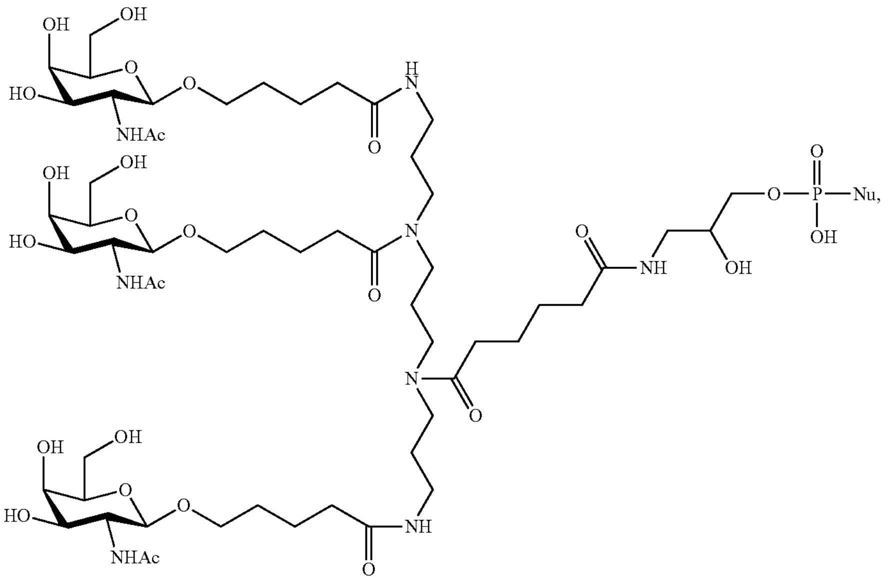
(Formula 414)
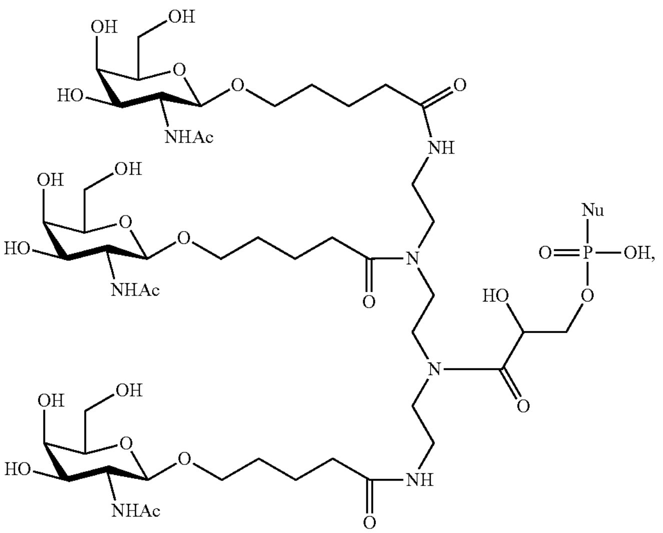

-continued
Formula (415)
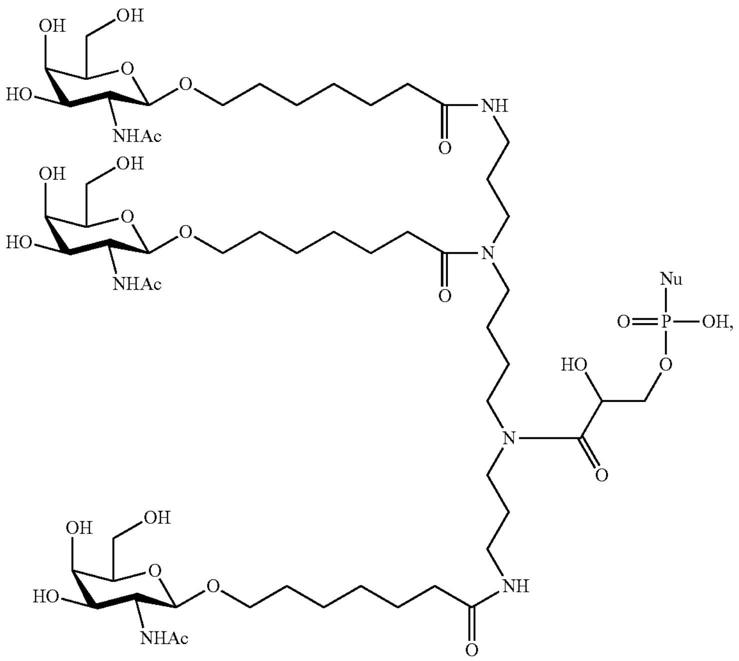
Formula (416)
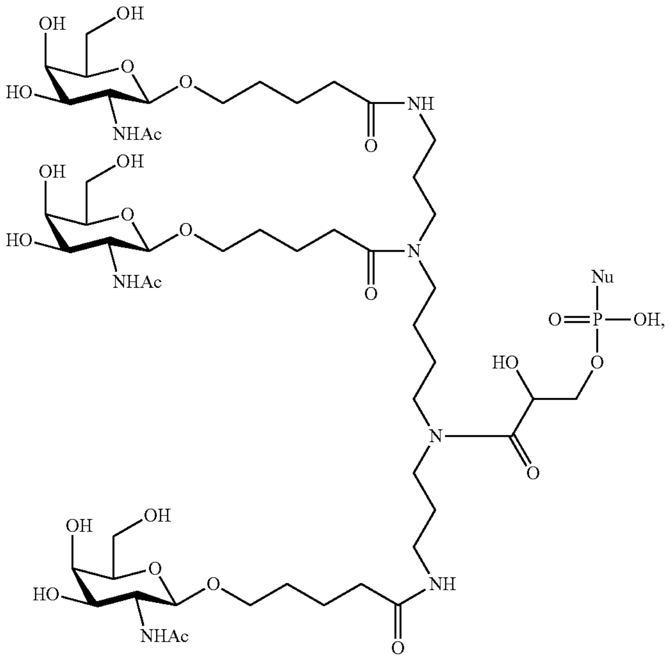

-continued
Formula (417)
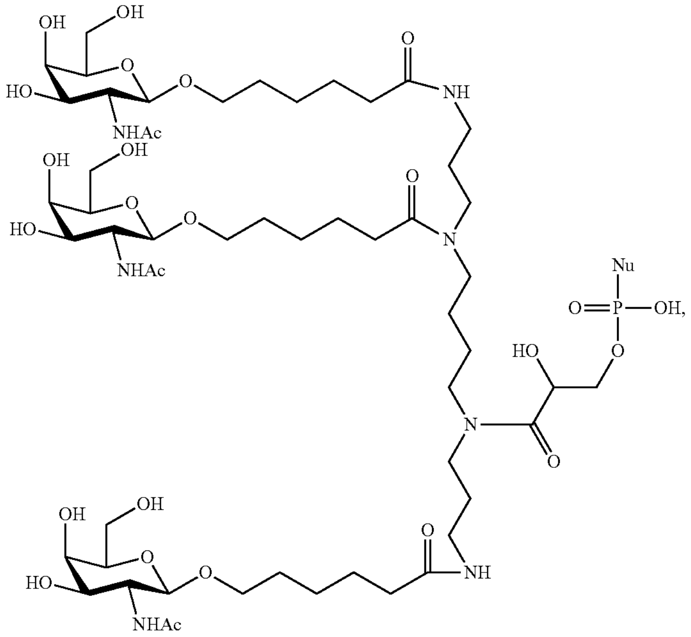
Formula (418)
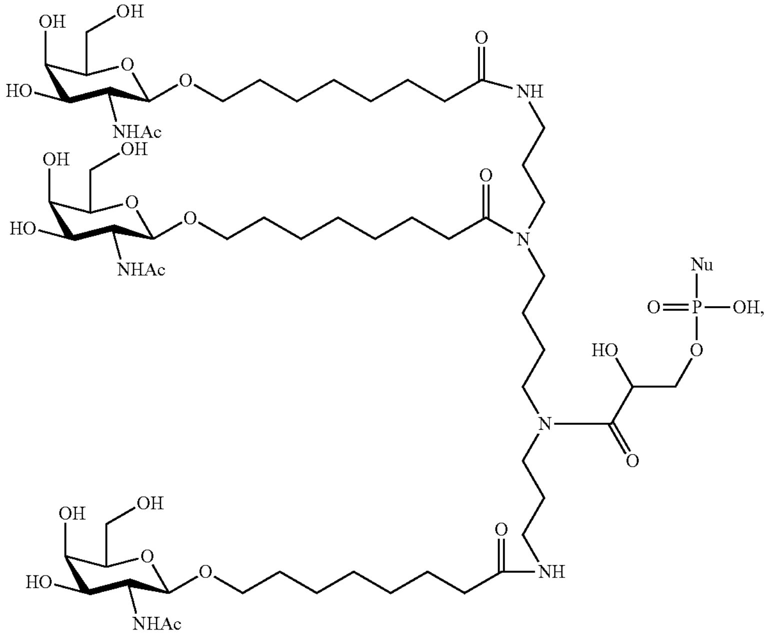

-continued
Formula (419)
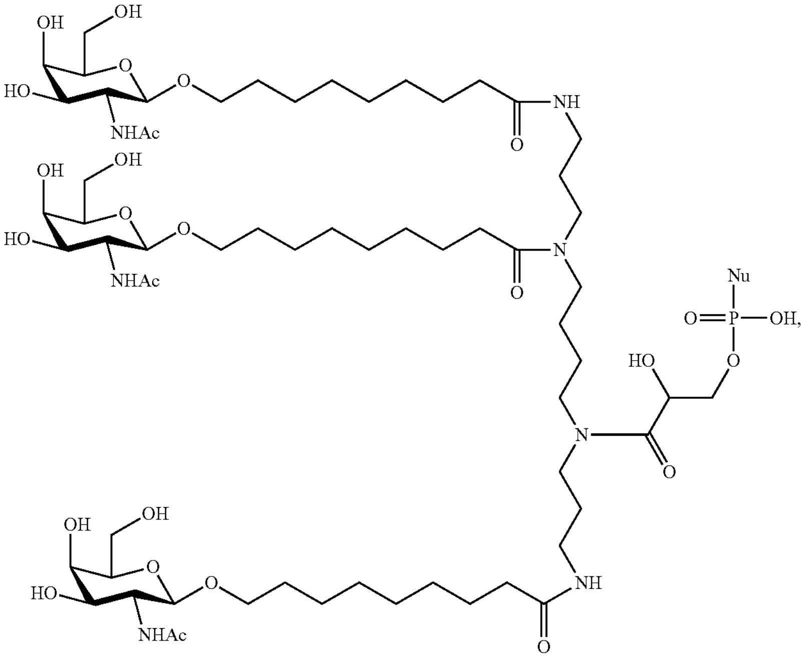
Formula (420)
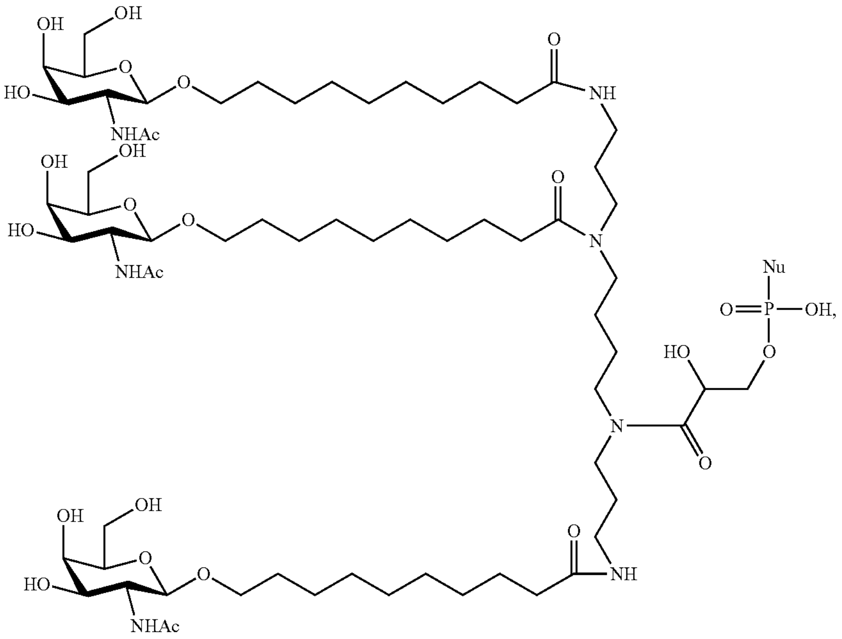

-continued
Formula (421)
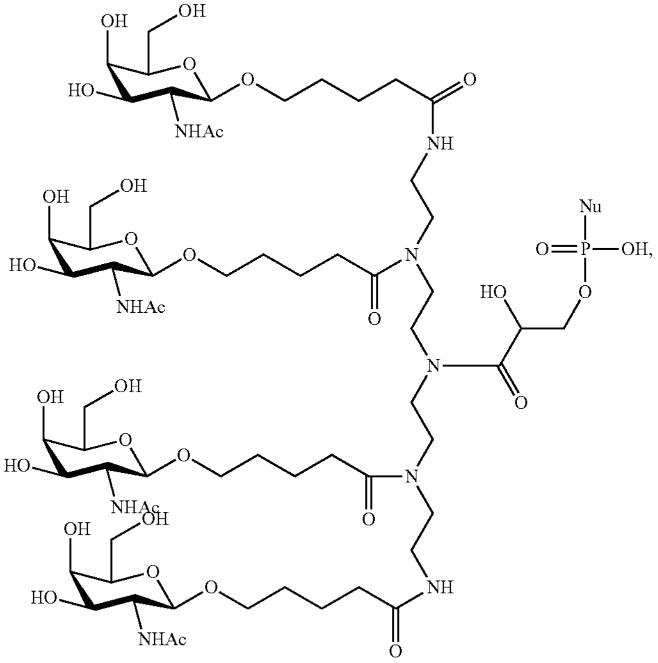
Formula (422)
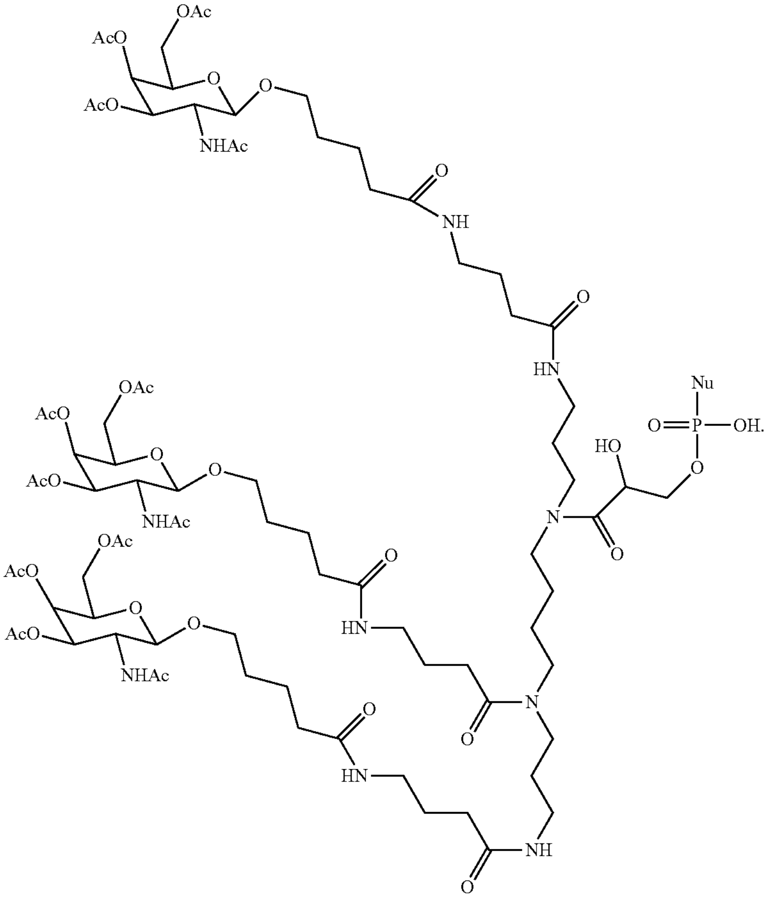
21. The siRNA conjugate according to claim 1, wherein the P atom in Formula (A59) is linked to 3' terminal of the sense strand of the siRNA.
22. The siRNA conjugate according to claim 21, wherein the siRNA conjugate is L10-siFXIf1M1S, wherein L10 has the structure as shown by Formula (403), and the sense strand of the siFXIf1M1S has the nucleotide sequence as shown by SEQ ID NO: 541, and the antisense strand of the siFXIf1M1S has the nucleotide sequence as shown by SEQ ID NO: 542:

5'-GmsUmsAmCmGmUmGfGfAfCmUmGmGmAmU-mUmCmUmGm-3' (SEQ ID NO: 541)

5'-CmsAfsGmAmAmUfCmCmAmGmUmCmCmA-fCmGfUmAmCmsUmsUm-3' (SEQ ID NO: 542), wherein C, G, U, and A represent base composition of a nucleotide; m represents that a nucleotide adjacent to a left side of letter m is a methoxy modified nucleotide; f represents that a nucleotide adjacent to a left side of letter f is a fluoro modified nucleotide; s represents that two nucleotides adjacent to both sides of letter s are linked by a thiophosphate linkage.

23. The siRNA conjugate according to claim 1, wherein there is no more than 1 nucleotide difference between the nucleotide sequence I and the nucleotide sequence as shown by SEQ ID NO: 1, and/or there is no more than 1 nucleotide difference between the nucleotide sequence II and the nucleotide sequence as shown by SEQ ID NO: 2; the nucleotide difference between the nucleotide sequence II and the nucleotide sequence as shown by SEQ ID NO: 2 includes a difference at the position $Z_4$, where $Z_4$ is selected from U, C or G; or there is no more than 1 nucleotide difference between the nucleotide sequence I and the nucleotide sequence as shown by SEQ ID NO: 61, and/or there is no more than 1 nucleotide difference between the nucleotide sequence II and the nucleotide sequence as shown by SEQ ID NO: 62; the nucleotide difference between the nucleotide sequence II and the nucleotide sequence as shown by SEQ ID NO: 62 includes a difference at the position $Z_8$, where $Z_8$ is selected from U, C or G; or there is no more than 1 nucleotide difference between the nucleotide sequence I and the nucleotide sequence as shown by SEQ ID NO: 121, and/or there is no more than 1 nucleotide difference between the nucleotide sequence II and the nucleotide sequence as shown by SEQ ID NO: 122; the nucleotide difference between the nucleotide sequence II and the nucleotide sequence as shown by SEQ ID NO: 122 includes a difference at the position $Z_{12}$, where $Z_{12}$ is selected from A, C or G; or there is no more than 1 nucleotide difference between the nucleotide sequence I and the nucleotide sequence as shown by SEQ ID NO: 181, and/or there is no more than 1 nucleotide difference between the nucleotide sequence II and the nucleotide sequence as shown by SEQ ID NO: 182; the nucleotide difference between the nucleotide sequence II and the nucleotide sequence as shown by SEQ ID NO: 182 includes a difference at the position $Z_{16}$, where $Z_{16}$ is selected from U, C or G; or there is no more than 1 nucleotide difference between the nucleotide sequence I and the nucleotide sequence as shown by SEQ ID NO: 241, and/or there is no more than 1 nucleotide difference between the nucleotide sequence II and the nucleotide sequence as shown by SEQ ID NO: 242; the nucleotide difference between the nucleotide sequence II and the nucleotide sequence as shown by SEQ ID NO: 242 includes a difference at the position $Z_{20}$, where $Z_{20}$ is selected from U, C or G; or there is no more than 1 nucleotide difference between the nucleotide sequence I and the nucleotide sequence as shown by SEQ ID NO: 301, and/or there is no more than 1 nucleotide difference between the nucleotide sequence II and the nucleotide sequence as shown by SEQ ID NO: 302; the nucleotide difference between the nucleotide sequence II and the nucleotide sequence as shown by SEQ ID NO: 302 includes a difference at the position $Z_{24}$, where $Z_{24}$ is selected from A, U or G; or there is no more than 1 nucleotide difference between the nucleotide sequence I and the nucleotide sequence as shown by SEQ ID NO: 361, and/or there is no more than 1 nucleotide difference between the nucleotide sequence II and the nucleotide sequence as shown by SEQ ID NO: 362; the nucleotide difference between the nucleotide sequence II and the nucleotide sequence as shown by SEQ ID NO: 362 includes a difference at the position $Z_{28}$, where $Z_{28}$ is selected from A, C or G; or there is no more than 1 nucleotide difference between the nucleotide sequence I and the nucleotide sequence as shown by SEQ ID NO: 421, and/or there is no more than 1 nucleotide difference between the nucleotide sequence II and the nucleotide sequence as shown by SEQ ID NO: 422; the nucleotide difference between the nucleotide sequence II and the nucleotide sequence as shown by SEQ ID NO: 422 includes a difference at the position $Z_{32}$, where $Z_{32}$ is selected from U, C or G; or there is no more than 1 nucleotide difference between the nucleotide sequence I and the nucleotide sequence as shown by SEQ ID NO: 481, and/or there is no more than 1 nucleotide difference between the nucleotide sequence II and the nucleotide sequence as shown by SEQ ID NO: 482; the nucleotide difference between the nucleotide sequence II and the nucleotide sequence as shown by SEQ ID NO: 482 includes a difference at the position $Z_{36}$, where $Z_{36}$ is selected from A, C or G.

24. The siRNA conjugate according to claim 1, wherein $Z_3$ is a nucleotide complementary to $Z_4$; or $Z_7$ is a nucleotide complementary to $Z_8$; or $Z_{11}$ is a nucleotide complementary to $Z_{12}$; or $Z_{15}$ is a nucleotide complementary to $Z_{16}$; or $Z_{19}$ is a nucleotide complementary to $Z_{20}$; or $Z_{23}$ is a nucleotide complementary to $Z_{24}$; or $Z_{27}$ is a nucleotide complementary to $Z_{28}$; or $Z_{31}$ is a nucleotide complementary to $Z_{32}$; or $Z_{35}$ is a nucleotide complementary to $Z_{36}$.

25. The siRNA conjugate according to claim 1, wherein $R_{10}$, $R_{11}$, $R_{12}$, $R_{13}$, $R_{14}$, and $R_{15}$ independently of one another are selected from H, methyl and ethyl.

26. The siRNA conjugate according to claim 1, wherein the nucleotide at 5' terminal of the antisense strand is a 5'-phosphate nucleotide or a 5'-phosphate analogue modified nucleotide; or, the 5'-phosphate nucleotide is a nucleotide having a structure represented by Formula (2), and the 5'-phosphate analogue modified nucleotide is a nucleotide having a structure represented by any of Formulae (3)-(6):

Formula (2)

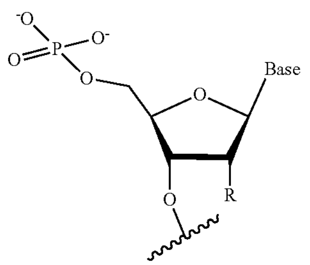

-continued
Formula (3)
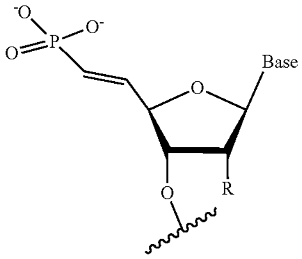
Formula (4)
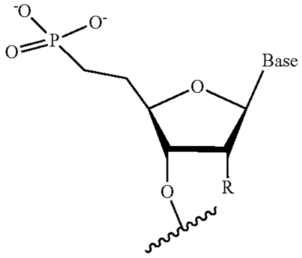
-continued
Formula (5)
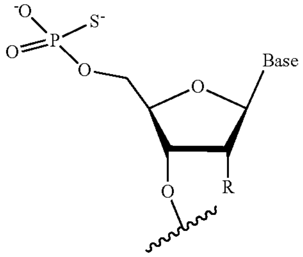
Formula (6)
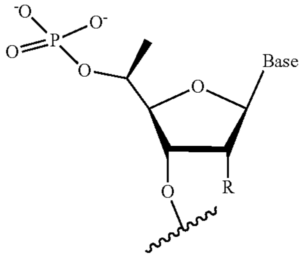
wherein R is selected from H, OH methoxy, or F; Base represents a nucleic acid base selected from A, U, C, G, or T.
* * * * *

SEQUENCE LISTING

```
<160> NUMBER OF SEQ ID NOS: 577

<210> SEQ ID NO 1
<211> LENGTH: 19
<212> TYPE: RNA
<213> ORGANISM: Artificial Sequence
<220> FEATURE:
<223> OTHER INFORMATION: Sense sequence for the first siRNA
<220> FEATURE:
<221> NAME/KEY: misc-feature
<222> LOCATION: (19)..(19)
<223> OTHER INFORMATION: n is Z1, Z1 is U

<400> SEQUENCE: 1

ggguauucuu ucaagcaan                                    19


<210> SEQ ID NO 2
<211> LENGTH: 19
<212> TYPE: RNA
<213> ORGANISM: Artificial Sequence
<220> FEATURE:
<223> OTHER INFORMATION: Antisense sequence for the first siRNA
<220> FEATURE:
<221> NAME/KEY: misc-feature
<222> LOCATION: (1)..(1)
<223> OTHER INFORMATION: n is Z2, Z2 is A

<400> SEQUENCE: 2

nuugcuugaa agaauaccc                                    19


<210> SEQ ID NO 3
<211> LENGTH: 19
<212> TYPE: RNA
<213> ORGANISM: Artificial Sequence
<220> FEATURE:
<223> OTHER INFORMATION: Sense sequence for the first siRNA
<220> FEATURE:
<221> NAME/KEY: misc-feature
<222> LOCATION: (19)..(19)
<223> OTHER INFORMATION: n is Z3, Z3 is A, U, G or C

<400> SEQUENCE: 3

ggguauucuu ucaagcaan                                    19
```

<210> SEQ ID NO 4
<211> LENGTH: 19
<212> TYPE: RNA
<213> ORGANISM: Artificial Sequence
<220> FEATURE:
<223> OTHER INFORMATION: Antisense sequence for the first siRNA
<220> FEATURE:
<221> NAME/KEY: misc-feature
<222> LOCATION: (1)..(1)
<223> OTHER INFORMATION: n is Z4, Z4 is a nucleotide complementary to
Z3, Z3 is selected from A, U, G or C

<400> SEQUENCE: 4
nuugcuugaa agaauaccc 19

<210> SEQ ID NO 5
<211> LENGTH: 19
<212> TYPE: RNA
<213> ORGANISM: Artificial Sequence
<220> FEATURE:
<223> OTHER INFORMATION: Sense sequence for the first siRNA
<220> FEATURE:
<221> NAME/KEY: misc-feature
<222> LOCATION: (19)..(19)
<223> OTHER INFORMATION: n is Z3, Z3 is A, U, G or C

<400> SEQUENCE: 5
ggguauucuu ucaagcaan 19

<210> SEQ ID NO 6
<211> LENGTH: 21
<212> TYPE: RNA
<213> ORGANISM: Artificial Sequence
<220> FEATURE:
<223> OTHER INFORMATION: Antisense sequence for the first siRNA
<220> FEATURE:
<221> NAME/KEY: misc-feature
<222> LOCATION: (1)..(1)
<223> OTHER INFORMATION: n is Z4, Z4 is a nucleotide complementary to
Z3, Z3 is selected from A,U,G or C

<400> SEQUENCE: 6
nuugcuugaa agaauaccca g 21

<210> SEQ ID NO 7
<211> LENGTH: 21
<212> TYPE: RNA
<213> ORGANISM: Artificial Sequence
<220> FEATURE:
<223> OTHER INFORMATION: Sense sequence for the first siRNA
<220> FEATURE:
<221> NAME/KEY: misc-feature
<222> LOCATION: (21)..(21)
<223> OTHER INFORMATION: n is Z3, Z3 is A, U, G or C

<400> SEQUENCE: 7
cuggguauuc uuucaagcaa n 21

<210> SEQ ID NO 8
<211> LENGTH: 23
<212> TYPE: RNA
<213> ORGANISM: Artificial Sequence
<220> FEATURE:
<223> OTHER INFORMATION: Antisense sequence for the first siRNA
<220> FEATURE:
<221> NAME/KEY: misc-feature
<222> LOCATION: (1)..(1)
<223> OTHER INFORMATION: n is Z4, Z4 is a nucleotide complementary to
Z3, Z3 is selected from A,U,G or C

<400> SEQUENCE: 8
nuugcuugaa agaauaccca gaa 23

<210> SEQ ID NO 9
<211> LENGTH: 19
<212> TYPE: RNA
<213> ORGANISM: Artificial Sequence
<220> FEATURE:
<223> OTHER INFORMATION: Sense sequence for siFXIa1

<400> SEQUENCE: 9
ggguauucuu ucaagcaau 19

<210> SEQ ID NO 10
<211> LENGTH: 21
<212> TYPE: RNA
<213> ORGANISM: Artificial Sequence
<220> FEATURE:
<223> OTHER INFORMATION: Antisense sequence for siFXIa1

<400> SEQUENCE: 10
auugcuugaa agaauaccca g 21

<210> SEQ ID NO 11
<211> LENGTH: 21
<212> TYPE: RNA
<213> ORGANISM: Artificial Sequence
<220> FEATURE:
<223> OTHER INFORMATION: Sense sequence for siFXIa2

<400> SEQUENCE: 11
cuggguauuc uuucaagcaa u 21

<210> SEQ ID NO 12
<211> LENGTH: 23
<212> TYPE: RNA
<213> ORGANISM: Artificial Sequence
<220> FEATURE:
<223> OTHER INFORMATION: Antisense sequence for siFXIa2

<400> SEQUENCE: 12
auugcuugaa agaauaccca gaa 23

<210> SEQ ID NO 13
<211> LENGTH: 19
<212> TYPE: RNA
<213> ORGANISM: Artificial Sequence
<220> FEATURE:
<223> OTHER INFORMATION: Sense sequence for siFXIa1-M1

<400> SEQUENCE: 13
ggguauucuu ucaagcaau 19

<210> SEQ ID NO 14
<211> LENGTH: 21
<212> TYPE: RNA
<213> ORGANISM: Artificial Sequence
<220> FEATURE:
<223> OTHER INFORMATION: Antisense sequence for siFXIa1-M1

<400> SEQUENCE: 14
auugcuugaa agaauaccca g 21

<210> SEQ ID NO 15
<211> LENGTH: 19

<212> TYPE: RNA
<213> ORGANISM: Artificial Sequence
<220> FEATURE:
<223> OTHER INFORMATION: Sense sequence for siFXIa1-M2

<400> SEQUENCE: 15
ggguauucuu ucaagcaau 19

<210> SEQ ID NO 16
<211> LENGTH: 21
<212> TYPE: RNA
<213> ORGANISM: Artificial Sequence
<220> FEATURE:
<223> OTHER INFORMATION: Antisense sequence for siFXIa1-M2

<400> SEQUENCE: 16
auugcuugaa agaauaccca g 21

<210> SEQ ID NO 17
<211> LENGTH: 19
<212> TYPE: RNA
<213> ORGANISM: Artificial Sequence
<220> FEATURE:
<223> OTHER INFORMATION: Sense sequence for siFXIa1-M3

<400> SEQUENCE: 17
ggguauucuu ucaagcaau 19

<210> SEQ ID NO 18
<211> LENGTH: 21
<212> TYPE: RNA
<213> ORGANISM: Artificial Sequence
<220> FEATURE:
<223> OTHER INFORMATION: Antisense sequence for siFXIa1-M3

<400> SEQUENCE: 18
auugcuugaa agaauaccca g 21

<210> SEQ ID NO 19
<211> LENGTH: 21
<212> TYPE: RNA
<213> ORGANISM: Artificial Sequence
<220> FEATURE:
<223> OTHER INFORMATION: Sense sequence for siFXIa2-M1

<400> SEQUENCE: 19
cuggguauuc uuucaagcaa u 21

<210> SEQ ID NO 20
<211> LENGTH: 23
<212> TYPE: RNA
<213> ORGANISM: Artificial Sequence
<220> FEATURE:
<223> OTHER INFORMATION: Antisense sequence for siFXIa2-M1

<400> SEQUENCE: 20
auugcuugaa agaauaccca gaa 23

<210> SEQ ID NO 21
<211> LENGTH: 21
<212> TYPE: RNA
<213> ORGANISM: Artificial Sequence
<220> FEATURE:
<223> OTHER INFORMATION: Sense sequence for siFXIa2-M2

<400> SEQUENCE: 21
cuggguauuc uuucaagcaa u 21

<210> SEQ ID NO 22
<211> LENGTH: 23
<212> TYPE: RNA
<213> ORGANISM: Artificial Sequence
<220> FEATURE:
<223> OTHER INFORMATION: Antisense sequence for siFXIa2-M2

<400> SEQUENCE: 22
auugcuugaa agaauaccca gaa 23

<210> SEQ ID NO 23
<211> LENGTH: 21
<212> TYPE: RNA
<213> ORGANISM: Artificial Sequence
<220> FEATURE:
<223> OTHER INFORMATION: Sense sequence for siFXIa2-M3

<400> SEQUENCE: 23
cuggguauuc uuucaagcaau 21

<210> SEQ ID NO 24
<211> LENGTH: 23
<212> TYPE: RNA
<213> ORGANISM: Artificial Sequence
<220> FEATURE:
<223> OTHER INFORMATION: Antisense sequence for siFXIa2-M3

<400> SEQUENCE: 24
auugcuugaa agaauaccca gaa 23

<210> SEQ ID NO 25
<211> LENGTH: 19
<212> TYPE: RNA
<213> ORGANISM: Artificial Sequence
<220> FEATURE:
<223> OTHER INFORMATION: Sense sequence for siFXIa1-M1S

<400> SEQUENCE: 25
ggguauucuu ucaagcaau 19

<210> SEQ ID NO 26
<211> LENGTH: 21
<212> TYPE: RNA
<213> ORGANISM: Artificial Sequence
<220> FEATURE:
<223> OTHER INFORMATION: Antisense sequence for siFXIa1-M1S

<400> SEQUENCE: 26
auugcuugaa agaauaccca g 21

<210> SEQ ID NO 27
<211> LENGTH: 19
<212> TYPE: RNA
<213> ORGANISM: Artificial Sequence
<220> FEATURE:
<223> OTHER INFORMATION: Sense sequence for siFXIa1-M2S

<400> SEQUENCE: 27
ggguauucuu ucaagcaau 19

<210> SEQ ID NO 28
<211> LENGTH: 21
<212> TYPE: RNA
<213> ORGANISM: Artificial Sequence
<220> FEATURE:
<223> OTHER INFORMATION: Antisense sequence for siFXIa1-M2S

<400> SEQUENCE: 28
auugcuugaa agaauaccca g 21

<210> SEQ ID NO 29
<211> LENGTH: 19
<212> TYPE: RNA
<213> ORGANISM: Artificial Sequence
<220> FEATURE:
<223> OTHER INFORMATION: Sense sequence for siFXIa1-M3S

<400> SEQUENCE: 29
ggguauucuu ucaagcaau 19

<210> SEQ ID NO 30
<211> LENGTH: 21
<212> TYPE: RNA
<213> ORGANISM: Artificial Sequence
<220> FEATURE:
<223> OTHER INFORMATION: Antisense sequence for siFXIa1-M3S

<400> SEQUENCE: 30
auugcuugaa agaauaccca g 21

<210> SEQ ID NO 31
<211> LENGTH: 21
<212> TYPE: RNA
<213> ORGANISM: Artificial Sequence
<220> FEATURE:
<223> OTHER INFORMATION: Sense sequence for siFXIa2-M1S

<400> SEQUENCE: 31
cuggguauuc uuucaagcaa u 21

<210> SEQ ID NO 32
<211> LENGTH: 23
<212> TYPE: RNA
<213> ORGANISM: Artificial Sequence
<220> FEATURE:
<223> OTHER INFORMATION: Antisense sequence for siFXIa2-M1S

<400> SEQUENCE: 32
auugcuugaa agaauaccca gaa 23

<210> SEQ ID NO 33
<211> LENGTH: 21
<212> TYPE: RNA
<213> ORGANISM: Artificial Sequence
<220> FEATURE:
<223> OTHER INFORMATION: Sense sequence for siFXIa2-M2S

<400> SEQUENCE: 33
cuggguauuc uuucaagcaa u 21

<210> SEQ ID NO 34
<211> LENGTH: 23
<212> TYPE: RNA
<213> ORGANISM: Artificial Sequence
<220> FEATURE:
<223> OTHER INFORMATION: Antisense sequence for siFXIa2-M2S

<400> SEQUENCE: 34
auugcuugaa agaauaccca gaa 23

<210> SEQ ID NO 35
<211> LENGTH: 21
<212> TYPE: RNA
<213> ORGANISM: Artificial Sequence
<220> FEATURE:
<223> OTHER INFORMATION: Sense sequence for siFXIa2-M3S

<400> SEQUENCE: 35
cuggguauuc uuucaagcaa u 21

<210> SEQ ID NO 36
<211> LENGTH: 23
<212> TYPE: RNA
<213> ORGANISM: Artificial Sequence
<220> FEATURE:
<223> OTHER INFORMATION: Antisense sequence for siFXIa2-M3S

<400> SEQUENCE: 36
auugcuugaa agaauaccca gaa 23

<210> SEQ ID NO 37
<211> LENGTH: 19
<212> TYPE: RNA
<213> ORGANISM: Artificial Sequence
<220> FEATURE:
<223> OTHER INFORMATION: Sense sequence for siFXIa1-M1P1

<400> SEQUENCE: 37
ggguauucuu ucaagcaau 19

<210> SEQ ID NO 38
<211> LENGTH: 21
<212> TYPE: RNA
<213> ORGANISM: Artificial Sequence
<220> FEATURE:
<223> OTHER INFORMATION: Antisense sequence for siFXIa1-M1P1

<400> SEQUENCE: 38
auugcuugaa agaauaccca g 21

<210> SEQ ID NO 39
<211> LENGTH: 19
<212> TYPE: RNA
<213> ORGANISM: Artificial Sequence
<220> FEATURE:
<223> OTHER INFORMATION: Sense sequence for siFXIa1-M2P1

<400> SEQUENCE: 39
ggguauucuu ucaagcaau 19

<210> SEQ ID NO 40
<211> LENGTH: 21
<212> TYPE: RNA
<213> ORGANISM: Artificial Sequence
<220> FEATURE:
<223> OTHER INFORMATION: Antisense sequence for siFXIa1-M2P1

<400> SEQUENCE: 40
auugcuugaa agaauaccca g 21

<210> SEQ ID NO 41
<211> LENGTH: 19
<212> TYPE: RNA
<213> ORGANISM: Artificial Sequence
<220> FEATURE:
<223> OTHER INFORMATION: Sense sequence for siFXIa1-M3P1

<400> SEQUENCE: 41
ggguauucuu ucaagcaau 19

<210> SEQ ID NO 42
<211> LENGTH: 21
<212> TYPE: RNA
<213> ORGANISM: Artificial Sequence
<220> FEATURE:
<223> OTHER INFORMATION: Antisense sequence for siFXIa1-M3P1

<400> SEQUENCE: 42
auugcuugaa agaauaccca g 21

<210> SEQ ID NO 43
<211> LENGTH: 21
<212> TYPE: RNA
<213> ORGANISM: Artificial Sequence
<220> FEATURE:
<223> OTHER INFORMATION: Sense sequence for siFXIa2-M1P1

<400> SEQUENCE: 43
cuggguauuc uuucaagcaa u 21

<210> SEQ ID NO 44
<211> LENGTH: 23
<212> TYPE: RNA
<213> ORGANISM: Artificial Sequence
<220> FEATURE:
<223> OTHER INFORMATION: Antisense sequence for siFXIa2-M1P1

<400> SEQUENCE: 44
auugcuugaa agaauaccca gaa 23

<210> SEQ ID NO 45
<211> LENGTH: 21
<212> TYPE: RNA
<213> ORGANISM: Artificial Sequence
<220> FEATURE:
<223> OTHER INFORMATION: Sense sequence for siFXIa2-M2P1

<400> SEQUENCE: 45
cuggguauuc uuucaagcaa u 21

<210> SEQ ID NO 46
<211> LENGTH: 23
<212> TYPE: RNA
<213> ORGANISM: Artificial Sequence
<220> FEATURE:
<223> OTHER INFORMATION: Antisense sequence for siFXIa2-M2P1

<400> SEQUENCE: 46
auugcuugaa agaauaccca gaa 23

<210> SEQ ID NO 47
<211> LENGTH: 21
<212> TYPE: RNA
<213> ORGANISM: Artificial Sequence
<220> FEATURE:
<223> OTHER INFORMATION: Sense sequence for siFXIa2-M3P1

<400> SEQUENCE: 47
cuggguauuc uuucaagcaa u 21

<210> SEQ ID NO 48

<211> LENGTH: 23
<212> TYPE: RNA
<213> ORGANISM: Artificial Sequence
<220> FEATURE:
<223> OTHER INFORMATION: Antisense sequence for siFXIa2-M3P1

<400> SEQUENCE: 48
auugcuugaa agaauaccca gaa 23

<210> SEQ ID NO 49
<211> LENGTH: 19
<212> TYPE: RNA
<213> ORGANISM: Artificial Sequence
<220> FEATURE:
<223> OTHER INFORMATION: Sense sequence for siFXIa1-M1SP1

<400> SEQUENCE: 49
ggguauucuu ucaagcaau 19

<210> SEQ ID NO 50
<211> LENGTH: 21
<212> TYPE: RNA
<213> ORGANISM: Artificial Sequence
<220> FEATURE:
<223> OTHER INFORMATION: Antisense sequence for siFXIa1-M1SP1

<400> SEQUENCE: 50
auugcuugaa agaauaccca g 21

<210> SEQ ID NO 51
<211> LENGTH: 19
<212> TYPE: RNA
<213> ORGANISM: Artificial Sequence
<220> FEATURE:
<223> OTHER INFORMATION: Sense sequence for siFXIa1-M2SP1

<400> SEQUENCE: 51
ggguauucuu ucaagcaau 19

<210> SEQ ID NO 52
<211> LENGTH: 21
<212> TYPE: RNA
<213> ORGANISM: Artificial Sequence
<220> FEATURE:
<223> OTHER INFORMATION: Antisense sequence for siFXIa1-M2SP1

<400> SEQUENCE: 52
auugcuugaa agaauaccca g 21

<210> SEQ ID NO 53
<211> LENGTH: 19
<212> TYPE: RNA
<213> ORGANISM: Artificial Sequence
<220> FEATURE:
<223> OTHER INFORMATION: Sense sequence for siFXIa1-M3SP1

<400> SEQUENCE: 53
ggguauucuu ucaagcaau 19

<210> SEQ ID NO 54
<211> LENGTH: 21
<212> TYPE: RNA
<213> ORGANISM: Artificial Sequence
<220> FEATURE:
<223> OTHER INFORMATION: Antisense sequence for siFXIa1-M3SP1

<400> SEQUENCE: 54
auugcuugaa agaauaccca g 21

<210> SEQ ID NO 55
<211> LENGTH: 21
<212> TYPE: RNA
<213> ORGANISM: Artificial Sequence
<220> FEATURE:
<223> OTHER INFORMATION: Sense sequence for siFXIa2-M1SP1

<400> SEQUENCE: 55
cuggguauuc uuucaagcaa u 21

<210> SEQ ID NO 56
<211> LENGTH: 23
<212> TYPE: RNA
<213> ORGANISM: Artificial Sequence
<220> FEATURE:
<223> OTHER INFORMATION: Antisense sequence for siFXIa2-M1SP1

<400> SEQUENCE: 56
auugcuugaa agaauaccca gaa 23

<210> SEQ ID NO 57
<211> LENGTH: 21
<212> TYPE: RNA
<213> ORGANISM: Artificial Sequence
<220> FEATURE:
<223> OTHER INFORMATION: Sense sequence for siFXIa2-M2SP1

<400> SEQUENCE: 57
cuggguauuc uuucaagcaa u 21

<210> SEQ ID NO 58
<211> LENGTH: 23
<212> TYPE: RNA
<213> ORGANISM: Artificial Sequence
<220> FEATURE:
<223> OTHER INFORMATION: Antisense sequence for siFXIa2-M2SP1

<400> SEQUENCE: 58
auugcuugaa agaauaccca gaa 23

<210> SEQ ID NO 59
<211> LENGTH: 21
<212> TYPE: RNA
<213> ORGANISM: Artificial Sequence
<220> FEATURE:
<223> OTHER INFORMATION: Sense sequence for siFXIa2-M3SP1

<400> SEQUENCE: 59
cuggguauuc uuucaagcaa u 21

<210> SEQ ID NO 60
<211> LENGTH: 23
<212> TYPE: RNA
<213> ORGANISM: Artificial Sequence
<220> FEATURE:
<223> OTHER INFORMATION: Antisense sequence for siFXIa2-M3SP1

<400> SEQUENCE: 60
auugcuugaa agaauaccca gaa 23

<210> SEQ ID NO 61
<211> LENGTH: 19
<212> TYPE: RNA

<213> ORGANISM: Artificial Sequence
<220> FEATURE:
<223> OTHER INFORMATION: Sense sequence for the second siRNA
<220> FEATURE:
<221> NAME/KEY: misc-feature
<222> LOCATION: (19)..(19)
<223> OTHER INFORMATION: n is Z5, Z5 is U

<400> SEQUENCE: 61
ggcauaaacu auaacagcn 19

<210> SEQ ID NO 62
<211> LENGTH: 19
<212> TYPE: RNA
<213> ORGANISM: Artificial Sequence
<220> FEATURE:
<223> OTHER INFORMATION: Antisense sequence for the second siRNA
<220> FEATURE:
<221> NAME/KEY: misc-feature
<222> LOCATION: (1)..(1)
<223> OTHER INFORMATION: n is Z6, Z6 is A

<400> SEQUENCE: 62
ngcuguuaua guuuaugcc 19

<210> SEQ ID NO 63
<211> LENGTH: 19
<212> TYPE: RNA
<213> ORGANISM: Artificial Sequence
<220> FEATURE:
<223> OTHER INFORMATION: Sense sequence for the second siRNA
<220> FEATURE:
<221> NAME/KEY: misc-feature
<222> LOCATION: (19)..(19)
<223> OTHER INFORMATION: n is Z7, Z7 is A, U,G or C

<400> SEQUENCE: 63
ggcauaaacu auaacagcn 19

<210> SEQ ID NO 64
<211> LENGTH: 19
<212> TYPE: RNA
<213> ORGANISM: Artificial Sequence
<220> FEATURE:
<223> OTHER INFORMATION: Antisense sequence for the second siRNA
<220> FEATURE:
<221> NAME/KEY: misc-feature
<222> LOCATION: (1)..(1)
<223> OTHER INFORMATION: n is Z8, Z8 is a nucleotide complementary to
Z7, Z7 is selected from A, U, G or C

<400> SEQUENCE: 64
ngcuguuaua guuuaugcc 19

<210> SEQ ID NO 65
<211> LENGTH: 19
<212> TYPE: RNA
<213> ORGANISM: Artificial Sequence
<220> FEATURE:
<223> OTHER INFORMATION: Sense sequence for the second siRNA
<220> FEATURE:
<221> NAME/KEY: misc-feature
<222> LOCATION: (19)..(19)
<223> OTHER INFORMATION: n is Z7, Z7 is A, U, G or C

<400> SEQUENCE: 65
ggcauaaacu auaacagcn 19

<210> SEQ ID NO 66

<211> LENGTH: 21
<212> TYPE: RNA
<213> ORGANISM: Artificial Sequence
<220> FEATURE:
<223> OTHER INFORMATION: Antisense sequence for the second siRNA
<220> FEATURE:
<221> NAME/KEY: misc-feature
<222> LOCATION: (1)..(1)
<223> OTHER INFORMATION: n is Z8, Z8 is a nucleotide complementary to
Z7, Z7 is selected from A, U, G or C

<400> SEQUENCE: 66
ngcuguuaua guuuaugccc u 21

<210> SEQ ID NO 67
<211> LENGTH: 21
<212> TYPE: RNA
<213> ORGANISM: Artificial Sequence
<220> FEATURE:
<223> OTHER INFORMATION: Sense sequence for the second siRNA
<220> FEATURE:
<221> NAME/KEY: misc-feature
<222> LOCATION: (21)..(21)
<223> OTHER INFORMATION: n is Z7, Z7 is A, U, G or C

<400> SEQUENCE: 67
agggcauaaa cuauaacagc n 21

<210> SEQ ID NO 68
<211> LENGTH: 23
<212> TYPE: RNA
<213> ORGANISM: Artificial Sequence
<220> FEATURE:
<223> OTHER INFORMATION: Antisense sequence for the second siRNA
<220> FEATURE:
<221> NAME/KEY: misc-feature
<222> LOCATION: (1)..(1)
<223> OTHER INFORMATION: n is Z8, Z8 is a nucleotide complementary to
Z7, Z7 is selected from A, U, G or C

<400> SEQUENCE: 68
ngcuguuaua guuuaugccc uuc 23

<210> SEQ ID NO 69
<211> LENGTH: 19
<212> TYPE: RNA
<213> ORGANISM: Artificial Sequence
<220> FEATURE:
<223> OTHER INFORMATION: Sense sequence for siFXIb1

<400> SEQUENCE: 69
ggcauaaacu auaacagcu 19

<210> SEQ ID NO 70
<211> LENGTH: 21
<212> TYPE: RNA
<213> ORGANISM: Artificial Sequence
<220> FEATURE:
<223> OTHER INFORMATION: Antisense sequence for siFXIb1

<400> SEQUENCE: 70
agcuguuaua guuuaugccc u 21

<210> SEQ ID NO 71
<211> LENGTH: 21
<212> TYPE: RNA
<213> ORGANISM: Artificial Sequence
<220> FEATURE:
<223> OTHER INFORMATION: Sense sequence for siFXIb2

-continued

<400> SEQUENCE: 71
agggcauaaa cuauaacagc u 21

<210> SEQ ID NO 72
<211> LENGTH: 23
<212> TYPE: RNA
<213> ORGANISM: Artificial Sequence
<220> FEATURE:
<223> OTHER INFORMATION: Antisense sequence for siFXIb2

<400> SEQUENCE: 72
agcuguuaua guuuaugccc uuc 23

<210> SEQ ID NO 73
<211> LENGTH: 19
<212> TYPE: RNA
<213> ORGANISM: Artificial Sequence
<220> FEATURE:
<223> OTHER INFORMATION: Sense sequence for siFXIb1-M1

<400> SEQUENCE: 73
ggcauaaacu auaacagcu 19

<210> SEQ ID NO 74
<211> LENGTH: 21
<212> TYPE: RNA
<213> ORGANISM: Artificial Sequence
<220> FEATURE:
<223> OTHER INFORMATION: Antisense sequence for siFXIb1-M1

<400> SEQUENCE: 74
agcuguuaua guuuaugccc u 21

<210> SEQ ID NO 75
<211> LENGTH: 19
<212> TYPE: RNA
<213> ORGANISM: Artificial Sequence
<220> FEATURE:
<223> OTHER INFORMATION: Sense sequence for siFXIb1-M2

<400> SEQUENCE: 75
ggcauaaacu auaacagcu 19

<210> SEQ ID NO 76
<211> LENGTH: 21
<212> TYPE: RNA
<213> ORGANISM: Artificial Sequence
<220> FEATURE:
<223> OTHER INFORMATION: Antisense sequence for siFXIb1-M2

<400> SEQUENCE: 76
agcuguuaua guuuaugccc u 21

<210> SEQ ID NO 77
<211> LENGTH: 19
<212> TYPE: RNA
<213> ORGANISM: Artificial Sequence
<220> FEATURE:
<223> OTHER INFORMATION: Sense sequence for siFXIb1-M3

<400> SEQUENCE: 77
ggcauaaacu auaacagcu 19

<210> SEQ ID NO 78

<211> LENGTH: 21
<212> TYPE: RNA
<213> ORGANISM: Artificial Sequence
<220> FEATURE:
<223> OTHER INFORMATION: Antisense sequence for siFXIb1-M3

<400> SEQUENCE: 78
agcuguuaua guuuaugccc u 21

<210> SEQ ID NO 79
<211> LENGTH: 21
<212> TYPE: RNA
<213> ORGANISM: Artificial Sequence
<220> FEATURE:
<223> OTHER INFORMATION: Sense sequence for siFXIb2-M1

<400> SEQUENCE: 79
agggcauaaa cuauaacagc u 21

<210> SEQ ID NO 80
<211> LENGTH: 23
<212> TYPE: RNA
<213> ORGANISM: Artificial Sequence
<220> FEATURE:
<223> OTHER INFORMATION: Antisense sequence for siFXIb2-M1

<400> SEQUENCE: 80
agcuguuaua guuuaugccc uuc 23

<210> SEQ ID NO 81
<211> LENGTH: 21
<212> TYPE: RNA
<213> ORGANISM: Artificial Sequence
<220> FEATURE:
<223> OTHER INFORMATION: Sense sequence for siFXIb2-M2

<400> SEQUENCE: 81
agggcauaaa cuauaacagc u 21

<210> SEQ ID NO 82
<211> LENGTH: 23
<212> TYPE: RNA
<213> ORGANISM: Artificial Sequence
<220> FEATURE:
<223> OTHER INFORMATION: Antisense sequence for siFXIb2-M2

<400> SEQUENCE: 82
agcuguuaua guuuaugccc uuc 23

<210> SEQ ID NO 83
<211> LENGTH: 21
<212> TYPE: RNA
<213> ORGANISM: Artificial Sequence
<220> FEATURE:
<223> OTHER INFORMATION: Sense sequence for siFXIb2-M3

<400> SEQUENCE: 83
agggcauaaa cuauaacagc u 21

<210> SEQ ID NO 84
<211> LENGTH: 23
<212> TYPE: RNA
<213> ORGANISM: Artificial Sequence
<220> FEATURE:
<223> OTHER INFORMATION: Antisense sequence for siFXIb2-M3

<400> SEQUENCE: 84
agcuguuaua guuuaugccc uuc 23

<210> SEQ ID NO 85
<211> LENGTH: 19
<212> TYPE: RNA
<213> ORGANISM: Artificial Sequence
<220> FEATURE:
<223> OTHER INFORMATION: Sense sequence for siFXIb1-M1S

<400> SEQUENCE: 85
ggcauaaacu auaacagcu 19

<210> SEQ ID NO 86
<211> LENGTH: 21
<212> TYPE: RNA
<213> ORGANISM: Artificial Sequence
<220> FEATURE:
<223> OTHER INFORMATION: Antisense sequence for siFXIb1-M1S

<400> SEQUENCE: 86
agcuguuaua guuuaugccc u 21

<210> SEQ ID NO 87
<211> LENGTH: 19
<212> TYPE: RNA
<213> ORGANISM: Artificial Sequence
<220> FEATURE:
<223> OTHER INFORMATION: Sense sequence for siFXIb1-M2S

<400> SEQUENCE: 87
ggcauaaacu auaacagcu 19

<210> SEQ ID NO 88
<211> LENGTH: 21
<212> TYPE: RNA
<213> ORGANISM: Artificial Sequence
<220> FEATURE:
<223> OTHER INFORMATION: Antisense sequence for siFXIb1-M2S

<400> SEQUENCE: 88
agcuguuaua guuuaugccc u 21

<210> SEQ ID NO 89
<211> LENGTH: 19
<212> TYPE: RNA
<213> ORGANISM: Artificial Sequence
<220> FEATURE:
<223> OTHER INFORMATION: Sense sequence for siFXIb1-M3S

<400> SEQUENCE: 89
ggcauaaacu auaacagcu 19

<210> SEQ ID NO 90
<211> LENGTH: 21
<212> TYPE: RNA
<213> ORGANISM: Artificial Sequence
<220> FEATURE:
<223> OTHER INFORMATION: Antisense sequence for siFXIb1-M3S

<400> SEQUENCE: 90
agcuguuaua guuuaugccc u 21

<210> SEQ ID NO 91
<211> LENGTH: 21
<212> TYPE: RNA

<213> ORGANISM: Artificial Sequence
<220> FEATURE:
<223> OTHER INFORMATION: Sense sequence for siFXIb2-M1S

<400> SEQUENCE: 91
agggcauaaa cuauaacagc u 21

<210> SEQ ID NO 92
<211> LENGTH: 23
<212> TYPE: RNA
<213> ORGANISM: Artificial Sequence
<220> FEATURE:
<223> OTHER INFORMATION: Antisense sequence for siFXIb2-M1S

<400> SEQUENCE: 92
agcuguuaua guuuaugccc uuc 23

<210> SEQ ID NO 93
<211> LENGTH: 19
<212> TYPE: RNA
<213> ORGANISM: Artificial Sequence
<220> FEATURE:
<223> OTHER INFORMATION: Sense sequence for siFXIb2-M2S

<400> SEQUENCE: 93
ggcauaaacu auaacagcu 19

<210> SEQ ID NO 94
<211> LENGTH: 23
<212> TYPE: RNA
<213> ORGANISM: Artificial Sequence
<220> FEATURE:
<223> OTHER INFORMATION: Antisense sequence for siFXIb2-M2S

<400> SEQUENCE: 94
agcuguuaua guuuaugccc uuc 23

<210> SEQ ID NO 95
<211> LENGTH: 21
<212> TYPE: RNA
<213> ORGANISM: Artificial Sequence
<220> FEATURE:
<223> OTHER INFORMATION: Sense sequence for siFXIb2-M3S

<400> SEQUENCE: 95
agggcauaaa cuauaacagc u 21

<210> SEQ ID NO 96
<211> LENGTH: 23
<212> TYPE: RNA
<213> ORGANISM: Artificial Sequence
<220> FEATURE:
<223> OTHER INFORMATION: Antisense sequence for siFXIb2-M3S

<400> SEQUENCE: 96
agcuguuaua guuuaugccc uuc 23

<210> SEQ ID NO 97
<211> LENGTH: 19
<212> TYPE: RNA
<213> ORGANISM: Artificial Sequence
<220> FEATURE:
<223> OTHER INFORMATION: Sense sequence for siFXIb1-M1P1

<400> SEQUENCE: 97
ggcauaaacu auaacagcu 19

<210> SEQ ID NO 98
<211> LENGTH: 21
<212> TYPE: RNA
<213> ORGANISM: Artificial Sequence
<220> FEATURE:
<223> OTHER INFORMATION: Antisense sequence for siFXIb1-M1P1

<400> SEQUENCE: 98
agcuguuaua guuuaugccc u 21

<210> SEQ ID NO 99
<211> LENGTH: 19
<212> TYPE: RNA
<213> ORGANISM: Artificial Sequence
<220> FEATURE:
<223> OTHER INFORMATION: Sense sequence for siFXIb1-M2P1

<400> SEQUENCE: 99
ggcauaaacu auaacagcu 19

<210> SEQ ID NO 100
<211> LENGTH: 21
<212> TYPE: RNA
<213> ORGANISM: Artificial Sequence
<220> FEATURE:
<223> OTHER INFORMATION: Antisense sequence for siFXIb1-M2P1

<400> SEQUENCE: 100
agcuguuaua guuuaugccc u 21

<210> SEQ ID NO 101
<211> LENGTH: 19
<212> TYPE: RNA
<213> ORGANISM: Artificial Sequence
<220> FEATURE:
<223> OTHER INFORMATION: Sense sequence for siFXIb1-M3P1

<400> SEQUENCE: 101
ggcauaaacu auaacagcu 19

<210> SEQ ID NO 102
<211> LENGTH: 21
<212> TYPE: RNA
<213> ORGANISM: Artificial Sequence
<220> FEATURE:
<223> OTHER INFORMATION: Antisense sequence for siFXIb1-M3P1

<400> SEQUENCE: 102
agcuguuaua guuuaugccc u 21

<210> SEQ ID NO 103
<211> LENGTH: 21
<212> TYPE: RNA
<213> ORGANISM: Artificial Sequence
<220> FEATURE:
<223> OTHER INFORMATION: Sense sequence for siFXIb2-M1P1

<400> SEQUENCE: 103
agggcauaaa cuauaacagc u 21

<210> SEQ ID NO 104
<211> LENGTH: 23
<212> TYPE: RNA
<213> ORGANISM: Artificial Sequence
<220> FEATURE:

<223> OTHER INFORMATION: Antisense sequence for siFXIb2-M1P1

<400> SEQUENCE: 104
agcuguuaua guuuaugccc uuc 23

<210> SEQ ID NO 105
<211> LENGTH: 21
<212> TYPE: RNA
<213> ORGANISM: Artificial Sequence
<220> FEATURE:
<223> OTHER INFORMATION: Sense sequence for siFXIb2-M2P1

<400> SEQUENCE: 105
agggcauaaa cuauaacagc u 21

<210> SEQ ID NO 106
<211> LENGTH: 23
<212> TYPE: RNA
<213> ORGANISM: Artificial Sequence
<220> FEATURE:
<223> OTHER INFORMATION: Antisense sequence for siFXIb2-M2P1

<400> SEQUENCE: 106
agcuguuaua guuuaugccc uuc 23

<210> SEQ ID NO 107
<211> LENGTH: 21
<212> TYPE: RNA
<213> ORGANISM: Artificial Sequence
<220> FEATURE:
<223> OTHER INFORMATION: Sense sequence for siFXIb2-M3P1

<400> SEQUENCE: 107
agggcauaaa cuauaacagc u 21

<210> SEQ ID NO 108
<211> LENGTH: 23
<212> TYPE: RNA
<213> ORGANISM: Artificial Sequence
<220> FEATURE:
<223> OTHER INFORMATION: Antisense sequence for siFXIb2-M3P1

<400> SEQUENCE: 108
agcuguuaua guuuaugccc uuc 23

<210> SEQ ID NO 109
<211> LENGTH: 19
<212> TYPE: RNA
<213> ORGANISM: Artificial Sequence
<220> FEATURE:
<223> OTHER INFORMATION: Sense sequence for siFXIb1-M1SP1

<400> SEQUENCE: 109
ggcauaaacu auaacagcu 19

<210> SEQ ID NO 110
<211> LENGTH: 21
<212> TYPE: RNA
<213> ORGANISM: Artificial Sequence
<220> FEATURE:
<223> OTHER INFORMATION: Antisense sequence for siFXIb1-M1SP1

<400> SEQUENCE: 110
agcuguuaua guuuaugccc u 21

<210> SEQ ID NO 111
<211> LENGTH: 19
<212> TYPE: RNA
<213> ORGANISM: Artificial Sequence
<220> FEATURE:
<223> OTHER INFORMATION: Sense sequence for siFXIb1-M2SP1

<400> SEQUENCE: 111
ggcauaaacu auaacagcu 19

<210> SEQ ID NO 112
<211> LENGTH: 21
<212> TYPE: RNA
<213> ORGANISM: Artificial Sequence
<220> FEATURE:
<223> OTHER INFORMATION: Antisense sequence for siFXIb1-M2SP1

<400> SEQUENCE: 112
agcuguuaua guuuaugccc u 21

<210> SEQ ID NO 113
<211> LENGTH: 19
<212> TYPE: RNA
<213> ORGANISM: Artificial Sequence
<220> FEATURE:
<223> OTHER INFORMATION: Sense sequence for siFXIb1-M3SP1

<400> SEQUENCE: 113
ggcauaaacu auaacagcu 19

<210> SEQ ID NO 114
<211> LENGTH: 21
<212> TYPE: RNA
<213> ORGANISM: Artificial Sequence
<220> FEATURE:
<223> OTHER INFORMATION: Antisense sequence for siFXIb1-M3SP1

<400> SEQUENCE: 114
agcuguuaua guuuaugccc u 21

<210> SEQ ID NO 115
<211> LENGTH: 21
<212> TYPE: RNA
<213> ORGANISM: Artificial Sequence
<220> FEATURE:
<223> OTHER INFORMATION: Sense sequence for siFXIb2-M1SP1

<400> SEQUENCE: 115
agggcauaaa cuauaacagc u 21

<210> SEQ ID NO 116
<211> LENGTH: 23
<212> TYPE: RNA
<213> ORGANISM: Artificial Sequence
<220> FEATURE:
<223> OTHER INFORMATION: Antisense sequence for siFXIb2-M1SP1

<400> SEQUENCE: 116
agcuguuaua guuuaugccc uuc 23

<210> SEQ ID NO 117
<211> LENGTH: 21
<212> TYPE: RNA
<213> ORGANISM: Artificial Sequence
<220> FEATURE:
<223> OTHER INFORMATION: Sense sequence for siFXIb2-M2SP1

<400> SEQUENCE: 117
agggcauaaa cuauaacagc u 21

<210> SEQ ID NO 118
<211> LENGTH: 23
<212> TYPE: RNA
<213> ORGANISM: Artificial Sequence
<220> FEATURE:
<223> OTHER INFORMATION: Antisense sequence for siFXIb2-M2SP1

<400> SEQUENCE: 118
agcuguuaua guuuaugccc uuc 23

<210> SEQ ID NO 119
<211> LENGTH: 21
<212> TYPE: RNA
<213> ORGANISM: Artificial Sequence
<220> FEATURE:
<223> OTHER INFORMATION: Sense sequence for siFXIb2-M3SP1

<400> SEQUENCE: 119
agggcauaaa cuauaacagc u 21

<210> SEQ ID NO 120
<211> LENGTH: 23
<212> TYPE: RNA
<213> ORGANISM: Artificial Sequence
<220> FEATURE:
<223> OTHER INFORMATION: Antisense sequence for siFXIb2-M3SP1

<400> SEQUENCE: 120
agcuguuaua guuuaugccc uuc 23

<210> SEQ ID NO 121
<211> LENGTH: 19
<212> TYPE: RNA
<213> ORGANISM: Artificial Sequence
<220> FEATURE:
<223> OTHER INFORMATION: Sense sequence for the third siRNA
<220> FEATURE:
<221> NAME/KEY: misc-feature
<222> LOCATION: (19)..(19)
<223> OTHER INFORMATION: n is Z9, Z9 is A

<400> SEQUENCE: 121
gcucaagaau gccaagaan 19

<210> SEQ ID NO 122
<211> LENGTH: 19
<212> TYPE: RNA
<213> ORGANISM: Artificial Sequence
<220> FEATURE:
<223> OTHER INFORMATION: Antisense sequence for the third siRNA
<220> FEATURE:
<221> NAME/KEY: misc-feature
<222> LOCATION: (1)..(1)
<223> OTHER INFORMATION: n is Z10, Z10 is U

<400> SEQUENCE: 122
nuucuuggca uucuugagc 19

<210> SEQ ID NO 123
<211> LENGTH: 19
<212> TYPE: RNA
<213> ORGANISM: Artificial Sequence
<220> FEATURE:
<223> OTHER INFORMATION: Sense sequence for the third siRNA
<220> FEATURE:
<221> NAME/KEY: misc-feature
<222> LOCATION: (19)..(19)
<223> OTHER INFORMATION: n is Z11, Z11 is A, U, G or C

<400> SEQUENCE: 123
gcucaagaau gccaagaan 19

<210> SEQ ID NO 124
<211> LENGTH: 19
<212> TYPE: RNA
<213> ORGANISM: Artificial Sequence
<220> FEATURE:
<223> OTHER INFORMATION: Antisense sequence for the third siRNA
<220> FEATURE:
<221> NAME/KEY: misc-feature
<222> LOCATION: (1)..(1)
<223> OTHER INFORMATION: n is Z12, Z12 is a nucleotide complementary to Z11, Z11 is selected from A, U, G or C

<400> SEQUENCE: 124
nuucuuggca uucuugagc 19

<210> SEQ ID NO 125
<211> LENGTH: 19
<212> TYPE: RNA
<213> ORGANISM: Artificial Sequence
<220> FEATURE:
<223> OTHER INFORMATION: Sense sequence for the third siRNA
<220> FEATURE:
<221> NAME/KEY: misc-feature
<222> LOCATION: (19)..(19)
<223> OTHER INFORMATION: n is Z11, Z11 is A, U, G or C

<400> SEQUENCE: 125
gcucaagaau gccaagaan 19

<210> SEQ ID NO 126
<211> LENGTH: 21
<212> TYPE: RNA
<213> ORGANISM: Artificial Sequence
<220> FEATURE:
<223> OTHER INFORMATION: Antisense sequence for the third siRNA
<220> FEATURE:
<221> NAME/KEY: misc-feature
<222> LOCATION: (1)..(1)
<223> OTHER INFORMATION: n is Z12, Z12 is a nucleotide complementary to Z11, Z11 is selected from A, U, G or C

<400> SEQUENCE: 126
nuucuuggca uucuugagca c 21

<210> SEQ ID NO 127
<211> LENGTH: 21
<212> TYPE: RNA
<213> ORGANISM: Artificial Sequence
<220> FEATURE:
<223> OTHER INFORMATION: Sense sequence for the third siRNA
<220> FEATURE:
<221> NAME/KEY: misc-feature
<222> LOCATION: (21)..(21)
<223> OTHER INFORMATION: n is Z11, Z11 is A, U, G or C

<400> SEQUENCE: 127
gugcucaaga augccaagaa n 21

<210> SEQ ID NO 128
<211> LENGTH: 23
<212> TYPE: RNA

<213> ORGANISM: Artificial Sequence
<220> FEATURE:
<223> OTHER INFORMATION: Antisense sequence for the third siRNA
<220> FEATURE:
<221> NAME/KEY: misc-feature
<222> LOCATION: (1)..(1)
<223> OTHER INFORMATION: n is Z12, Z12 is a nucleotide complementary to Z11, Z11 is selected from A, U, G or C

<400> SEQUENCE: 128
nuucuuggca uucuugagca cuc 23

<210> SEQ ID NO 129
<211> LENGTH: 19
<212> TYPE: RNA
<213> ORGANISM: Artificial Sequence
<220> FEATURE:
<223> OTHER INFORMATION: Sense sequence for siFXIc1

<400> SEQUENCE: 129
gcucaagaau gccaagaaa 19

<210> SEQ ID NO 130
<211> LENGTH: 21
<212> TYPE: RNA
<213> ORGANISM: Artificial Sequence
<220> FEATURE:
<223> OTHER INFORMATION: Antisense sequence for siFXIc1

<400> SEQUENCE: 130
uuucuuggca uucuugagca c 21

<210> SEQ ID NO 131
<211> LENGTH: 21
<212> TYPE: RNA
<213> ORGANISM: Artificial Sequence
<220> FEATURE:
<223> OTHER INFORMATION: Sense sequence for siFXIc2

<400> SEQUENCE: 131
gugcucaaga augccaagaa a 21

<210> SEQ ID NO 132
<211> LENGTH: 23
<212> TYPE: RNA
<213> ORGANISM: Artificial Sequence
<220> FEATURE:
<223> OTHER INFORMATION: Antisense sequence for siFXIc2

<400> SEQUENCE: 132
uuucuuggca uucuugagca cuc 23

<210> SEQ ID NO 133
<211> LENGTH: 19
<212> TYPE: RNA
<213> ORGANISM: Artificial Sequence
<220> FEATURE:
<223> OTHER INFORMATION: Sense sequence for siFXIc1-M1

<400> SEQUENCE: 133
gcucaagaau gccaagaaa 19

<210> SEQ ID NO 134
<211> LENGTH: 21
<212> TYPE: RNA
<213> ORGANISM: Artificial Sequence
<220> FEATURE:

<223> OTHER INFORMATION: Antisense sequence for siFXIc1-M1

<400> SEQUENCE: 134
uuucuuggca uucuugagca c 21

<210> SEQ ID NO 135
<211> LENGTH: 19
<212> TYPE: RNA
<213> ORGANISM: Artificial Sequence
<220> FEATURE:
<223> OTHER INFORMATION: Sense sequence for siFXIc1-M2

<400> SEQUENCE: 135
gcucaagaau gccaagaaa 19

<210> SEQ ID NO 136
<211> LENGTH: 21
<212> TYPE: RNA
<213> ORGANISM: Artificial Sequence
<220> FEATURE:
<223> OTHER INFORMATION: Antisense sequence for siFXIc1-M2

<400> SEQUENCE: 136
uuucuuggca uucuugagca c 21

<210> SEQ ID NO 137
<211> LENGTH: 19
<212> TYPE: RNA
<213> ORGANISM: Artificial Sequence
<220> FEATURE:
<223> OTHER INFORMATION: Sense sequence for siFXIc1-M3

<400> SEQUENCE: 137
gcucaagaau gccaagaaa 19

<210> SEQ ID NO 138
<211> LENGTH: 21
<212> TYPE: RNA
<213> ORGANISM: Artificial Sequence
<220> FEATURE:
<223> OTHER INFORMATION: Antisense sequence for siFXIc1-M3

<400> SEQUENCE: 138
uuucuuggca uucuugagca c 21

<210> SEQ ID NO 139
<211> LENGTH: 21
<212> TYPE: RNA
<213> ORGANISM: Artificial Sequence
<220> FEATURE:
<223> OTHER INFORMATION: Sense sequence for siFXIc2-M1

<400> SEQUENCE: 139
gugcucaaga augccaagaa a 21

<210> SEQ ID NO 140
<211> LENGTH: 23
<212> TYPE: RNA
<213> ORGANISM: Artificial Sequence
<220> FEATURE:
<223> OTHER INFORMATION: Antisense sequence for siFXIc2-M1

<400> SEQUENCE: 140
uuucuuggca uucuugagca cuc 23

<210> SEQ ID NO 141
<211> LENGTH: 21
<212> TYPE: RNA
<213> ORGANISM: Artificial Sequence
<220> FEATURE:
<223> OTHER INFORMATION: Sense sequence for siFXIc2-M2

<400> SEQUENCE: 141
gugcucaaga augccaagaa a 21

<210> SEQ ID NO 142
<211> LENGTH: 23
<212> TYPE: RNA
<213> ORGANISM: Artificial Sequence
<220> FEATURE:
<223> OTHER INFORMATION: Antisense sequence for siFXIc2-M2

<400> SEQUENCE: 142
uuucuuggca uucuugagca cuc 23

<210> SEQ ID NO 143
<211> LENGTH: 21
<212> TYPE: RNA
<213> ORGANISM: Artificial Sequence
<220> FEATURE:
<223> OTHER INFORMATION: Sense sequence for siFXIc2-M3

<400> SEQUENCE: 143
gugcucaaga augccaagaa a 21

<210> SEQ ID NO 144
<211> LENGTH: 23
<212> TYPE: RNA
<213> ORGANISM: Artificial Sequence
<220> FEATURE:
<223> OTHER INFORMATION: Antisense sequence for siFXIc2-M3

<400> SEQUENCE: 144
uuucuuggca uucuugagca cuc 23

<210> SEQ ID NO 145
<211> LENGTH: 19
<212> TYPE: RNA
<213> ORGANISM: Artificial Sequence
<220> FEATURE:
<223> OTHER INFORMATION: Sense sequence for siFXIc1-M1S

<400> SEQUENCE: 145
gcucaagaau gccaagaaa 19

<210> SEQ ID NO 146
<211> LENGTH: 21
<212> TYPE: RNA
<213> ORGANISM: Artificial Sequence
<220> FEATURE:
<223> OTHER INFORMATION: Antisense sequence for siFXIc1-M1S

<400> SEQUENCE: 146
uuucuuggca uucuugagca c 21

<210> SEQ ID NO 147
<211> LENGTH: 19
<212> TYPE: RNA
<213> ORGANISM: Artificial Sequence
<220> FEATURE:
<223> OTHER INFORMATION: Sense sequence for siFXIc1-M2S

<400> SEQUENCE: 147
gcucaagaau gccaagaaa 19

<210> SEQ ID NO 148
<211> LENGTH: 21
<212> TYPE: RNA
<213> ORGANISM: Artificial Sequence
<220> FEATURE:
<223> OTHER INFORMATION: Antisense sequence for siFXIc1-M2S

<400> SEQUENCE: 148
uuucuuggca uucuugagca c 21

<210> SEQ ID NO 149
<211> LENGTH: 19
<212> TYPE: RNA
<213> ORGANISM: Artificial Sequence
<220> FEATURE:
<223> OTHER INFORMATION: Sense sequence for siFXIc1-M3S

<400> SEQUENCE: 149
gcucaagaau gccaagaaa 19

<210> SEQ ID NO 150
<211> LENGTH: 21
<212> TYPE: RNA
<213> ORGANISM: Artificial Sequence
<220> FEATURE:
<223> OTHER INFORMATION: Antisense sequence for siFXIc1-M3S

<400> SEQUENCE: 150
uuucuuggca uucuugagca c 21

<210> SEQ ID NO 151
<211> LENGTH: 21
<212> TYPE: RNA
<213> ORGANISM: Artificial Sequence
<220> FEATURE:
<223> OTHER INFORMATION: Sense sequence for siFXIc2-M1S

<400> SEQUENCE: 151
gugcucaaga augccaagaa a 21

<210> SEQ ID NO 152
<211> LENGTH: 23
<212> TYPE: RNA
<213> ORGANISM: Artificial Sequence
<220> FEATURE:
<223> OTHER INFORMATION: Antisense sequence for siFXIc2-M1S

<400> SEQUENCE: 152
uuucuuggca uucuugagca cuc 23

<210> SEQ ID NO 153
<211> LENGTH: 21
<212> TYPE: RNA
<213> ORGANISM: Artificial Sequence
<220> FEATURE:
<223> OTHER INFORMATION: Sense sequence for siFXIc2-M2S

<400> SEQUENCE: 153
gugcucaaga augccaagaa a 21

<210> SEQ ID NO 154
<211> LENGTH: 23

<212> TYPE: RNA
<213> ORGANISM: Artificial Sequence
<220> FEATURE:
<223> OTHER INFORMATION: Antisense sequence for siFXIc2-M2S

<400> SEQUENCE: 154
uuucuuggca uucuugagca cuc 23

<210> SEQ ID NO 155
<211> LENGTH: 21
<212> TYPE: RNA
<213> ORGANISM: Artificial Sequence
<220> FEATURE:
<223> OTHER INFORMATION: Sense sequence for siFXIc2-M3S

<400> SEQUENCE: 155
gugcucaaga augccaagaa a 21

<210> SEQ ID NO 156
<211> LENGTH: 23
<212> TYPE: RNA
<213> ORGANISM: Artificial Sequence
<220> FEATURE:
<223> OTHER INFORMATION: Antisense sequence for siFXIc2-M3S

<400> SEQUENCE: 156
uuucuuggca uucuugagca cuc 23

<210> SEQ ID NO 157
<211> LENGTH: 19
<212> TYPE: RNA
<213> ORGANISM: Artificial Sequence
<220> FEATURE:
<223> OTHER INFORMATION: Sense sequence for siFXIc1-M1P1

<400> SEQUENCE: 157
gcucaagaau gccaagaaa 19

<210> SEQ ID NO 158
<211> LENGTH: 21
<212> TYPE: RNA
<213> ORGANISM: Artificial Sequence
<220> FEATURE:
<223> OTHER INFORMATION: Antisense sequence for siFXIc1-M1P1

<400> SEQUENCE: 158
uuucuuggca uucuugagca c 21

<210> SEQ ID NO 159
<211> LENGTH: 19
<212> TYPE: RNA
<213> ORGANISM: Artificial Sequence
<220> FEATURE:
<223> OTHER INFORMATION: Sense sequence for siFXIc1-M2P1

<400> SEQUENCE: 159
gcucaagaau gccaagaaa 19

<210> SEQ ID NO 160
<211> LENGTH: 21
<212> TYPE: RNA
<213> ORGANISM: Artificial Sequence
<220> FEATURE:
<223> OTHER INFORMATION: Antisense sequence for siFXIc1-M2P1

<400> SEQUENCE: 160
uuucuuggca uucuugagca c 21

<210> SEQ ID NO 161
<211> LENGTH: 19
<212> TYPE: RNA
<213> ORGANISM: Artificial Sequence
<220> FEATURE:
<223> OTHER INFORMATION: Sense sequence for siFXIc1-M3P1

<400> SEQUENCE: 161
gcucaagaau gccaagaaa 19

<210> SEQ ID NO 162
<211> LENGTH: 21
<212> TYPE: RNA
<213> ORGANISM: Artificial Sequence
<220> FEATURE:
<223> OTHER INFORMATION: Antisense sequence for siFXIc1-M3P1

<400> SEQUENCE: 162
uuucuuggca uucuugagca c 21

<210> SEQ ID NO 163
<211> LENGTH: 21
<212> TYPE: RNA
<213> ORGANISM: Artificial Sequence
<220> FEATURE:
<223> OTHER INFORMATION: Sense sequence for siFXIc2-M1P1

<400> SEQUENCE: 163
gugcucaaga augccaagaa a 21

<210> SEQ ID NO 164
<211> LENGTH: 23
<212> TYPE: RNA
<213> ORGANISM: Artificial Sequence
<220> FEATURE:
<223> OTHER INFORMATION: Antisense sequence for siFXIc2-M1P1

<400> SEQUENCE: 164
uuucuuggca uucuugagca cuc 23

<210> SEQ ID NO 165
<211> LENGTH: 21
<212> TYPE: RNA
<213> ORGANISM: Artificial Sequence
<220> FEATURE:
<223> OTHER INFORMATION: Sense sequence for siFXIc2-M2P1

<400> SEQUENCE: 165
gugcucaaga augccaagaa a 21

<210> SEQ ID NO 166
<211> LENGTH: 23
<212> TYPE: RNA
<213> ORGANISM: Artificial Sequence
<220> FEATURE:
<223> OTHER INFORMATION: Antisense sequence for siFXIc2-M2P1

<400> SEQUENCE: 166
uuucuuggca uucuugagca cuc 23

<210> SEQ ID NO 167
<211> LENGTH: 21
<212> TYPE: RNA
<213> ORGANISM: Artificial Sequence
<220> FEATURE:
<223> OTHER INFORMATION: Sense sequence for siFXIc2-M3P1

<400> SEQUENCE: 167
gugcucaaga augccaagaa a 21

<210> SEQ ID NO 168
<211> LENGTH: 23
<212> TYPE: RNA
<213> ORGANISM: Artificial Sequence
<220> FEATURE:
<223> OTHER INFORMATION: Antisense sequence for siFXIc2-M3P1

<400> SEQUENCE: 168
uuucuuggca uucuugagca cuc 23

<210> SEQ ID NO 169
<211> LENGTH: 19
<212> TYPE: RNA
<213> ORGANISM: Artificial Sequence
<220> FEATURE:
<223> OTHER INFORMATION: Sense sequence for siFXIc1-M1SP1

<400> SEQUENCE: 169
gcucaagaau gccaagaaa 19

<210> SEQ ID NO 170
<211> LENGTH: 21
<212> TYPE: RNA
<213> ORGANISM: Artificial Sequence
<220> FEATURE:
<223> OTHER INFORMATION: Antisense sequence for siFXIc1-M1SP1

<400> SEQUENCE: 170
uuucuuggca uucuugagca c 21

<210> SEQ ID NO 171
<211> LENGTH: 19
<212> TYPE: RNA
<213> ORGANISM: Artificial Sequence
<220> FEATURE:
<223> OTHER INFORMATION: Sense sequence for siFXIc1-M2SP1

<400> SEQUENCE: 171
gcucaagaau gccaagaaa 19

<210> SEQ ID NO 172
<211> LENGTH: 21
<212> TYPE: RNA
<213> ORGANISM: Artificial Sequence
<220> FEATURE:
<223> OTHER INFORMATION: Antisense sequence for siFXIc1-M2SP1

<400> SEQUENCE: 172
uuucuuggca uucuugagca c 21

<210> SEQ ID NO 173
<211> LENGTH: 19
<212> TYPE: RNA
<213> ORGANISM: Artificial Sequence
<220> FEATURE:
<223> OTHER INFORMATION: Sense sequence for siFXIc1-M3SP1

<400> SEQUENCE: 173
gcucaagaau gccaagaaa 19

<210> SEQ ID NO 174
<211> LENGTH: 21
<212> TYPE: RNA
<213> ORGANISM: Artificial Sequence
<220> FEATURE:
<223> OTHER INFORMATION: Antisense sequence for siFXIc1-M3SP1

<400> SEQUENCE: 174
uuucuuggca uucuugagca c 21

<210> SEQ ID NO 175
<211> LENGTH: 21
<212> TYPE: RNA
<213> ORGANISM: Artificial Sequence
<220> FEATURE:
<223> OTHER INFORMATION: Sense sequence for siFXIc2-M1SP1

<400> SEQUENCE: 175
gugcucaaga augccaagaa a 21

<210> SEQ ID NO 176
<211> LENGTH: 23
<212> TYPE: RNA
<213> ORGANISM: Artificial Sequence
<220> FEATURE:
<223> OTHER INFORMATION: Antisense sequence for siFXIc2-M1SP1

<400> SEQUENCE: 176
uuucuuggca uucuugagca cuc 23

<210> SEQ ID NO 177
<211> LENGTH: 21
<212> TYPE: RNA
<213> ORGANISM: Artificial Sequence
<220> FEATURE:
<223> OTHER INFORMATION: Sense sequence for siFXIc2-M2SP1

<400> SEQUENCE: 177
gugcucaaga augccaagaa a 21

<210> SEQ ID NO 178
<211> LENGTH: 23
<212> TYPE: RNA
<213> ORGANISM: Artificial Sequence
<220> FEATURE:
<223> OTHER INFORMATION: Antisense sequence for siFXIc2-M2SP1

<400> SEQUENCE: 178
uuucuuggca uucuugagca cuc 23

<210> SEQ ID NO 179
<211> LENGTH: 21
<212> TYPE: RNA
<213> ORGANISM: Artificial Sequence
<220> FEATURE:
<223> OTHER INFORMATION: Sense sequence for siFXIc2-M3SP1

<400> SEQUENCE: 179
gugcucaaga augccaagaa a 21

<210> SEQ ID NO 180
<211> LENGTH: 23
<212> TYPE: RNA
<213> ORGANISM: Artificial Sequence
<220> FEATURE:
<223> OTHER INFORMATION: Antisense sequence for siFXIc2-M3SP1

<400> SEQUENCE: 180
uuucuuggca uucuugagca cuc 23

<210> SEQ ID NO 181
<211> LENGTH: 19
<212> TYPE: RNA
<213> ORGANISM: Artificial Sequence
<220> FEATURE:
<223> OTHER INFORMATION: Sense sequence for the fourth siRNA
<220> FEATURE:
<221> NAME/KEY: misc-feature
<222> LOCATION: (19)..(19)
<223> OTHER INFORMATION: n is Z13, Z13 is U

<400> SEQUENCE: 181
gcaacaaaga cauuuaugn 19

<210> SEQ ID NO 182
<211> LENGTH: 19
<212> TYPE: RNA
<213> ORGANISM: Artificial Sequence
<220> FEATURE:
<223> OTHER INFORMATION: Antisense sequence for the fourth siRNA
<220> FEATURE:
<221> NAME/KEY: misc-feature
<222> LOCATION: (1)..(1)
<223> OTHER INFORMATION: n is Z14, Z14 is A

<400> SEQUENCE: 182
ncauaaaugu cuuuguugc 19

<210> SEQ ID NO 183
<211> LENGTH: 19
<212> TYPE: RNA
<213> ORGANISM: Artificial Sequence
<220> FEATURE:
<223> OTHER INFORMATION: Sense sequence for the fourth siRNA
<220> FEATURE:
<221> NAME/KEY: misc-feature
<222> LOCATION: (19)..(19)
<223> OTHER INFORMATION: n is Z15, Z15 is A, U, G or C

<400> SEQUENCE: 183
gcaacaaaga cauuuaugn 19

<210> SEQ ID NO 184
<211> LENGTH: 19
<212> TYPE: RNA
<213> ORGANISM: Artificial Sequence
<220> FEATURE:
<223> OTHER INFORMATION: Antisense sequence for the fourth siRNA
<220> FEATURE:
<221> NAME/KEY: misc-feature
<222> LOCATION: (1)..(1)
<223> OTHER INFORMATION: n is Z16, Z16 is a nucleotide complementary to
Z15, Z15 is selected from A, U, G or C

<400> SEQUENCE: 184
ncauaaaugu cuuuguugc 19

<210> SEQ ID NO 185
<211> LENGTH: 19
<212> TYPE: RNA
<213> ORGANISM: Artificial Sequence
<220> FEATURE:
<223> OTHER INFORMATION: Sense sequence for the fourth siRNA
<220> FEATURE:
<221> NAME/KEY: misc-feature
<222> LOCATION: (19)..(19)
<223> OTHER INFORMATION: n is Z15, Z15 is A, U, G or C

<400> SEQUENCE: 185
gcaacaaaga cauuuaugn 19

<210> SEQ ID NO 186
<211> LENGTH: 21
<212> TYPE: RNA
<213> ORGANISM: Artificial Sequence
<220> FEATURE:
<223> OTHER INFORMATION: Antisense sequence for the fourth siRNA
<220> FEATURE:
<221> NAME/KEY: misc-feature
<222> LOCATION: (1)..(1)
<223> OTHER INFORMATION: n is Z16, Z16 is a nucleotide complementary to
Z15, Z15 is selected from A, U, G or C

<400> SEQUENCE: 186
ncauaaaugu cuuuguugca a 21

<210> SEQ ID NO 187
<211> LENGTH: 21
<212> TYPE: RNA
<213> ORGANISM: Artificial Sequence
<220> FEATURE:
<223> OTHER INFORMATION: Sense sequence for the fourth siRNA
<220> FEATURE:
<221> NAME/KEY: misc-feature
<222> LOCATION: (21)..(21)
<223> OTHER INFORMATION: n is Z15, Z15 is A, U, G or C

<400> SEQUENCE: 187
uugcaacaaa gacauuuaug n 21

<210> SEQ ID NO 188
<211> LENGTH: 23
<212> TYPE: RNA
<213> ORGANISM: Artificial Sequence
<220> FEATURE:
<223> OTHER INFORMATION: Antisense sequence for the fourth siRNA
<220> FEATURE:
<221> NAME/KEY: misc-feature
<222> LOCATION: (1)..(1)
<223> OTHER INFORMATION: n is Z16, Z16 is a nucleotide complementary to
Z15, Z15 is selected from A, U, G or C

<400> SEQUENCE: 188
ncauaaaugu cuuuguugca agc 23

<210> SEQ ID NO 189
<211> LENGTH: 19
<212> TYPE: RNA
<213> ORGANISM: Artificial Sequence
<220> FEATURE:
<223> OTHER INFORMATION: Sense sequence for siFXId1

<400> SEQUENCE: 189
gcaacaaaga cauuuaugu 19

<210> SEQ ID NO 190
<211> LENGTH: 21
<212> TYPE: RNA
<213> ORGANISM: Artificial Sequence
<220> FEATURE:
<223> OTHER INFORMATION: Antisense sequence for siFXId1

<400> SEQUENCE: 190
acauaaaugu cuuuguugca a 21

<210> SEQ ID NO 191
<211> LENGTH: 21
<212> TYPE: RNA
<213> ORGANISM: Artificial Sequence
<220> FEATURE:
<223> OTHER INFORMATION: Sense sequence for siFXId2

<400> SEQUENCE: 191
uugcaacaaa gacauuuaug u 21

<210> SEQ ID NO 192
<211> LENGTH: 23
<212> TYPE: RNA
<213> ORGANISM: Artificial Sequence
<220> FEATURE:
<223> OTHER INFORMATION: Antisense sequence for siFXId2

<400> SEQUENCE: 192
acauaaaugu cuuuguugca agc 23

<210> SEQ ID NO 193
<211> LENGTH: 19
<212> TYPE: RNA
<213> ORGANISM: Artificial Sequence
<220> FEATURE:
<223> OTHER INFORMATION: Sense sequence for siFXId1-M1

<400> SEQUENCE: 193
gcaacaaaga cauuuaugu 19

<210> SEQ ID NO 194
<211> LENGTH: 21
<212> TYPE: RNA
<213> ORGANISM: Artificial Sequence
<220> FEATURE:
<223> OTHER INFORMATION: Antisense sequence for siFXId1-M1

<400> SEQUENCE: 194
acauaaaugu cuuuguugca a 21

<210> SEQ ID NO 195
<211> LENGTH: 19
<212> TYPE: RNA
<213> ORGANISM: Artificial Sequence
<220> FEATURE:
<223> OTHER INFORMATION: Sense sequence for siFXId1-M2

<400> SEQUENCE: 195
gcaacaaaga cauuuaugu 19

<210> SEQ ID NO 196
<211> LENGTH: 21
<212> TYPE: RNA
<213> ORGANISM: Artificial Sequence
<220> FEATURE:
<223> OTHER INFORMATION: Antisense sequence for siFXId1-M2

<400> SEQUENCE: 196
acauaaaugu cuuuguugca a 21

<210> SEQ ID NO 197
<211> LENGTH: 19
<212> TYPE: RNA
<213> ORGANISM: Artificial Sequence
<220> FEATURE:
<223> OTHER INFORMATION: Sense sequence for siFXId1-M3

<400> SEQUENCE: 197
gcaacaaaga cauuuaugu 19

<210> SEQ ID NO 198
<211> LENGTH: 21
<212> TYPE: RNA
<213> ORGANISM: Artificial Sequence
<220> FEATURE:
<223> OTHER INFORMATION: Antisense sequence for siFXId1-M3

<400> SEQUENCE: 198
acauaaaugu cuuuguugca a 21

<210> SEQ ID NO 199
<211> LENGTH: 21
<212> TYPE: RNA
<213> ORGANISM: Artificial Sequence
<220> FEATURE:
<223> OTHER INFORMATION: Sense sequence for siFXId2-M1

<400> SEQUENCE: 199
uugcaacaaa gacauuuaug u 21

<210> SEQ ID NO 200
<211> LENGTH: 23
<212> TYPE: RNA
<213> ORGANISM: Artificial Sequence
<220> FEATURE:
<223> OTHER INFORMATION: Antisense sequence for siFXId2-M1

<400> SEQUENCE: 200
acauaaaugu cuuuguugca agc 23

<210> SEQ ID NO 201
<211> LENGTH: 21
<212> TYPE: RNA
<213> ORGANISM: Artificial Sequence
<220> FEATURE:
<223> OTHER INFORMATION: Sense sequence for siFXId2-M2

<400> SEQUENCE: 201
uugcaacaaa gacauuuaug u 21

<210> SEQ ID NO 202
<211> LENGTH: 23
<212> TYPE: RNA
<213> ORGANISM: Artificial Sequence
<220> FEATURE:
<223> OTHER INFORMATION: Antisense sequence for siFXId2-M2

<400> SEQUENCE: 202
acauaaaugu cuuuguugca agc 23

<210> SEQ ID NO 203
<211> LENGTH: 21
<212> TYPE: RNA
<213> ORGANISM: Artificial Sequence
<220> FEATURE:
<223> OTHER INFORMATION: Sense sequence for siFXId2-M3

<400> SEQUENCE: 203
uugcaacaaa gacauuuaug u 21

<210> SEQ ID NO 204
<211> LENGTH: 23
<212> TYPE: RNA
<213> ORGANISM: Artificial Sequence
<220> FEATURE:
<223> OTHER INFORMATION: Antisense sequence for siFXId2-M3

<400> SEQUENCE: 204
acauaaaugu cuuuguugca agc 23

<210> SEQ ID NO 205
<211> LENGTH: 19
<212> TYPE: RNA
<213> ORGANISM: Artificial Sequence
<220> FEATURE:
<223> OTHER INFORMATION: Sense sequence for siFXId1-M1S

<400> SEQUENCE: 205
gcaacaaaga cauuuaugu 19

<210> SEQ ID NO 206
<211> LENGTH: 21
<212> TYPE: RNA
<213> ORGANISM: Artificial Sequence
<220> FEATURE:
<223> OTHER INFORMATION: Antisense sequence for siFXId1-M1S

<400> SEQUENCE: 206
acauaaaugu cuuuguugca a 21

<210> SEQ ID NO 207
<211> LENGTH: 19
<212> TYPE: RNA
<213> ORGANISM: Artificial Sequence
<220> FEATURE:
<223> OTHER INFORMATION: Sense sequence for siFXId1-M2S

<400> SEQUENCE: 207
gcaacaaaga cauuuaugu 19

<210> SEQ ID NO 208
<211> LENGTH: 21
<212> TYPE: RNA
<213> ORGANISM: Artificial Sequence
<220> FEATURE:
<223> OTHER INFORMATION: Antisense sequence for siFXId1-M2S

<400> SEQUENCE: 208
acauaaaugu cuuuguugca a 21

<210> SEQ ID NO 209
<211> LENGTH: 19
<212> TYPE: RNA
<213> ORGANISM: Artificial Sequence
<220> FEATURE:
<223> OTHER INFORMATION: Sense sequence for siFXId1-M3S

<400> SEQUENCE: 209
gcaacaaaga cauuuaugu 19

<210> SEQ ID NO 210
<211> LENGTH: 21
<212> TYPE: RNA
<213> ORGANISM: Artificial Sequence
<220> FEATURE:
<223> OTHER INFORMATION: Anrisense sequence for siFXId1-M3S

<400> SEQUENCE: 210
acauaaaugu cuuuguugca a 21

<210> SEQ ID NO 211
<211> LENGTH: 21
<212> TYPE: RNA
<213> ORGANISM: Artificial Sequence
<220> FEATURE:
<223> OTHER INFORMATION: Sense sequence for siFXId2-M1S

<400> SEQUENCE: 211
uugcaacaaa gacauuuaug u 21

<210> SEQ ID NO 212
<211> LENGTH: 23
<212> TYPE: RNA
<213> ORGANISM: Artificial Sequence
<220> FEATURE:
<223> OTHER INFORMATION: Antisense sequence for siFXId2-M1S

<400> SEQUENCE: 212
acauaaaugu cuuuguugca agc 23

<210> SEQ ID NO 213
<211> LENGTH: 21
<212> TYPE: RNA
<213> ORGANISM: Artificial Sequence
<220> FEATURE:
<223> OTHER INFORMATION: Sense sequence for siFXId2-M2S

<400> SEQUENCE: 213
uugcaacaaa gacauuuaug u 21

<210> SEQ ID NO 214
<211> LENGTH: 23
<212> TYPE: RNA
<213> ORGANISM: Artificial Sequence
<220> FEATURE:
<223> OTHER INFORMATION: Antisense sequence for siFXId2-M2S

<400> SEQUENCE: 214
acauaaaugu cuuuguugca agc 23

<210> SEQ ID NO 215
<211> LENGTH: 21
<212> TYPE: RNA
<213> ORGANISM: Artificial Sequence
<220> FEATURE:
<223> OTHER INFORMATION: Sense sequence for siFXId2-M3S

<400> SEQUENCE: 215
uugcaacaaa gacauuuaug u 21

<210> SEQ ID NO 216
<211> LENGTH: 23
<212> TYPE: RNA
<213> ORGANISM: Artificial Sequence
<220> FEATURE:
<223> OTHER INFORMATION: Antisense sequence for siFXId2-M3S

<400> SEQUENCE: 216
acauaaaugu cuuuguugca agc 23

<210> SEQ ID NO 217

<211> LENGTH: 19
<212> TYPE: RNA
<213> ORGANISM: Artificial Sequence
<220> FEATURE:
<223> OTHER INFORMATION: Sense sequence for siFXId1-M1P1

<400> SEQUENCE: 217
gcaacaaaga cauuuaugu 19

<210> SEQ ID NO 218
<211> LENGTH: 21
<212> TYPE: RNA
<213> ORGANISM: Artificial Sequence
<220> FEATURE:
<223> OTHER INFORMATION: Antisense sequence for siFXId1-M1P1

<400> SEQUENCE: 218
acauaaaugu cuuuguugca a 21

<210> SEQ ID NO 219
<211> LENGTH: 19
<212> TYPE: RNA
<213> ORGANISM: Artificial Sequence
<220> FEATURE:
<223> OTHER INFORMATION: Sense sequence for siFXId1-M2P1

<400> SEQUENCE: 219
gcaacaaaga cauuuaugu 19

<210> SEQ ID NO 220
<211> LENGTH: 21
<212> TYPE: RNA
<213> ORGANISM: Artificial Sequence
<220> FEATURE:
<223> OTHER INFORMATION: Antisense sequence for siFXId1-M2P1

<400> SEQUENCE: 220
acauaaaugu cuuuguugca a 21

<210> SEQ ID NO 221
<211> LENGTH: 19
<212> TYPE: RNA
<213> ORGANISM: Artificial Sequence
<220> FEATURE:
<223> OTHER INFORMATION: Sense sequence for siFXId1-M3P1

<400> SEQUENCE: 221
gcaacaaaga cauuuaugu 19

<210> SEQ ID NO 222
<211> LENGTH: 21
<212> TYPE: RNA
<213> ORGANISM: Artificial Sequence
<220> FEATURE:
<223> OTHER INFORMATION: Antisense sequence for siFXId1-M3P1

<400> SEQUENCE: 222
acauaaaugu cuuuguugca a 21

<210> SEQ ID NO 223
<211> LENGTH: 21
<212> TYPE: RNA
<213> ORGANISM: Artificial Sequence
<220> FEATURE:
<223> OTHER INFORMATION: Sense sequence for siFXId2-M1P1

<400> SEQUENCE: 223
uugcaacaaa gacauuuaug u 21

<210> SEQ ID NO 224
<211> LENGTH: 23
<212> TYPE: RNA
<213> ORGANISM: Artificial Sequence
<220> FEATURE:
<223> OTHER INFORMATION: Antisense sequence for siFXId2-M1P1

<400> SEQUENCE: 224
acauaaaugu cuuuguugca agc 23

<210> SEQ ID NO 225
<211> LENGTH: 21
<212> TYPE: RNA
<213> ORGANISM: Artificial Sequence
<220> FEATURE:
<223> OTHER INFORMATION: Sense sequence for siFXId2-M2P1

<400> SEQUENCE: 225
uugcaacaaa gacauuuaug u 21

<210> SEQ ID NO 226
<211> LENGTH: 23
<212> TYPE: RNA
<213> ORGANISM: Artificial Sequence
<220> FEATURE:
<223> OTHER INFORMATION: Antisense sequence for siFXId2-M2P1

<400> SEQUENCE: 226
acauaaaugu cuuuguugca agc 23

<210> SEQ ID NO 227
<211> LENGTH: 21
<212> TYPE: RNA
<213> ORGANISM: Artificial Sequence
<220> FEATURE:
<223> OTHER INFORMATION: Sense sequence for siFXId2-M3P1

<400> SEQUENCE: 227
uugcaacaaa gacauuuaug u 21

<210> SEQ ID NO 228
<211> LENGTH: 23
<212> TYPE: RNA
<213> ORGANISM: Artificial Sequence
<220> FEATURE:
<223> OTHER INFORMATION: Antisense sequence for siFXId2-M3P1

<400> SEQUENCE: 228
acauaaaugu cuuuguugca agc 23

<210> SEQ ID NO 229
<211> LENGTH: 19
<212> TYPE: RNA
<213> ORGANISM: Artificial Sequence
<220> FEATURE:
<223> OTHER INFORMATION: Sense sequence for siFXId1-M1SP1

<400> SEQUENCE: 229
gcaacaaaga cauuuaugu 19

<210> SEQ ID NO 230
<211> LENGTH: 21
<212> TYPE: RNA

<213> ORGANISM: Artificial Sequence
<220> FEATURE:
<223> OTHER INFORMATION: Antisense sequence for siFXId1-M1SP1

<400> SEQUENCE: 230
acauaaaugu cuuuguugca a 21

<210> SEQ ID NO 231
<211> LENGTH: 19
<212> TYPE: RNA
<213> ORGANISM: Artificial Sequence
<220> FEATURE:
<223> OTHER INFORMATION: Sense sequence for siFXId1-M2SP1

<400> SEQUENCE: 231
gcaacaaaga cauuuaugu 19

<210> SEQ ID NO 232
<211> LENGTH: 21
<212> TYPE: RNA
<213> ORGANISM: Artificial Sequence
<220> FEATURE:
<223> OTHER INFORMATION: Antisense sequence for siFXId1-M2SP1

<400> SEQUENCE: 232
acauaaaugu cuuuguugca a 21

<210> SEQ ID NO 233
<211> LENGTH: 19
<212> TYPE: RNA
<213> ORGANISM: Artificial Sequence
<220> FEATURE:
<223> OTHER INFORMATION: Sense sequence for siFXId1-M3SP1

<400> SEQUENCE: 233
gcaacaaaga cauuuaugu 19

<210> SEQ ID NO 234
<211> LENGTH: 21
<212> TYPE: RNA
<213> ORGANISM: Artificial Sequence
<220> FEATURE:
<223> OTHER INFORMATION: Antisense sequence for siFXId1-M3SP1

<400> SEQUENCE: 234
acauaaaugu cuuuguugca a 21

<210> SEQ ID NO 235
<211> LENGTH: 21
<212> TYPE: RNA
<213> ORGANISM: Artificial Sequence
<220> FEATURE:
<223> OTHER INFORMATION: Sense sequence for siFXId2-M1SP1

<400> SEQUENCE: 235
uugcaacaaa gacauuuaug u 21

<210> SEQ ID NO 236
<211> LENGTH: 23
<212> TYPE: RNA
<213> ORGANISM: Artificial Sequence
<220> FEATURE:
<223> OTHER INFORMATION: Antisense sequence for siFXId2-M1SP1

<400> SEQUENCE: 236
acauaaaugu cuuuguugca agc 23

<210> SEQ ID NO 237
<211> LENGTH: 21
<212> TYPE: RNA
<213> ORGANISM: Artificial Sequence
<220> FEATURE:
<223> OTHER INFORMATION: Sense sequence for siFXId2-M2SP1

<400> SEQUENCE: 237
uugcaacaaa gacauuuaug u 21

<210> SEQ ID NO 238
<211> LENGTH: 23
<212> TYPE: RNA
<213> ORGANISM: Artificial Sequence
<220> FEATURE:
<223> OTHER INFORMATION: Antisense sequence for siFXId2-M2SP1

<400> SEQUENCE: 238
acauaaaugu cuuuguugca agc 23

<210> SEQ ID NO 239
<211> LENGTH: 21
<212> TYPE: RNA
<213> ORGANISM: Artificial Sequence
<220> FEATURE:
<223> OTHER INFORMATION: Sense sequence for siFXId2-M3SP1

<400> SEQUENCE: 239
uugcaacaaa gacauuuaug u 21

<210> SEQ ID NO 240
<211> LENGTH: 23
<212> TYPE: RNA
<213> ORGANISM: Artificial Sequence
<220> FEATURE:
<223> OTHER INFORMATION: Antisense sequence for siFXId2-M3SP1

<400> SEQUENCE: 240
acauaaaugu cuuuguugca agc 23

<210> SEQ ID NO 241
<211> LENGTH: 19
<212> TYPE: RNA
<213> ORGANISM: Artificial Sequence
<220> FEATURE:
<223> OTHER INFORMATION: Sense sequence for the fifth siRNA
<220> FEATURE:
<221> NAME/KEY: misc-feature
<222> LOCATION: (19)..(19)
<223> OTHER INFORMATION: n is Z17, Z17 is U

<400> SEQUENCE: 241
gaaucucaaa gaaaucuun 19

<210> SEQ ID NO 242
<211> LENGTH: 19
<212> TYPE: RNA
<213> ORGANISM: Artificial Sequence
<220> FEATURE:
<223> OTHER INFORMATION: Antisense sequence for the fifth siRNA
<220> FEATURE:
<221> NAME/KEY: misc-feature
<222> LOCATION: (1)..(1)
<223> OTHER INFORMATION: n is Z18, Z18 is A

<400> SEQUENCE: 242
naagauuucu uugagauuc 19

<210> SEQ ID NO 243
<211> LENGTH: 19
<212> TYPE: RNA
<213> ORGANISM: Artificial Sequence
<220> FEATURE:
<223> OTHER INFORMATION: Sense sequence for the fifth siRNA
<220> FEATURE:
<221> NAME/KEY: misc-feature
<222> LOCATION: (19)..(19)
<223> OTHER INFORMATION: n is Z19,Z19 is A, U, G or C

<400> SEQUENCE: 243
gaaucucaaa gaaaucuun 19

<210> SEQ ID NO 244
<211> LENGTH: 19
<212> TYPE: RNA
<213> ORGANISM: Artificial Sequence
<220> FEATURE:
<223> OTHER INFORMATION: Antisense sequence for the fifth siRNA
<220> FEATURE:
<221> NAME/KEY: misc-feature
<222> LOCATION: (1)..(1)
<223> OTHER INFORMATION: n is Z20, Z20 is a nucleotide complementary to
Z19, Z19 is selected from A, U, G or C

<400> SEQUENCE: 244
naagauuucu uugagauuc 19

<210> SEQ ID NO 245
<211> LENGTH: 19
<212> TYPE: RNA
<213> ORGANISM: Artificial Sequence
<220> FEATURE:
<223> OTHER INFORMATION: Sense sequence for the fifth siRNA
<220> FEATURE:
<221> NAME/KEY: misc-feature
<222> LOCATION: (19)..(19)
<223> OTHER INFORMATION: n is Z19,Z19 is A, U, G or C

<400> SEQUENCE: 245
gaaucucaaa gaaaucuun 19

<210> SEQ ID NO 246
<211> LENGTH: 21
<212> TYPE: RNA
<213> ORGANISM: Artificial Sequence
<220> FEATURE:
<223> OTHER INFORMATION: Antisense sequence for the fifth siRNA
<220> FEATURE:
<221> NAME/KEY: misc-feature
<222> LOCATION: (1)..(1)
<223> OTHER INFORMATION: n is Z20, Z20 is a nucleotide complementary to
Z19, Z19 is selected from A, U, G or C

<400> SEQUENCE: 246
naagauuucu uugagauucu u 21

<210> SEQ ID NO 247
<211> LENGTH: 21
<212> TYPE: RNA
<213> ORGANISM: Artificial Sequence
<220> FEATURE:
<223> OTHER INFORMATION: Sense sequence for the fifth siRNA
<220> FEATURE:
<221> NAME/KEY: misc-feature
<222> LOCATION: (21)..(21)
<223> OTHER INFORMATION: n is Z19,Z19 is A, U, G or C

<400> SEQUENCE: 247
aagaaucuca aagaaaucuu n 21

<210> SEQ ID NO 248
<211> LENGTH: 23
<212> TYPE: RNA
<213> ORGANISM: Artificial Sequence
<220> FEATURE:
<223> OTHER INFORMATION: Antisense sequence for the fifth siRNA
<220> FEATURE:
<221> NAME/KEY: misc-feature
<222> LOCATION: (1)..(1)
<223> OTHER INFORMATION: n is Z20, Z20 is a nucleotide complementary to Z19, Z19 is selected from A, U, G or C

<400> SEQUENCE: 248
naagauuucu uugagauucu uug 23

<210> SEQ ID NO 249
<211> LENGTH: 19
<212> TYPE: RNA
<213> ORGANISM: Artificial Sequence
<220> FEATURE:
<223> OTHER INFORMATION: Sense sequence for siFXIe1

<400> SEQUENCE: 249
gaaucucaaa gaaaucuuu 19

<210> SEQ ID NO 250
<211> LENGTH: 21
<212> TYPE: RNA
<213> ORGANISM: Artificial Sequence
<220> FEATURE:
<223> OTHER INFORMATION: Antisense sequence for siFXIe1

<400> SEQUENCE: 250
aaagauuucu uugagauucu u 21

<210> SEQ ID NO 251
<211> LENGTH: 21
<212> TYPE: RNA
<213> ORGANISM: Artificial Sequence
<220> FEATURE:
<223> OTHER INFORMATION: Sense sequence for siFXIe2

<400> SEQUENCE: 251
aagaaucuca aagaaaucuu u 21

<210> SEQ ID NO 252
<211> LENGTH: 23
<212> TYPE: RNA
<213> ORGANISM: Artificial Sequence
<220> FEATURE:
<223> OTHER INFORMATION: Antisense sequence for siFXIe2

<400> SEQUENCE: 252
aaagauuucu uugagauucu uug 23

<210> SEQ ID NO 253
<211> LENGTH: 19
<212> TYPE: RNA
<213> ORGANISM: Artificial Sequence
<220> FEATURE:
<223> OTHER INFORMATION: Sense sequence for siFXIe1-M1

<400> SEQUENCE: 253

```
gaaucucaaa gaaaucuuu                                              19


<210> SEQ ID NO 254
<211> LENGTH: 21
<212> TYPE: RNA
<213> ORGANISM: Artificial Sequence
<220> FEATURE:
<223> OTHER INFORMATION: Antisense sequence for siFXIe1-M1

<400> SEQUENCE: 254

aaagauuucu uugagauucu u                                           21


<210> SEQ ID NO 255
<211> LENGTH: 19
<212> TYPE: RNA
<213> ORGANISM: Artificial Sequence
<220> FEATURE:
<223> OTHER INFORMATION: Sense sequence for siFXIe1-M2

<400> SEQUENCE: 255

gaaucucaaa gaaaucuuu                                              19


<210> SEQ ID NO 256
<211> LENGTH: 21
<212> TYPE: RNA
<213> ORGANISM: Artificial Sequence
<220> FEATURE:
<223> OTHER INFORMATION: Antisense sequence for siFXIe1-M2

<400> SEQUENCE: 256

aaagauuucu uugagauucu u                                           21


<210> SEQ ID NO 257
<211> LENGTH: 19
<212> TYPE: RNA
<213> ORGANISM: Artificial Sequence
<220> FEATURE:
<223> OTHER INFORMATION: Sense sequence for siFXIe1-M3

<400> SEQUENCE: 257

gaaucucaaa gaaaucuuu                                              19


<210> SEQ ID NO 258
<211> LENGTH: 21
<212> TYPE: RNA
<213> ORGANISM: Artificial Sequence
<220> FEATURE:
<223> OTHER INFORMATION: Antisense sequence for siFXIe1-M3

<400> SEQUENCE: 258

aaagauuucu uugagauucu u                                           21


<210> SEQ ID NO 259
<211> LENGTH: 21
<212> TYPE: RNA
<213> ORGANISM: Artificial Sequence
<220> FEATURE:
<223> OTHER INFORMATION: Sense sequence for siFXIe2-M1

<400> SEQUENCE: 259

aagaaucuca aagaaaucuu u                                           21


<210> SEQ ID NO 260
<211> LENGTH: 23
<212> TYPE: RNA
```

<213> ORGANISM: Artificial Sequence
<220> FEATURE:
<223> OTHER INFORMATION: Antisense sequence for siFXIe2-M1

<400> SEQUENCE: 260
aaagauuucu uugagauucu uug 23

<210> SEQ ID NO 261
<211> LENGTH: 21
<212> TYPE: RNA
<213> ORGANISM: Artificial Sequence
<220> FEATURE:
<223> OTHER INFORMATION: Sense sequence for siFXIe2-M2

<400> SEQUENCE: 261
aagaaucuca aagaaaucuu u 21

<210> SEQ ID NO 262
<211> LENGTH: 23
<212> TYPE: RNA
<213> ORGANISM: Artificial Sequence
<220> FEATURE:
<223> OTHER INFORMATION: Antisense sequence for siFXIe2-M2

<400> SEQUENCE: 262
aaagauuucu uugagauucu uug 23

<210> SEQ ID NO 263
<211> LENGTH: 21
<212> TYPE: RNA
<213> ORGANISM: Artificial Sequence
<220> FEATURE:
<223> OTHER INFORMATION: Sense sequence for siFXIe2-M3

<400> SEQUENCE: 263
aagaaucuca aagaaaucuu u 21

<210> SEQ ID NO 264
<211> LENGTH: 23
<212> TYPE: RNA
<213> ORGANISM: Artificial Sequence
<220> FEATURE:
<223> OTHER INFORMATION: Antisense sequence for siFXIe2-M3

<400> SEQUENCE: 264
aaagauuucu uugagauucu uug 23

<210> SEQ ID NO 265
<211> LENGTH: 19
<212> TYPE: RNA
<213> ORGANISM: Artificial Sequence
<220> FEATURE:
<223> OTHER INFORMATION: Sense sequence for siFXIe1-M1S

<400> SEQUENCE: 265
gaaucucaaa gaaaucuuu 19

<210> SEQ ID NO 266
<211> LENGTH: 21
<212> TYPE: RNA
<213> ORGANISM: Artificial Sequence
<220> FEATURE:
<223> OTHER INFORMATION: Antisense sequence for siFXIe1-M1S

<400> SEQUENCE: 266
aaagauuucu uugagauucu u 21

<210> SEQ ID NO 267
<211> LENGTH: 19
<212> TYPE: RNA
<213> ORGANISM: Artificial Sequence
<220> FEATURE:
<223> OTHER INFORMATION: Sense sequence for siFXIe1-M2S

<400> SEQUENCE: 267
gaaucucaaa gaaaucuuu 19

<210> SEQ ID NO 268
<211> LENGTH: 21
<212> TYPE: RNA
<213> ORGANISM: Artificial Sequence
<220> FEATURE:
<223> OTHER INFORMATION: Antisense sequence for siFXIe1-M2S

<400> SEQUENCE: 268
aaagauuucu uugagauucu u 21

<210> SEQ ID NO 269
<211> LENGTH: 19
<212> TYPE: RNA
<213> ORGANISM: Artificial Sequence
<220> FEATURE:
<223> OTHER INFORMATION: Sense sequence for siFXIe1-M3S

<400> SEQUENCE: 269
gaaucucaaa gaaaucuuu 19

<210> SEQ ID NO 270
<211> LENGTH: 21
<212> TYPE: RNA
<213> ORGANISM: Artificial Sequence
<220> FEATURE:
<223> OTHER INFORMATION: Antisense sequence for siFXIe1-M3S

<400> SEQUENCE: 270
aaagauuucu uugagauucu u 21

<210> SEQ ID NO 271
<211> LENGTH: 21
<212> TYPE: RNA
<213> ORGANISM: Artificial Sequence
<220> FEATURE:
<223> OTHER INFORMATION: Sense sequence for siFXIe1-M3S

<400> SEQUENCE: 271
aagaaucuca aagaaaucuu u 21

<210> SEQ ID NO 272
<211> LENGTH: 23
<212> TYPE: RNA
<213> ORGANISM: Artificial Sequence
<220> FEATURE:
<223> OTHER INFORMATION: Antisense sequence for siFXIe1-M3S

<400> SEQUENCE: 272
aaagauuucu uugagauucu uug 23

<210> SEQ ID NO 273
<211> LENGTH: 21
<212> TYPE: RNA
<213> ORGANISM: Artificial Sequence
<220> FEATURE:

<223> OTHER INFORMATION: Sense sequence for siFXIe2-M2S

<400> SEQUENCE: 273
aagaaucuca aagaaaucuu u 21

<210> SEQ ID NO 274
<211> LENGTH: 23
<212> TYPE: RNA
<213> ORGANISM: Artificial Sequence
<220> FEATURE:
<223> OTHER INFORMATION: Antisense sequence for siFXIe2-M2S

<400> SEQUENCE: 274
aaagauuucu uugagauucu uug 23

<210> SEQ ID NO 275
<211> LENGTH: 21
<212> TYPE: RNA
<213> ORGANISM: Artificial Sequence
<220> FEATURE:
<223> OTHER INFORMATION: Sense sequence for siFXIe2-M3S

<400> SEQUENCE: 275
aagaaucuca aagaaaucuu u 21

<210> SEQ ID NO 276
<211> LENGTH: 23
<212> TYPE: RNA
<213> ORGANISM: Artificial Sequence
<220> FEATURE:
<223> OTHER INFORMATION: Antisense sequence for siFXIe2-M3S

<400> SEQUENCE: 276
aaagauuucu uugagauucu uug 23

<210> SEQ ID NO 277
<211> LENGTH: 19
<212> TYPE: RNA
<213> ORGANISM: Artificial Sequence
<220> FEATURE:
<223> OTHER INFORMATION: Sense sequence for siFXIe1-M1P1

<400> SEQUENCE: 277
gaaucucaaa gaaaucuuu 19

<210> SEQ ID NO 278
<211> LENGTH: 21
<212> TYPE: RNA
<213> ORGANISM: Artificial Sequence
<220> FEATURE:
<223> OTHER INFORMATION: Antisense sequence for siFXIe1-M1P1

<400> SEQUENCE: 278
aaagauuucu uugagauucu u 21

<210> SEQ ID NO 279
<211> LENGTH: 19
<212> TYPE: RNA
<213> ORGANISM: Artificial Sequence
<220> FEATURE:
<223> OTHER INFORMATION: Sense sequence for siFXIe1-M2P1

<400> SEQUENCE: 279
gaaucucaaa gaaaucuuu 19

<210> SEQ ID NO 280
<211> LENGTH: 21
<212> TYPE: RNA
<213> ORGANISM: Artificial Sequence
<220> FEATURE:
<223> OTHER INFORMATION: Antisense sequence for siFXIe1-M2P1

<400> SEQUENCE: 280
aaagauuucu uugagauucu u 21

<210> SEQ ID NO 281
<211> LENGTH: 19
<212> TYPE: RNA
<213> ORGANISM: Artificial Sequence
<220> FEATURE:
<223> OTHER INFORMATION: Sense sequence for siFXIe1-M3P1

<400> SEQUENCE: 281
gaaucucaaa gaaaucuuu 19

<210> SEQ ID NO 282
<211> LENGTH: 21
<212> TYPE: RNA
<213> ORGANISM: Artificial Sequence
<220> FEATURE:
<223> OTHER INFORMATION: Antisense sequence for siFXIe1-M3P1

<400> SEQUENCE: 282
aaagauuucu uugagauucu u 21

<210> SEQ ID NO 283
<211> LENGTH: 21
<212> TYPE: RNA
<213> ORGANISM: Artificial Sequence
<220> FEATURE:
<223> OTHER INFORMATION: Sense sequence for siFXIe2-M1P1

<400> SEQUENCE: 283
aagaaucuca aagaaaucuu u 21

<210> SEQ ID NO 284
<211> LENGTH: 23
<212> TYPE: RNA
<213> ORGANISM: Artificial Sequence
<220> FEATURE:
<223> OTHER INFORMATION: Antisense sequence for siFXIe2-M1P1

<400> SEQUENCE: 284
aaagauuucu uugagauucu uug 23

<210> SEQ ID NO 285
<211> LENGTH: 21
<212> TYPE: RNA
<213> ORGANISM: Artificial Sequence
<220> FEATURE:
<223> OTHER INFORMATION: Sense sequence for siFXIe2-M2P1

<400> SEQUENCE: 285
aagaaucuca aagaaaucuu u 21

<210> SEQ ID NO 286
<211> LENGTH: 23
<212> TYPE: RNA
<213> ORGANISM: Artificial Sequence
<220> FEATURE:
<223> OTHER INFORMATION: Antisense sequence for siFXIe2-M2P1

<400> SEQUENCE: 286
aaagauuucu uugagauucu uug 23

<210> SEQ ID NO 287
<211> LENGTH: 21
<212> TYPE: RNA
<213> ORGANISM: Artificial Sequence
<220> FEATURE:
<223> OTHER INFORMATION: Sense sequence for siFXIe2-M3P1

<400> SEQUENCE: 287
aagaaucuca aagaaaucuu u 21

<210> SEQ ID NO 288
<211> LENGTH: 23
<212> TYPE: RNA
<213> ORGANISM: Artificial Sequence
<220> FEATURE:
<223> OTHER INFORMATION: Antisense sequence for siFXIe2-M3P1

<400> SEQUENCE: 288
aaagauuucu uugagauucu uug 23

<210> SEQ ID NO 289
<211> LENGTH: 19
<212> TYPE: RNA
<213> ORGANISM: Artificial Sequence
<220> FEATURE:
<223> OTHER INFORMATION: Sense sequence for siFXIe1-M1SP1

<400> SEQUENCE: 289
gaaucucaaa gaaaucuuu 19

<210> SEQ ID NO 290
<211> LENGTH: 21
<212> TYPE: RNA
<213> ORGANISM: Artificial Sequence
<220> FEATURE:
<223> OTHER INFORMATION: Antisense sequence for siFXIe1-M1SP1

<400> SEQUENCE: 290
aaagauuucu uugagauucu u 21

<210> SEQ ID NO 291
<211> LENGTH: 19
<212> TYPE: RNA
<213> ORGANISM: Artificial Sequence
<220> FEATURE:
<223> OTHER INFORMATION: Sense sequence for siFXIe1-M2SP1

<400> SEQUENCE: 291
gaaucucaaa gaaaucuuu 19

<210> SEQ ID NO 292
<211> LENGTH: 21
<212> TYPE: RNA
<213> ORGANISM: Artificial Sequence
<220> FEATURE:
<223> OTHER INFORMATION: Antisense sequence for siFXIe1-M2SP1

<400> SEQUENCE: 292
aaagauuucu uugagauucu u 21

<210> SEQ ID NO 293
<211> LENGTH: 19

<212> TYPE: RNA
<213> ORGANISM: Artificial Sequence
<220> FEATURE:
<223> OTHER INFORMATION: Sense sequence for siFXIe1-M3SP1

<400> SEQUENCE: 293
gaaucucaaa gaaaucuuu 19

<210> SEQ ID NO 294
<211> LENGTH: 21
<212> TYPE: RNA
<213> ORGANISM: Artificial Sequence
<220> FEATURE:
<223> OTHER INFORMATION: Antisense sequence for siFXIe1-M3SP1

<400> SEQUENCE: 294
aaagauuucu uugagauucu u 21

<210> SEQ ID NO 295
<211> LENGTH: 21
<212> TYPE: RNA
<213> ORGANISM: Artificial Sequence
<220> FEATURE:
<223> OTHER INFORMATION: Sense sequence for siFXIe2-M1SP1

<400> SEQUENCE: 295
aagaaucuca aagaaaucuu u 21

<210> SEQ ID NO 296
<211> LENGTH: 23
<212> TYPE: RNA
<213> ORGANISM: Artificial Sequence
<220> FEATURE:
<223> OTHER INFORMATION: Antisense sequence for siFXIe2-M1SP1

<400> SEQUENCE: 296
aaagauuucu uugagauucu uug 23

<210> SEQ ID NO 297
<211> LENGTH: 21
<212> TYPE: RNA
<213> ORGANISM: Artificial Sequence
<220> FEATURE:
<223> OTHER INFORMATION: Sense sequence for siFXIe2-M2SP1

<400> SEQUENCE: 297
aagaaucuca aagaaaucuu u 21

<210> SEQ ID NO 298
<211> LENGTH: 23
<212> TYPE: RNA
<213> ORGANISM: Artificial Sequence
<220> FEATURE:
<223> OTHER INFORMATION: Antisense sequence for siFXIe2-M2SP1

<400> SEQUENCE: 298
aaagauuucu uugagauucu uug 23

<210> SEQ ID NO 299
<211> LENGTH: 21
<212> TYPE: RNA
<213> ORGANISM: Artificial Sequence
<220> FEATURE:
<223> OTHER INFORMATION: Sense sequence for siFXIe2-M3SP1

<400> SEQUENCE: 299
aagaaucuca aagaaaucuu u 21

<210> SEQ ID NO 300
<211> LENGTH: 23
<212> TYPE: RNA
<213> ORGANISM: Artificial Sequence
<220> FEATURE:
<223> OTHER INFORMATION: Antisense sequence for siFXIe2-M3SP1

<400> SEQUENCE: 300
aaagauuucu uugagauucu uug 23

<210> SEQ ID NO 301
<211> LENGTH: 19
<212> TYPE: RNA
<213> ORGANISM: Artificial Sequence
<220> FEATURE:
<223> OTHER INFORMATION: Sense sequence for the sixth siRNA
<220> FEATURE:
<221> NAME/KEY: misc-feature
<222> LOCATION: (19)..(19)
<223> OTHER INFORMATION: n is Z21, Z21 is G

<400> SEQUENCE: 301
guacguggac uggauucun 19

<210> SEQ ID NO 302
<211> LENGTH: 19
<212> TYPE: RNA
<213> ORGANISM: Artificial Sequence
<220> FEATURE:
<223> OTHER INFORMATION: Antisense sequence for the sixth siRNA
<220> FEATURE:
<221> NAME/KEY: misc-feature
<222> LOCATION: (1)..(1)
<223> OTHER INFORMATION: n is Z22, Z22 is C

<400> SEQUENCE: 302
nagaauccag uccacguac 19

<210> SEQ ID NO 303
<211> LENGTH: 19
<212> TYPE: RNA
<213> ORGANISM: Artificial Sequence
<220> FEATURE:
<223> OTHER INFORMATION: Sense sequence for the sixth siRNA
<220> FEATURE:
<221> NAME/KEY: misc-feature
<222> LOCATION: (19)..(19)
<223> OTHER INFORMATION: n is Z23, Z23 is A, U, G or C

<400> SEQUENCE: 303
guacguggac uggauucun 19

<210> SEQ ID NO 304
<211> LENGTH: 19
<212> TYPE: RNA
<213> ORGANISM: Artificial Sequence
<220> FEATURE:
<223> OTHER INFORMATION: Antisense sequence for the sixth siRNA
<220> FEATURE:
<221> NAME/KEY: misc-feature
<222> LOCATION: (1)..(1)
<223> OTHER INFORMATION: n is Z24, Z24 is a nucleotide complementary to
Z23, Z23 is selected from A, U, G or C

<400> SEQUENCE: 304
nagaauccag uccacguac 19

<210> SEQ ID NO 305
<211> LENGTH: 19
<212> TYPE: RNA
<213> ORGANISM: Artificial Sequence
<220> FEATURE:
<223> OTHER INFORMATION: Sense sequence for the sixth siRNA
<220> FEATURE:
<221> NAME/KEY: misc-feature
<222> LOCATION: (19)..(19)
<223> OTHER INFORMATION: n is Z23, Z23 is A, U, G or C

<400> SEQUENCE: 305
guacguggac uggauucun 19

<210> SEQ ID NO 306
<211> LENGTH: 21
<212> TYPE: RNA
<213> ORGANISM: Artificial Sequence
<220> FEATURE:
<223> OTHER INFORMATION: Antisense sequence for the sixth siRNA
<220> FEATURE:
<221> NAME/KEY: misc-feature
<222> LOCATION: (1)..(1)
<223> OTHER INFORMATION: n is Z24, Z24 is a nucleotide complementary to
Z23, Z23 is selected from A, U, G or C

<400> SEQUENCE: 306
nagaauccag uccacguacu c 21

<210> SEQ ID NO 307
<211> LENGTH: 21
<212> TYPE: RNA
<213> ORGANISM: Artificial Sequence
<220> FEATURE:
<223> OTHER INFORMATION: Sense sequence for the sixth siRNA
<220> FEATURE:
<221> NAME/KEY: misc-feature
<222> LOCATION: (21)..(21)
<223> OTHER INFORMATION: n is Z23, Z23 is A, U, G or C

<400> SEQUENCE: 307
gaguacgugg acuggauucu n 21

<210> SEQ ID NO 308
<211> LENGTH: 23
<212> TYPE: RNA
<213> ORGANISM: Artificial Sequence
<220> FEATURE:
<223> OTHER INFORMATION: Antisense sequence for the sixth siRNA
<220> FEATURE:
<221> NAME/KEY: misc-feature
<222> LOCATION: (1)..(1)
<223> OTHER INFORMATION: n is Z24, Z24 is a nucleotide complementary to
Z23, Z23 is selected from A, U, G or C

<400> SEQUENCE: 308
nagaauccag uccacguacu cga 23

<210> SEQ ID NO 309
<211> LENGTH: 19
<212> TYPE: RNA
<213> ORGANISM: Artificial Sequence
<220> FEATURE:
<223> OTHER INFORMATION: Sense sequence for siFXIf1

<400> SEQUENCE: 309 guacguggacu ggauucug 19

<210> SEQ ID NO 310

```
<211> LENGTH: 21
<212> TYPE: RNA
<213> ORGANISM: Artificial Sequence
<220> FEATURE:
<223> OTHER INFORMATION: Antisense sequence for siFXIf1

<400> SEQUENCE: 310

cagaauccag uccacguacu c                                           21


<210> SEQ ID NO 311
<211> LENGTH: 21
<212> TYPE: RNA
<213> ORGANISM: Artificial Sequence
<220> FEATURE:
<223> OTHER INFORMATION: Sense sequence for siFXIf2

<400> SEQUENCE: 311

gaguacgugg acuggauucu g                                           21


<210> SEQ ID NO 312
<211> LENGTH: 23
<212> TYPE: RNA
<213> ORGANISM: Artificial Sequence
<220> FEATURE:
<223> OTHER INFORMATION: Antisense sequence for siFXIf2

<400> SEQUENCE: 312

cagaauccag uccacguacu cga                                         23


<210> SEQ ID NO 313
<211> LENGTH: 19
<212> TYPE: RNA
<213> ORGANISM: Artificial Sequence
<220> FEATURE:
<223> OTHER INFORMATION: Sense sequence for siFXIf1-M1

<400> SEQUENCE: 313

guacguggac uggauucug                                              19


<210> SEQ ID NO 314
<211> LENGTH: 21
<212> TYPE: RNA
<213> ORGANISM: Artificial Sequence
<220> FEATURE:
<223> OTHER INFORMATION: Antisense sequence for siFXIf1-M1

<400> SEQUENCE: 314

cagaauccag uccacguacu c                                           21


<210> SEQ ID NO 315
<211> LENGTH: 19
<212> TYPE: RNA
<213> ORGANISM: Artificial Sequence
<220> FEATURE:
<223> OTHER INFORMATION: Sense sequence for siFXIf1-M2

<400> SEQUENCE: 315

guacguggac uggauucug                                              19


<210> SEQ ID NO 316
<211> LENGTH: 21
<212> TYPE: RNA
<213> ORGANISM: Artificial Sequence
<220> FEATURE:
<223> OTHER INFORMATION: Antisense sequence for siFXIf1-M2

<400> SEQUENCE: 316
```

cagaauccag uccacguacu c 21

<210> SEQ ID NO 317
<211> LENGTH: 19
<212> TYPE: RNA
<213> ORGANISM: Artificial Sequence
<220> FEATURE:
<223> OTHER INFORMATION: Sense sequence for siFXIf1-M3

<400> SEQUENCE: 317
guacguggac uggauucug 19

<210> SEQ ID NO 318
<211> LENGTH: 21
<212> TYPE: RNA
<213> ORGANISM: Artificial Sequence
<220> FEATURE:
<223> OTHER INFORMATION: Antisense sequence for siFXIf1-M3

<400> SEQUENCE: 318
cagaauccag uccacguacu c 21

<210> SEQ ID NO 319
<211> LENGTH: 21
<212> TYPE: RNA
<213> ORGANISM: Artificial Sequence
<220> FEATURE:
<223> OTHER INFORMATION: Sense sequence for siFXIf2-M1

<400> SEQUENCE: 319
gaguacgugg acuggauucu g 21

<210> SEQ ID NO 320
<211> LENGTH: 23
<212> TYPE: RNA
<213> ORGANISM: Artificial Sequence
<220> FEATURE:
<223> OTHER INFORMATION: Antisense sequence for siFXIf2-M1

<400> SEQUENCE: 320
cagaauccag uccacguacu cga 23

<210> SEQ ID NO 321
<211> LENGTH: 21
<212> TYPE: RNA
<213> ORGANISM: Artificial Sequence
<220> FEATURE:
<223> OTHER INFORMATION: Sense sequence for siFXIf2-M2

<400> SEQUENCE: 321
gaguacgugg acuggauucu g 21

<210> SEQ ID NO 322
<211> LENGTH: 23
<212> TYPE: RNA
<213> ORGANISM: Artificial Sequence
<220> FEATURE:
<223> OTHER INFORMATION: Antisense sequence for siFXIf2-M2

<400> SEQUENCE: 322
cagaauccag uccacguacu cga 23

<210> SEQ ID NO 323
<211> LENGTH: 21
<212> TYPE: RNA

<213> ORGANISM: Artificial Sequence
<220> FEATURE:
<223> OTHER INFORMATION: Sense sequence for siFXIf2-M3

<400> SEQUENCE: 323
gaguacgugg acuggauucu g 21

<210> SEQ ID NO 324
<211> LENGTH: 23
<212> TYPE: RNA
<213> ORGANISM: Artificial Sequence
<220> FEATURE:
<223> OTHER INFORMATION: Antisense sequence for siFXIf2-M3

<400> SEQUENCE: 324
cagaauccag uccacguacu cga 23

<210> SEQ ID NO 325
<211> LENGTH: 19
<212> TYPE: RNA
<213> ORGANISM: Artificial Sequence
<220> FEATURE:
<223> OTHER INFORMATION: Sense sequence for siFXIf1-M1S

<400> SEQUENCE: 325
guacguggac uggauucug 19

<210> SEQ ID NO 326
<211> LENGTH: 21
<212> TYPE: RNA
<213> ORGANISM: Artificial Sequence
<220> FEATURE:
<223> OTHER INFORMATION: Antisense sequence for siFXIf1-M1S

<400> SEQUENCE: 326
cagaauccag uccacguacu c 21

<210> SEQ ID NO 327
<211> LENGTH: 19
<212> TYPE: RNA
<213> ORGANISM: Artificial Sequence
<220> FEATURE:
<223> OTHER INFORMATION: Sense sequence for siFXIf1-M2S

<400> SEQUENCE: 327
guacguggac uggauucug 19

<210> SEQ ID NO 328
<211> LENGTH: 21
<212> TYPE: RNA
<213> ORGANISM: Artificial Sequence
<220> FEATURE:
<223> OTHER INFORMATION: Antisense sequence for siFXIf1-M2S

<400> SEQUENCE: 328
cagaauccag uccacguacu c 21

<210> SEQ ID NO 329
<211> LENGTH: 19
<212> TYPE: RNA
<213> ORGANISM: Artificial Sequence
<220> FEATURE:
<223> OTHER INFORMATION: Sense sequence for siFXIf1-M3S

<400> SEQUENCE: 329
guacguggac uggauucug 19

<210> SEQ ID NO 330
<211> LENGTH: 21
<212> TYPE: RNA
<213> ORGANISM: Artificial Sequence
<220> FEATURE:
<223> OTHER INFORMATION: Antisense sequence for siFXIf1-M3S

<400> SEQUENCE: 330
cagaauccag uccacguacu c 21

<210> SEQ ID NO 331
<211> LENGTH: 21
<212> TYPE: RNA
<213> ORGANISM: Artificial Sequence
<220> FEATURE:
<223> OTHER INFORMATION: Sense sequence for siFXIf2-M1S

<400> SEQUENCE: 331
gaguacgugg acuggauucu g 21

<210> SEQ ID NO 332
<211> LENGTH: 23
<212> TYPE: RNA
<213> ORGANISM: Artificial Sequence
<220> FEATURE:
<223> OTHER INFORMATION: Antisense sequence for siFXIf2-M1S

<400> SEQUENCE: 332
cagaauccag uccacguacu cga 23

<210> SEQ ID NO 333
<211> LENGTH: 21
<212> TYPE: RNA
<213> ORGANISM: Artificial Sequence
<220> FEATURE:
<223> OTHER INFORMATION: Sense sequence for siFXIf2-M2S

<400> SEQUENCE: 333
gaguacgugg acuggauucu g 21

<210> SEQ ID NO 334
<211> LENGTH: 23
<212> TYPE: RNA
<213> ORGANISM: Artificial Sequence
<220> FEATURE:
<223> OTHER INFORMATION: Antisense sequence for siFXIf2-M2S

<400> SEQUENCE: 334
cagaauccag uccacguacu cga 23

<210> SEQ ID NO 335
<211> LENGTH: 21
<212> TYPE: RNA
<213> ORGANISM: Artificial Sequence
<220> FEATURE:
<223> OTHER INFORMATION: Sense sequence for siFXIf2-M3S

<400> SEQUENCE: 335
gaguacgugg acuggauucu g 21

<210> SEQ ID NO 336
<211> LENGTH: 23
<212> TYPE: RNA
<213> ORGANISM: Artificial Sequence
<220> FEATURE:

<223> OTHER INFORMATION: Antisense sequence for siFXIf2-M3S

<400> SEQUENCE: 336
cagaauccag uccacguacu cga 23

<210> SEQ ID NO 337
<211> LENGTH: 19
<212> TYPE: RNA
<213> ORGANISM: Artificial Sequence
<220> FEATURE:
<223> OTHER INFORMATION: Sense sequence for siFXIf1-M1P1

<400> SEQUENCE: 337
guacguggac uggauucug 19

<210> SEQ ID NO 338
<211> LENGTH: 21
<212> TYPE: RNA
<213> ORGANISM: Artificial Sequence
<220> FEATURE:
<223> OTHER INFORMATION: Antisense sequence for siFXIf1-M1P1

<400> SEQUENCE: 338
cagaauccag uccacguacu c 21

<210> SEQ ID NO 339
<211> LENGTH: 19
<212> TYPE: RNA
<213> ORGANISM: Artificial Sequence
<220> FEATURE:
<223> OTHER INFORMATION: Sense sequence for siFXIf1-M2P1

<400> SEQUENCE: 339
guacguggac uggauucug 19

<210> SEQ ID NO 340
<211> LENGTH: 21
<212> TYPE: RNA
<213> ORGANISM: Artificial Sequence
<220> FEATURE:
<223> OTHER INFORMATION: Antisense sequence for siFXIf1-M2P1

<400> SEQUENCE: 340
cagaauccag uccacguacu c 21

<210> SEQ ID NO 341
<211> LENGTH: 19
<212> TYPE: RNA
<213> ORGANISM: Artificial Sequence
<220> FEATURE:
<223> OTHER INFORMATION: Sense sequence for siFXIf1-M3P1

<400> SEQUENCE: 341
guacguggac uggauucug 19

<210> SEQ ID NO 342
<211> LENGTH: 21
<212> TYPE: RNA
<213> ORGANISM: Artificial Sequence
<220> FEATURE:
<223> OTHER INFORMATION: Antisense sequence for siFXIf1-M3P1

<400> SEQUENCE: 342
cagaauccag uccacguacu c 21

<210> SEQ ID NO 343
<211> LENGTH: 21
<212> TYPE: RNA
<213> ORGANISM: Artificial Sequence
<220> FEATURE:
<223> OTHER INFORMATION: Sense sequence for siFXIf2-M1P1

<400> SEQUENCE: 343
gaguacgugg acuggauucu g 21

<210> SEQ ID NO 344
<211> LENGTH: 23
<212> TYPE: RNA
<213> ORGANISM: Artificial Sequence
<220> FEATURE:
<223> OTHER INFORMATION: Antisense sequence for siFXIf2-M1P1

<400> SEQUENCE: 344
cagaauccag uccacguacu cga 23

<210> SEQ ID NO 345
<211> LENGTH: 21
<212> TYPE: RNA
<213> ORGANISM: Artificial Sequence
<220> FEATURE:
<223> OTHER INFORMATION: Sense sequence for siFXIf2-M2P1

<400> SEQUENCE: 345
gaguacgugg acuggauucu g 21

<210> SEQ ID NO 346
<211> LENGTH: 23
<212> TYPE: RNA
<213> ORGANISM: Artificial Sequence
<220> FEATURE:
<223> OTHER INFORMATION: Antisense sequence for siFXIf2-M2P1

<400> SEQUENCE: 346
cagaauccag uccacguacu cga 23

<210> SEQ ID NO 347
<211> LENGTH: 21
<212> TYPE: RNA
<213> ORGANISM: Artificial Sequence
<220> FEATURE:
<223> OTHER INFORMATION: Sense sequence for siFXIf2-M3P1

<400> SEQUENCE: 347
gaguacgugg acuggauucu g 21

<210> SEQ ID NO 348
<211> LENGTH: 23
<212> TYPE: RNA
<213> ORGANISM: Artificial Sequence
<220> FEATURE:
<223> OTHER INFORMATION: Antisense sequence for siFXIf2-M3P1

<400> SEQUENCE: 348
cagaauccag uccacguacu cga 23

<210> SEQ ID NO 349
<211> LENGTH: 19
<212> TYPE: RNA
<213> ORGANISM: Artificial Sequence
<220> FEATURE:
<223> OTHER INFORMATION: Sense sequence for siFXIf1-M1SP1

<400> SEQUENCE: 349
guacguggac uggauucug 19

<210> SEQ ID NO 350
<211> LENGTH: 21
<212> TYPE: RNA
<213> ORGANISM: Artificial Sequence
<220> FEATURE:
<223> OTHER INFORMATION: Antisense sequence for siFXIf1-M1SP1

<400> SEQUENCE: 350
cagaauccag uccacguacu c 21

<210> SEQ ID NO 351
<211> LENGTH: 19
<212> TYPE: RNA
<213> ORGANISM: Artificial Sequence
<220> FEATURE:
<223> OTHER INFORMATION: Sense sequence for siFXIf1-M2SP1

<400> SEQUENCE: 351
guacguggac uggauucug 19

<210> SEQ ID NO 352
<211> LENGTH: 21
<212> TYPE: RNA
<213> ORGANISM: Artificial Sequence
<220> FEATURE:
<223> OTHER INFORMATION: Antisense sequence for siFXIf1-M2SP1

<400> SEQUENCE: 352
cagaauccag uccacguacu c 21

<210> SEQ ID NO 353
<211> LENGTH: 19
<212> TYPE: RNA
<213> ORGANISM: Artificial Sequence
<220> FEATURE:
<223> OTHER INFORMATION: Sense sequence for siFXIf1-M3SP1

<400> SEQUENCE: 353
guacguggac uggauucug 19

<210> SEQ ID NO 354
<211> LENGTH: 21
<212> TYPE: RNA
<213> ORGANISM: Artificial Sequence
<220> FEATURE:
<223> OTHER INFORMATION: Antisense sequence for siFXIf1-M3SP1

<400> SEQUENCE: 354
cagaauccag uccacguacu c 21

<210> SEQ ID NO 355
<211> LENGTH: 21
<212> TYPE: RNA
<213> ORGANISM: Artificial Sequence
<220> FEATURE:
<223> OTHER INFORMATION: Sense sequence for siFXIf2-M1SP1

<400> SEQUENCE: 355
gaguacgugg acuggauucu g 21

<210> SEQ ID NO 356
<211> LENGTH: 23

<212> TYPE: RNA
<213> ORGANISM: Artificial Sequence
<220> FEATURE:
<223> OTHER INFORMATION: Antisense sequence for siFXIf2-M1SP1

<400> SEQUENCE: 356
cagaauccag uccacguacu cga 23

<210> SEQ ID NO 357
<211> LENGTH: 21
<212> TYPE: RNA
<213> ORGANISM: Artificial Sequence
<220> FEATURE:
<223> OTHER INFORMATION: Sense sequence for siFXIf2-M2SP1

<400> SEQUENCE: 357
gaguacgugg acuggauucu g 21

<210> SEQ ID NO 358
<211> LENGTH: 23
<212> TYPE: RNA
<213> ORGANISM: Artificial Sequence
<220> FEATURE:
<223> OTHER INFORMATION: Antisense sequence for siFXIf2-M2SP1

<400> SEQUENCE: 358
cagaauccag uccacguacu cga 23

<210> SEQ ID NO 359
<211> LENGTH: 21
<212> TYPE: RNA
<213> ORGANISM: Artificial Sequence
<220> FEATURE:
<223> OTHER INFORMATION: Sense sequence for siFXIf2-M3SP1

<400> SEQUENCE: 359
gaguacgugg acuggauucu g 21

<210> SEQ ID NO 360
<211> LENGTH: 23
<212> TYPE: RNA
<213> ORGANISM: Artificial Sequence
<220> FEATURE:
<223> OTHER INFORMATION: Antisense sequence for siFXIf2-M3SP1

<400> SEQUENCE: 360
cagaauccag uccacguacu cga 23

<210> SEQ ID NO 361
<211> LENGTH: 19
<212> TYPE: RNA
<213> ORGANISM: Artificial Sequence
<220> FEATURE:
<223> OTHER INFORMATION: Sense sequence for the seventh siRNA
<220> FEATURE:
<221> NAME/KEY: misc-feature
<222> LOCATION: (19)..(19)
<223> OTHER INFORMATION: n is Z25, Z25 is A

<400> SEQUENCE: 361
auuucugggu auucuuucn 19

<210> SEQ ID NO 362
<211> LENGTH: 19
<212> TYPE: RNA
<213> ORGANISM: Artificial Sequence
<220> FEATURE:

<223> OTHER INFORMATION: Antisense sequence for the seventh siRNA
<220> FEATURE:
<221> NAME/KEY: misc-feature
<222> LOCATION: (1)..(1)
<223> OTHER INFORMATION: n is Z26, Z26 is U

<400> SEQUENCE: 362
ngaaagaaua cccagaaau 19

<210> SEQ ID NO 363
<211> LENGTH: 19
<212> TYPE: RNA
<213> ORGANISM: Artificial Sequence
<220> FEATURE:
<223> OTHER INFORMATION: Sense sequence for the seventh siRNA
<220> FEATURE:
<221> NAME/KEY: misc-feature
<222> LOCATION: (19)..(19)
<223> OTHER INFORMATION: n is Z27,Z27 is A, U, G or C

<400> SEQUENCE: 363
auuucugggu auucuuucn 19

<210> SEQ ID NO 364
<211> LENGTH: 19
<212> TYPE: RNA
<213> ORGANISM: Artificial Sequence
<220> FEATURE:
<223> OTHER INFORMATION: Antisense sequence for the seventh siRNA
<220> FEATURE:
<221> NAME/KEY: misc-feature
<222> LOCATION: (1)..(1)
<223> OTHER INFORMATION: n is Z28, Z28 is a nucleotide complementary to Z27, Z27 is selected from A, U, G or C

<400> SEQUENCE: 364
ngaaagaaua cccagaaau 19

<210> SEQ ID NO 365
<211> LENGTH: 19
<212> TYPE: RNA
<213> ORGANISM: Artificial Sequence
<220> FEATURE:
<223> OTHER INFORMATION: Sense sequence for the seventh siRNA
<220> FEATURE:
<221> NAME/KEY: misc-feature
<222> LOCATION: (19)..(19)
<223> OTHER INFORMATION: n is Z27,Z27 is A, U, G or C

<400> SEQUENCE: 365
auuucugggu auucuuucn 19

<210> SEQ ID NO 366
<211> LENGTH: 21
<212> TYPE: RNA
<213> ORGANISM: Artificial Sequence
<220> FEATURE:
<223> OTHER INFORMATION: Antisense sequence for the seventh siRNA
<220> FEATURE:
<221> NAME/KEY: misc-feature
<222> LOCATION: (1)..(1)
<223> OTHER INFORMATION: n is Z28, Z28 is a nucleotide complementary to Z27, Z27 is selected from A, U, G or C

<400> SEQUENCE: 366
ngaaagaaua cccagaaauc g 21

<210> SEQ ID NO 367
<211> LENGTH: 21

<212> TYPE: RNA
<213> ORGANISM: Artificial Sequence
<220> FEATURE:
<223> OTHER INFORMATION: Sense sequence for the seventh siRNA
<220> FEATURE:
<221> NAME/KEY: misc-feature
<222> LOCATION: (21)..(21)
<223> OTHER INFORMATION: n is Z27,Z27 is A, U, G or C

<400> SEQUENCE: 367
cgauuucugg guauucuuuc n 21

<210> SEQ ID NO 368
<211> LENGTH: 23
<212> TYPE: RNA
<213> ORGANISM: Artificial Sequence
<220> FEATURE:
<223> OTHER INFORMATION: Antisense sequence for the seventh siRNA
<220> FEATURE:
<221> NAME/KEY: misc-feature
<222> LOCATION: (1)..(1)
<223> OTHER INFORMATION: n is Z28, Z28 is a nucleotide complementary to Z27, Z27 is selected from A, U, G or C

<400> SEQUENCE: 368
ngaaagaaua cccagaaauc gcu 23

<210> SEQ ID NO 369
<211> LENGTH: 19
<212> TYPE: RNA
<213> ORGANISM: Artificial Sequence
<220> FEATURE:
<223> OTHER INFORMATION: Sense sequence for siFXIg1

<400> SEQUENCE: 369
auuucugggu auucuuuca 19

<210> SEQ ID NO 370
<211> LENGTH: 21
<212> TYPE: RNA
<213> ORGANISM: Artificial Sequence
<220> FEATURE:
<223> OTHER INFORMATION: Antisense sequence for siFXIg1

<400> SEQUENCE: 370
ugaaagaaua cccagaaauc g 21

<210> SEQ ID NO 371
<211> LENGTH: 21
<212> TYPE: RNA
<213> ORGANISM: Artificial Sequence
<220> FEATURE:
<223> OTHER INFORMATION: Sense sequence for siFXIg2

<400> SEQUENCE: 371
cgauuucugg guauucuuuc a 21

<210> SEQ ID NO 372
<211> LENGTH: 23
<212> TYPE: RNA
<213> ORGANISM: Artificial Sequence
<220> FEATURE:
<223> OTHER INFORMATION: Antisense sequence for siFXIg2

<400> SEQUENCE: 372
ugaaagaaua cccagaaauc gcu 23

<210> SEQ ID NO 373
<211> LENGTH: 19
<212> TYPE: RNA
<213> ORGANISM: Artificial Sequence
<220> FEATURE:
<223> OTHER INFORMATION: Sense sequence for siFXIg1-M1

<400> SEQUENCE: 373
auuucugggu auucuuuca 19

<210> SEQ ID NO 374
<211> LENGTH: 21
<212> TYPE: RNA
<213> ORGANISM: Artificial Sequence
<220> FEATURE:
<223> OTHER INFORMATION: Antisense sequence for siFXIg1-M1

<400> SEQUENCE: 374
ugaaagaaua cccagaaauc g 21

<210> SEQ ID NO 375
<211> LENGTH: 19
<212> TYPE: RNA
<213> ORGANISM: Artificial Sequence
<220> FEATURE:
<223> OTHER INFORMATION: Sense sequence for siFXIg1-M2

<400> SEQUENCE: 375
auuucugggu auucuuuca 19

<210> SEQ ID NO 376
<211> LENGTH: 21
<212> TYPE: RNA
<213> ORGANISM: Artificial Sequence
<220> FEATURE:
<223> OTHER INFORMATION: Antisense sequence for siFXIg1-M2

<400> SEQUENCE: 376
ugaaagaaua cccagaaauc g 21

<210> SEQ ID NO 377
<211> LENGTH: 19
<212> TYPE: RNA
<213> ORGANISM: Artificial Sequence
<220> FEATURE:
<223> OTHER INFORMATION: Sense sequence for siFXIg1-M3

<400> SEQUENCE: 377
auuucugggu auucuuuca 19

<210> SEQ ID NO 378
<211> LENGTH: 21
<212> TYPE: RNA
<213> ORGANISM: Artificial Sequence
<220> FEATURE:
<223> OTHER INFORMATION: Antisense sequence for siFXIg1-M3

<400> SEQUENCE: 378
ugaaagaaua cccagaaauc g 21

<210> SEQ ID NO 379
<211> LENGTH: 21
<212> TYPE: RNA
<213> ORGANISM: Artificial Sequence
<220> FEATURE:
<223> OTHER INFORMATION: Sense sequence for siFXIg2-M1

<400> SEQUENCE: 379
cgauuucugg guauucuuuc a 21

<210> SEQ ID NO 380
<211> LENGTH: 23
<212> TYPE: RNA
<213> ORGANISM: Artificial Sequence
<220> FEATURE:
<223> OTHER INFORMATION: Antisense sequence for siFXIg2-M1

<400> SEQUENCE: 380
ugaaagaaua cccagaaauc gcu 23

<210> SEQ ID NO 381
<211> LENGTH: 21
<212> TYPE: RNA
<213> ORGANISM: Artificial Sequence
<220> FEATURE:
<223> OTHER INFORMATION: Sense sequence for siFXIg2-M2

<400> SEQUENCE: 381
cgauuucugg guauucuuuc a 21

<210> SEQ ID NO 382
<211> LENGTH: 23
<212> TYPE: RNA
<213> ORGANISM: Artificial Sequence
<220> FEATURE:
<223> OTHER INFORMATION: Antisense sequence for siFXIg2-M2

<400> SEQUENCE: 382
ugaaagaaua cccagaaauc gcu 23

<210> SEQ ID NO 383
<211> LENGTH: 21
<212> TYPE: RNA
<213> ORGANISM: Artificial Sequence
<220> FEATURE:
<223> OTHER INFORMATION: Sense sequence for siFXIg2-M3

<400> SEQUENCE: 383
cgauuucugg guauucuuuc a 21

<210> SEQ ID NO 384
<211> LENGTH: 23
<212> TYPE: RNA
<213> ORGANISM: Artificial Sequence
<220> FEATURE:
<223> OTHER INFORMATION: Antisense sequence for siFXIg2-M3

<400> SEQUENCE: 384
ugaaagaaua cccagaaauc gcu 23

<210> SEQ ID NO 385
<211> LENGTH: 19
<212> TYPE: RNA
<213> ORGANISM: Artificial Sequence
<220> FEATURE:
<223> OTHER INFORMATION: Sense sequence for siFXIg1-M1S

<400> SEQUENCE: 385
auuucugggu auucuuuca 19

<210> SEQ ID NO 386
<211> LENGTH: 21

<212> TYPE: RNA
<213> ORGANISM: Artificial Sequence
<220> FEATURE:
<223> OTHER INFORMATION: Antisense sequence for siFXIg1-M1S

<400> SEQUENCE: 386
ugaaagaaua cccagaaauc g 21

<210> SEQ ID NO 387
<211> LENGTH: 19
<212> TYPE: RNA
<213> ORGANISM: Artificial Sequence
<220> FEATURE:
<223> OTHER INFORMATION: Sense sequence for siFXIg1-M2S

<400> SEQUENCE: 387
auuucugggu auucuuuca 19

<210> SEQ ID NO 388
<211> LENGTH: 21
<212> TYPE: RNA
<213> ORGANISM: Artificial Sequence
<220> FEATURE:
<223> OTHER INFORMATION: Antisense sequence for siFXIg1-M2S

<400> SEQUENCE: 388
ugaaagaaua cccagaaauc g 21

<210> SEQ ID NO 389
<211> LENGTH: 19
<212> TYPE: RNA
<213> ORGANISM: Artificial Sequence
<220> FEATURE:
<223> OTHER INFORMATION: Sense sequence for siFXIg1-M3S

<400> SEQUENCE: 389
auuucugggu auucuuuca 19

<210> SEQ ID NO 390
<211> LENGTH: 21
<212> TYPE: RNA
<213> ORGANISM: Artificial Sequence
<220> FEATURE:
<223> OTHER INFORMATION: Antisense sequence for siFXIg1-M3S

<400> SEQUENCE: 390
ugaaagaaua cccagaaauc g 21

<210> SEQ ID NO 391
<211> LENGTH: 21
<212> TYPE: RNA
<213> ORGANISM: Artificial Sequence
<220> FEATURE:
<223> OTHER INFORMATION: Sense sequence for siFXIg2-M1S

<400> SEQUENCE: 391
cgauuucugg guauucuuuc a 21

<210> SEQ ID NO 392
<211> LENGTH: 23
<212> TYPE: RNA
<213> ORGANISM: Artificial Sequence
<220> FEATURE:
<223> OTHER INFORMATION: Antisense sequence for siFXIg2-M1S

<400> SEQUENCE: 392
ugaaagaaua cccagaaauc gcu 23

<210> SEQ ID NO 393
<211> LENGTH: 21
<212> TYPE: RNA
<213> ORGANISM: Artificial Sequence
<220> FEATURE:
<223> OTHER INFORMATION: Sense sequence for siFXIg2-M2S

<400> SEQUENCE: 393
cgauuucugg guauucuuuc a 21

<210> SEQ ID NO 394
<211> LENGTH: 23
<212> TYPE: RNA
<213> ORGANISM: Artificial Sequence
<220> FEATURE:
<223> OTHER INFORMATION: Antisense sequence for siFXIg2-M2S

<400> SEQUENCE: 394
ugaaagaaua cccagaaauc gcu 23

<210> SEQ ID NO 395
<211> LENGTH: 21
<212> TYPE: RNA
<213> ORGANISM: Artificial Sequence
<220> FEATURE:
<223> OTHER INFORMATION: Sense sequence for siFXIg2-M3S

<400> SEQUENCE: 395
cgauuucugg guauucuuuc a 21

<210> SEQ ID NO 396
<211> LENGTH: 23
<212> TYPE: RNA
<213> ORGANISM: Artificial Sequence
<220> FEATURE:
<223> OTHER INFORMATION: Antisense sequence for siFXIg2-M3S

<400> SEQUENCE: 396
ugaaagaaua cccagaaauc gcu 23

<210> SEQ ID NO 397
<211> LENGTH: 19
<212> TYPE: RNA
<213> ORGANISM: Artificial Sequence
<220> FEATURE:
<223> OTHER INFORMATION: Sense sequence for siFXIg1-M1P1

<400> SEQUENCE: 397
auuucugggu auucuuuca 19

<210> SEQ ID NO 398
<211> LENGTH: 21
<212> TYPE: RNA
<213> ORGANISM: Artificial Sequence
<220> FEATURE:
<223> OTHER INFORMATION: Antisense sequence for siFXIg1-M1P1

<400> SEQUENCE: 398
ugaaagaaua cccagaaauc g 21

<210> SEQ ID NO 399
<211> LENGTH: 19
<212> TYPE: RNA
<213> ORGANISM: Artificial Sequence
<220> FEATURE:
<223> OTHER INFORMATION: Sense sequence for siFXIg1-M2P1

<400> SEQUENCE: 399
auuucugggu auucuuuca 19

<210> SEQ ID NO 400
<211> LENGTH: 21
<212> TYPE: RNA
<213> ORGANISM: Artificial Sequence
<220> FEATURE:
<223> OTHER INFORMATION: Antisense sequence for siFXIg1-M2P1

<400> SEQUENCE: 400
ugaaagaaua cccagaaauc g 21

<210> SEQ ID NO 401
<211> LENGTH: 19
<212> TYPE: RNA
<213> ORGANISM: Artificial Sequence
<220> FEATURE:
<223> OTHER INFORMATION: Sense sequence for siFXIg1-M3P1

<400> SEQUENCE: 401
auuucugggu auucuuuca 19

<210> SEQ ID NO 402
<211> LENGTH: 21
<212> TYPE: RNA
<213> ORGANISM: Artificial Sequence
<220> FEATURE:
<223> OTHER INFORMATION: Antisense sequence for siFXIg1-M3P1

<400> SEQUENCE: 402
ugaaagaaua cccagaaauc g 21

<210> SEQ ID NO 403
<211> LENGTH: 21
<212> TYPE: RNA
<213> ORGANISM: Artificial Sequence
<220> FEATURE:
<223> OTHER INFORMATION: Sense sequence for siFXIg2-M1P1

<400> SEQUENCE: 403
cgauuucugg guauucuuuc a 21

<210> SEQ ID NO 404
<211> LENGTH: 23
<212> TYPE: RNA
<213> ORGANISM: Artificial Sequence
<220> FEATURE:
<223> OTHER INFORMATION: Antisense sequence for siFXIg2-M1P1

<400> SEQUENCE: 404
ugaaagaaua cccagaaauc gcu 23

<210> SEQ ID NO 405
<211> LENGTH: 21
<212> TYPE: RNA
<213> ORGANISM: Artificial Sequence
<220> FEATURE:
<223> OTHER INFORMATION: Sense sequence for siFXIg2-M2P1

<400> SEQUENCE: 405
cgauuucugg guauucuuuc a 21

<210> SEQ ID NO 406
<211> LENGTH: 23
<212> TYPE: RNA
<213> ORGANISM: Artificial Sequence
<220> FEATURE:
<223> OTHER INFORMATION: Antisense sequence for siFXIg2-M2P1

<400> SEQUENCE: 406
ugaaagaaua cccagaaauc gcu 23

<210> SEQ ID NO 407
<211> LENGTH: 21
<212> TYPE: RNA
<213> ORGANISM: Artificial Sequence
<220> FEATURE:
<223> OTHER INFORMATION: Sense sequence for siFXIg2-M3P1

<400> SEQUENCE: 407
cgauuucugg guauucuuuc a 21

<210> SEQ ID NO 408
<211> LENGTH: 23
<212> TYPE: RNA
<213> ORGANISM: Artificial Sequence
<220> FEATURE:
<223> OTHER INFORMATION: Antisense sequence for siFXIg2-M3P1

<400> SEQUENCE: 408
ugaaagaaua cccagaaauc gcu 23

<210> SEQ ID NO 409
<211> LENGTH: 19
<212> TYPE: RNA
<213> ORGANISM: Artificial Sequence
<220> FEATURE:
<223> OTHER INFORMATION: Sense sequence for siFXIg1-M1SP1

<400> SEQUENCE: 409
auuucugggu auucuuuca 19

<210> SEQ ID NO 410
<211> LENGTH: 21
<212> TYPE: RNA
<213> ORGANISM: Artificial Sequence
<220> FEATURE:
<223> OTHER INFORMATION: Antisense sequence for siFXIg1-M1SP1

<400> SEQUENCE: 410
ugaaagaaua cccagaaauc g 21

<210> SEQ ID NO 411
<211> LENGTH: 19
<212> TYPE: RNA
<213> ORGANISM: Artificial Sequence
<220> FEATURE:
<223> OTHER INFORMATION: Sense sequence for siFXIg1-M2SP1

<400> SEQUENCE: 411
auuucugggu auucuuuca 19

<210> SEQ ID NO 412
<211> LENGTH: 21
<212> TYPE: RNA
<213> ORGANISM: Artificial Sequence
<220> FEATURE:
<223> OTHER INFORMATION: Antisense sequence for siFXIg1-M2SP1

<400> SEQUENCE: 412
ugaaagaaua cccagaaauc g 21

<210> SEQ ID NO 413
<211> LENGTH: 19
<212> TYPE: RNA
<213> ORGANISM: Artificial Sequence
<220> FEATURE:
<223> OTHER INFORMATION: Sense sequence for siFXIg1-M3SP1

<400> SEQUENCE: 413
auuucugggu auucuuuca 19

<210> SEQ ID NO 414
<211> LENGTH: 21
<212> TYPE: RNA
<213> ORGANISM: Artificial Sequence
<220> FEATURE:
<223> OTHER INFORMATION: Antisense sequence for siFXIg1-M3SP1

<400> SEQUENCE: 414
ugaaagaaua cccagaaauc g 21

<210> SEQ ID NO 415
<211> LENGTH: 21
<212> TYPE: RNA
<213> ORGANISM: Artificial Sequence
<220> FEATURE:
<223> OTHER INFORMATION: Sense sequence for siFXIg2-M1SP1

<400> SEQUENCE: 415
cgauuucugg guauucuuuc a 21

<210> SEQ ID NO 416
<211> LENGTH: 23
<212> TYPE: RNA
<213> ORGANISM: Artificial Sequence
<220> FEATURE:
<223> OTHER INFORMATION: Antisense sequence for siFXIg2-M1SP1

<400> SEQUENCE: 416
ugaaagaaua cccagaaauc gcu 23

<210> SEQ ID NO 417
<211> LENGTH: 21
<212> TYPE: RNA
<213> ORGANISM: Artificial Sequence
<220> FEATURE:
<223> OTHER INFORMATION: Sense sequence for siFXIg2-M2SP1

<400> SEQUENCE: 417
cgauuucugg guauucuuuc a 21

<210> SEQ ID NO 418
<211> LENGTH: 23
<212> TYPE: RNA
<213> ORGANISM: Artificial Sequence
<220> FEATURE:
<223> OTHER INFORMATION: Antisense sequence for siFXIg2-M2SP1

<400> SEQUENCE: 418
ugaaagaaua cccagaaauc gcu 23

<210> SEQ ID NO 419

<211> LENGTH: 21
<212> TYPE: RNA
<213> ORGANISM: Artificial Sequence
<220> FEATURE:
<223> OTHER INFORMATION: Sense sequence for siFXIg2-M3SP1

<400> SEQUENCE: 419
cgauuucugg guauucuuuc a 21

<210> SEQ ID NO 420
<211> LENGTH: 23
<212> TYPE: RNA
<213> ORGANISM: Artificial Sequence
<220> FEATURE:
<223> OTHER INFORMATION: Antisense sequence for siFXIg2-M3SP1

<400> SEQUENCE: 420
ugaaagaaua cccagaaauc gcu 23

<210> SEQ ID NO 421
<211> LENGTH: 19
<212> TYPE: RNA
<213> ORGANISM: Artificial Sequence
<220> FEATURE:
<223> OTHER INFORMATION: Sense sequence for the eighth siRNA
<220> FEATURE:
<221> NAME/KEY: misc-feature
<222> LOCATION: (19)..(19)
<223> OTHER INFORMATION: n is Z29, Z29 is U

<400> SEQUENCE: 421
caugaagggc auaaacuan 19

<210> SEQ ID NO 422
<211> LENGTH: 19
<212> TYPE: RNA
<213> ORGANISM: Artificial Sequence
<220> FEATURE:
<223> OTHER INFORMATION: Antisense sequence for the eighth siRNA
<220> FEATURE:
<221> NAME/KEY: misc-feature
<222> LOCATION: (1)..(1)
<223> OTHER INFORMATION: n is Z30, Z30 is A

<400> SEQUENCE: 422
nuaguuuaug cccuucaug 19

<210> SEQ ID NO 423
<211> LENGTH: 19
<212> TYPE: RNA
<213> ORGANISM: Artificial Sequence
<220> FEATURE:
<223> OTHER INFORMATION: Sense sequence for the eighth siRNA
<220> FEATURE:
<221> NAME/KEY: misc-feature
<222> LOCATION: (19)..(19)
<223> OTHER INFORMATION: n is Z31, Z31 is A, U, G or C

<400> SEQUENCE: 423
caugaagggc auaaacuan 19

<210> SEQ ID NO 424
<211> LENGTH: 19
<212> TYPE: RNA
<213> ORGANISM: Artificial Sequence
<220> FEATURE:
<223> OTHER INFORMATION: Antisense sequence for the eighth siRNA
<220> FEATURE:
<221> NAME/KEY: misc-feature
<222> LOCATION: (1)..(1)
<223> OTHER INFORMATION: n is Z32, Z32 is a nucleotide complementary to
Z31, Z31 is selected from A, U, G or C

<400> SEQUENCE: 424
nuaguuuaug cccuucaug 19

<210> SEQ ID NO 425
<211> LENGTH: 19
<212> TYPE: RNA
<213> ORGANISM: Artificial Sequence
<220> FEATURE:
<223> OTHER INFORMATION: Sense sequence for the eighth siRNA
<220> FEATURE:
<221> NAME/KEY: misc-feature
<222> LOCATION: (19)..(19)
<223> OTHER INFORMATION: n is Z31, Z31 is A, U, G or C

<400> SEQUENCE: 425
caugaagggc auaaacuan 19

<210> SEQ ID NO 426
<211> LENGTH: 21
<212> TYPE: RNA
<213> ORGANISM: Artificial Sequence
<220> FEATURE:
<223> OTHER INFORMATION: Antisense sequence for the eighth siRNA
<220> FEATURE:
<221> NAME/KEY: misc-feature
<222> LOCATION: (1)..(1)
<223> OTHER INFORMATION: n is Z32, Z32 is a nucleotide complementary to
Z31, Z31 is selected from A, U, G or C

<400> SEQUENCE: 426
nuaguuuaug cccuucaugu c 21

<210> SEQ ID NO 427
<211> LENGTH: 21
<212> TYPE: RNA
<213> ORGANISM: Artificial Sequence
<220> FEATURE:
<223> OTHER INFORMATION: Sense sequence for the eighth siRNA
<220> FEATURE:
<221> NAME/KEY: misc-feature
<222> LOCATION: (21)..(21)
<223> OTHER INFORMATION: n is Z31, Z31 is A, U, G or C

<400> SEQUENCE: 427
gacaugaagg gcauaaacua n 21

<210> SEQ ID NO 428
<211> LENGTH: 23
<212> TYPE: RNA
<213> ORGANISM: Artificial Sequence
<220> FEATURE:
<223> OTHER INFORMATION: Antisense sequence for the eighth siRNA
<220> FEATURE:
<221> NAME/KEY: misc-feature
<222> LOCATION: (1)..(1)
<223> OTHER INFORMATION: n is Z32, Z32 is a nucleotide complementary to
Z31, Z31 is selected from A, U, G or C

<400> SEQUENCE: 428
nuaguuuaug cccuucaugu cua 23

<210> SEQ ID NO 429
<211> LENGTH: 19
<212> TYPE: RNA
<213> ORGANISM: Artificial Sequence
<220> FEATURE:
<223> OTHER INFORMATION: Sense sequence for siFXIh1

<400> SEQUENCE: 429
caugaagggc auaaacuau 19

<210> SEQ ID NO 430
<211> LENGTH: 21
<212> TYPE: RNA
<213> ORGANISM: Artificial Sequence
<220> FEATURE:
<223> OTHER INFORMATION: Antisense sequence for siFXIh1

<400> SEQUENCE: 430
auaguuuaug cccuucaugu c 21

<210> SEQ ID NO 431
<211> LENGTH: 21
<212> TYPE: RNA
<213> ORGANISM: Artificial Sequence
<220> FEATURE:
<223> OTHER INFORMATION: Sense sequence for siFXIh2

<400> SEQUENCE: 431
gacaugaagg gcauaaacua u 21

<210> SEQ ID NO 432
<211> LENGTH: 23
<212> TYPE: RNA
<213> ORGANISM: Artificial Sequence
<220> FEATURE:
<223> OTHER INFORMATION: Antisense sequence for siFXIh2

<400> SEQUENCE: 432
auaguuuaug cccuucaugu cua 23

<210> SEQ ID NO 433
<211> LENGTH: 19
<212> TYPE: RNA
<213> ORGANISM: Artificial Sequence
<220> FEATURE:
<223> OTHER INFORMATION: Sense sequence for siFXIh1-M1

<400> SEQUENCE: 433
caugaagggc auaaacuau 19

<210> SEQ ID NO 434
<211> LENGTH: 21
<212> TYPE: RNA
<213> ORGANISM: Artificial Sequence
<220> FEATURE:
<223> OTHER INFORMATION: Antisense sequence for siFXIh1-M1

<400> SEQUENCE: 434
auaguuuaug cccuucaugu c 21

<210> SEQ ID NO 435
<211> LENGTH: 19
<212> TYPE: RNA
<213> ORGANISM: Artificial Sequence
<220> FEATURE:
<223> OTHER INFORMATION: Sense sequence for siFXIh1-M2

<400> SEQUENCE: 435
caugaagggc auaaacuau 19

<210> SEQ ID NO 436
<211> LENGTH: 21
<212> TYPE: RNA
<213> ORGANISM: Artificial Sequence
<220> FEATURE:
<223> OTHER INFORMATION: Antisense sequence for siFXIh1-M2

<400> SEQUENCE: 436
auaguuuaug cccuucaugu c 21

<210> SEQ ID NO 437
<211> LENGTH: 19
<212> TYPE: RNA
<213> ORGANISM: Artificial Sequence
<220> FEATURE:
<223> OTHER INFORMATION: Sense sequence for siFXIh1-M3

<400> SEQUENCE: 437
caugaagggc auaaacuau 19

<210> SEQ ID NO 438
<211> LENGTH: 21
<212> TYPE: RNA
<213> ORGANISM: Artificial Sequence
<220> FEATURE:
<223> OTHER INFORMATION: Antisense sequence for siFXIh1-M3

<400> SEQUENCE: 438
auaguuuaug cccuucaugu c 21

<210> SEQ ID NO 439
<211> LENGTH: 21
<212> TYPE: RNA
<213> ORGANISM: Artificial Sequence
<220> FEATURE:
<223> OTHER INFORMATION: Sense sequence for siFXIh2-M1

<400> SEQUENCE: 439
gacaugaagg gcauaaacua u 21

<210> SEQ ID NO 440
<211> LENGTH: 23
<212> TYPE: RNA
<213> ORGANISM: Artificial Sequence
<220> FEATURE:
<223> OTHER INFORMATION: Antisense sequence for siFXIh2-M1

<400> SEQUENCE: 440
auaguuuaug cccuucaugu cua 23

<210> SEQ ID NO 441
<211> LENGTH: 21
<212> TYPE: RNA
<213> ORGANISM: Artificial Sequence
<220> FEATURE:
<223> OTHER INFORMATION: Sense sequence for siFXIh2-M2

<400> SEQUENCE: 441
gacaugaagg gcauaaacua u 21

<210> SEQ ID NO 442
<211> LENGTH: 23
<212> TYPE: RNA
<213> ORGANISM: Artificial Sequence
<220> FEATURE:
<223> OTHER INFORMATION: Antisense sequence for siFXIh2-M2

<400> SEQUENCE: 442
auaguuuaug cccuucaugu cua 23

<210> SEQ ID NO 443
<211> LENGTH: 21
<212> TYPE: RNA
<213> ORGANISM: Artificial Sequence
<220> FEATURE:
<223> OTHER INFORMATION: Sense sequence for siFXIh2-M3

<400> SEQUENCE: 443
gacaugaagg gcauaaacua u 21

<210> SEQ ID NO 444
<211> LENGTH: 23
<212> TYPE: RNA
<213> ORGANISM: Artificial Sequence
<220> FEATURE:
<223> OTHER INFORMATION: Antisense sequence for siFXIh2-M3

<400> SEQUENCE: 444
auaguuuaug cccuucaugu cua 23

<210> SEQ ID NO 445
<211> LENGTH: 19
<212> TYPE: RNA
<213> ORGANISM: Artificial Sequence
<220> FEATURE:
<223> OTHER INFORMATION: Sense sequence for siFXIh1-M1S

<400> SEQUENCE: 445
caugaagggc auaaacuau 19

<210> SEQ ID NO 446
<211> LENGTH: 21
<212> TYPE: RNA
<213> ORGANISM: Artificial Sequence
<220> FEATURE:
<223> OTHER INFORMATION: Antisense sequence for siFXIh1-M1S

<400> SEQUENCE: 446
auaguuuaug cccuucaugu c 21

<210> SEQ ID NO 447
<211> LENGTH: 19
<212> TYPE: RNA
<213> ORGANISM: Artificial Sequence
<220> FEATURE:
<223> OTHER INFORMATION: Sense sequence for siFXIh1-M2S

<400> SEQUENCE: 447
caugaagggc auaaacuau 19

<210> SEQ ID NO 448
<211> LENGTH: 21
<212> TYPE: RNA
<213> ORGANISM: Artificial Sequence
<220> FEATURE:
<223> OTHER INFORMATION: Antisense sequence for siFXIh1-M2S

<400> SEQUENCE: 448
auaguuuaug cccuucaugu c 21

<210> SEQ ID NO 449

<211> LENGTH: 19
<212> TYPE: RNA
<213> ORGANISM: Artificial Sequence
<220> FEATURE:
<223> OTHER INFORMATION: Sense sequence for siFXIh1-M3S

<400> SEQUENCE: 449
caugaagggc auaaacuau 19

<210> SEQ ID NO 450
<211> LENGTH: 21
<212> TYPE: RNA
<213> ORGANISM: Artificial Sequence
<220> FEATURE:
<223> OTHER INFORMATION: Antisense sequence for siFXIh1-M3S

<400> SEQUENCE: 450
auaguuuaug cccuucaugu c 21

<210> SEQ ID NO 451
<211> LENGTH: 21
<212> TYPE: RNA
<213> ORGANISM: Artificial Sequence
<220> FEATURE:
<223> OTHER INFORMATION: Sense sequence for siFXIh2-M1S

<400> SEQUENCE: 451
gacaugaagg gcauaaacua u 21

<210> SEQ ID NO 452
<211> LENGTH: 23
<212> TYPE: RNA
<213> ORGANISM: Artificial Sequence
<220> FEATURE:
<223> OTHER INFORMATION: Antisense sequence for siFXIh2-M1S

<400> SEQUENCE: 452
auaguuuaug cccuucaugu cua 23

<210> SEQ ID NO 453
<211> LENGTH: 21
<212> TYPE: RNA
<213> ORGANISM: Artificial Sequence
<220> FEATURE:
<223> OTHER INFORMATION: Sense sequence for siFXIh2-M2S

<400> SEQUENCE: 453
gacaugaagg gcauaaacua u 21

<210> SEQ ID NO 454
<211> LENGTH: 23
<212> TYPE: RNA
<213> ORGANISM: Artificial Sequence
<220> FEATURE:
<223> OTHER INFORMATION: Antisense sequence for siFXIh2-M2S

<400> SEQUENCE: 454
auaguuuaug cccuucaugu cua 23

<210> SEQ ID NO 455
<211> LENGTH: 21
<212> TYPE: RNA
<213> ORGANISM: Artificial Sequence
<220> FEATURE:
<223> OTHER INFORMATION: Sense sequence for siFXIh2-M3S

<400> SEQUENCE: 455
gacaugaagg gcauaaacua u 21

<210> SEQ ID NO 456
<211> LENGTH: 23
<212> TYPE: RNA
<213> ORGANISM: Artificial Sequence
<220> FEATURE:
<223> OTHER INFORMATION: Antisense sequence for siFXIh2-M3S

<400> SEQUENCE: 456
auaguuuaug cccuucaugu cua 23

<210> SEQ ID NO 457
<211> LENGTH: 19
<212> TYPE: RNA
<213> ORGANISM: Artificial Sequence
<220> FEATURE:
<223> OTHER INFORMATION: Sense sequence for siFXIh1-M1P1

<400> SEQUENCE: 457
caugaagggc auaaacuau 19

<210> SEQ ID NO 458
<211> LENGTH: 21
<212> TYPE: RNA
<213> ORGANISM: Artificial Sequence
<220> FEATURE:
<223> OTHER INFORMATION: Antisense sequence for siFXIh1-M1P1

<400> SEQUENCE: 458
auaguuuaug cccuucaugu c 21

<210> SEQ ID NO 459
<211> LENGTH: 19
<212> TYPE: RNA
<213> ORGANISM: Artificial Sequence
<220> FEATURE:
<223> OTHER INFORMATION: Sense sequence for siFXIh1-M2P1

<400> SEQUENCE: 459
caugaagggc auaaacuau 19

<210> SEQ ID NO 460
<211> LENGTH: 21
<212> TYPE: RNA
<213> ORGANISM: Artificial Sequence
<220> FEATURE:
<223> OTHER INFORMATION: Antisense sequence for siFXIh1-M2P1

<400> SEQUENCE: 460
auaguuuaug cccuucaugu c 21

<210> SEQ ID NO 461
<211> LENGTH: 19
<212> TYPE: RNA
<213> ORGANISM: Artificial Sequence
<220> FEATURE:
<223> OTHER INFORMATION: Sense sequence for siFXIh1-M3P1

<400> SEQUENCE: 461
caugaagggc auaaacuau 19

<210> SEQ ID NO 462
<211> LENGTH: 21
<212> TYPE: RNA

```
<213> ORGANISM: Artificial Sequence
<220> FEATURE:
<223> OTHER INFORMATION: Antisense sequence for siFXIh1-M3P1

<400> SEQUENCE: 462

auaguuuaug cccuucaugu c                                          21


<210> SEQ ID NO 463
<211> LENGTH: 21
<212> TYPE: RNA
<213> ORGANISM: Artificial Sequence
<220> FEATURE:
<223> OTHER INFORMATION: Sense sequence for siFXIh2-M1P1

<400> SEQUENCE: 463

gacaugaagg gcauaaacua u                                          21


<210> SEQ ID NO 464
<211> LENGTH: 23
<212> TYPE: RNA
<213> ORGANISM: Artificial Sequence
<220> FEATURE:
<223> OTHER INFORMATION: Antisense sequence for siFXIh2-M1P1

<400> SEQUENCE: 464

auaguuuaug cccuucaugu cua                                        23


<210> SEQ ID NO 465
<211> LENGTH: 21
<212> TYPE: RNA
<213> ORGANISM: Artificial Sequence
<220> FEATURE:
<223> OTHER INFORMATION: Sense sequence for siFXIh2-M2P1

<400> SEQUENCE: 465

gacaugaaggg cauaaacua u                                          21

<210> SEQ ID NO 466
<211> LENGTH: 23
<212> TYPE: RNA
<213> ORGANISM: Artificial Sequence
<220> FEATURE:
<223> OTHER INFORMATION: Antisense sequence for siFXIh2-M2P1

<400> SEQUENCE: 466

auaguuuaug cccuucaugu cua                                        23


<210> SEQ ID NO 467
<211> LENGTH: 21
<212> TYPE: RNA
<213> ORGANISM: Artificial Sequence
<220> FEATURE:
<223> OTHER INFORMATION: Sense sequence for siFXIh2-M3P1

<400> SEQUENCE: 467

gacaugaagg gcauaaacua u                                          21


<210> SEQ ID NO 468
<211> LENGTH: 23
<212> TYPE: RNA
<213> ORGANISM: Artificial Sequence
<220> FEATURE:
<223> OTHER INFORMATION: Antisense sequence for siFXIh2-M3P1

<400> SEQUENCE: 468

auaguuuaug cccuucaugu cua                                        23
```

<210> SEQ ID NO 469
<211> LENGTH: 19
<212> TYPE: RNA
<213> ORGANISM: Artificial Sequence
<220> FEATURE:
<223> OTHER INFORMATION: Sense sequence for siFXIh1-M1SP1

<400> SEQUENCE: 469
caugaagggc auaaacuau 19

<210> SEQ ID NO 470
<211> LENGTH: 21
<212> TYPE: RNA
<213> ORGANISM: Artificial Sequence
<220> FEATURE:
<223> OTHER INFORMATION: Antisense sequence for siFXIh1-M1SP1

<400> SEQUENCE: 470
auaguuuaug cccuucaugu c 21

<210> SEQ ID NO 471
<211> LENGTH: 19
<212> TYPE: RNA
<213> ORGANISM: Artificial Sequence
<220> FEATURE:
<223> OTHER INFORMATION: Sense sequence for siFXIh1-M2SP1

<400> SEQUENCE: 471
caugaagggc auaaacuau 19

<210> SEQ ID NO 472
<211> LENGTH: 21
<212> TYPE: RNA
<213> ORGANISM: Artificial Sequence
<220> FEATURE:
<223> OTHER INFORMATION: Antisense sequence for siFXIh1-M2SP1

<400> SEQUENCE: 472
auaguuuaug cccuucaugu c 21

<210> SEQ ID NO 473
<211> LENGTH: 19
<212> TYPE: RNA
<213> ORGANISM: Artificial Sequence
<220> FEATURE:
<223> OTHER INFORMATION: Sense sequence for siFXIh1-M3SP1

<400> SEQUENCE: 473
caugaagggc auaaacuau 19

<210> SEQ ID NO 474
<211> LENGTH: 21
<212> TYPE: RNA
<213> ORGANISM: Artificial Sequence
<220> FEATURE:
<223> OTHER INFORMATION: Antisense sequence for siFXIh1-M3SP1

<400> SEQUENCE: 474
auaguuuaug cccuucaugu c 21

<210> SEQ ID NO 475
<211> LENGTH: 21
<212> TYPE: RNA
<213> ORGANISM: Artificial Sequence
<220> FEATURE:
<223> OTHER INFORMATION: Sense sequence for siFXIh2-M1SP1

<400> SEQUENCE: 475
gacaugaagg gcauaaacua u 21

<210> SEQ ID NO 476
<211> LENGTH: 23
<212> TYPE: RNA
<213> ORGANISM: Artificial Sequence
<220> FEATURE:
<223> OTHER INFORMATION: Antisense sequence for siFXIh2-M1SP1

<400> SEQUENCE: 476
auaguuuaug cccuucaugu cua 23

<210> SEQ ID NO 477
<211> LENGTH: 21
<212> TYPE: RNA
<213> ORGANISM: Artificial Sequence
<220> FEATURE:
<223> OTHER INFORMATION: Sense sequence for siFXIh2-M2SP1

<400> SEQUENCE: 477
gacaugaagg gcauaaacua u 21

<210> SEQ ID NO 478
<211> LENGTH: 23
<212> TYPE: RNA
<213> ORGANISM: Artificial Sequence
<220> FEATURE:
<223> OTHER INFORMATION: Antisense sequence for siFXIh2-M2SP1

<400> SEQUENCE: 478
auaguuuaug cccuucaugu cua 23

<210> SEQ ID NO 479
<211> LENGTH: 21
<212> TYPE: RNA
<213> ORGANISM: Artificial Sequence
<220> FEATURE:
<223> OTHER INFORMATION: Sense sequence for siFXIh2-M3SP1

<400> SEQUENCE: 479
gacaugaagg gcauaaacua u 21

<210> SEQ ID NO 480
<211> LENGTH: 23
<212> TYPE: RNA
<213> ORGANISM: Artificial Sequence
<220> FEATURE:
<223> OTHER INFORMATION: Antisense sequence for siFXIh2-M3SP1

<400> SEQUENCE: 480
auaguuuaug cccuucaugu cua 23

<210> SEQ ID NO 481
<211> LENGTH: 19
<212> TYPE: RNA
<213> ORGANISM: Artificial Sequence
<220> FEATURE:
<223> OTHER INFORMATION: Sense sequence for the ninth siRNA
<220> FEATURE:
<221> NAME/KEY: misc-feature
<222> LOCATION: (19)..(19)
<223> OTHER INFORMATION: n is Z33, Z33 is A

<400> SEQUENCE: 481
ggauucugga gaaaacucn 19

<210> SEQ ID NO 482
<211> LENGTH: 19
<212> TYPE: RNA
<213> ORGANISM: Artificial Sequence
<220> FEATURE:
<223> OTHER INFORMATION: Antisense sequence for the ninth siRNA
<220> FEATURE:
<221> NAME/KEY: misc-feature
<222> LOCATION: (1)..(1)
<223> OTHER INFORMATION: n is Z34, Z34 is U

<400> SEQUENCE: 482 ngaguuucu ccagaaucc 19

<210> SEQ ID NO 483
<211> LENGTH: 19
<212> TYPE: RNA
<213> ORGANISM: Artificial Sequence
<220> FEATURE:
<223> OTHER INFORMATION: Sense sequence for the ninth siRNA
<220> FEATURE:
<221> NAME/KEY: misc-feature
<222> LOCATION: (19)..(19)
<223> OTHER INFORMATION: n is Z35, Z35 is A, U, G or C

<400> SEQUENCE: 483
ggauucugga gaaaacucn 19

<210> SEQ ID NO 484
<211> LENGTH: 19
<212> TYPE: RNA
<213> ORGANISM: Artificial Sequence
<220> FEATURE:
<223> OTHER INFORMATION: Antisense sequence for the ninth siRNA
<220> FEATURE:
<221> NAME/KEY: misc-feature
<222> LOCATION: (1)..(1)
<223> OTHER INFORMATION: n is Z36, Z36 is a nucleotide complementary to
Z35, Z35 is selected from A, U, G or C

<400> SEQUENCE: 484 ngaguuucu ccagaaucc 19

<210> SEQ ID NO 485
<211> LENGTH: 19
<212> TYPE: RNA
<213> ORGANISM: Artificial Sequence
<220> FEATURE:
<223> OTHER INFORMATION: Sense sequence for the ninth siRNA
<220> FEATURE:
<221> NAME/KEY: misc-feature
<222> LOCATION: (19)..(19)
<223> OTHER INFORMATION: n is Z35, Z35 is A, U, G or C

<400> SEQUENCE: 485
ggauucugga gaaaacucn 19

<210> SEQ ID NO 486
<211> LENGTH: 21
<212> TYPE: RNA
<213> ORGANISM: Artificial Sequence
<220> FEATURE:
<223> OTHER INFORMATION: Antisense sequence for the ninth siRNA
<220> FEATURE:
<221> NAME/KEY: misc-feature
<222> LOCATION: (1)..(1)
<223> OTHER INFORMATION: n is Z36, Z36 is a nucleotide complementary to
Z35, Z35 is selected from A, U, G or C

<400> SEQUENCE: 486
ngaguuuucu ccagaaucca g 21

<210> SEQ ID NO 487
<211> LENGTH: 21
<212> TYPE: RNA
<213> ORGANISM: Artificial Sequence
<220> FEATURE:
<223> OTHER INFORMATION: Sense sequence for the ninth siRNA
<220> FEATURE:
<221> NAME/KEY: misc-feature
<222> LOCATION: (21)..(21)
<223> OTHER INFORMATION: n is Z35, Z35 is A, U, G or C

<400> SEQUENCE: 487
cuggauucug gagaaaacuc n 21

<210> SEQ ID NO 488
<211> LENGTH: 23
<212> TYPE: RNA
<213> ORGANISM: Artificial Sequence
<220> FEATURE:
<223> OTHER INFORMATION: Antisense sequence for the ninth siRNA
<220> FEATURE:
<221> NAME/KEY: misc-feature
<222> LOCATION: (1)..(1)
<223> OTHER INFORMATION: n is Z36, Z36 is a nucleotide complementary to
Z35, Z35 is selected from A, U, G or C

<400> SEQUENCE: 488
ngaguuuucu ccagaaucca guc 23

<210> SEQ ID NO 489
<211> LENGTH: 19
<212> TYPE: RNA
<213> ORGANISM: Artificial Sequence
<220> FEATURE:
<223> OTHER INFORMATION: Sense sequence for siFXIi1

<400> SEQUENCE: 489
ggauucugga gaaaacuca 19

<210> SEQ ID NO 490
<211> LENGTH: 21
<212> TYPE: RNA
<213> ORGANISM: Artificial Sequence
<220> FEATURE:
<223> OTHER INFORMATION: Antisense sequence for siFXIi1

<400> SEQUENCE: 490
ugaguuuucu ccagaaucca g 21

<210> SEQ ID NO 491
<211> LENGTH: 21
<212> TYPE: RNA
<213> ORGANISM: Artificial Sequence
<220> FEATURE:
<223> OTHER INFORMATION: Sense sequence for siFXIi2

<400> SEQUENCE: 491
cuggauucug gagaaaacuc a 21

<210> SEQ ID NO 492
<211> LENGTH: 23
<212> TYPE: RNA
<213> ORGANISM: Artificial Sequence
<220> FEATURE:
<223> OTHER INFORMATION: Antisense sequence for siFXIi2

<400> SEQUENCE: 492
ugaguuuucu ccagaaucca guc 23

<210> SEQ ID NO 493
<211> LENGTH: 19
<212> TYPE: RNA
<213> ORGANISM: Artificial Sequence
<220> FEATURE:
<223> OTHER INFORMATION: Sense sequence for siFXIi1-M1

<400> SEQUENCE: 493
ggauucugga gaaaacuca 19

<210> SEQ ID NO 494
<211> LENGTH: 21
<212> TYPE: RNA
<213> ORGANISM: Artificial Sequence
<220> FEATURE:
<223> OTHER INFORMATION: Antisense sequence for siFXIi1-M1

<400> SEQUENCE: 494
ugaguuuucu ccagaaucca g 21

<210> SEQ ID NO 495
<211> LENGTH: 19
<212> TYPE: RNA
<213> ORGANISM: Artificial Sequence
<220> FEATURE:
<223> OTHER INFORMATION: Sense sequence for siFXIi1-M2

<400> SEQUENCE: 495
ggauucugga gaaaacuca 19

<210> SEQ ID NO 496
<211> LENGTH: 21
<212> TYPE: RNA
<213> ORGANISM: Artificial Sequence
<220> FEATURE:
<223> OTHER INFORMATION: Antisense sequence for siFXIi1-M2

<400> SEQUENCE: 496
ugaguuuucu ccagaaucca g 21

<210> SEQ ID NO 497
<211> LENGTH: 19
<212> TYPE: RNA
<213> ORGANISM: Artificial Sequence
<220> FEATURE:
<223> OTHER INFORMATION: Sense sequence for siFXIi1-M3

<400> SEQUENCE: 497
ggauucugga gaaaacuca 19

<210> SEQ ID NO 498
<211> LENGTH: 21
<212> TYPE: RNA
<213> ORGANISM: Artificial Sequence
<220> FEATURE:
<223> OTHER INFORMATION: Antisense sequence for siFXIi1-M3

<400> SEQUENCE: 498
ugaguuuucu ccagaaucca g 21

<210> SEQ ID NO 499
<211> LENGTH: 21
<212> TYPE: RNA
<213> ORGANISM: Artificial Sequence
<220> FEATURE:
<223> OTHER INFORMATION: Sense sequence for siFXIi2-M1

<400> SEQUENCE: 499
cuggauucug gagaaaacuc a 21

<210> SEQ ID NO 500
<211> LENGTH: 23
<212> TYPE: RNA
<213> ORGANISM: Artificial Sequence
<220> FEATURE:
<223> OTHER INFORMATION: Antisense sequence for siFXIi2-M1

<400> SEQUENCE: 500
ugaguuuucu ccagaaucca guc 23

<210> SEQ ID NO 501
<211> LENGTH: 21
<212> TYPE: RNA
<213> ORGANISM: Artificial Sequence
<220> FEATURE:
<223> OTHER INFORMATION: Sense sequence for siFXIi2-M2

<400> SEQUENCE: 501
cuggauucug gagaaaacuc a 21

<210> SEQ ID NO 502
<211> LENGTH: 23
<212> TYPE: RNA
<213> ORGANISM: Artificial Sequence
<220> FEATURE:
<223> OTHER INFORMATION: Antisense sequence for siFXIi2-M2

<400> SEQUENCE: 502
ugaguuuucu ccagaaucca guc 23

<210> SEQ ID NO 503
<211> LENGTH: 21
<212> TYPE: RNA
<213> ORGANISM: Artificial Sequence
<220> FEATURE:
<223> OTHER INFORMATION: Sense sequence for siFXIi2-M3

<400> SEQUENCE: 503
cuggauucug gagaaaacuc a 21

<210> SEQ ID NO 504
<211> LENGTH: 23
<212> TYPE: RNA
<213> ORGANISM: Artificial Sequence
<220> FEATURE:
<223> OTHER INFORMATION: Antisense sequence for siFXIi2-M3

<400> SEQUENCE: 504
ugaguuuucu ccagaaucca guc 23

<210> SEQ ID NO 505
<211> LENGTH: 19
<212> TYPE: RNA
<213> ORGANISM: Artificial Sequence
<220> FEATURE:
<223> OTHER INFORMATION: Sense sequence for siFXIi1-M1S

<400> SEQUENCE: 505
ggauucugga gaaaacuca 19

<210> SEQ ID NO 506
<211> LENGTH: 21
<212> TYPE: RNA
<213> ORGANISM: Artificial Sequence
<220> FEATURE:
<223> OTHER INFORMATION: Antisense sequence for siFXIi1-M1S

<400> SEQUENCE: 506
ugaguuuucu ccagaaucca g 21

<210> SEQ ID NO 507
<211> LENGTH: 19
<212> TYPE: RNA
<213> ORGANISM: Artificial Sequence
<220> FEATURE:
<223> OTHER INFORMATION: Sense sequence for siFXIi1-M2S

<400> SEQUENCE: 507
ggauucugga gaaaacuca 19

<210> SEQ ID NO 508
<211> LENGTH: 21
<212> TYPE: RNA
<213> ORGANISM: Artificial Sequence
<220> FEATURE:
<223> OTHER INFORMATION: Antisense sequence for siFXIi1-M2S

<400> SEQUENCE: 508
ugaguuuucu ccagaaucca g 21

<210> SEQ ID NO 509
<211> LENGTH: 19
<212> TYPE: RNA
<213> ORGANISM: Artificial Sequence
<220> FEATURE:
<223> OTHER INFORMATION: Sense sequence for siFXIi1-M3S

<400> SEQUENCE: 509
ggauucugga gaaaacuca 19

<210> SEQ ID NO 510
<211> LENGTH: 21
<212> TYPE: RNA
<213> ORGANISM: Artificial Sequence
<220> FEATURE:
<223> OTHER INFORMATION: Antisense sequence for siFXIi1-M3S

<400> SEQUENCE: 510
ugaguuuucu ccagaaucca g 21

<210> SEQ ID NO 511
<211> LENGTH: 21
<212> TYPE: RNA
<213> ORGANISM: Artificial Sequence
<220> FEATURE:
<223> OTHER INFORMATION: Sense sequence for siFXIi2-M1S

<400> SEQUENCE: 511
cuggauucug gagaaaacuc a 21

<210> SEQ ID NO 512

<211> LENGTH: 23
<212> TYPE: RNA
<213> ORGANISM: Artificial Sequence
<220> FEATURE:
<223> OTHER INFORMATION: Antisense sequence for siFXIi2-M1S

<400> SEQUENCE: 512
ugaguuuucu ccagaaucca guc 23

<210> SEQ ID NO 513
<211> LENGTH: 21
<212> TYPE: RNA
<213> ORGANISM: Artificial Sequence
<220> FEATURE:
<223> OTHER INFORMATION: Sense sequence for siFXIi2-M2S

<400> SEQUENCE: 513
cuggauucug gagaaaacuc a 21

<210> SEQ ID NO 514
<211> LENGTH: 23
<212> TYPE: RNA
<213> ORGANISM: Artificial Sequence
<220> FEATURE:
<223> OTHER INFORMATION: Antisense sequence for siFXIi2-M2S

<400> SEQUENCE: 514
ugaguuuucu ccagaaucca guc 23

<210> SEQ ID NO 515
<211> LENGTH: 21
<212> TYPE: RNA
<213> ORGANISM: Artificial Sequence
<220> FEATURE:
<223> OTHER INFORMATION: Sense sequence for siFXIi2-M3S

<400> SEQUENCE: 515
cuggauucug gagaaaacuc a 21

<210> SEQ ID NO 516
<211> LENGTH: 23
<212> TYPE: RNA
<213> ORGANISM: Artificial Sequence
<220> FEATURE:
<223> OTHER INFORMATION: Antisense sequence for siFXIi2-M3S

<400> SEQUENCE: 516
ugaguuuucu ccagaaucca guc 23

<210> SEQ ID NO 517
<211> LENGTH: 19
<212> TYPE: RNA
<213> ORGANISM: Artificial Sequence
<220> FEATURE:
<223> OTHER INFORMATION: Sense sequence for siFXIi1-M1P1

<400> SEQUENCE: 517
ggauucugga gaaaacuca 19

<210> SEQ ID NO 518
<211> LENGTH: 21
<212> TYPE: RNA
<213> ORGANISM: Artificial Sequence
<220> FEATURE:
<223> OTHER INFORMATION: Antisense sequence for siFXIi1-M1P1

<400> SEQUENCE: 518
ugaguuuucu ccagaaucca g 21

<210> SEQ ID NO 519
<211> LENGTH: 19
<212> TYPE: RNA
<213> ORGANISM: Artificial Sequence
<220> FEATURE:
<223> OTHER INFORMATION: Sense sequence for siFXIi1-M2P1

<400> SEQUENCE: 519
ggauucugga gaaaacuca 19

<210> SEQ ID NO 520
<211> LENGTH: 21
<212> TYPE: RNA
<213> ORGANISM: Artificial Sequence
<220> FEATURE:
<223> OTHER INFORMATION: Antisense sequence for siFXIi1-M2P1

<400> SEQUENCE: 520
ugaguuuucu ccagaaucca g 21

<210> SEQ ID NO 521
<211> LENGTH: 19
<212> TYPE: RNA
<213> ORGANISM: Artificial Sequence
<220> FEATURE:
<223> OTHER INFORMATION: Sense sequence for siFXIi1-M3P1

<400> SEQUENCE: 521
ggauucugga gaaaacuca 19

<210> SEQ ID NO 522
<211> LENGTH: 21
<212> TYPE: RNA
<213> ORGANISM: Artificial Sequence
<220> FEATURE:
<223> OTHER INFORMATION: Antisense sequence for siFXIi1-M3P1

<400> SEQUENCE: 522
ugaguuuucu ccagaaucca g 21

<210> SEQ ID NO 523
<211> LENGTH: 21
<212> TYPE: RNA
<213> ORGANISM: Artificial Sequence
<220> FEATURE:
<223> OTHER INFORMATION: Sense sequence for siFXIi2-M1P1

<400> SEQUENCE: 523
cuggauucug gagaaaacuc a 21

<210> SEQ ID NO 524
<211> LENGTH: 23
<212> TYPE: RNA
<213> ORGANISM: Artificial Sequence
<220> FEATURE:
<223> OTHER INFORMATION: Antisense sequence for siFXIi2-M1P1

<400> SEQUENCE: 524
ugaguuuucu ccagaaucca guc 23

<210> SEQ ID NO 525
<211> LENGTH: 21
<212> TYPE: RNA

<213> ORGANISM: Artificial Sequence
<220> FEATURE:
<223> OTHER INFORMATION: Sense sequence for siFXIi2-M2P1

<400> SEQUENCE: 525
cuggauucug gagaaaacuc a 21

<210> SEQ ID NO 526
<211> LENGTH: 23
<212> TYPE: RNA
<213> ORGANISM: Artificial Sequence
<220> FEATURE:
<223> OTHER INFORMATION: Antisense sequence for siFXIi2-M2P1

<400> SEQUENCE: 526
ugaguuuucu ccagaaucca guc 23

<210> SEQ ID NO 527
<211> LENGTH: 21
<212> TYPE: RNA
<213> ORGANISM: Artificial Sequence
<220> FEATURE:
<223> OTHER INFORMATION: Sense sequence for siFXIi2-M3P1

<400> SEQUENCE: 527
cuggauucug gagaaaacuc a 21

<210> SEQ ID NO 528
<211> LENGTH: 23
<212> TYPE: RNA
<213> ORGANISM: Artificial Sequence
<220> FEATURE:
<223> OTHER INFORMATION: Antisense sequence for siFXIi2-M3P1

<400> SEQUENCE: 528
ugaguuuucu ccagaaucca guc 23

<210> SEQ ID NO 529
<211> LENGTH: 19
<212> TYPE: RNA
<213> ORGANISM: Artificial Sequence
<220> FEATURE:
<223> OTHER INFORMATION: Sense sequence for siFXIi1-M1SP1

<400> SEQUENCE: 529
ggauucugga gaaaacuca 19

<210> SEQ ID NO 530
<211> LENGTH: 21
<212> TYPE: RNA
<213> ORGANISM: Artificial Sequence
<220> FEATURE:
<223> OTHER INFORMATION: Antisense sequence for siFXIi1-M1SP1

<400> SEQUENCE: 530
ugaguuuucu ccagaaucca g 21

<210> SEQ ID NO 531
<211> LENGTH: 19
<212> TYPE: RNA
<213> ORGANISM: Artificial Sequence
<220> FEATURE:
<223> OTHER INFORMATION: Sense sequence for siFXIi1-M2SP1

<400> SEQUENCE: 531
ggauucugga gaaaacuca 19

<210> SEQ ID NO 532
<211> LENGTH: 21
<212> TYPE: RNA
<213> ORGANISM: Artificial Sequence
<220> FEATURE:
<223> OTHER INFORMATION: Antisense sequence for siFXIi1-M2SP1

<400> SEQUENCE: 532
ugaguuuucu ccagaaucca g 21

<210> SEQ ID NO 533
<211> LENGTH: 19
<212> TYPE: RNA
<213> ORGANISM: Artificial Sequence
<220> FEATURE:
<223> OTHER INFORMATION: Sense sequence for siFXIi1-M3SP1

<400> SEQUENCE: 533
ggauucugga gaaaacuca 19

<210> SEQ ID NO 534
<211> LENGTH: 21
<212> TYPE: RNA
<213> ORGANISM: Artificial Sequence
<220> FEATURE:
<223> OTHER INFORMATION: Antisense sequence for siFXIi1-M3SP1

<400> SEQUENCE: 534
ugaguuuucu ccagaaucca g 21

<210> SEQ ID NO 535
<211> LENGTH: 21
<212> TYPE: RNA
<213> ORGANISM: Artificial Sequence
<220> FEATURE:
<223> OTHER INFORMATION: Sense sequence for siFXIi2-M1SP1

<400> SEQUENCE: 535
cuggauucug gagaaaacuc a 21

<210> SEQ ID NO 536
<211> LENGTH: 23
<212> TYPE: RNA
<213> ORGANISM: Artificial Sequence
<220> FEATURE:
<223> OTHER INFORMATION: Antisense sequence for siFXIi2-M1SP1

<400> SEQUENCE: 536
ugaguuuucu ccagaaucca guc 23

<210> SEQ ID NO 537
<211> LENGTH: 21
<212> TYPE: RNA
<213> ORGANISM: Artificial Sequence
<220> FEATURE:
<223> OTHER INFORMATION: Sense sequence for siFXIi2-M2SP1

<400> SEQUENCE: 537
cuggauucug gagaaaacuc a 21

<210> SEQ ID NO 538
<211> LENGTH: 23
<212> TYPE: RNA
<213> ORGANISM: Artificial Sequence
<220> FEATURE:

<223> OTHER INFORMATION: Antisense sequence for siFXIi2-M2SP1

<400> SEQUENCE: 538
ugaguuuucu ccagaaucca guc 23

<210> SEQ ID NO 539
<211> LENGTH: 21
<212> TYPE: RNA
<213> ORGANISM: Artificial Sequence
<220> FEATURE:
<223> OTHER INFORMATION: Sense sequence for siFXIi2-M3SP1

<400> SEQUENCE: 539
cuggauucug gagaaaacuc a 21

<210> SEQ ID NO 540
<211> LENGTH: 23
<212> TYPE: RNA
<213> ORGANISM: Artificial Sequence
<220> FEATURE:
<223> OTHER INFORMATION: Antisense sequence for siFXIi2-M3SP1

<400> SEQUENCE: 540
ugaguuuucu ccagaaucca guc 23

<210> SEQ ID NO 541
<211> LENGTH: 19
<212> TYPE: RNA
<213> ORGANISM: Artificial Sequence
<220> FEATURE:
<223> OTHER INFORMATION: Sense sequence for L10-siFXIf1M1S

<400> SEQUENCE: 541
guacguggac uggauucug 19

<210> SEQ ID NO 542
<211> LENGTH: 21
<212> TYPE: RNA
<213> ORGANISM: Artificial Sequence
<220> FEATURE:
<223> OTHER INFORMATION: Antisense sequence for L10-siFXIf1M1S

<400> SEQUENCE: 542
cagaauccag uccacguacu u 21

<210> SEQ ID NO 543
<211> LENGTH: 19
<212> TYPE: RNA
<213> ORGANISM: Artificial Sequence
<220> FEATURE:
<223> OTHER INFORMATION: Sense sequence for L10-siFXIa1M1SP

<400> SEQUENCE: 543
ggguauucuu ucaagcaau 19

<210> SEQ ID NO 544
<211> LENGTH: 21
<212> TYPE: RNA
<213> ORGANISM: Artificial Sequence
<220> FEATURE:
<223> OTHER INFORMATION: Antisense sequence for L10-siFXIa1M1SP

<400> SEQUENCE: 544
auugcuugaa agaauaccca g 21

<210> SEQ ID NO 545
<211> LENGTH: 19
<212> TYPE: RNA
<213> ORGANISM: Artificial Sequence
<220> FEATURE:
<223> OTHER INFORMATION: Sense sequence for L10-siFXIb1M1SP

<400> SEQUENCE: 545
ggcauaaacu auaacagcu 19

<210> SEQ ID NO 546
<211> LENGTH: 21
<212> TYPE: RNA
<213> ORGANISM: Artificial Sequence
<220> FEATURE:
<223> OTHER INFORMATION: Antisense sequence for L10-siFXIb1M1SP

<400> SEQUENCE: 546
agcuguuaua guuuaugccc u 21

<210> SEQ ID NO 547
<211> LENGTH: 19
<212> TYPE: RNA
<213> ORGANISM: Artificial Sequence
<220> FEATURE:
<223> OTHER INFORMATION: Sense sequence for L10-siFXIc1M1SP

<400> SEQUENCE: 547
gcucaagaau gccaagaaa 19

<210> SEQ ID NO 548
<211> LENGTH: 21
<212> TYPE: RNA
<213> ORGANISM: Artificial Sequence
<220> FEATURE:
<223> OTHER INFORMATION: Antisense sequence for L10-siFXIc1M1SP

<400> SEQUENCE: 548
uuucuuggca uucuugagca c 21

<210> SEQ ID NO 549
<211> LENGTH: 19
<212> TYPE: RNA
<213> ORGANISM: Artificial Sequence
<220> FEATURE:
<223> OTHER INFORMATION: Sense sequence for L10-siFXId1M1SP

<400> SEQUENCE: 549
gcaacaaaga cauuuaugu 19

<210> SEQ ID NO 550
<211> LENGTH: 21
<212> TYPE: RNA
<213> ORGANISM: Artificial Sequence
<220> FEATURE:
<223> OTHER INFORMATION: Antisense sequence for L10-siFXId1M1SP

<400> SEQUENCE: 550
acauaaaugu cuuuguugca a 21

<210> SEQ ID NO 551
<211> LENGTH: 19
<212> TYPE: RNA
<213> ORGANISM: Artificial Sequence
<220> FEATURE:
<223> OTHER INFORMATION: Sense sequence for L10-siFXIe1M1SPP

<400> SEQUENCE: 551
gaaucucaaa gaaaucuuu 19

<210> SEQ ID NO 552
<211> LENGTH: 21
<212> TYPE: RNA
<213> ORGANISM: Artificial Sequence
<220> FEATURE:
<223> OTHER INFORMATION: Antisense sequence for L10-siFXIe1M1SP

<400> SEQUENCE: 552
aaagauuucu uugagauucu u 21

<210> SEQ ID NO 553
<211> LENGTH: 19
<212> TYPE: RNA
<213> ORGANISM: Artificial Sequence
<220> FEATURE:
<223> OTHER INFORMATION: Sense sequence for L10-siFXIg1M1SP

<400> SEQUENCE: 553
auuucugggu auucuuuca 19

<210> SEQ ID NO 554
<211> LENGTH: 21
<212> TYPE: RNA
<213> ORGANISM: Artificial Sequence
<220> FEATURE:
<223> OTHER INFORMATION: Antisense sequence for L10-siFXIg1M1SP

<400> SEQUENCE: 554
ugaaagaaua cccagaaauc g 21

<210> SEQ ID NO 555
<211> LENGTH: 19
<212> TYPE: RNA
<213> ORGANISM: Artificial Sequence
<220> FEATURE:
<223> OTHER INFORMATION: Sense sequence for L10-siFXIh1M1SP

<400> SEQUENCE: 555
caugaagggc auaaacuau 19

<210> SEQ ID NO 556
<211> LENGTH: 21
<212> TYPE: RNA
<213> ORGANISM: Artificial Sequence
<220> FEATURE:
<223> OTHER INFORMATION: Antisense sequence for L10-siFXIh1M1SP

<400> SEQUENCE: 556
auaguuuaug cccuucaugu c 21

<210> SEQ ID NO 557
<211> LENGTH: 19
<212> TYPE: RNA
<213> ORGANISM: Artificial Sequence
<220> FEATURE:
<223> OTHER INFORMATION: Sense sequence for L10-siFXIi1M1S

<400> SEQUENCE: 557
ggauucugga gaaaacuca 19

<210> SEQ ID NO 558
<211> LENGTH: 21

<212> TYPE: RNA
<213> ORGANISM: Artificial Sequence
<220> FEATURE:
<223> OTHER INFORMATION: Antisense sequence for L10-siFXIi1M1S

<400> SEQUENCE: 558
ugaguuuucu ccagaaucca g 21

<210> SEQ ID NO 559
<211> LENGTH: 19
<212> TYPE: RNA
<213> ORGANISM: Artificial Sequence
<220> FEATURE:
<223> OTHER INFORMATION: Sense sequence for L10-siFXIi1M1SP

<400> SEQUENCE: 559
ggauucugga gaaaacuca 19

<210> SEQ ID NO 560
<211> LENGTH: 21
<212> TYPE: RNA
<213> ORGANISM: Artificial Sequence
<220> FEATURE:
<223> OTHER INFORMATION: Antisense sequence for L10-siFXIi1M1SP

<400> SEQUENCE: 560
ugaguuuucu ccagaaucca g 21

<210> SEQ ID NO 561
<211> LENGTH: 19
<212> TYPE: RNA
<213> ORGANISM: Artificial Sequence
<220> FEATURE:
<223> OTHER INFORMATION: Sense sequence for siFXIe1

<400> SEQUENCE: 561
gaaucucaaa gaaaucuuu 19

<210> SEQ ID NO 562
<211> LENGTH: 19
<212> TYPE: RNA
<213> ORGANISM: Artificial Sequence
<220> FEATURE:
<223> OTHER INFORMATION: Antisense sequence for siFXIe1

<400> SEQUENCE: 562
aaagauuucu uugagauuc 19

<210> SEQ ID NO 563
<211> LENGTH: 19
<212> TYPE: RNA
<213> ORGANISM: Artificial Sequence
<220> FEATURE:
<223> OTHER INFORMATION: Sense sequence for NC

<400> SEQUENCE: 563
uucuccgaac gugucacgu 19

<210> SEQ ID NO 564
<211> LENGTH: 21
<212> TYPE: RNA
<213> ORGANISM: Artificial Sequence
<220> FEATURE:
<223> OTHER INFORMATION: Antisense sequence for NC

<400> SEQUENCE: 564
acgugacacg uucggagaac u 21

<210> SEQ ID NO 565
<211> LENGTH: 19
<212> TYPE: DNA
<213> ORGANISM: Artificial Sequence
<220> FEATURE:
<223> OTHER INFORMATION: The target sequence for siFXIe1

<400> SEQUENCE: 565
gaatctcaaa gaaatcttt 19

<210> SEQ ID NO 566
<211> LENGTH: 19
<212> TYPE: DNA
<213> ORGANISM: Artificial Sequence
<220> FEATURE:
<223> OTHER INFORMATION: Upstream Primer for Human FXI

<400> SEQUENCE: 566
tcacggcgga atcaccatc 19

<210> SEQ ID NO 567
<211> LENGTH: 22
<212> TYPE: DNA
<213> ORGANISM: Artificial Sequence
<220> FEATURE:
<223> OTHER INFORMATION: Downstream Primer for Human FXI

<400> SEQUENCE: 567
tgtcctattc actcttggca gt 22

<210> SEQ ID NO 568
<211> LENGTH: 19
<212> TYPE: DNA
<213> ORGANISM: Artificial Sequence
<220> FEATURE:
<223> OTHER INFORMATION: Upstream Primer for Human GAPDH

<400> SEQUENCE: 568
ggtcggagtc aacggattt 19

<210> SEQ ID NO 569
<211> LENGTH: 19
<212> TYPE: DNA
<213> ORGANISM: Artificial Sequence
<220> FEATURE:
<223> OTHER INFORMATION: Downstream Primer for Human GAPDH

<400> SEQUENCE: 569
ccagcatcgc cccacttga 19

<210> SEQ ID NO 570
<211> LENGTH: 19
<212> TYPE: DNA
<213> ORGANISM: Artificial Sequence
<220> FEATURE:
<223> OTHER INFORMATION: Upstream Primer for Human FXI

<400> SEQUENCE: 570
tcacggcgga atcaccatc 19

<210> SEQ ID NO 571
<211> LENGTH: 22
<212> TYPE: DNA
<213> ORGANISM: Artificial Sequence
<220> FEATURE:
<223> OTHER INFORMATION: Downstream Primer for Human FXI

<400> SEQUENCE: 571
tgtcctattc actcttggca gt 22

<210> SEQ ID NO 572
<211> LENGTH: 24
<212> TYPE: DNA
<213> ORGANISM: Artificial Sequence
<220> FEATURE:
<223> OTHER INFORMATION: Upstream Primer for Mouse GAPDH

<400> SEQUENCE: 572
aactttggca ttgtggaagg gctc 24

<210> SEQ ID NO 573
<211> LENGTH: 24
<212> TYPE: DNA
<213> ORGANISM: Artificial Sequence
<220> FEATURE:
<223> OTHER INFORMATION: Downstream Primer for Mouse GAPDH

<400> SEQUENCE: 573
tggaagagtg ggagttgctg ttga 24

<210> SEQ ID NO 574
<211> LENGTH: 23
<212> TYPE: DNA
<213> ORGANISM: Artificial Sequence
<220> FEATURE:
<223> OTHER INFORMATION: Upstream Primer for Mouse FXI

<400> SEQUENCE: 574
gccctgttaa aactggaatc agc 23

<210> SEQ ID NO 575
<211> LENGTH: 23
<212> TYPE: DNA
<213> ORGANISM: Artificial Sequence
<220> FEATURE:
<223> OTHER INFORMATION: Downstream Primer for Mouse FXI

<400> SEQUENCE: 575
cgtttctatc tcctttggaa ggc 23

<210> SEQ ID NO 576
<211> LENGTH: 19
<212> TYPE: DNA
<213> ORGANISM: Artificial Sequence
<220> FEATURE:
<223> OTHER INFORMATION: Upstream Primer for Mouse GAPDH

<400> SEQUENCE: 576
tgcaccacca actgcttag 19

<210> SEQ ID NO 577
<211> LENGTH: 19
<212> TYPE: DNA
<213> ORGANISM: Artificial Sequence
<220> FEATURE:
<223> OTHER INFORMATION: Downstream Primer for Mouse GAPDH

<400> SEQUENCE: 577
ggatgcaggg atgatgttc 19